United States Patent
Ensley et al.

(10) Patent No.: US 9,114,128 B2
(45) Date of Patent: Aug. 25, 2015

(54) TROPOELASTINS AND USES THEREOF

(71) Applicant: Protein Genomics, Inc., Sedona, AZ (US)

(72) Inventors: Burt D. Ensley, Sedona, AZ (US); Robert Kellar, Flagstaff, AZ (US)

(73) Assignee: Protein Genomics, Inc., Sedona, AZ (US)

( * ) Notice: Subject to any disclaimer, the term of this patent is extended or adjusted under 35 U.S.C. 154(b) by 0 days.

(21) Appl. No.: 13/631,139

(22) Filed: Sep. 28, 2012

(65) Prior Publication Data

US 2013/0164340 A1 Jun. 27, 2013

Related U.S. Application Data

(60) Provisional application No. 61/541,696, filed on Sep. 30, 2011.

(51) Int. Cl.

| | |
|---|---|
| C07H 21/04 | (2006.01) |
| C07K 14/78 | (2006.01) |
| A61K 38/39 | (2006.01) |
| A61K 35/28 | (2015.01) |
| A61K 9/00 | (2006.01) |
| C12N 5/0775 | (2010.01) |
| C12N 5/00 | (2006.01) |
| C12N 5/077 | (2010.01) |
| A61L 27/24 | (2006.01) |
| A61L 27/26 | (2006.01) |
| A61L 27/38 | (2006.01) |
| A61L 27/58 | (2006.01) |

(52) U.S. Cl.
CPC ............... *A61K 38/39* (2013.01); *A61K 9/0024* (2013.01); *A61K 35/28* (2013.01); *A61L 27/24* (2013.01); *A61L 27/26* (2013.01); *A61L 27/3804* (2013.01); *A61L 27/58* (2013.01); *C07K 14/78* (2013.01); *C12N 5/0068* (2013.01); *C12N 5/0652* (2013.01); *C12N 5/0654* (2013.01); *C12N 5/0663* (2013.01); *A61L 2300/252* (2013.01); *C12N 2533/50* (2013.01)

(58) Field of Classification Search
CPC ..................................... C07K 14/78
See application file for complete search history.

(56) References Cited

FOREIGN PATENT DOCUMENTS

WO 2008/067195 * 6/2008

OTHER PUBLICATIONS

Indik et al. 1987; Alternative splicing of human elastin mRNA indicated by sequence analysis of cloned genomic and complementary DNA. PNAS 84(16): 5680-5684.*

Amarzguioui et al., "Secondary structure prediction and in vitro accessibility of mRNA as tools in the selection of target sites for ribozymes," *Nucleic Acids Res*. (2000), 28(21): 4113-4124.

Boyd et al., "Mammalian Tropoelastin: Multiple Domains of the Protein Define an Evolutionarily Divergent Amino Acid Sequence", *Matrix* (1991), 11: 235-241.

Buttafoco et al., "Electrospinning of collagen and elastin for tissue engineering applications", *Biomaterials* (2006), 27: 724-734.

Clarke et al., "Tropoelastin massively associates during coacervation to form quantized protein spheres", *Biochemistry* (2006), 45: 9989-9996.

Cummings et al., "Histologic evaluation of autogenous connective tissue and acellular dermal matrix grafts in humans", J Periodontol. (2005), 76(2):178-186.

Fazio et al. "Cloning of full-length elastin cDNAs from a human skin fibroblast recombinant cDNA library: Further elucidation of alternative splicing utilizing exonspecific oligonucleotides", *J. Invest. Dermatol.* (1988), 91:458-464.

Fazio et al., "Isolation and characterization of human elastin cDNAs, and age-associated variation in elastin gene expression in cultured skin fibroblasts", *Lab. Invest.* (1988), 58(3): 270-277.

Fazio et al., "Regulation of Elastin Gene Expression: Evidence for Functional Promoter Activity in the 5'-Flanking Region of the human Gene", *Journal of Investigative Dermatology* (1990), 94(2): 191-196.

Gapski et al., "Acellular Dermal Matrix for Mucogingival Surgery: A Meta-Analysis", *J Periodontol* (2005), 76(11): 1814-1822.

Hinds et al., "Development of a reinforced porcine elastin composite vascular scaffold", *J. Biomed. Mater. Res. Part A* (2006), 77: 458-469.

Indik et al., "Production of Recombinant Human Tropoelastin: Characterization and Demonstration of Immunologic and Chemotactic Activity", *Arch. Biochem. Biophys.* (1990), 280(1): 80-86.

Indik et al., "Structure of the 3' Region of the Human Elastin Gene: Great Abundance of Alu Repetitive Sequences and Few Coding Sequences", *Connect. Tissue Res.* (1987), 16: 197-211.

Indik et al., "Alternative splicing of human elastin mRNA indicated by sequence analysis of cloned genomic and complementary DNA", P.N.A.S. USA (1987), 84(16): 5680-5684.

Kapoor et al., "Effects of Epicatechin Gallate on Wound Healing and Scar Formation in a Full Thickness Incisional Wound Healing Model in Rats", *Am. J. Path.* (2004), 165(1): 299-307.

Kellar et al., "Characterization of angiogenesis and inflammation surrounding ePTFE implanted on the epicardium", *Journal of Biomedical Materials Research* (2002), 61(2): 226-233.

Kidd et al., "A comparative evaluation of the tissue responses associated with polymeric implants in the rat and mouse", *Journal of Biomedical Materials Research* (2002), 59(4): 682-689.

Kundu and Putnam, "Vitronectin and collagen I differentially regulate osteogenesis in mesenchymal stem cells", *Biochem Biophys Res Commun.* (2006), 347-357.

(Continued)

*Primary Examiner* — Karen Cochrane Carlson

(74) *Attorney, Agent, or Firm* — Cooley LLP

(57) ABSTRACT

The present invention relates to biocompatible polymeric scaffold materials, methods for making the materials and methods of using the materials. More particularly, the present invention relates to implants and grafts comprising polymeric scaffold materials of cross-linked human tropoelastin polypeptides and methods of making and using the same. In addition, the present invention provides alternatively spliced tropoelastin polynucleotides and polypeptides.

8 Claims, 3 Drawing Sheets

(56) References Cited

OTHER PUBLICATIONS

Kundu et al., "Extracellular Matrix Remodeling, Integrin Expression, and Downstream Signaling Pathways Influence the Osteogenic Differentiation of Mesenchymal Stem Cells on Poly(Lactide-Co-Glycolide) Substrates", *Tissue Engineering: Part A* (2009), 15(2): 273-283.

Martin et al., "Total synthesis and expression in *Escherichia coli* of a gene encoding human tropoelastin", *Gene* (1995), 154: 159-166.

Mithieux et al., "Synthetic elastin hydrogels derived from massive elastic assemblies of self-organized human protein monomers", *Biomaterials* (2004), 25: 4921-4927.

Papageorgakopoulos et al., "Root coverage using acellular dermal matrix and comparing a coronally positioned tunnel to a coronally positioned flap approach", *J Periodontol.* (2008), 79(6): 1022-1030.

Parks and Deak, "Tropoelastin Heterogeneity: Implications for Protein Function and Disease", *Am. J. Respir. Cell Mol. Biol.* (1990), 2:399-406.

Parks et al., "Posttranscriptional Regulation of Lung Elastin Production", *Am. J. Respir. Cell Mol. Biol.* (1997), 17(1):1-2.

Ragnarsson et al., "Isolation and growth of human periodontal ligament cells in vitro", *Journal of Dental Research* (1985), 64: 1026-1030.

Rosenbloom et al., "Extracellular matrix 4: the elastic fiber", *FASEB J.* (1993), 7: 1208-1218.

Santerre et al., "Understanding the biodegradation of polyurethanes: From classical implants to tissue engineering materials", *Biomaterials* (2005), 26: 7457-7470.

Shapiro, S.D., "Elastolytic Metalloproteinases Produced by Human Mononuclear Phagocytes", *Am. J. Respir. Crit. Care Med.* (1994) 150: S160-S164.

Stitzel et al., "Controlled fabrication of a biological vascular substitute", *Biomaterials* (2006), 27: 1088-1094.

\* cited by examiner

SEQUENCE LISTING

```
<160> NUMBER OF SEQ ID NOS: 87

<210> SEQ ID NO 1
<211> LENGTH: 822
<212> TYPE: PRT
<213> ORGANISM: Homo sapiens

<400> SEQUENCE: 1

Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Gly Lys Pro Leu Lys
                50                  55                  60

Pro Val Pro Gly Gly Leu Ala Gly Ala Gly Leu Gly Ala Gly Pro His
65                  70                  75                  80

Pro Ile Leu Pro Ser Ala Gly Leu Gly Ala Phe Pro Ala Val Thr Phe
                85                  90                  95

Pro Gly Ala Leu Val Pro Gly Gly Val Ala Asp Ala Ala Ala Ala Tyr
                100                 105                 110

Lys Ala Ala Lys Ala Gly Ala Gly Leu Gly Gly Val Pro Gly Val Gly
                115                 120                 125

Gly Leu Gly Val Ser Ala Ala Pro Ser Val Pro Gly Ala Val Val Pro
                130                 135                 140

Gln Pro Gly Ala Gly Val Lys Pro Gly Lys Val Pro Gly Val Gly Leu
145                 150                 155                 160

Pro Gly Val Tyr Pro Gly Gly Val Leu Pro Gly Pro Ala Arg Pro Ala
                165                 170                 175

Phe Leu His Ser Leu Leu Cys Pro Pro Ala Gly Ala Arg Phe Pro Gly
                180                 185                 190

Val Gly Val Leu Pro Gly Val Pro Thr Gly Ala Gly Val Lys Pro Lys
                195                 200                 205

Ala Pro Gly Val Gly Gly Ala Phe Ala Gly Ile Pro Gly Val Gly Pro
                210                 215                 220

Phe Gly Gly Pro Gln Pro Gly Val Pro Leu Gly Tyr Pro Ile Lys Ala
225                 230                 235                 240

Pro Lys Leu Pro Gly Gly Tyr Gly Leu Pro Tyr Thr Thr Gly Lys Leu
                245                 250                 255

Pro Tyr Gly Tyr Gly Pro Gly Gly Val Ala Gly Ala Ala Gly Lys Ala
                260                 265                 270

Gly Tyr Pro Thr Gly Thr Gly Val Gly Pro Gln Ala Ala Ala Ala Ala
                275                 280                 285

Ala Ala Lys Ala Ala Ala Lys Phe Gly Ala Gly Ala Ala Gly Val Leu
                290                 295                 300
```

```
Pro Gly Val Gly Gly Ala Gly Val Pro Gly Val Pro Gly Ala Ile Pro
305                 310                 315                 320

Gly Ile Gly Gly Ile Ala Gly Val Gly Thr Pro Ala Ala Ala Ala
            325                 330                 335

Ala Ala Ala Ala Ala Lys Ala Ala Lys Tyr Gly Ala Ala Gly Leu
            340                 345                 350

Val Pro Gly Gly Pro Gly Phe Gly Pro Gly Val Val Gly Val Pro Gly
            355                 360                 365

Ala Gly Val Pro Gly Val Gly Val Pro Gly Ala Gly Ile Pro Val Val
            370                 375                 380

Pro Gly Ala Gly Ile Pro Gly Ala Ala Val Pro Gly Val Val Ser Pro
385                 390                 395                 400

Glu Ala Ala Ala Lys Ala Ala Ala Lys Ala Ala Lys Tyr Gly Ala Arg
                405                 410                 415

Pro Gly Val Gly Val Gly Gly Ile Pro Thr Tyr Gly Val Gly Ala Gly
            420                 425                 430

Gly Phe Pro Gly Phe Gly Val Gly Val Gly Gly Ile Pro Gly Val Ala
            435                 440                 445

Gly Val Pro Gly Val Gly Val Pro Gly Val Gly Gly Val Pro Gly
450                 455                 460

Val Gly Ile Ser Pro Glu Ala Gln Ala Ala Ala Ala Lys Ala Ala
465                 470                 475                 480

Lys Tyr Gly Ala Ala Gly Ala Gly Val Leu Gly Gly Leu Val Pro Gly
            485                 490                 495

Ala Pro Gly Ala Val Pro Gly Val Pro Gly Thr Gly Val Pro Gly
            500                 505                 510

Val Gly Thr Pro Ala Ala Ala Ala Lys Ala Ala Lys Ala Ala
            515                 520                 525

Gln Phe Ala Leu Leu Asn Leu Ala Gly Leu Val Pro Gly Val Gly Val
530                 535                 540

Ala Pro Gly Val Gly Val Ala Pro Gly Val Gly Val Ala Pro Gly Val
545                 550                 555                 560

Gly Leu Ala Pro Gly Val Gly Val Ala Pro Gly Val Gly Val Ala Pro
            565                 570                 575

Gly Val Gly Val Ala Pro Gly Ile Gly Pro Gly Gly Val Ala Ala Ala
            580                 585                 590

Ala Lys Ser Ala Ala Lys Val Ala Ala Lys Ala Gln Leu Arg Ala Ala
            595                 600                 605

Ala Gly Leu Gly Ala Gly Ile Pro Gly Leu Gly Val Gly Val Gly Val
            610                 615                 620

Pro Gly Leu Gly Val Gly Ala Gly Val Pro Gly Leu Gly Val Gly Ala
625                 630                 635                 640

Gly Val Pro Gly Phe Gly Ala Gly Ala Asp Glu Gly Val Arg Arg Ser
                645                 650                 655

Leu Ser Pro Glu Leu Arg Glu Gly Asp Pro Ser Ser Gln His Leu
            660                 665                 670

Pro Ser Thr Pro Ser Ser Pro Arg Val Pro Gly Ala Leu Ala Ala Ala
            675                 680                 685

Lys Ala Ala Lys Tyr Gly Ala Ala Val Pro Gly Val Leu Gly Gly Leu
            690                 695                 700

Gly Ala Leu Gly Gly Val Gly Ile Pro Gly Gly Val Val Gly Ala Gly
705                 710                 715                 720
```

Pro Ala Ala Ala Ala Ala Ala Lys Ala Ala Lys Ala Ala Gln
         725                 730             735

Phe Gly Leu Val Gly Ala Ala Gly Leu Gly Gly Leu Val Gly Gly
         740                 745             750

Leu Gly Val Pro Gly Val Gly Gly Leu Gly Gly Ile Pro Pro Ala Ala
         755                 760             765

Ala Ala Lys Ala Ala Lys Tyr Gly Ala Ala Gly Leu Gly Gly Val Leu
         770                 775             780

Gly Gly Ala Gly Gln Phe Pro Leu Gly Gly Val Ala Ala Arg Pro Gly
785              790                 795             800

Phe Gly Leu Ser Pro Ile Phe Pro Gly Gly Ala Cys Leu Gly Lys Ala
             805                 810             815

Cys Gly Arg Lys Arg Lys
             820

<210> SEQ ID NO 2
<211> LENGTH: 697
<212> TYPE: PRT
<213> ORGANISM: Homo sapiens

<400> SEQUENCE: 2

Met Ala Gly Leu Thr Ala Ala Pro Arg Pro Gly Val Leu Leu Leu
 1               5                  10              15

Leu Leu Ser Ile Leu His Pro Ser Arg Pro Gly Val Phe Tyr Pro Gly
             20                  25              30

Ala Gly Leu Gly Ala Leu Gly Gly Gly Ala Leu Gly Pro Gly Gly Lys
             35                  40              45

Pro Leu Lys Pro Val Pro Gly Gly Leu Ala Gly Ala Gly Leu Gly Ala
50                   55                  60

Gly Leu Gly Ala Phe Pro Ala Val Thr Phe Pro Gly Ala Leu Val Pro
65                   70                  75                  80

Gly Gly Val Ala Asp Ala Ala Ala Tyr Lys Ala Ala Lys Ala Gly
                 85                  90                  95

Ala Gly Leu Gly Gly Val Pro Gly Val Gly Gly Leu Gly Val Ser Ala
             100                 105                 110

Ala Pro Ser Val Pro Gly Ala Val Pro Gln Pro Gly Ala Gly Val
             115                 120                 125

Lys Pro Gly Lys Val Pro Gly Val Gly Leu Pro Gly Val Tyr Pro Gly
         130                 135                 140

Gly Val Leu Pro Gly Ala Arg Phe Pro Gly Val Gly Val Leu Pro Gly
145                 150                 155                 160

Val Pro Thr Gly Ala Gly Val Lys Pro Lys Ala Pro Gly Val Gly Gly
             165                 170                 175

Ala Phe Ala Gly Ile Pro Gly Val Gly Pro Phe Gly Gly Pro Gln Pro
             180                 185                 190

Gly Val Pro Leu Gly Tyr Pro Ile Lys Ala Pro Lys Leu Pro Gly Gly
             195                 200                 205

Tyr Gly Leu Pro Tyr Thr Thr Gly Lys Leu Pro Tyr Gly Tyr Gly Pro
         210                 215                 220

Gly Gly Val Ala Gly Ala Ala Gly Lys Ala Gly Tyr Pro Thr Gly Thr
225                 230                 235                 240

Gly Val Gly Pro Gln Ala Ala Ala Ala Ala Lys Ala Ala Ala
                 245                 250                 255

Lys Phe Gly Ala Gly Ala Ala Gly Val Leu Pro Gly Val Gly Gly Ala
             260                 265                 270

```
Gly Val Pro Gly Val Pro Gly Ala Ile Pro Gly Ile Gly Ile Ala
            275                 280                 285

Gly Val Gly Thr Pro Ala Ala Ala Ala Ala Ala Ala Ala Ala Lys
            290                 295                 300

Ala Ala Lys Tyr Gly Ala Ala Gly Leu Val Pro Gly Gly Pro Gly
305                 310                 315                 320

Phe Gly Pro Gly Val Val Gly Val Pro Gly Ala Gly Val Pro Gly Val
                    325                 330                 335

Gly Val Pro Gly Ala Gly Ile Pro Val Val Pro Gly Ala Gly Ile Pro
                    340                 345                 350

Gly Ala Ala Val Pro Gly Val Val Ser Pro Glu Ala Ala Lys Ala
            355                 360                 365

Ala Ala Lys Ala Ala Lys Tyr Gly Ala Arg Pro Gly Val Gly Val Gly
370                 375                 380

Gly Ile Pro Thr Tyr Gly Val Gly Ala Gly Gly Phe Pro Gly Phe Gly
385                 390                 395                 400

Val Gly Val Gly Gly Ile Pro Gly Val Ala Gly Val Pro Gly Val Gly
                    405                 410                 415

Gly Val Pro Gly Val Gly Val Pro Gly Val Gly Ile Ser Pro Glu
            420                 425                 430

Ala Gln Ala Ala Ala Ala Lys Ala Ala Lys Tyr Gly Leu Val Pro
            435                 440                 445

Gly Val Gly Val Ala Pro Gly Val Gly Val Ala Pro Gly Val Gly Val
450                 455                 460

Ala Pro Gly Val Gly Leu Ala Pro Gly Val Gly Val Ala Pro Gly Val
465                 470                 475                 480

Gly Val Ala Pro Gly Val Gly Val Ala Pro Gly Ile Gly Pro Gly Gly
                    485                 490                 495

Val Ala Ala Ala Ala Lys Ser Ala Ala Lys Val Ala Ala Lys Ala Gln
                    500                 505                 510

Leu Arg Ala Ala Ala Gly Leu Gly Ala Gly Ile Pro Gly Leu Gly Val
            515                 520                 525

Gly Val Gly Val Pro Gly Leu Gly Val Gly Ala Gly Val Pro Gly Leu
            530                 535                 540

Gly Val Gly Ala Gly Val Pro Gly Phe Gly Ala Val Pro Gly Ala Leu
545                 550                 555                 560

Ala Ala Ala Lys Ala Ala Lys Tyr Gly Ala Ala Val Pro Gly Val Leu
                    565                 570                 575

Gly Gly Leu Gly Ala Leu Gly Gly Val Gly Ile Pro Gly Gly Val Val
            580                 585                 590

Gly Ala Gly Pro Ala Ala Ala Ala Ala Ala Lys Ala Ala Ala Lys
            595                 600                 605

Ala Ala Gln Phe Gly Leu Val Gly Ala Ala Gly Leu Gly Gly Leu Gly
610                 615                 620

Val Gly Gly Leu Gly Val Pro Gly Val Gly Gly Leu Gly Gly Ile Pro
625                 630                 635                 640

Pro Ala Ala Ala Ala Lys Ala Ala Lys Tyr Gly Ala Ala Gly Leu Gly
                    645                 650                 655

Gly Val Leu Gly Gly Ala Gly Gln Phe Pro Leu Gly Gly Val Ala Ala
            660                 665                 670

Arg Pro Gly Phe Gly Leu Ser Pro Ile Phe Pro Gly Gly Ala Cys Leu
            675                 680                 685
```

```
Gly Lys Ala Cys Gly Arg Lys Arg Lys
    690                 695

<210> SEQ ID NO 3
<211> LENGTH: 724
<212> TYPE: PRT
<213> ORGANISM: Homo sapiens

<400> SEQUENCE: 3

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
             20                  25                  30

Ile Pro Gly Gly Val Pro Gly Gly Val Phe Tyr Pro Gly Ala Gly Leu
             35                  40                  45

Gly Ala Leu Gly Gly Gly Ala Leu Gly Pro Gly Gly Lys Pro Leu Lys
 50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
            130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
            210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Val Pro Gly Ala Gly Ile Pro
            340                 345                 350

Val Val Pro Gly Ala Gly Ile Pro Gly Ala Ala Val Pro Gly Val Val
            355                 360                 365
```

Ser Pro Glu Ala Ala Ala Lys Ala Ala Ala Lys Ala Ala Lys Tyr Gly
370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
            405                 410                 415

Val Ala Gly Val Pro Gly Val Gly Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Val Gly Thr Pro Ala Ala Ala Ala Ala Lys Ala
450                 455                 460

Ala Ala Lys Ala Ala His Phe Gly Leu Val Pro Gly Val Gly Val Ala
465                 470                 475                 480

Pro Gly Val Gly Val Ala Pro Gly Val Gly Val Ala Pro Gly Val Gly
            485                 490                 495

Leu Ala Pro Gly Val Gly Val Ala Pro Gly Val Gly Val Ala Pro Gly
            500                 505                 510

Val Gly Val Ala Pro Gly Ile Gly Pro Gly Gly Val Ala Ala Ala Ala
            515                 520                 525

Lys Ser Ala Ala Lys Val Ala Ala Lys Ala Gln Leu Arg Ala Ala
530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
            565                 570                 575

Val Pro Gly Phe Gly Ala Val Pro Gly Ala Leu Ala Ala Ala Lys Ala
            580                 585                 590

Ala Lys Tyr Gly Ala Ala Val Pro Gly Val Leu Gly Gly Leu Gly Ala
            595                 600                 605

Leu Gly Gly Val Gly Ile Pro Gly Gly Val Val Gly Ala Gly Pro Ala
610                 615                 620

Ala Ala Ala Ala Ala Ala Lys Ala Ala Lys Ala Ala Gln Phe Gly
625                 630                 635                 640

Leu Val Gly Ala Ala Gly Leu Gly Gly Leu Gly Val Gly Gly Leu Gly
            645                 650                 655

Val Pro Gly Val Gly Gly Leu Gly Gly Ile Pro Pro Ala Ala Ala Ala
            660                 665                 670

Lys Ala Ala Lys Tyr Gly Ala Ala Gly Leu Gly Gly Val Leu Gly Gly
            675                 680                 685

Ala Gly Gln Phe Pro Leu Gly Gly Val Ala Ala Arg Pro Gly Phe Gly
690                 695                 700

Leu Ser Pro Ile Phe Pro Gly Gly Ala Cys Leu Gly Lys Ala Cys Gly
705                 710                 715                 720

Arg Lys Arg Lys

<210> SEQ ID NO 4
<211> LENGTH: 724
<212> TYPE: PRT
<213> ORGANISM: Homo sapiens

<400> SEQUENCE: 4

Met Ala Gly Leu Thr Ala Ala Ala Pro Arg Pro Gly Val Leu Leu Leu
1               5                   10                  15

```
Leu Leu Ser Ile Leu His Pro Ser Arg Pro Gly Gly Val Pro Gly Ala
            20                  25                  30

Ile Pro Gly Gly Val Pro Gly Val Phe Tyr Pro Gly Ala Gly Leu
        35                  40                  45

Gly Ala Leu Gly Gly Ala Leu Gly Pro Gly Lys Pro Leu Lys
 50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
 130                 135                 140

Gly Leu Pro Gly Val Tyr Pro Gly Gly Val Leu Pro Gly Ala Arg Phe
 145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
 210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
            245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Lys Ala Ala Lys Tyr Gly
            370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430
```

-continued

```
Pro Gly Val Gly Ile Ser Pro Glu Ala Gln Ala Ala Ala Ala Lys
            435                 440                 445

Ala Ala Lys Tyr Gly Val Gly Thr Pro Ala Ala Ala Ala Lys Ala
450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
                500                 505                 510

Val Gly Val Ala Pro Gly Ile Gly Pro Gly Gly Val Ala Ala Ala
            515                 520                 525

Lys Ser Ala Ala Lys Val Ala Ala Lys Ala Gln Leu Arg Ala Ala
530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Val Pro Gly Ala Leu Ala Ala Ala Lys Ala
                580                 585                 590

Ala Lys Tyr Gly Ala Ala Val Pro Gly Val Leu Gly Gly Leu Gly Ala
            595                 600                 605

Leu Gly Gly Val Gly Ile Pro Gly Gly Val Val Gly Ala Gly Pro Ala
            610                 615                 620

Ala Ala Ala Ala Ala Lys Ala Ala Ala Lys Ala Ala Gln Phe Gly
625                 630                 635                 640

Leu Val Gly Ala Ala Gly Leu Gly Gly Leu Gly Val Gly Gly Leu Gly
                645                 650                 655

Val Pro Gly Val Gly Gly Leu Gly Gly Ile Pro Pro Ala Ala Ala Ala
                660                 665                 670

Lys Ala Ala Lys Tyr Gly Ala Ala Gly Leu Gly Gly Val Leu Gly Gly
            675                 680                 685

Ala Gly Gln Phe Pro Leu Gly Gly Val Ala Ala Arg Pro Gly Phe Gly
            690                 695                 700

Leu Ser Pro Ile Phe Pro Gly Gly Ala Cys Leu Gly Lys Ala Cys Gly
705                 710                 715                 720

Arg Lys Arg Lys

<210> SEQ ID NO 5
<211> LENGTH: 724
<212> TYPE: PRT
<213> ORGANISM: Homo sapiens

<400> SEQUENCE: 5

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80
```

```
Ala Phe Pro Ala Val Thr Phe Pro Gly Ala Leu Val Pro Gly Gly Val
                    85                  90                  95

Ala Asp Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
        290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Val Gly Thr Pro Ala Ala Ala Ala Lys Ala
    450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
            485                 490                 495

Leu Ala Pro Gly Val Gly Val Ala Pro Gly Val Gly Val Ala Pro Gly
```

```
                    500                 505                 510
Val Gly Val Ala Pro Gly Ile Gly Pro Gly Gly Val Ala Ala Ala
            515                 520                 525

Lys Ser Ala Ala Lys Val Ala Ala Lys Ala Gln Leu Arg Ala Ala
            530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Val Pro Gly Ala Leu Ala Ala Ala Lys Ala
                580                 585                 590

Ala Lys Tyr Gly Ala Ala Val Pro Gly Val Leu Gly Gly Leu Gly Ala
            595                 600                 605

Leu Gly Gly Val Gly Ile Pro Gly Gly Val Val Gly Ala Gly Pro Ala
            610                 615                 620

Ala Ala Ala Ala Ala Ala Lys Ala Ala Ala Lys Ala Ala Gln Phe Gly
625                 630                 635                 640

Leu Val Gly Ala Ala Gly Leu Gly Gly Leu Gly Val Gly Gly Leu Gly
                645                 650                 655

Val Pro Gly Val Gly Gly Leu Gly Gly Ile Pro Pro Ala Ala Ala Ala
                660                 665                 670

Lys Ala Ala Lys Tyr Gly Ala Ala Gly Leu Gly Gly Val Leu Gly Gly
            675                 680                 685

Ala Gly Gln Phe Pro Leu Gly Gly Val Ala Ala Arg Pro Gly Phe Gly
            690                 695                 700

Leu Ser Pro Ile Phe Pro Gly Gly Ala Cys Leu Gly Lys Ala Cys Gly
705                 710                 715                 720

Arg Lys Arg Lys

<210> SEQ ID NO 6
<211> LENGTH: 693
<212> TYPE: PRT
<213> ORGANISM: Homo sapiens

<400> SEQUENCE: 6

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
                20                  25                  30

Ala Gly Leu Gly Ala Leu Gly Gly Gly Ala Leu Gly Pro Gly Gly Lys
            35                  40                  45

Pro Leu Lys Pro Val Pro Gly Gly Leu Ala Gly Ala Gly Leu Gly Ala
        50                  55                  60

Gly Leu Gly Ala Phe Pro Ala Val Thr Phe Pro Gly Ala Leu Val Pro
65              70                  75                  80

Gly Gly Val Ala Asp Ala Ala Ala Tyr Lys Ala Ala Lys Ala Gly
                85                  90                  95

Ala Gly Leu Gly Gly Val Pro Gly Val Gly Gly Leu Gly Val Ser Ala
            100                 105                 110

Gly Ala Val Val Pro Gln Pro Gly Ala Gly Val Lys Pro Gly Lys Val
        115                 120                 125

Pro Gly Val Gly Leu Pro Gly Val Tyr Pro Gly Gly Val Leu Pro Gly
        130                 135                 140

Ala Arg Phe Pro Gly Val Gly Val Leu Pro Gly Val Pro Thr Gly Ala
```

-continued

```
        145                 150                 155                 160
Gly Val Lys Pro Lys Ala Pro Gly Val Gly Ala Phe Ala Gly Ile
                165                 170                 175
Pro Gly Val Gly Pro Phe Gly Gly Pro Gln Pro Gly Val Pro Leu Gly
                180                 185                 190
Tyr Pro Ile Lys Ala Pro Lys Leu Pro Gly Gly Tyr Gly Leu Pro Tyr
                195                 200                 205
Thr Thr Gly Lys Leu Pro Tyr Gly Tyr Gly Pro Gly Gly Val Ala Gly
    210                  215                 220
Ala Ala Gly Lys Ala Gly Tyr Pro Thr Gly Thr Gly Val Gly Pro Gln
225                 230                 235                 240
Ala Ala Ala Ala Ala Ala Lys Ala Ala Lys Phe Gly Ala Gly
                245                 250                 255
Ala Ala Gly Val Leu Pro Gly Val Gly Gly Ala Gly Val Pro Gly Val
                260                 265                 270
Pro Gly Ala Ile Pro Gly Ile Gly Gly Ile Ala Gly Val Gly Thr Pro
                275                 280                 285
Ala Ala Ala Ala Ala Ala Ala Ala Lys Ala Ala Lys Tyr Gly
    290                 295                 300
Ala Ala Ala Gly Leu Val Pro Gly Pro Gly Phe Gly Pro Gly Val
305                 310                 315                 320
Val Gly Val Pro Gly Ala Gly Val Pro Gly Val Gly Val Pro Gly Ala
                325                 330                 335
Gly Ile Pro Val Val Pro Gly Ala Gly Ile Pro Gly Ala Ala Val Pro
                340                 345                 350
Gly Val Val Ser Pro Glu Ala Ala Lys Ala Ala Ala Lys Ala Ala
                355                 360                 365
Lys Tyr Gly Ala Arg Pro Gly Val Gly Val Gly Ile Pro Thr Tyr
    370                 375                 380
Gly Val Gly Ala Gly Phe Pro Gly Phe Gly Val Gly Val Gly Gly
385                 390                 395                 400
Ile Pro Gly Val Ala Gly Val Pro Gly Val Gly Val Pro Gly Val
                405                 410                 415
Gly Gly Val Pro Gly Val Gly Ile Ser Pro Glu Ala Gln Ala Ala
                420                 425                 430
Ala Ala Lys Ala Ala Lys Tyr Gly Val Gly Thr Pro Ala Ala Ala Ala
                435                 440                 445
Ala Lys Ala Ala Ala Lys Ala Ala Gln Phe Gly Leu Val Pro Gly Val
    450                 455                 460
Gly Val Ala Pro Gly Val Gly Val Ala Pro Gly Val Gly Val Ala Pro
465                 470                 475                 480
Gly Val Gly Leu Ala Pro Gly Val Gly Ala Pro Gly Val Gly Val
                485                 490                 495
Ala Pro Gly Val Gly Val Ala Pro Gly Ile Gly Pro Gly Gly Val Ala
                500                 505                 510
Ala Ala Ala Lys Ser Ala Ala Lys Val Ala Ala Lys Ala Gln Leu Arg
                515                 520                 525
Ala Ala Ala Gly Leu Gly Ala Gly Ile Pro Gly Leu Gly Val Gly Val
                530                 535                 540
Gly Val Pro Gly Leu Gly Val Gly Ala Gly Val Pro Gly Leu Gly Val
545                 550                 555                 560
Gly Ala Gly Val Pro Gly Phe Gly Ala Val Pro Gly Ala Leu Ala Ala
                565                 570                 575
```

```
Ala Lys Ala Ala Lys Tyr Gly Ala Val Pro Gly Val Leu Gly Gly
            580                 585                 590

Leu Gly Ala Leu Gly Gly Val Gly Ile Pro Gly Gly Val Val Gly Ala
        595                 600                 605

Gly Pro Ala Ala Ala Ala Ala Ala Lys Ala Ala Lys Ala Ala
    610                 615                 620

Gln Phe Gly Leu Val Gly Ala Ala Gly Leu Gly Gly Leu Gly Val Gly
625                 630                 635                 640

Gly Leu Gly Val Pro Gly Val Gly Gly Leu Gly Gly Ile Pro Pro Ala
                645                 650                 655

Ala Ala Ala Lys Ala Ala Lys Tyr Gly Val Ala Ala Arg Pro Gly Phe
                660                 665                 670

Gly Leu Ser Pro Ile Phe Pro Gly Gly Ala Cys Leu Gly Lys Ala Cys
                675                 680                 685

Gly Arg Lys Arg Lys
            690

<210> SEQ ID NO 7
<211> LENGTH: 706
<212> TYPE: PRT
<213> ORGANISM: Homo sapiens

<400> SEQUENCE: 7

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
                 20                  25                  30

Ile Pro Gly Gly Val Pro Gly Gly Val Phe Tyr Pro Gly Ala Gly Leu
             35                  40                  45

Gly Ala Leu Gly Gly Gly Ala Leu Gly Pro Gly Gly Lys Pro Leu Lys
         50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
        130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
```

```
                245                 250                 255
Ala Ala Ala Ala Lys Ala Ala Lys Phe Gly Ala Gly Ala Ala Gly
            260                 265                 270
Val Leu Pro Gly Val Gly Gly Ala Gly Val Pro Gly Val Pro Gly Ala
            275                 280                 285
Ile Pro Gly Ile Gly Gly Ile Ala Gly Val Gly Thr Pro Ala Ala Ala
        290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
            355                 360                 365
Ser Pro Glu Ala Ala Ala Lys Ala Ala Ala Lys Ala Ala Lys Tyr Gly
        370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Gly Val Gly Val Pro Gly Val Gly Gly Val
            420                 425                 430
Pro Gly Val Gly Ile Ser Pro Glu Ala Gln Ala Ala Ala Ala Lys
            435                 440                 445
Ala Ala Lys Tyr Gly Val Gly Thr Pro Ala Ala Ala Ala Lys Ala
        450                 455                 460
Ala Ala Lys Ala Ala Gln Phe Gly Leu Val Pro Gly Val Gly Val Ala
465                 470                 475                 480
Pro Gly Val Gly Val Ala Pro Gly Val Gly Val Ala Pro Gly Val Gly
                485                 490                 495
Leu Ala Pro Gly Val Gly Val Ala Pro Gly Val Gly Val Ala Pro Gly
            500                 505                 510
Val Gly Val Ala Pro Gly Ile Gly Pro Gly Gly Val Ala Ala Ala
        515                 520                 525
Lys Ser Ala Ala Lys Val Ala Ala Lys Ala Gln Leu Arg Ala Ala
530                 535                 540
Gly Leu Gly Ala Gly Ile Pro Gly Leu Gly Val Gly Val Gly Val Pro
545                 550                 555                 560
Gly Leu Gly Val Gly Ala Gly Val Pro Gly Leu Gly Val Gly Ala Gly
                565                 570                 575
Val Pro Gly Phe Arg Ala Val Pro Gly Ala Leu Ala Ala Ala Lys Ala
            580                 585                 590
Ala Lys Tyr Gly Ala Ala Val Pro Gly Val Leu Gly Gly Leu Gly Ala
        595                 600                 605
Leu Gly Gly Val Gly Ile Pro Gly Gly Val Val Gly Ala Gly Pro Ala
610                 615                 620
Ala Ala Ala Ala Ala Ala Lys Ala Ala Ala Lys Ala Ala Gln Phe Gly
625                 630                 635                 640
Leu Val Gly Ala Ala Gly Leu Gly Gly Leu Gly Val Gly Gly Leu Gly
                645                 650                 655
Val Pro Gly Val Gly Gly Leu Gly Gly Ile Pro Pro Ala Ala Ala Ala
            660                 665                 670
```

```
Lys Ala Ala Lys Tyr Gly Val Ala Arg Pro Gly Phe Gly Leu Ser
        675                 680                 685

Pro Ile Phe Pro Gly Gly Ala Cys Leu Gly Lys Ala Cys Gly Arg Lys
690                 695                 700

Arg Lys
705

<210> SEQ ID NO 8
<211> LENGTH: 706
<212> TYPE: PRT
<213> ORGANISM: Homo sapiens

<400> SEQUENCE: 8

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
```

```
                    325                 330                 335
Pro Gly Ala Gly Val Pro Gly Val Pro Gly Ala Gly Ile Pro
                340                 345                 350
Val Val Pro Gly Ala Gly Ile Pro Gly Ala Ala Val Pro Gly Val Val
            355                 360                 365
Ser Pro Glu Ala Ala Lys Ala Ala Lys Ala Ala Lys Tyr Gly
        370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Ile Pro Gly
                405                 410                 415
Val Ala Gly Val Pro Ser Val Gly Val Pro Gly Val Gly Gly Val
            420                 425                 430
Pro Gly Val Gly Ile Ser Pro Glu Ala Gln Ala Ala Ala Ala Lys
        435                 440                 445
Ala Ala Lys Tyr Gly Val Gly Thr Pro Ala Ala Ala Ala Lys Ala
    450                 455                 460
Ala Ala Lys Ala Ala Gln Phe Gly Leu Val Pro Gly Val Gly Val Ala
465                 470                 475                 480
Pro Gly Val Gly Val Ala Pro Gly Val Gly Val Ala Pro Gly Val Gly
                485                 490                 495
Leu Ala Pro Gly Val Gly Val Ala Pro Gly Val Gly Val Ala Pro Gly
            500                 505                 510
Val Gly Val Ala Pro Gly Ile Gly Pro Gly Gly Val Ala Ala Ala
        515                 520                 525
Lys Ser Ala Ala Lys Val Ala Ala Lys Ala Gln Leu Arg Ala Ala Ala
530                 535                 540
Gly Leu Gly Ala Gly Ile Pro Gly Leu Gly Val Gly Val Gly Val Pro
545                 550                 555                 560
Gly Leu Gly Val Gly Ala Gly Val Pro Gly Leu Gly Val Gly Ala Gly
                565                 570                 575
Val Pro Gly Phe Gly Ala Val Pro Gly Ala Leu Ala Ala Ala Lys Ala
            580                 585                 590
Ala Lys Tyr Gly Ala Ala Val Pro Gly Val Leu Gly Gly Leu Gly Ala
        595                 600                 605
Leu Gly Gly Val Gly Ile Pro Gly Gly Val Val Gly Ala Gly Pro Ala
    610                 615                 620
Ala Ala Ala Ala Ala Lys Ala Ala Ala Lys Ala Ala Gln Phe Gly
625                 630                 635                 640
Leu Val Gly Ala Ala Gly Leu Gly Gly Leu Gly Val Gly Gly Leu Gly
                645                 650                 655
Val Pro Gly Val Gly Gly Leu Gly Gly Ile Pro Pro Ala Ala Ala Ala
            660                 665                 670
Lys Ala Ala Lys Tyr Gly Val Ala Ala Arg Pro Gly Phe Gly Leu Ser
        675                 680                 685
Pro Ile Phe Pro Gly Gly Ala Cys Leu Gly Lys Ala Cys Gly Arg Lys
        690                 695                 700
Arg Lys
705

<210> SEQ ID NO 9
<211> LENGTH: 706
<212> TYPE: PRT
<213> ORGANISM: Homo sapiens
```

<400> SEQUENCE: 9

```
Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Ala Phe Ala Gly Ile Pro Gly Val
        180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
        210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
        290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
        370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
```

```
                405                 410                 415
Val Ala Gly Val Pro Gly Val Gly Val Pro Gly Val Gly Val
            420                 425                 430
Pro Gly Val Gly Ile Ser Pro Glu Ala Gln Ala Ala Ala Lys
            435                 440                 445
Ala Ala Lys Tyr Gly Val Gly Thr Pro Ala Ala Ala Lys Ala
            450                 455                 460
Ala Ala Lys Ala Ala Gln Phe Gly Leu Val Pro Gly Val Ala
465                 470                 475                 480
Pro Gly Val Gly Val Ala Pro Gly Val Gly Val Ala Pro Val Gly
            485                 490                 495
Leu Ala Pro Gly Val Gly Val Ala Pro Gly Val Gly Val Ala Pro Gly
            500                 505                 510
Val Gly Val Ala Pro Gly Ile Gly Pro Gly Gly Val Ala Ala Ala
            515                 520                 525
Lys Ser Ala Ala Lys Val Ala Ala Lys Ala Gln Leu Arg Ala Ala
            530                 535                 540
Gly Leu Gly Ala Gly Ile Pro Gly Leu Gly Val Gly Val Gly Val Pro
545                 550                 555                 560
Gly Leu Gly Val Gly Ala Gly Val Pro Gly Leu Gly Val Gly Ala Gly
            565                 570                 575
Val Pro Gly Phe Gly Ala Val Pro Gly Ala Leu Ala Ala Ala Lys Ala
            580                 585                 590
Ala Lys Tyr Gly Ala Ala Val Pro Gly Val Leu Gly Gly Leu Gly Ala
            595                 600                 605
Leu Gly Gly Val Gly Ile Pro Gly Gly Val Val Gly Ala Gly Pro Ala
            610                 615                 620
Ala Ala Ala Ala Ala Lys Ala Ala Ala Lys Ala Ala Gln Phe Gly
625                 630                 635                 640
Leu Val Gly Ala Ala Gly Leu Gly Gly Leu Gly Val Gly Gly Leu Gly
            645                 650                 655
Val Pro Gly Val Gly Gly Leu Gly Gly Ile Pro Pro Ala Ala Ala Ala
            660                 665                 670
Lys Ala Ala Lys Tyr Gly Val Ala Ala Arg Pro Gly Phe Gly Leu Ser
            675                 680                 685
Pro Ile Phe Pro Gly Gly Ala Cys Leu Gly Lys Ala Cys Gly Arg Lys
            690                 695                 700
Arg Lys
705

<210> SEQ ID NO 10
<211> LENGTH: 688
<212> TYPE: PRT
<213> ORGANISM: Homo sapiens

<400> SEQUENCE: 10

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
                20                  25                  30

Ala Gly Leu Gly Ala Leu Gly Gly Gly Ala Leu Gly Pro Gly Gly Lys
            35                  40                  45

Pro Leu Lys Pro Val Pro Gly Gly Leu Ala Gly Ala Gly Leu Gly Ala
        50                  55                  60
```

-continued

Gly Leu Gly Ala Phe Pro Ala Val Thr Phe Pro Gly Ala Leu Val Pro
65                  70                  75                  80

Gly Gly Val Ala Asp Ala Ala Ala Tyr Lys Ala Ala Lys Ala Gly
            85                  90                  95

Ala Gly Leu Gly Gly Val Pro Gly Val Gly Leu Gly Val Ser Ala
        100                 105                 110

Gly Ala Val Val Pro Gln Pro Ala Gly Val Lys Pro Gly Lys Val
        115                 120                 125

Pro Gly Val Gly Leu Pro Gly Val Tyr Pro Gly Val Leu Pro Gly
    130                 135                 140

Ala Arg Phe Pro Gly Val Gly Val Leu Pro Gly Val Pro Thr Gly Ala
145                 150                 155                 160

Gly Val Lys Pro Lys Ala Pro Gly Val Gly Ala Phe Ala Gly Ile
            165                 170                 175

Pro Gly Val Gly Pro Phe Gly Gly Pro Gln Pro Gly Val Pro Leu Gly
            180                 185                 190

Tyr Pro Ile Lys Ala Pro Lys Leu Pro Gly Gly Tyr Gly Leu Pro Tyr
        195                 200                 205

Thr Thr Gly Lys Leu Pro Tyr Gly Tyr Gly Pro Gly Gly Val Ala Gly
    210                 215                 220

Ala Ala Gly Lys Ala Gly Tyr Pro Thr Gly Thr Gly Val Gly Pro Gln
225                 230                 235                 240

Ala Ala Ala Ala Ala Ala Lys Ala Ala Lys Phe Gly Ala Gly
                245                 250                 255

Ala Ala Gly Val Leu Pro Gly Val Gly Gly Ala Gly Val Pro Gly Val
        260                 265                 270

Pro Gly Ala Ile Pro Gly Val Gly Ile Ala Ala Ala Ala Ala
        275                 280                 285

Ala Ala Ala Ala Ala Thr Gly Ser Gln Tyr Gly Ala Ala Ser Leu
        290                 295                 300

Val Pro Ala Gly Pro Gly Phe Gly Pro Gly Val Val Gly Val Pro Gly
305                 310                 315                 320

Ala Gly Val Pro Gly Val Gly Val Pro Gly Ala Gly Ile Pro Val Val
            325                 330                 335

Pro Gly Ala Gly Ile Pro Gly Ala Ala Val Pro Gly Val Val Ser Pro
        340                 345                 350

Glu Ala Ala Ala Lys Ala Ala Ala Lys Ala Ala Lys Tyr Gly Ala Arg
            355                 360                 365

Pro Gly Val Gly Val Gly Gly Ile Pro Thr Tyr Gly Val Gly Ala Gly
    370                 375                 380

Gly Phe Pro Gly Phe Gly Val Gly Val Gly Ile Pro Gly Val Ala
385                 390                 395                 400

Gly Val Pro Gly Val Gly Val Pro Gly Val Gly Val Pro Gly
            405                 410                 415

Val Gly Ile Ser Pro Glu Ala Gln Ala Ala Ala Ala Lys Ala Ala
            420                 425                 430

Lys Tyr Gly Val Gly Thr Pro Ala Ala Ala Ala Lys Ala Ala Ala
        435                 440                 445

Lys Ala Ala Gln Phe Gly Leu Val Pro Gly Val Gly Val Ala Pro Gly
        450                 455                 460

Val Gly Val Ala Pro Gly Val Gly Val Ala Pro Gly Val Gly Leu Ala
465                 470                 475                 480

Pro Gly Val Gly Val Ala Pro Gly Val Gly Val Ala Pro Gly Val Gly

-continued

```
                485                 490                 495
Val Ala Pro Gly Ile Gly Pro Gly Gly Val Ala Ala Ala Lys Ser
            500                 505                 510

Ala Ala Lys Val Ala Ala Lys Ala Gln Leu Arg Ala Ala Gly Leu
        515                 520                 525

Gly Ala Gly Ile Pro Gly Leu Gly Val Gly Val Pro Gly Leu
    530                 535                 540

Gly Val Gly Ala Gly Val Pro Gly Leu Gly Val Gly Ala Gly Val Pro
545                 550                 555                 560

Gly Phe Gly Ala Val Pro Gly Ala Leu Ala Ala Lys Ala Ala Lys
                565                 570                 575

Tyr Gly Ala Ala Val Pro Gly Val Leu Gly Gly Leu Gly Ala Leu Gly
                580                 585                 590

Gly Val Gly Ile Pro Gly Gly Val Val Gly Ala Gly Pro Ala Ala Ala
            595                 600                 605

Ala Ala Ala Ala Lys Ala Ala Lys Ala Ala Gln Phe Gly Leu Val
        610                 615                 620

Gly Ala Ala Gly Leu Gly Gly Leu Gly Val Gly Gly Leu Gly Val Pro
625                 630                 635                 640

Gly Val Gly Gly Leu Gly Gly Ile Pro Pro Ala Ala Ala Lys Ala
                645                 650                 655

Ala Lys Tyr Gly Val Ala Ala Arg Pro Gly Phe Gly Leu Ser Pro Ile
            660                 665                 670

Phe Pro Gly Gly Ala Cys Leu Gly Lys Ala Cys Gly Arg Lys Arg Lys
                675                 680                 685

<210> SEQ ID NO 11
<211> LENGTH: 674
<212> TYPE: PRT
<213> ORGANISM: Homo sapiens

<400> SEQUENCE: 11

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
            20                  25                  30

Ala Gly Leu Gly Ala Leu Gly Gly Gly Ala Leu Gly Pro Gly Gly Lys
        35                  40                  45

Pro Leu Lys Pro Val Pro Gly Gly Leu Ala Gly Ala Gly Leu Gly Ala
    50                  55                  60

Gly Leu Gly Ala Phe Pro Ala Val Thr Phe Pro Gly Ala Leu Val Pro
65                  70                  75                  80

Gly Gly Val Ala Asp Ala Ala Ala Ala Tyr Lys Ala Ala Lys Ala Gly
                85                  90                  95

Ala Gly Leu Gly Gly Val Pro Gly Val Gly Gly Leu Gly Val Ser Ala
            100                 105                 110

Gly Ala Val Val Pro Gln Pro Gly Ala Gly Val Lys Pro Gly Lys Val
        115                 120                 125

Pro Gly Val Gly Leu Pro Gly Val Tyr Pro Gly Gly Val Leu Pro Gly
    130                 135                 140

Ala Arg Phe Pro Gly Val Gly Val Leu Pro Gly Val Pro Thr Gly Ala
145                 150                 155                 160

Gly Val Lys Pro Lys Ala Pro Gly Val Gly Gly Ala Phe Ala Gly Ile
                165                 170                 175
```

-continued

```
Pro Gly Val Gly Pro Phe Gly Gly Pro Gln Pro Gly Val Pro Leu Gly
            180                 185                 190
Tyr Pro Ile Lys Ala Pro Lys Leu Pro Gly Gly Tyr Gly Leu Pro Tyr
        195                 200                 205
Thr Thr Gly Lys Leu Pro Tyr Gly Tyr Gly Pro Gly Gly Val Ala Gly
    210                 215                 220
Ala Ala Gly Lys Ala Gly Tyr Pro Thr Gly Thr Gly Val Gly Pro Gln
225                 230                 235                 240
Ala Ala Ala Ala Ala Ala Lys Ala Ala Lys Phe Gly Ala Gly
                245                 250                 255
Ala Ala Gly Val Leu Pro Gly Val Gly Gly Ala Gly Val Pro Gly Val
            260                 265                 270
Pro Gly Ala Ile Pro Gly Ile Gly Gly Ile Ala Gly Val Gly Thr Pro
        275                 280                 285
Ala Ala Ala Ala Ala Ala Ala Ala Lys Ala Ala Lys Tyr Gly
    290                 295                 300
Ala Ala Ala Gly Leu Val Pro Gly Gly Pro Gly Phe Gly Pro Gly Val
305                 310                 315                 320
Val Gly Val Pro Gly Ala Gly Val Pro Gly Val Gly Val Pro Gly Ala
                325                 330                 335
Gly Ile Pro Val Val Pro Gly Ala Gly Ile Pro Gly Ala Ala Val Pro
            340                 345                 350
Gly Val Val Ser Pro Glu Ala Ala Lys Ala Ala Ala Lys Ala Ala
        355                 360                 365
Lys Tyr Gly Ala Arg Pro Gly Val Gly Val Gly Ile Pro Thr Tyr
    370                 375                 380
Gly Val Gly Ala Gly Gly Phe Pro Gly Phe Gly Val Gly Val Gly Gly
385                 390                 395                 400
Ile Pro Gly Val Ala Gly Val Pro Gly Val Gly Val Pro Gly Val
                405                 410                 415
Gly Gly Val Pro Gly Val Gly Ile Ser Pro Glu Ala Gln Ala Ala Ala
            420                 425                 430
Ala Ala Lys Ala Ala Lys Tyr Gly Leu Val Pro Gly Val Gly Val Ala
        435                 440                 445
Pro Gly Val Gly Val Ala Pro Gly Val Gly Val Ala Pro Gly Val Gly
    450                 455                 460
Leu Ala Pro Gly Val Gly Val Ala Pro Gly Val Gly Val Ala Pro Gly
465                 470                 475                 480
Val Gly Val Ala Pro Gly Ile Gly Pro Gly Gly Val Ala Ala Ala
                485                 490                 495
Lys Ser Ala Ala Lys Val Ala Ala Lys Ala Gln Leu Arg Ala Ala Ala
            500                 505                 510
Gly Leu Gly Ala Gly Ile Pro Gly Leu Gly Val Gly Val Gly Val Pro
        515                 520                 525
Gly Leu Gly Val Gly Ala Gly Val Pro Gly Leu Gly Val Gly Ala Gly
    530                 535                 540
Val Pro Gly Phe Gly Ala Val Pro Gly Ala Leu Ala Ala Ala Lys Ala
545                 550                 555                 560
Ala Lys Tyr Gly Ala Ala Val Pro Gly Val Leu Gly Gly Leu Gly Ala
                565                 570                 575
Leu Gly Gly Val Gly Ile Pro Gly Gly Val Val Gly Ala Gly Pro Ala
            580                 585                 590
Ala Ala Ala Ala Ala Ala Lys Ala Ala Ala Lys Ala Ala Gln Phe Gly
```

```
                595                 600                 605

Leu Val Gly Ala Ala Gly Leu Gly Gly Leu Gly Val Gly Gly Leu Gly
        610                 615                 620

Val Pro Gly Val Gly Gly Leu Gly Gly Ile Pro Pro Ala Ala Ala Ala
625                 630                 635                 640

Lys Ala Ala Lys Tyr Gly Val Ala Ala Arg Pro Gly Phe Gly Leu Ser
                645                 650                 655

Pro Ile Phe Pro Gly Gly Ala Cys Leu Gly Lys Ala Cys Gly Arg Lys
                660                 665                 670

Arg Lys

<210> SEQ ID NO 12
<211> LENGTH: 687
<212> TYPE: PRT
<213> ORGANISM: Homo sapiens

<400> SEQUENCE: 12

Met Ala Gly Leu Thr Ala Ala Pro Arg Pro Gly Val Leu Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
```

```
                290                 295                 300
Ala Ala Ala Ala Ala Lys Ala Lys Tyr Gly Ala Ala
305                 310                 315                 320
Gly Leu Val Pro Gly Pro Gly Phe Gly Pro Val Val Gly Val
                    325                 330                 335
Pro Gly Ala Gly Val Pro Val Gly Ile Pro Gly Ala Gly Ile Pro
                340                 345                 350
Val Val Pro Gly Ala Gly Ile Pro Gly Ala Ala Val Pro Gly Val Val
            355                 360                 365
Ser Pro Glu Ala Ala Lys Ala Ala Lys Ala Ala Lys Tyr Gly
370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Gly Val Gly Val Pro Gly Val Gly Gly Val
            420                 425                 430
Pro Gly Val Gly Ile Ser Pro Glu Ala Gln Ala Ala Ala Ala Lys
            435                 440                 445
Ala Ala Lys Tyr Gly Leu Val Pro Gly Val Gly Val Ala Pro Gly Val
450                 455                 460
Gly Val Ala Pro Gly Val Gly Val Ala Pro Gly Val Gly Leu Ala Pro
465                 470                 475                 480
Gly Val Gly Val Ala Pro Gly Val Gly Val Ala Pro Gly Val Gly Val
                485                 490                 495
Ala Pro Gly Ile Gly Pro Gly Gly Val Ala Ala Ala Lys Ser Ala
            500                 505                 510
Ala Lys Val Ala Ala Lys Ala Gln Leu Arg Ala Ala Gly Leu Gly
            515                 520                 525
Ala Gly Ile Pro Gly Leu Gly Val Gly Val Gly Val Pro Gly Leu Gly
530                 535                 540
Val Gly Ala Gly Val Pro Gly Leu Gly Val Gly Ala Gly Val Pro Gly
545                 550                 555                 560
Phe Gly Ala Val Pro Gly Ala Leu Ala Ala Ala Lys Ala Ala Lys Tyr
                565                 570                 575
Gly Ala Ala Val Pro Gly Val Leu Gly Gly Leu Gly Ala Leu Gly Gly
                580                 585                 590
Val Gly Ile Pro Gly Gly Val Val Gly Ala Gly Pro Ala Ala Ala
            595                 600                 605
Ala Ala Ala Lys Ala Ala Ala Lys Ala Ala Gln Phe Gly Leu Val Gly
            610                 615                 620
Ala Ala Gly Leu Gly Gly Leu Gly Val Gly Gly Leu Gly Val Pro Gly
625                 630                 635                 640
Val Gly Gly Leu Gly Gly Ile Pro Pro Ala Ala Ala Lys Ala Ala
                645                 650                 655
Lys Tyr Gly Val Ala Ala Arg Pro Gly Phe Gly Leu Ser Pro Ile Phe
            660                 665                 670
Pro Gly Gly Ala Cys Leu Gly Lys Ala Cys Gly Arg Lys Arg Lys
            675                 680                 685

<210> SEQ ID NO 13
<211> LENGTH: 687
<212> TYPE: PRT
<213> ORGANISM: Homo sapiens
```

<400> SEQUENCE: 13

```
Met Ala Gly Leu Thr Ala Ala Ala Pro Arg Pro Gly Val Leu Leu Leu
 1               5                  10                  15
Leu Leu Ser Ile Leu His Pro Ser Arg Pro Gly Gly Val Pro Gly Ala
             20                  25                  30
Ile Pro Gly Gly Val Pro Gly Gly Val Phe Tyr Pro Gly Ala Gly Leu
         35                  40                  45
Gly Ala Leu Gly Gly Gly Ala Leu Gly Pro Gly Gly Lys Pro Leu Lys
     50                  55                  60
Pro Val Pro Gly Gly Leu Ala Gly Ala Gly Leu Gly Ala Gly Leu Gly
 65                  70                  75                  80
Ala Phe Pro Ala Val Thr Phe Pro Gly Ala Leu Val Pro Gly Gly Val
                 85                  90                  95
Ala Asp Ala Ala Ala Ala Tyr Lys Ala Ala Lys Ala Gly Ala Gly Leu
            100                 105                 110
Gly Gly Val Pro Gly Val Gly Gly Leu Gly Val Ser Ala Gly Ala Val
        115                 120                 125
Val Pro Gln Pro Gly Ala Gly Val Lys Pro Lys Val Pro Gly Val
    130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
            180                 185                 190
Gly Pro Phe Gly Gly Pro Gln Pro Gly Val Pro Leu Gly Tyr Pro Ile
        195                 200                 205
Lys Ala Pro Lys Leu Pro Gly Gly Tyr Gly Leu Pro Tyr Thr Thr Gly
    210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Ala Lys Phe Gly Ala Gly Ala Ala Gly
            260                 265                 270
Val Leu Pro Gly Val Gly Gly Ala Gly Val Pro Gly Val Pro Gly Ala
        275                 280                 285
Ile Pro Gly Ile Gly Gly Ile Ala Gly Val Gly Thr Pro Ala Ala Ala
    290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
        355                 360                 365
Ser Pro Glu Ala Ala Ala Lys Ala Ala Ala Lys Ala Ala Lys Tyr Gly
    370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
```

```
            405                 410                 415
Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Leu Val Pro Gly Val Gly Val Ala Pro Gly Val
            450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
            485                 490                 495

Ala Pro Gly Ile Gly Pro Gly Val Ala Ala Ala Lys Ser Ala
            500                 505                 510

Ala Lys Val Ala Ala Lys Ala Gln Leu Arg Ala Ala Ala Gly Leu Gly
            515                 520                 525

Ala Gly Ile Pro Gly Leu Gly Val Gly Val Pro Gly Leu Gly
            530                 535                 540

Val Gly Ala Gly Val Pro Gly Leu Gly Val Gly Ala Gly Val Pro Gly
545                 550                 555                 560

Phe Gly Ala Val Pro Gly Ala Leu Ala Ala Ala Lys Ala Ala Lys Tyr
            565                 570                 575

Gly Ala Ala Val Pro Gly Val Leu Gly Gly Leu Gly Ala Leu Gly Gly
            580                 585                 590

Val Gly Ile Pro Gly Gly Val Val Gly Ala Gly Pro Ala Ala Ala Ala
            595                 600                 605

Ala Ala Ala Lys Ala Ala Ala Lys Ala Ala Gln Phe Gly Leu Val Gly
            610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Pro Ala Ala Ala Ala Lys Ala Ala
            645                 650                 655

Lys Tyr Gly Val Ala Ala Arg Pro Gly Phe Gly Leu Ser Pro Ile Phe
            660                 665                 670

Pro Gly Gly Ala Cys Leu Gly Lys Ala Cys Gly Arg Lys Arg Lys
            675                 680                 685

<210> SEQ ID NO 14
<211> LENGTH: 692
<212> TYPE: PRT
<213> ORGANISM: Homo sapiens

<400> SEQUENCE: 14

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
            20                  25                  30

Ala Gly Leu Gly Ala Leu Gly Gly Gly Ala Leu Gly Pro Gly Gly Lys
            35                  40                  45

Pro Leu Lys Pro Val Pro Gly Gly Leu Ala Gly Ala Gly Leu Gly Ala
            50                  55                  60

Gly Leu Gly Ala Phe Pro Ala Val Thr Phe Pro Gly Ala Leu Val Pro
65                  70                  75                  80

Gly Gly Val Ala Asp Ala Ala Ala Tyr Lys Ala Ala Lys Ala Gly
            85                  90                  95
```

-continued

```
Ala Gly Leu Gly Gly Val Pro Gly Val Gly Leu Gly Val Ser Ala
            100                 105                 110
Gly Ala Val Val Pro Gln Pro Gly Ala Gly Val Lys Pro Gly Lys Val
        115                 120                 125
Pro Gly Val Gly Leu Pro Gly Val Tyr Pro Gly Gly Val Leu Pro Gly
    130                 135                 140
Ala Arg Phe Pro Gly Val Gly Val Leu Pro Gly Val Pro Thr Gly Ala
145                 150                 155                 160
Gly Val Lys Pro Lys Ala Pro Gly Val Gly Ala Phe Ala Gly Ile
            165                 170                 175
Pro Gly Val Gly Pro Phe Gly Gly Pro Gln Pro Gly Val Pro Leu Gly
    180                 185                 190
Tyr Pro Ile Lys Ala Pro Lys Leu Pro Gly Gly Tyr Gly Leu Pro Tyr
            195                 200                 205
Thr Thr Gly Lys Leu Pro Tyr Gly Tyr Gly Pro Gly Gly Val Ala Gly
    210                 215                 220
Ala Ala Gly Lys Ala Gly Tyr Pro Thr Gly Thr Gly Val Gly Pro Gln
225                 230                 235                 240
Ala Ala Ala Ala Ala Ala Lys Ala Ala Lys Phe Gly Ala Gly
                245                 250                 255
Ala Ala Gly Val Leu Pro Gly Val Gly Ala Gly Val Pro Gly Val
            260                 265                 270
Pro Gly Ala Ile Pro Gly Ile Gly Ile Ala Gly Val Gly Thr Pro
    275                 280                 285
Ala Ala Ala Ala Ala Ala Ala Ala Lys Ala Ala Lys Tyr Gly
            290                 295                 300
Ala Ala Ala Gly Leu Val Pro Gly Gly Pro Gly Phe Gly Pro Gly Val
305                 310                 315                 320
Val Gly Val Pro Gly Ala Gly Val Pro Gly Val Val Pro Gly Ala
            325                 330                 335
Gly Ile Pro Val Val Pro Gly Ala Gly Ile Pro Gly Ala Ala Val Pro
            340                 345                 350
Gly Val Val Ser Pro Glu Ala Ala Ala Lys Ala Ala Ala Lys Ala Ala
            355                 360                 365
Lys Tyr Gly Ala Arg Pro Gly Val Gly Val Gly Gly Ile Pro Thr Tyr
370                 375                 380
Gly Val Gly Ala Gly Gly Phe Pro Gly Phe Gly Val Gly Val Gly Gly
385                 390                 395                 400
Ile Pro Gly Val Ala Gly Val Pro Gly Val Gly Val Pro Gly Val
            405                 410                 415
Gly Gly Val Pro Gly Val Gly Ile Ser Pro Glu Ala Gln Ala Ala Ala
            420                 425                 430
Ala Ala Lys Ala Ala Lys Tyr Gly Leu Val Pro Gly Val Gly Val Ala
        435                 440                 445
Pro Gly Val Gly Val Ala Pro Gly Val Gly Val Ala Pro Gly Val Gly
    450                 455                 460
Leu Ala Pro Gly Val Gly Val Ala Pro Gly Val Gly Val Ala Pro Gly
465                 470                 475                 480
Val Gly Val Ala Pro Gly Ile Gly Pro Gly Gly Val Ala Ala Ala Ala
                485                 490                 495
Lys Ser Ala Ala Lys Val Ala Ala Lys Ala Gln Leu Arg Ala Ala Ala
            500                 505                 510
Gly Leu Gly Ala Gly Ile Pro Gly Leu Gly Val Gly Val Gly Val Pro
```

```
              515                 520                 525
Gly Leu Gly Val Gly Ala Gly Pro Gly Leu Gly Val Gly Ala Gly
            530                 535                 540

Val Pro Gly Phe Gly Ala Val Pro Gly Ala Leu Ala Ala Lys Ala
545                 550                 555                 560

Ala Lys Tyr Gly Ala Ala Val Pro Gly Val Leu Gly Gly Leu Gly Ala
                565                 570                 575

Leu Gly Gly Val Gly Ile Pro Gly Gly Val Val Gly Ala Gly Pro Ala
                580                 585                 590

Ala Ala Ala Ala Ala Lys Ala Ala Lys Ala Ala Gln Phe Gly
            595                 600                 605

Leu Val Gly Ala Ala Gly Leu Gly Gly Leu Gly Val Gly Gly Leu Gly
            610                 615                 620

Val Pro Gly Val Gly Gly Leu Gly Gly Ile Pro Pro Ala Ala Ala
625                 630                 635                 640

Lys Ala Ala Lys Tyr Gly Ala Ala Gly Leu Gly Gly Val Leu Gly Gly
                645                 650                 655

Ala Gly Gln Phe Pro Leu Gly Gly Val Ala Ala Arg Pro Gly Phe Gly
            660                 665                 670

Leu Ser Pro Ile Phe Pro Gly Gly Ala Cys Leu Gly Lys Ala Cys Gly
            675                 680                 685

Arg Lys Arg Lys
            690

<210> SEQ ID NO 15
<211> LENGTH: 692
<212> TYPE: PRT
<213> ORGANISM: Homo sapiens

<400> SEQUENCE: 15

Met Ala Gly Leu Thr Ala Ala Pro Arg Pro Gly Val Leu Leu Leu
1               5                   10                  15

Leu Leu Ser Ile Leu His Pro Ser Arg Pro Gly Val Phe Tyr Pro Gly
                20                  25                  30

Ala Gly Leu Gly Ala Leu Gly Gly Gly Ala Leu Gly Pro Gly Gly Lys
            35                  40                  45

Pro Leu Lys Pro Val Pro Gly Gly Leu Ala Gly Ala Gly Leu Gly Ala
50                  55                  60

Gly Leu Gly Ala Phe Pro Ala Val Thr Phe Pro Gly Ala Leu Val Pro
65                  70                  75                  80

Gly Gly Val Ala Asp Ala Ala Ala Tyr Lys Ala Ala Lys Ala Gly
                85                  90                  95

Ala Gly Leu Gly Gly Val Pro Gly Val Gly Gly Leu Gly Val Ser Ala
            100                 105                 110

Gly Ala Val Val Pro Gln Pro Gly Ala Gly Val Lys Pro Gly Lys Val
            115                 120                 125

Pro Gly Val Gly Leu Pro Gly Val Tyr Pro Gly Gly Val Leu Pro Gly
            130                 135                 140

Ala Arg Phe Pro Gly Val Gly Val Leu Pro Gly Val Pro Thr Gly Ala
145                 150                 155                 160

Gly Val Lys Pro Lys Ala Pro Gly Val Gly Gly Ala Phe Ala Gly Ile
                165                 170                 175

Pro Gly Val Gly Pro Phe Gly Gly Pro Gln Pro Gly Val Pro Leu Gly
            180                 185                 190
```

```
Tyr Pro Ile Lys Ala Pro Lys Leu Pro Gly Gly Tyr Leu Pro Tyr
        195                 200                 205

Thr Thr Gly Lys Leu Pro Tyr Gly Tyr Gly Pro Gly Gly Val Ala Gly
    210                 215                 220

Ala Ala Gly Lys Ala Gly Tyr Pro Thr Gly Thr Gly Val Gly Pro Gln
225                 230                 235                 240

Ala Ala Ala Ala Ala Ala Lys Ala Ala Lys Phe Gly Ala Gly
                245                 250                 255

Ala Ala Gly Val Leu Pro Gly Val Gly Ala Gly Val Pro Gly Val
                260                 265                 270

Pro Gly Ala Ile Pro Gly Ile Gly Ile Ala Gly Val Gly Thr Pro
            275                 280                 285

Ala Ala Ala Ala Ala Ala Ala Ala Lys Ala Ala Lys Tyr Gly
        290                 295                 300

Ala Ala Ala Gly Leu Val Pro Gly Pro Gly Phe Gly Pro Gly Val
305                 310                 315                 320

Val Gly Val Pro Gly Ala Gly Val Pro Gly Val Gly Val Pro Gly Ala
                325                 330                 335

Gly Ile Pro Val Val Pro Gly Ala Gly Ile Pro Gly Ala Ala Val Pro
            340                 345                 350

Gly Val Val Ser Pro Glu Ala Ala Lys Ala Ala Ala Lys Ala Ala
        355                 360                 365

Lys Tyr Gly Ala Arg Pro Gly Val Gly Val Gly Gly Ile Pro Thr Tyr
    370                 375                 380

Gly Val Gly Ala Gly Gly Phe Pro Gly Phe Gly Val Gly Val Gly Gly
385                 390                 395                 400

Ile Pro Gly Val Ala Gly Val Pro Gly Val Gly Val Pro Gly Val
                405                 410                 415

Gly Gly Val Pro Gly Val Gly Ile Ser Pro Glu Ala Gln Ala Ala Ala
                420                 425                 430

Ala Ala Lys Ala Ala Lys Tyr Gly Leu Val Pro Gly Val Gly Val Ala
        435                 440                 445

Pro Gly Val Gly Val Ala Pro Gly Val Gly Val Ala Pro Gly Val Gly
    450                 455                 460

Leu Ala Pro Gly Val Gly Val Ala Pro Gly Val Gly Val Ala Pro Gly
465                 470                 475                 480

Val Gly Val Ala Pro Gly Ile Gly Pro Gly Gly Val Ala Ala Ala
                485                 490                 495

Lys Ser Ala Ala Lys Val Ala Lys Ala Gln Leu Arg Ala Ala Ala
        500                 505                 510

Gly Leu Gly Ala Gly Ile Pro Gly Leu Gly Val Gly Val Gly Val Pro
            515                 520                 525

Gly Leu Gly Val Gly Ala Gly Val Pro Gly Leu Gly Val Gly Ala Gly
        530                 535                 540

Val Pro Gly Phe Arg Ala Val Pro Gly Ala Leu Ala Ala Ala Lys Ala
545                 550                 555                 560

Ala Lys Tyr Gly Ala Ala Val Pro Gly Val Leu Gly Gly Leu Gly Ala
                565                 570                 575

Leu Gly Gly Val Gly Ile Pro Gly Gly Val Val Gly Ala Gly Pro Ala
                580                 585                 590

Ala Ala Ala Ala Ala Ala Lys Ala Ala Ala Lys Val Ala Gln Phe Gly
        595                 600                 605

Leu Val Gly Ala Ala Gly Leu Gly Gly Leu Gly Val Gly Gly Leu Gly
```

```
            610                 615                 620
Val Pro Gly Val Gly Leu Gly Gly Ile Pro Pro Ala Ala Ala
625                 630                 635                 640

Lys Ala Ala Lys Tyr Gly Ala Ala Gly Leu Gly Val Leu Gly Gly
                    645                 650                 655

Ala Gly Gln Phe Pro Leu Gly Gly Val Ala Ala Arg Pro Phe Gly
                660                 665                 670

Leu Ser Pro Ile Phe Pro Gly Ala Cys Leu Gly Lys Ala Cys Gly
            675                 680                 685

Arg Lys Arg Lys
        690

<210> SEQ ID NO 16
<211> LENGTH: 705
<212> TYPE: PRT
<213> ORGANISM: Homo sapiens

<400> SEQUENCE: 16

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285
```

```
Ile Pro Gly Ile Gly Ile Ala Gly Val Gly Thr Pro Ala Ala Ala
    290                 295                 300

Ala Ala Ala Ala Ala Ala Lys Ala Ala Lys Tyr Gly Ala Ala Ala
305                 310                 315                 320

Gly Leu Val Pro Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Ala Lys Ala Ala Lys Ala Ala Lys Tyr Gly
370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Val Pro Gly Val Gly Gly Val
        420                 425                 430

Pro Gly Val Gly Ile Ser Pro Glu Ala Gln Ala Ala Ala Ala Lys
        435                 440                 445

Ala Ala Lys Tyr Gly Leu Val Pro Gly Val Gly Val Ala Pro Gly Val
450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
                485                 490                 495

Ala Pro Gly Ile Gly Pro Gly Gly Val Ala Ala Ala Lys Ser Ala
            500                 505                 510

Ala Lys Val Ala Ala Lys Ala Gln Leu Arg Ala Ala Gly Leu Gly
        515                 520                 525

Ala Gly Ile Pro Gly Leu Gly Val Gly Val Gly Val Pro Gly Leu Gly
        530                 535                 540

Val Gly Ala Gly Val Pro Gly Leu Gly Val Gly Ala Gly Val Pro Gly
545                 550                 555                 560

Phe Gly Ala Val Pro Gly Ala Leu Ala Ala Lys Ala Ala Lys Tyr
                565                 570                 575

Gly Ala Ala Val Pro Gly Val Leu Gly Gly Leu Gly Ala Leu Gly Gly
                580                 585                 590

Val Gly Ile Pro Gly Gly Val Val Gly Ala Gly Pro Ala Ala Ala Ala
        595                 600                 605

Ala Ala Ala Lys Ala Ala Ala Lys Ala Ala Gln Phe Gly Leu Val Gly
610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Ala Ala Ala Lys Ala Ala
                645                 650                 655

Lys Tyr Gly Ala Ala Gly Leu Gly Gly Val Leu Gly Ala Gly Gln
                660                 665                 670

Phe Pro Leu Gly Gly Val Ala Ala Arg Pro Gly Phe Gly Leu Ser Pro
            675                 680                 685

Ile Phe Pro Gly Gly Ala Cys Leu Gly Lys Ala Cys Gly Arg Lys Arg
    690                 695                 700

Lys
```

<210> SEQ ID NO 17
<211> LENGTH: 672
<212> TYPE: PRT
<213> ORGANISM: Homo sapiens

<400> SEQUENCE: 17

```
Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
             20                  25                  30

Ile Pro Gly Gly Val Pro Gly Gly Val Phe Tyr Pro Gly Ala Gly Leu
             35                  40                  45

Gly Ala Leu Gly Gly Gly Ala Leu Gly Pro Gly Gly Lys Pro Leu Lys
         50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
                115                 120                 125

Val Pro Gln Pro Gly Ala Gly Val Lys Pro Gly Lys Val Pro Gly Val
            130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
            275                 280                 285

Ile Pro Gly Ile Gly Gly Ile Ala Gly Val Gly Thr Pro Ala Ala Ala
            290                 295                 300

Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365
```

```
Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Ile Pro Gly
                405                 410                 415

Val Ala Gly Val Pro Gly Val Gly Val Pro Gly Val Gly Gly Val
                420                 425                 430

Pro Gly Val Gly Ile Ser Pro Glu Ala Gln Ala Ala Ala Ala Lys
                435                 440                 445

Ala Ala Lys Tyr Gly Leu Val Pro Gly Val Gly Val Ala Pro Gly Val
    450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
                485                 490                 495

Ala Pro Gly Ile Gly Pro Gly Gly Val Ala Gly Ala Ala Gly Leu
                500                 505                 510

Gly Ala Gly Ile Pro Gly Leu Gly Val Gly Val Gly Val Pro Gly Leu
    515                 520                 525

Gly Val Gly Ala Gly Val Pro Gly Leu Gly Val Gly Ala Gly Val Pro
530                 535                 540

Gly Phe Gly Ala Val Pro Gly Ala Leu Ala Ala Ala Lys Ala Ala Lys
545                 550                 555                 560

Tyr Gly Ala Ala Val Pro Gly Val Leu Gly Gly Leu Gly Ala Leu Gly
                565                 570                 575

Gly Val Gly Ile Pro Gly Gly Val Val Gly Ala Gly Pro Ala Ala Ala
                580                 585                 590

Ala Ala Ala Ala Lys Ala Ala Ala Lys Ala Ala Gln Phe Gly Leu Val
                595                 600                 605

Gly Ala Ala Gly Leu Gly Gly Leu Gly Val Gly Gly Leu Gly Val Pro
            610                 615                 620

Gly Val Gly Gly Leu Gly Gly Ile Pro Pro Ala Ala Ala Ala Lys Ala
625                 630                 635                 640

Ala Lys Tyr Gly Val Ala Ala Arg Pro Gly Phe Gly Leu Ser Pro Ile
                645                 650                 655

Phe Pro Gly Gly Ala Cys Leu Gly Lys Ala Cys Gly Arg Lys Arg Lys
                660                 665                 670

<210> SEQ ID NO 18
<211> LENGTH: 680
<212> TYPE: PRT
<213> ORGANISM: Homo sapiens

<400> SEQUENCE: 18

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
                20                  25                  30

Ala Gly Leu Gly Ala Leu Gly Gly Gly Ala Leu Gly Pro Gly Gly Lys
            35                  40                  45

Pro Leu Lys Pro Gly Leu Gly Ala Phe Pro Ala Val Thr Phe Pro Gly
    50                  55                  60

Ala Leu Val Pro Gly Gly Val Ala Asp Ala Ala Ala Tyr Lys Ala
65                  70                  75                  80
```

```
Ala Lys Ala Gly Ala Gly Leu Gly Gly Val Pro Val Gly Gly Leu
             85                  90                  95

Gly Val Ser Ala Gly Ala Val Val Pro Gln Pro Gly Ala Gly Val Lys
            100                 105                 110

Pro Gly Lys Val Pro Gly Val Gly Leu Pro Gly Val Tyr Pro Gly Gly
            115                 120                 125

Val Leu Pro Gly Ala Arg Phe Pro Gly Val Gly Val Leu Pro Gly Val
130                 135                 140

Pro Thr Gly Ala Gly Val Lys Pro Lys Ala Pro Gly Val Gly Gly Ala
145                 150                 155                 160

Phe Ala Gly Ile Pro Gly Val Gly Pro Phe Gly Pro Gln Pro Gly
             165                 170                 175

Val Pro Leu Gly Tyr Pro Ile Lys Ala Pro Lys Leu Pro Gly Gly Tyr
            180                 185                 190

Gly Leu Pro Tyr Thr Thr Gly Lys Leu Pro Tyr Gly Tyr Gly Pro Gly
            195                 200                 205

Gly Val Ala Gly Ala Ala Gly Lys Ala Gly Tyr Pro Thr Gly Thr Gly
            210                 215                 220

Val Gly Pro Gln Ala Ala Ala Ala Ala Ala Lys Ala Ala Ala Lys
225                 230                 235                 240

Phe Gly Ala Gly Ala Ala Gly Val Leu Pro Gly Val Gly Gly Ala Gly
             245                 250                 255

Val Pro Gly Val Pro Gly Ala Ile Pro Gly Ile Gly Gly Ile Ala Gly
             260                 265                 270

Val Gly Thr Pro Ala Ala Ala Ala Ala Ala Ala Ala Ala Lys Ala
             275                 280                 285

Ala Lys Tyr Gly Ala Ala Ala Gly Leu Val Pro Gly Gly Pro Gly Phe
            290                 295                 300

Gly Pro Gly Val Val Gly Val Pro Gly Ala Gly Val Pro Gly Val Gly
305                 310                 315                 320

Val Pro Gly Ala Gly Ile Pro Val Val Pro Gly Ala Gly Ile Pro Gly
             325                 330                 335

Ala Ala Val Pro Gly Val Val Ser Pro Glu Ala Ala Lys Ala Ala
             340                 345                 350

Ala Lys Ala Ala Lys Tyr Gly Ala Arg Pro Gly Val Gly Val Gly Gly
            355                 360                 365

Ile Pro Thr Tyr Gly Val Gly Ala Gly Phe Pro Gly Phe Gly Val
            370                 375                 380

Gly Val Gly Gly Ile Pro Gly Val Ala Gly Val Pro Gly Val Gly Gly
385                 390                 395                 400

Val Pro Gly Val Gly Gly Val Pro Gly Val Gly Ile Ser Pro Glu Ala
            405                 410                 415

Gln Ala Ala Ala Ala Lys Ala Ala Lys Tyr Gly Leu Val Pro Gly
            420                 425                 430

Val Gly Val Ala Pro Gly Val Gly Val Ala Pro Gly Val Gly Val Ala
            435                 440                 445

Pro Gly Val Gly Leu Ala Pro Gly Val Gly Val Ala Pro Gly Val Gly
            450                 455                 460

Val Ala Pro Gly Val Gly Val Ala Pro Gly Ile Gly Pro Gly Gly Val
465                 470                 475                 480

Ala Ala Ala Ala Lys Ser Ala Lys Val Ala Lys Ala Gln Leu
            485                 490                 495
```

```
Arg Ala Ala Ala Gly Leu Gly Ala Gly Ile Pro Gly Leu Gly Val Gly
                500                 505                 510

Val Gly Val Pro Gly Leu Gly Val Gly Ala Gly Val Pro Gly Leu Gly
            515                 520                 525

Val Gly Ala Gly Val Pro Gly Phe Gly Ala Val Pro Gly Ala Leu Ala
        530                 535                 540

Ala Ala Lys Ala Ala Lys Tyr Gly Ala Ala Val Pro Gly Val Leu Gly
545                 550                 555                 560

Gly Leu Gly Ala Leu Gly Gly Val Gly Ile Pro Gly Gly Val Val Gly
                565                 570                 575

Ala Gly Pro Ala Ala Ala Ala Ala Ala Lys Ala Ala Ala Lys Ala
            580                 585                 590

Ala Gln Phe Gly Leu Val Gly Ala Ala Gly Leu Gly Gly Leu Gly Val
            595                 600                 605

Gly Gly Leu Gly Val Pro Gly Val Gly Gly Leu Gly Gly Ile Pro Pro
            610                 615                 620

Ala Ala Ala Ala Lys Ala Ala Lys Tyr Gly Ala Ala Gly Leu Gly Gly
625                 630                 635                 640

Val Leu Gly Gly Ala Gly Gln Phe Pro Leu Gly Gly Val Ala Ala Arg
                645                 650                 655

Pro Gly Phe Gly Leu Ser Pro Ile Phe Pro Gly Gly Ala Cys Leu Gly
                660                 665                 670

Lys Ala Cys Gly Arg Lys Arg Lys
                675                 680

<210> SEQ ID NO 19
<211> LENGTH: 666
<212> TYPE: PRT
<213> ORGANISM: Homo sapiens

<400> SEQUENCE: 19

Met Ala Gly Leu Thr Ala Ala Ala Pro Arg Pro Gly Val Leu Leu Leu
  1               5                  10                  15

Leu Leu Ser Ile Leu His Pro Ser Arg Pro Gly Val Phe Tyr Pro Gly
             20                  25                  30

Ala Gly Leu Gly Ala Leu Gly Gly Gly Ala Leu Gly Pro Gly Gly Lys
         35                  40                  45

Pro Leu Lys Pro Gly Leu Gly Ala Phe Pro Ala Val Thr Phe Pro Gly
     50                  55                  60

Ala Leu Val Pro Gly Gly Val Ala Asp Ala Ala Ala Tyr Lys Ala
 65                  70                  75                  80

Ala Lys Ala Gly Ala Gly Leu Gly Gly Val Pro Gly Val Gly Gly Leu
                 85                  90                  95

Gly Val Ser Ala Gly Ala Val Val Pro Gln Pro Gly Ala Gly Val Lys
            100                 105                 110

Pro Gly Lys Val Pro Gly Val Gly Leu Pro Gly Val Tyr Pro Gly Gly
            115                 120                 125

Val Leu Pro Gly Ala Arg Phe Pro Gly Val Gly Val Leu Pro Gly Val
        130                 135                 140

Pro Thr Gly Ala Gly Val Lys Pro Lys Ala Pro Gly Val Gly Gly Ala
145                 150                 155                 160

Phe Ala Gly Ile Pro Gly Val Gly Pro Phe Gly Gly Pro Gln Pro Gly
                165                 170                 175

Val Pro Leu Gly Tyr Pro Ile Lys Ala Pro Lys Leu Pro Gly Tyr Gly
                180                 185                 190
```

-continued

Pro Gly Gly Val Ala Gly Ala Gly Lys Ala Gly Tyr Pro Thr Gly
            195                 200                 205

Thr Gly Val Gly Pro Gln Ala Ala Ala Ala Ala Ala Lys Ala Ala
        210                 215                 220

Ala Lys Phe Gly Ala Gly Ala Ala Gly Val Leu Pro Gly Val Gly
225                 230                 235                 240

Ala Gly Val Pro Gly Val Pro Gly Ala Ile Pro Gly Ile Gly Ile
                245                 250                 255

Ala Gly Val Gly Thr Pro Ala Ala Ala Ala Ala Ala Ala Ala Ala
                260                 265                 270

Lys Ala Ala Lys Tyr Gly Ala Ala Gly Leu Val Pro Gly Gly Pro
            275                 280                 285

Gly Phe Gly Pro Gly Val Gly Val Pro Gly Ala Gly Val Pro Gly
    290                 295                 300

Val Gly Val Pro Gly Ala Gly Ile Pro Val Val Pro Gly Ala Gly Ile
305                 310                 315                 320

Pro Gly Ala Ala Val Pro Gly Val Val Ser Pro Glu Ala Ala Lys
                325                 330                 335

Ala Ala Ala Lys Ala Ala Lys Tyr Gly Ala Arg Pro Gly Val Gly Val
            340                 345                 350

Gly Gly Ile Pro Thr Tyr Gly Val Gly Ala Gly Phe Pro Gly Phe
        355                 360                 365

Gly Val Gly Val Gly Gly Ile Pro Gly Val Ala Gly Val Pro Gly Val
    370                 375                 380

Gly Gly Val Pro Gly Val Gly Gly Val Pro Gly Val Gly Ile Ser Pro
385                 390                 395                 400

Glu Ala Gln Ala Ala Ala Ala Ala Lys Ala Ala Lys Tyr Gly Leu Val
            405                 410                 415

Pro Gly Val Gly Val Ala Pro Gly Val Gly Val Ala Pro Gly Val Gly
        420                 425                 430

Val Ala Pro Gly Val Gly Leu Ala Pro Gly Val Gly Val Ala Pro Gly
    435                 440                 445

Val Gly Val Ala Pro Gly Val Gly Val Ala Pro Gly Ile Gly Pro Gly
    450                 455                 460

Gly Val Ala Ala Ala Lys Ser Ala Ala Lys Val Ala Ala Lys Ala
465                 470                 475                 480

Gln Leu Arg Ala Ala Ala Gly Leu Gly Ala Gly Ile Pro Gly Leu Gly
            485                 490                 495

Val Gly Val Gly Val Pro Gly Leu Gly Val Gly Ala Gly Val Pro Gly
        500                 505                 510

Leu Gly Val Gly Ala Gly Val Pro Gly Phe Gly Ala Val Pro Gly Ala
    515                 520                 525

Leu Ala Ala Ala Lys Ala Ala Lys Tyr Gly Ala Ala Val Pro Gly Val
    530                 535                 540

Leu Gly Gly Leu Gly Ala Leu Gly Gly Val Gly Ile Pro Gly Gly Val
545                 550                 555                 560

Val Gly Ala Gly Pro Ala Ala Ala Ala Ala Ala Lys Ala Ala Ala
                565                 570                 575

Lys Ala Ala Gln Phe Gly Leu Val Gly Ala Ala Gly Leu Gly Gly Leu
            580                 585                 590

Gly Val Gly Gly Leu Gly Val Pro Gly Val Gly Gly Leu Gly Gly Ile
        595                 600                 605

```
Pro Pro Ala Ala Ala Lys Ala Ala Lys Tyr Gly Ala Ala Gly Leu
    610             615                 620

Gly Gly Val Leu Gly Gly Ala Gly Gln Phe Pro Leu Gly Gly Val Ala
625             630                 635                 640

Ala Arg Pro Gly Phe Gly Leu Ser Pro Ile Phe Pro Gly Gly Ala Cys
            645                 650                 655

Leu Gly Lys Ala Cys Gly Arg Lys Arg Lys
        660                 665

<210> SEQ ID NO 20
<211> LENGTH: 678
<212> TYPE: PRT
<213> ORGANISM: Homo sapiens

<400> SEQUENCE: 20

Met Ala Gly Leu Thr Ala Ala Pro Arg Pro Gly Val Leu Leu Leu
 1               5                  10                  15

Leu Leu Ser Ile Leu His Pro Ser Arg Pro Gly Val Phe Tyr Pro Gly
            20                  25                  30

Ala Gly Leu Gly Ala Leu Gly Gly Ala Leu Gly Pro Gly Gly Lys
        35                  40                  45

Pro Leu Lys Pro Val Pro Gly Gly Leu Ala Gly Ala Gly Leu Gly Ala
 50                  55                  60

Gly Leu Gly Ala Phe Pro Ala Val Thr Phe Pro Gly Ala Leu Val Pro
65                  70                  75                  80

Gly Gly Val Ala Asp Ala Ala Ala Tyr Lys Ala Ala Lys Ala Gly
                85                  90                  95

Ala Gly Leu Gly Gly Val Pro Gly Val Gly Leu Gly Val Ser Ala
            100                 105                 110

Gly Ala Val Val Pro Gln Pro Gly Ala Gly Val Lys Pro Gly Lys Val
            115                 120                 125

Pro Gly Val Gly Leu Pro Gly Val Tyr Pro Gly Gly Val Leu Pro Gly
            130                 135                 140

Ala Arg Phe Pro Gly Val Gly Val Leu Pro Gly Val Pro Thr Gly Ala
145                 150                 155                 160

Gly Val Lys Pro Lys Ala Pro Gly Val Gly Ala Phe Ala Gly Ile
                165                 170                 175

Pro Gly Val Gly Pro Phe Gly Gly Pro Gln Pro Gly Val Pro Leu Gly
            180                 185                 190

Tyr Pro Ile Lys Ala Pro Lys Leu Pro Gly Gly Tyr Gly Leu Pro Tyr
            195                 200                 205

Thr Thr Gly Lys Leu Pro Tyr Gly Tyr Gly Pro Gly Gly Val Ala Gly
210                 215                 220

Ala Ala Gly Lys Ala Gly Tyr Pro Thr Gly Thr Gly Val Gly Pro Gln
225                 230                 235                 240

Ala Ala Ala Ala Ala Ala Lys Ala Ala Lys Phe Gly Ala Gly
                245                 250                 255

Ala Ala Gly Val Leu Pro Gly Val Gly Gly Ala Gly Val Pro Gly Val
            260                 265                 270

Pro Gly Ala Ile Pro Gly Ile Gly Gly Ile Ala Gly Val Gly Thr Pro
            275                 280                 285

Ala Ala Ala Ala Ala Ala Ala Ala Lys Ala Ala Lys Tyr Gly
            290                 295                 300

Ala Ala Ala Gly Leu Val Pro Gly Gly Pro Gly Phe Gly Pro Gly Val
305                 310                 315                 320
```

```
Val Gly Val Pro Gly Ala Gly Val Pro Gly Val Val Pro Gly Ala
            325                 330                 335

Gly Ile Pro Val Val Pro Gly Ala Gly Ile Pro Gly Ala Ala Val Pro
            340                 345                 350

Gly Val Val Ser Pro Glu Ala Ala Lys Ala Ala Lys Ala Ala
            355                 360                 365

Lys Tyr Gly Ala Arg Pro Gly Val Gly Val Gly Ile Pro Thr Tyr
370                 375                 380

Gly Val Gly Ala Gly Gly Phe Pro Gly Phe Gly Val Gly Val Gly Gly
385                 390                 395                 400

Ile Pro Gly Val Ala Gly Val Pro Gly Val Gly Val Pro Gly Val
            405                 410                 415

Gly Gly Val Pro Gly Val Gly Ile Ser Pro Glu Ala Gln Ala Ala
            420                 425                 430

Ala Ala Lys Ala Ala Lys Tyr Gly Val Gly Thr Pro Ala Ala Ala
            435                 440                 445

Ala Lys Ala Ala Lys Ala Ala Gln Phe Gly Leu Val Pro Gly Val
450                 455                 460

Gly Val Ala Pro Gly Val Gly Val Ala Pro Gly Val Gly Val Ala Pro
465                 470                 475                 480

Gly Val Gly Leu Ala Pro Gly Val Gly Val Ala Pro Gly Val Gly Val
            485                 490                 495

Ala Pro Gly Val Gly Val Ala Pro Gly Ile Gly Pro Gly Gly Val Ala
            500                 505                 510

Ala Ala Ala Lys Ser Ala Ala Lys Val Ala Ala Lys Ala Gln Leu Arg
            515                 520                 525

Ala Ala Ala Gly Leu Gly Ala Gly Ile Pro Gly Leu Gly Val Gly Val
            530                 535                 540

Gly Val Pro Gly Leu Gly Val Gly Ala Gly Val Pro Gly Leu Gly Val
545                 550                 555                 560

Gly Ala Gly Val Pro Gly Phe Gly Ala Val Pro Gly Ala Leu Ala Ala
            565                 570                 575

Ala Lys Ala Ala Lys Tyr Gly Ala Ala Val Pro Gly Val Leu Gly Gly
            580                 585                 590

Leu Gly Ala Leu Gly Gly Val Gly Ile Pro Gly Gly Val Val Gly Ala
            595                 600                 605

Gly Pro Ala Ala Ala Ala Ala Ala Lys Ala Ala Ala Lys Ala Ala
            610                 615                 620

Gln Phe Gly Leu Val Gly Ala Ala Gly Leu Gly Gly Leu Gly Val Gly
625                 630                 635                 640

Gly Leu Gly Val Pro Gly Val Gly Gly Leu Gly Gly Ile Pro Pro Ala
            645                 650                 655

Ala Ala Ala Lys Ala Ala Lys Tyr Gly Gly Ala Cys Leu Gly Lys Ala
            660                 665                 670

Cys Gly Arg Lys Arg Lys
            675

<210> SEQ ID NO 21
<211> LENGTH: 729
<212> TYPE: PRT
<213> ORGANISM: Homo sapiens

<400> SEQUENCE: 21

Met Ala Gly Leu Thr Ala Ala Ala Pro Arg Pro Gly Val Leu Leu Leu
```

-continued

```
  1               5              10              15
Leu Leu Ser Ile Leu His Pro Ser Arg Pro Gly Gly Val Pro Gly Ala
             20              25              30
Ile Pro Gly Gly Val Pro Gly Gly Val Phe Tyr Pro Gly Ala Gly Leu
             35              40              45
Gly Ala Leu Gly Gly Ala Leu Gly Pro Gly Gly Lys Pro Leu Lys
 50              55              60
Pro Val Pro Gly Gly Leu Ala Gly Ala Gly Leu Gly Ala Gly Leu Gly
 65              70              75              80
Ala Phe Pro Ala Val Thr Phe Pro Gly Ala Leu Val Pro Gly Gly Val
             85              90              95
Ala Asp Ala Ala Ala Ala Tyr Lys Ala Ala Lys Ala Gly Ala Gly Leu
            100             105             110
Gly Gly Val Pro Gly Val Gly Gly Leu Gly Val Ser Ala Ala Pro Ser
            115             120             125
Val Pro Arg Ala Val Val Pro Gln Pro Ala Ala Gly Val Lys Pro Val
            130             135             140
Lys Val Pro Gly Val Gly Leu Pro Gly Val Tyr Pro Gly Gly Val Leu
145             150             155             160
Pro Gly Ala Arg Phe Pro Gly Val Gly Val Leu Pro Gly Val Pro Thr
            165             170             175
Gly Ala Gly Val Lys Pro Lys Ala Pro Gly Val Gly Gly Ala Phe Ala
            180             185             190
Gly Ile Pro Gly Val Gly Pro Phe Gly Gly Pro Gln Pro Gly Val Pro
            195             200             205
Leu Gly Tyr Pro Ile Lys Ala Pro Lys Leu Pro Gly Gly Tyr Gly Leu
            210             215             220
Pro Tyr Thr Thr Gly Lys Leu Pro Tyr Gly Tyr Gly Pro Gly Gly Val
225             230             235             240
Ala Gly Ala Ala Gly Lys Ala Gly Tyr Pro Thr Gly Thr Gly Val Gly
            245             250             255
Pro Gln Ala Ala Ala Ala Ala Ala Lys Ala Ala Ala Lys Phe Gly
            260             265             270
Ala Gly Ala Ala Gly Val Leu Pro Gly Val Gly Gly Ala Gly Val Pro
            275             280             285
Gly Val Pro Gly Ala Ile Pro Gly Ile Gly Ile Ala Gly Val Gly
            290             295             300
Thr Pro Ala Ala Ala Ala Ala Ala Ala Ala Lys Ala Ala Lys
305             310             315             320
Tyr Gly Ala Ala Ala Gly Leu Val Pro Gly Gly Pro Gly Phe Gly Pro
            325             330             335
Gly Val Val Gly Val Pro Gly Ala Gly Val Pro Gly Val Gly Val Pro
            340             345             350
Gly Ala Gly Ile Pro Val Val Pro Gly Ala Gly Ile Pro Gly Ala Ala
            355             360             365
Val Pro Gly Val Val Ser Pro Glu Ala Ala Lys Ala Ala Ala Lys
            370             375             380
Ala Ala Lys Tyr Gly Ala Arg Pro Gly Val Gly Val Gly Gly Ile Pro
385             390             395             400
Thr Tyr Gly Val Gly Ala Gly Gly Phe Pro Gly Phe Gly Val Gly Val
            405             410             415
Gly Gly Ile Pro Gly Val Ala Gly Val Pro Gly Val Gly Val Pro
            420             425             430
```

```
Gly Val Gly Gly Val Pro Gly Val Gly Ile Ser Pro Glu Ala Gln Ala
            435                 440                 445

Ala Ala Ala Ala Lys Ala Ala Lys Tyr Gly Val Gly Thr Ala Ala Ala
        450                 455                 460

Ala Ala Ala Glu Ala Ala Ala Lys Ala Ala Gln Tyr Gly Leu Val Pro
465                 470                 475                 480

Gly Val Gly Val Ala Pro Gly Val Gly Val Ala Pro Gly Val Gly Val
            485                 490                 495

Ala Pro Gly Val Gly Leu Ala Pro Gly Val Gly Val Ala Pro Gly Val
        500                 505                 510

Gly Val Ala Pro Gly Val Gly Val Ala Pro Gly Ile Gly Pro Gly Gly
            515                 520                 525

Val Ala Ala Ala Lys Ser Ala Ala Lys Val Ala Ala Lys Ala Gln
        530                 535                 540

Leu Arg Ala Ala Ala Gly Leu Gly Ala Gly Ile Pro Gly Leu Gly Val
545                 550                 555                 560

Gly Val Gly Val Pro Gly Leu Gly Val Gly Ala Gly Val Pro Gly Leu
            565                 570                 575

Gly Val Gly Ala Gly Val Pro Gly Phe Gly Ala Val Pro Gly Ala Leu
        580                 585                 590

Ala Ala Ala Lys Ala Ala Lys Tyr Gly Ala Ala Val Pro Gly Val Leu
            595                 600                 605

Gly Gly Leu Gly Ala Leu Gly Gly Val Gly Ile Pro Gly Gly Val Val
        610                 615                 620

Gly Ala Gly Pro Ala Ala Ala Ala Ala Ala Lys Ala Ala Lys
625                 630                 635                 640

Ala Ala Gln Phe Gly Leu Val Gly Ala Ala Gly Leu Gly Gly Leu Gly
            645                 650                 655

Val Gly Gly Leu Gly Val Pro Gly Val Gly Gly Leu Gly Gly Ile Pro
        660                 665                 670

Pro Ala Ala Ala Ala Lys Ala Ala Lys Tyr Gly Ala Ala Gly Leu Gly
            675                 680                 685

Gly Val Leu Gly Gly Ala Gly Gln Phe Pro Leu Gly Gly Val Ala Ala
        690                 695                 700

Arg Pro Gly Phe Gly Leu Ser Pro Ile Phe Pro Gly Gly Ala Cys Leu
705                 710                 715                 720

Gly Lys Ala Cys Gly Arg Lys Arg Lys
            725

<210> SEQ ID NO 22
<211> LENGTH: 271
<212> TYPE: PRT
<213> ORGANISM: Homo sapiens

<400> SEQUENCE: 22

Met Ala Gly Leu Thr Ala Ala Ala Pro Arg Pro Gly Val Leu Leu Leu
  1               5                  10                  15

Leu Leu Ser Ile Leu His Pro Ser Arg Pro Gly Gly Val Pro Gly Ala
                 20                  25                  30

Ile Pro Gly Gly Val Pro Gly Gly Val Phe Tyr Pro Gly Ala Gly Leu
             35                  40                  45

Gly Ala Leu Gly Gly Gly Ala Leu Gly Pro Gly Gly Lys Pro Leu Lys
         50                  55                  60

Pro Val Pro Gly Gly Leu Ala Gly Ala Gly Leu Gly Ala Gly Leu Gly
```

```
                65                  70                  75                  80
Ala Phe Pro Ala Val Thr Phe Pro Gly Ala Leu Val Pro Gly Gly Val
                    85                  90                  95

Ala Asp Ala Ala Ala Tyr Lys Ala Ala Lys Ala Gly Ala Gly Leu
            100                 105                 110

Gly Gly Val Pro Gly Val Gly Leu Gly Val Ser Ala Gly Ala Val
            115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Ala Phe Ala Gly Ile Pro Gly Val
            180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
            210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Ala Lys Phe Gly Ala Gly Ala Asp
            260                 265                 270

<210> SEQ ID NO 23
<211> LENGTH: 678
<212> TYPE: PRT
<213> ORGANISM: Homo sapiens

<400> SEQUENCE: 23

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                    85                  90                  95

Ala Asp Ala Ala Ala Tyr Lys Ala Ala Lys Ala Gly Ala Gly Leu
            100                 105                 110

Gly Gly Val Pro Gly Val Gly Leu Gly Val Ser Ala Gly Ala Val
            115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175
```

```
Pro Lys Ala Pro Gly Val Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
        290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
            355                 360                 365

Ser Pro Glu Ala Ala Ala Lys Ala Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Gly Val
            420                 425                 430

Pro Gly Val Gly Ile Ser Pro Glu Ala Gln Ala Ala Ala Ala Ala Lys
            435                 440                 445

Ala Ala Lys Tyr Gly Val Gly Thr Pro Ala Ala Ala Ala Lys Ala
    450                 455                 460

Ala Ala Lys Ala Ala Gln Phe Gly Leu Val Pro Gly Val Gly Val Ala
465                 470                 475                 480

Pro Gly Val Gly Val Ala Pro Gly Val Gly Val Ala Pro Gly Val Gly
                485                 490                 495

Leu Ala Pro Gly Val Gly Val Ala Pro Gly Val Gly Val Ala Pro Gly
                500                 505                 510

Val Gly Val Ala Pro Gly Ile Gly Pro Gly Gly Val Ala Ala Ala Ala
            515                 520                 525

Lys Ser Ala Ala Lys Val Ala Lys Ala Gln Leu Arg Ala Ala Ala
    530                 535                 540

Gly Leu Gly Ala Gly Ile Pro Gly Leu Gly Val Gly Val Gly Val Pro
545                 550                 555                 560

Gly Leu Gly Val Gly Ala Gly Val Pro Gly Leu Gly Val Gly Ala Gly
                565                 570                 575

Val Pro Gly Phe Gly Ala Val Pro Gly Ala Leu Ala Ala Ala Lys Ala
                580                 585                 590

Ala Lys Tyr Gly Ala Ala Val Pro Gly Val Leu Gly Gly Leu Gly Ala
```

```
                595                 600                 605
Leu Gly Gly Val Gly Ile Pro Gly Gly Val Val Gly Ala Gly Pro Ala
            610                 615                 620
Ala Ala Ala Ala Ala Lys Ala Ala Lys Ala Ala Gln Phe Gly
625                 630                 635                 640
Leu Val Gly Ala Ala Gly Leu Gly Gly Leu Val Gly Gly Leu Gly
                645                 650                 655
Val Pro Gly Val Gly Gly Leu Gly Gly Ala Cys Leu Gly Lys Ala
            660                 665                 670
Cys Gly Arg Lys Arg Lys
            675

<210> SEQ ID NO 24
<211> LENGTH: 685
<212> TYPE: PRT
<213> ORGANISM: Homo sapiens

<400> SEQUENCE: 24

Met Ala Gly Leu Thr Ala Ala Pro Arg Pro Gly Val Leu Leu Leu
  1               5                  10                  15
Leu Leu Ser Ile Leu His Pro Ser Arg Pro Gly Gly Val Pro Gly Ala
                20                  25                  30
Ile Pro Gly Gly Val Pro Gly Gly Val Phe Tyr Pro Gly Ala Gly Leu
            35                  40                  45
Gly Ala Leu Gly Gly Gly Ala Leu Gly Pro Gly Gly Lys Pro Leu Lys
        50                  55                  60
Pro Val Pro Gly Gly Leu Ala Gly Ala Gly Leu Ala Gly Leu Gly
65                  70                  75                  80
Ala Phe Pro Ala Val Thr Phe Pro Gly Ala Leu Val Pro Gly Val
                85                  90                  95
Ala Asp Ala Ala Ala Ala Tyr Lys Ala Ala Lys Ala Gly Ala Gly Leu
            100                 105                 110
Gly Gly Val Pro Gly Val Gly Gly Leu Gly Val Ser Ala Gly Ala Val
        115                 120                 125
Val Pro Gln Pro Gly Ala Gly Val Lys Pro Gly Lys Val Pro Gly Val
    130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
            180                 185                 190
Gly Pro Phe Gly Gly Pro Gln Pro Gly Val Pro Leu Gly Tyr Pro Ile
        195                 200                 205
Lys Ala Pro Lys Leu Pro Gly Gly Tyr Gly Leu Pro Tyr Thr Thr Gly
    210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Ala Lys Phe Gly Ala Gly Ala Ala Gly
            260                 265                 270
Val Leu Pro Gly Val Gly Gly Ala Gly Val Pro Gly Val Pro Gly Ala
        275                 280                 285
```

```
Ile Pro Gly Ile Gly Ile Ala Gly Ala Ala Ala Gly Leu Val Pro
    290                 295                 300

Gly Gly Pro Gly Phe Gly Pro Gly Val Val Gly Val Pro Gly Ala Gly
305                 310                 315                 320

Val Pro Gly Val Gly Val Pro Gly Ala Gly Ile Pro Val Val Pro Gly
                325                 330                 335

Ala Gly Ile Pro Gly Ala Ala Val Pro Gly Val Val Ser Pro Glu Ala
                340                 345                 350

Ala Ala Lys Ala Ala Ala Lys Ala Lys Tyr Gly Ala Arg Pro Gly
    355                 360                 365

Val Gly Val Gly Gly Ile Pro Thr Tyr Gly Val Gly Ala Gly Gly Phe
370                 375                 380

Pro Gly Phe Gly Val Gly Val Gly Gly Ile Pro Gly Val Ala Gly Val
385                 390                 395                 400

Pro Gly Val Gly Gly Val Pro Gly Val Gly Gly Val Pro Gly Val Gly
                405                 410                 415

Ile Ser Pro Glu Ala Gln Ala Ala Ala Ala Lys Ala Ala Lys Tyr
                420                 425                 430

Gly Leu Val Pro Gly Val Gly Val Ala Pro Gly Val Gly Val Ala Pro
    435                 440                 445

Gly Val Gly Val Ala Pro Gly Val Gly Leu Ala Pro Gly Val Gly Val
450                 455                 460

Ala Pro Gly Val Gly Val Ala Pro Gly Val Gly Val Ala Pro Gly Ile
465                 470                 475                 480

Gly Pro Gly Gly Val Ala Ala Ala Ala Lys Ser Ala Ala Lys Val Ala
                485                 490                 495

Ala Lys Ala Gln Leu Arg Ala Ala Gly Leu Gly Ala Gly Ile Pro
    500                 505                 510

Gly Leu Gly Val Gly Val Gly Val Pro Gly Leu Gly Val Gly Ala Gly
    515                 520                 525

Val Pro Gly Leu Gly Val Gly Ala Gly Val Pro Gly Phe Gly Ala Val
    530                 535                 540

Pro Gly Ala Leu Ala Ala Ala Lys Ala Ala Lys Tyr Gly Ala Ala Val
545                 550                 555                 560

Pro Gly Val Leu Gly Gly Leu Gly Ala Leu Gly Gly Val Gly Ile Pro
                565                 570                 575

Gly Gly Val Val Gly Ala Gly Pro Ala Ala Ala Ala Ala Ala Ala Lys
                580                 585                 590

Ala Ala Ala Lys Ala Ala Gln Phe Gly Leu Val Gly Ala Ala Gly Leu
    595                 600                 605

Gly Gly Leu Gly Val Gly Gly Leu Gly Val Pro Gly Val Gly Gly Leu
    610                 615                 620

Gly Gly Ile Pro Pro Ala Ala Ala Ala Lys Ala Ala Lys Tyr Gly Ala
625                 630                 635                 640

Ala Gly Leu Gly Gly Val Leu Gly Gly Ala Gly Gln Phe Pro Leu Gly
                645                 650                 655

Gly Val Ala Ala Arg Pro Gly Phe Gly Leu Ser Pro Ile Phe Pro Gly
                660                 665                 670

Gly Ala Cys Leu Gly Lys Ala Cys Gly Arg Lys Arg Lys
                675                 680                 685

<210> SEQ ID NO 25
<211> LENGTH: 671
<212> TYPE: PRT
```

<213> ORGANISM: Homo sapiens

<400> SEQUENCE: 25

```
Met Ala Gly Leu Thr Ala Ala Pro Arg Pro Gly Val Leu Leu Leu
 1               5                  10                  15
Leu Leu Ser Ile Leu His Pro Ser Arg Pro Gly Gly Val Pro Gly Ala
                20                  25                  30
Ile Pro Gly Gly Val Pro Gly Gly Val Phe Tyr Pro Gly Ala Gly Leu
                35                  40                  45
Gly Ala Leu Gly Gly Gly Ala Leu Gly Pro Gly Gly Lys Pro Leu Lys
            50                  55                  60
Pro Val Pro Gly Gly Leu Ala Gly Ala Gly Leu Gly Ala Gly Leu Gly
 65                  70                  75                  80
Ala Phe Pro Ala Val Thr Phe Pro Gly Ala Leu Val Pro Gly Gly Val
                85                  90                  95
Ala Asp Ala Ala Ala Ala Tyr Lys Ala Ala Lys Ala Gly Ala Gly Leu
                100                 105                 110
Gly Gly Val Pro Gly Val Gly Gly Leu Gly Val Ser Ala Gly Ala Val
            115                 120                 125
Val Pro Gln Pro Gly Ala Gly Val Lys Pro Gly Lys Val Pro Gly Val
130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
                180                 185                 190
Gly Pro Phe Gly Gly Pro Gln Pro Gly Val Pro Leu Gly Tyr Pro Ile
            195                 200                 205
Lys Ala Pro Lys Leu Pro Gly Tyr Gly Pro Gly Gly Val Ala Gly Ala
210                 215                 220
Ala Gly Lys Ala Gly Tyr Pro Thr Gly Thr Gly Val Gly Pro Gln Ala
225                 230                 235                 240
Ala Ala Ala Ala Ala Lys Ala Ala Lys Phe Gly Ala Gly Ala
                245                 250                 255
Ala Gly Val Leu Pro Gly Val Gly Gly Ala Gly Val Pro Gly Val Pro
                260                 265                 270
Gly Ala Ile Pro Gly Ile Gly Gly Ile Ala Gly Ala Ala Gly Leu
            275                 280                 285
Val Pro Gly Gly Pro Gly Phe Gly Pro Gly Val Val Gly Val Pro Gly
                290                 295                 300
Ala Gly Val Pro Gly Val Gly Val Pro Gly Ala Gly Ile Pro Val Val
305                 310                 315                 320
Pro Gly Ala Gly Ile Pro Gly Ala Ala Val Pro Gly Val Val Ser Pro
                325                 330                 335
Glu Ala Ala Ala Lys Ala Ala Ala Lys Ala Ala Lys Tyr Gly Ala Arg
                340                 345                 350
Pro Gly Val Gly Val Gly Gly Ile Pro Thr Tyr Gly Val Gly Ala Gly
            355                 360                 365
Gly Phe Pro Gly Phe Gly Val Gly Val Gly Gly Ile Pro Gly Val Ala
            370                 375                 380
Gly Val Pro Gly Val Gly Gly Val Pro Gly Val Gly Gly Val Pro Gly
385                 390                 395                 400
```

```
Val Gly Ile Ser Pro Glu Ala Gln Ala Ala Ala Ala Lys Ala Ala
                405                 410                 415

Lys Tyr Gly Leu Val Pro Gly Val Gly Val Ala Pro Gly Val Gly Val
            420                 425                 430

Ala Pro Gly Val Gly Val Ala Pro Gly Val Gly Leu Ala Pro Gly Val
            435                 440                 445

Gly Val Ala Pro Gly Val Gly Val Ala Pro Gly Val Gly Val Ala Pro
        450                 455                 460

Gly Ile Gly Pro Gly Gly Val Ala Ala Ala Lys Ser Ala Ala Lys
465                 470                 475                 480

Val Ala Ala Lys Ala Gln Leu Arg Ala Ala Gly Leu Gly Ala Gly
                485                 490                 495

Ile Pro Gly Leu Gly Val Gly Val Gly Val Pro Gly Leu Gly Val Gly
            500                 505                 510

Ala Gly Val Pro Gly Leu Gly Val Gly Ala Gly Val Pro Gly Phe Gly
            515                 520                 525

Ala Val Pro Gly Ala Leu Ala Ala Ala Lys Ala Ala Lys Tyr Gly Ala
        530                 535                 540

Ala Val Pro Gly Val Leu Gly Gly Leu Gly Ala Leu Gly Gly Val Gly
545                 550                 555                 560

Ile Pro Gly Gly Val Val Gly Ala Gly Pro Ala Ala Ala Ala Ala
                565                 570                 575

Ala Lys Ala Ala Ala Lys Ala Ala Gln Phe Gly Leu Val Gly Ala Ala
            580                 585                 590

Gly Leu Gly Gly Leu Gly Val Gly Gly Leu Gly Val Pro Gly Val Gly
        595                 600                 605

Gly Leu Gly Gly Ile Pro Pro Ala Ala Ala Lys Ala Ala Lys Tyr
                610                 615                 620

Gly Ala Ala Gly Leu Gly Gly Val Leu Gly Gly Ala Gly Gln Phe Pro
625                 630                 635                 640

Leu Gly Gly Val Ala Ala Arg Pro Gly Phe Gly Leu Ser Pro Ile Phe
                645                 650                 655

Pro Gly Gly Ala Cys Leu Gly Lys Ala Cys Gly Arg Lys Arg Lys
            660                 665                 670

<210> SEQ ID NO 26
<211> LENGTH: 661
<212> TYPE: PRT
<213> ORGANISM: Homo sapiens

<400> SEQUENCE: 26

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Gly Leu Gly Ala Phe Pro Ala Val Thr Phe Pro Gly Ala Leu Val
65                  70                  75                  80

Pro Gly Gly Val Ala Asp Ala Ala Ala Ala Tyr Lys Ala Ala Lys Ala
                85                  90                  95

Gly Ala Gly Leu Gly Gly Val Pro Gly Val Gly Gly Leu Gly Val Ser
            100                 105                 110
```

```
Ala Gly Ala Val Val Pro Gln Pro Gly Ala Gly Val Lys Pro Gly Lys
        115                 120                 125

Val Pro Gly Val Gly Leu Pro Gly Val Tyr Pro Gly Gly Val Leu Pro
    130                 135                 140

Gly Ala Arg Phe Pro Gly Val Gly Val Leu Pro Gly Val Pro Thr Gly
145                 150                 155                 160

Ala Gly Val Lys Pro Lys Ala Pro Gly Val Gly Gly Ala Phe Ala Gly
                165                 170                 175

Ile Pro Gly Val Gly Pro Phe Gly Gly Pro Gln Pro Gly Val Pro Leu
                180                 185                 190

Gly Tyr Pro Ile Lys Ala Pro Lys Leu Pro Gly Tyr Gly Pro Gly Gly
                195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Ala Lys Phe
225                 230                 235                 240

Gly Ala Gly Ala Ala Gly Val Leu Pro Gly Val Gly Ala Gly Val
                245                 250                 255

Pro Gly Val Pro Gly Ala Ile Pro Gly Ile Gly Gly Ile Ala Gly Val
                260                 265                 270

Gly Thr Pro Ala Ala Ala Ala Ala Ala Ala Ala Lys Ala Ala
            275                 280                 285

Lys Tyr Gly Ala Ala Gly Leu Val Pro Gly Gly Pro Gly Phe Gly
                290                 295                 300

Pro Gly Val Val Gly Val Pro Gly Ala Gly Val Pro Gly Val Gly Val
305                 310                 315                 320

Pro Gly Ala Gly Ile Pro Val Val Pro Gly Ala Gly Ile Pro Gly Ala
                325                 330                 335

Ala Val Pro Gly Val Val Ser Pro Glu Ala Ala Lys Ala Ala Ala
                340                 345                 350

Lys Ala Ala Lys Tyr Gly Ala Arg Pro Gly Val Gly Val Gly Gly Ile
        355                 360                 365

Pro Thr Tyr Gly Val Gly Ala Gly Gly Phe Pro Gly Phe Gly Val Gly
        370                 375                 380

Val Gly Gly Ile Pro Gly Val Ala Gly Val Pro Ser Val Gly Gly Val
385                 390                 395                 400

Pro Gly Val Gly Gly Val Pro Gly Val Gly Ile Ser Pro Glu Ala Gln
                405                 410                 415

Ala Ala Ala Ala Ala Lys Ala Ala Lys Tyr Gly Leu Val Pro Gly Val
                420                 425                 430

Gly Val Ala Pro Gly Val Gly Val Ala Pro Gly Val Gly Val Ala Pro
            435                 440                 445

Gly Val Gly Leu Ala Pro Gly Val Gly Val Ala Pro Gly Val Gly Val
            450                 455                 460

Ala Pro Gly Val Gly Val Ala Pro Gly Ile Gly Pro Gly Gly Val Ala
465                 470                 475                 480

Ala Ala Ala Lys Ser Ala Ala Lys Val Ala Lys Ala Gln Leu Arg
                485                 490                 495

Ala Ala Ala Gly Leu Gly Ala Gly Ile Pro Gly Leu Gly Val Gly Val
            500                 505                 510

Gly Val Pro Gly Leu Gly Val Gly Ala Gly Val Pro Gly Leu Gly Val
            515                 520                 525
```

-continued

```
Gly Ala Gly Val Pro Gly Phe Gly Ala Val Pro Gly Ala Leu Ala Ala
            530                 535                 540

Ala Lys Ala Ala Lys Tyr Gly Ala Ala Val Pro Gly Val Leu Gly Gly
545                 550                 555                 560

Leu Gly Ala Leu Gly Gly Val Gly Ile Pro Gly Gly Val Val Gly Ala
                565                 570                 575

Gly Pro Ala Ala Ala Ala Ala Ala Lys Ala Ala Lys Ala Ala
            580                 585                 590

Gln Phe Gly Leu Val Gly Ala Ala Gly Leu Gly Gly Leu Gly Val Gly
            595                 600                 605

Gly Leu Gly Val Pro Gly Val Gly Gly Leu Gly Gly Ile Pro Pro Ala
            610                 615                 620

Ala Ala Ala Lys Ala Ala Lys Tyr Gly Val Ala Ala Arg Pro Gly Phe
625                 630                 635                 640

Gly Leu Ser Pro Ile Phe Pro Gly Gly Ala Cys Leu Gly Lys Ala Cys
                645                 650                 655

Gly Arg Lys Arg Lys
            660

<210> SEQ ID NO 27
<211> LENGTH: 714
<212> TYPE: PRT
<213> ORGANISM: Homo sapiens

<400> SEQUENCE: 27

Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
         50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
        130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Pro Phe Gly Gly Pro Gln Pro Gly Val
            180                 185                 190

Pro Leu Gly Tyr Pro Ile Lys Ala Pro Lys Leu Pro Gly Gly Tyr Gly
            195                 200                 205

Leu Pro Tyr Thr Thr Gly Lys Leu Pro Tyr Gly Tyr Gly Pro Gly Gly
        210                 215                 220

Met Ala Gly Ala Ala Gly Lys Ala Gly Tyr Pro Thr Gly Thr Gly Val
225                 230                 235                 240
```

-continued

```
Gly Pro Gln Ala Pro Thr Ala Ala Ala Lys Ala Ala Lys Phe
                245                 250                 255
Gly Ala Gly Ala Ala Gly Val Leu Pro Gly Val Gly Ala Gly Val
            260                 265                 270
Pro Gly Val Pro Gly Ala Ile Pro Gly Ile Gly Gly Ile Ala Gly Val
        275                 280                 285
Gly Thr Pro Ala Ala Ala Ala Ala Ala Ala Ala Lys Ala Ala
            290                 295                 300
Lys Tyr Gly Ala Ala Gly Leu Val Pro Gly Pro Gly Phe Gly
305                 310                 315                 320
Pro Gly Val Val Gly Val Pro Gly Ala Gly Val Pro Gly Val Gly Val
            325                 330                 335
Pro Gly Ala Gly Ile Pro Val Val Pro Gly Ala Gly Ile Pro Gly Ala
            340                 345                 350
Ala Val Pro Gly Val Val Ser Pro Glu Ala Ala Lys Ala Ala Ala
            355                 360                 365
Lys Ala Ala Lys Tyr Gly Ala Arg Pro Gly Val Gly Val Gly Gly Ile
    370                 375                 380
Pro Thr Tyr Gly Val Gly Ala Gly Phe Pro Gly Phe Gly Val Gly
385                 390                 395                 400
Val Gly Gly Ile Pro Gly Val Ala Gly Val Pro Gly Val Gly Gly Val
            405                 410                 415
Pro Gly Val Gly Gly Val Pro Gly Val Gly Ile Ser Pro Glu Ala Gln
            420                 425                 430
Ala Ala Ala Ala Lys Ala Ala Lys Tyr Gly Val Gly Thr Pro Ala
            435                 440                 445
Ala Ala Ala Ala Lys Ala Ala Lys Ala Ala Gln Phe Gly Leu Val
    450                 455                 460
Pro Gly Val Gly Val Ala Pro Gly Val Gly Val Ala Pro Gly Val Gly
465                 470                 475                 480
Val Ala Pro Gly Val Gly Leu Ala Pro Gly Val Gly Val Ala Pro Gly
            485                 490                 495
Val Gly Val Ala Pro Gly Val Gly Val Ala Pro Gly Ile Gly Pro Gly
            500                 505                 510
Gly Val Ala Ala Ala Lys Ser Ala Ala Lys Val Ala Ala Lys Ala
            515                 520                 525
Gln Leu Arg Ala Ala Gly Leu Gly Ala Gly Ile Pro Gly Leu Gly
    530                 535                 540
Val Gly Val Gly Val Pro Gly Leu Gly Val Gly Ala Gly Val Pro Gly
545                 550                 555                 560
Leu Gly Val Gly Ala Gly Val Pro Gly Phe Gly Ala Val Pro Gly Ala
            565                 570                 575
Leu Ala Ala Ala Lys Ala Ala Lys Tyr Gly Ala Ala Val Pro Gly Val
            580                 585                 590
Leu Gly Gly Leu Gly Ala Leu Gly Gly Val Gly Ile Pro Gly Gly Val
            595                 600                 605
Val Gly Ala Gly Pro Ala Ala Ala Ala Ala Ala Lys Ala Ala Ala
            610                 615                 620
Lys Ala Ala Gln Phe Gly Leu Val Gly Ala Ala Gly Leu Gly Gly Leu
625                 630                 635                 640
Gly Val Gly Gly Leu Gly Val Pro Gly Val Gly Gly Leu Gly Gly Ile
            645                 650                 655
```

```
Pro Pro Ala Ala Ala Lys Ala Ala Lys Tyr Gly Ala Ala Gly Leu
            660                 665                 670

Gly Gly Val Leu Gly Gly Ala Gly Gln Phe Pro Leu Gly Gly Val Ala
        675                 680                 685

Ala Arg Pro Gly Phe Gly Leu Ser Pro Ile Phe Pro Gly Gly Ala Cys
690                 695                 700

Leu Gly Lys Ala Cys Gly Arg Lys Arg Lys
705                 710

<210> SEQ ID NO 28
<211> LENGTH: 714
<212> TYPE: PRT
<213> ORGANISM: Homo sapiens

<400> SEQUENCE: 28

Met Ala Gly Leu Thr Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Gly Ala Val
        115                 120                 125

Val Pro Gln Pro Gly Ala Gly Val Lys Pro Gly Lys Val Pro Gly Val
    130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
            180                 185                 190

Gly Pro Phe Gly Gly Pro Gln Pro Gly Val Pro Leu Gly Tyr Pro Ile
        195                 200                 205

Lys Ala Pro Lys Leu Pro Gly Gly Tyr Gly Leu Pro Tyr Thr Thr Gly
    210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
            260                 265                 270

Val Leu Pro Gly Val Gly Gly Ala Gly Val Pro Gly Val Pro Gly Ala
        275                 280                 285

Ile Pro Gly Ile Gly Gly Ile Ala Gly Val Gly Thr Pro Ala Ala Ala
    290                 295                 300

Ala Ala Ala Ala Ala Ala Lys Ala Ala Lys Tyr Gly Ala Ala Ala
305                 310                 315                 320
```

```
Gly Leu Val Pro Gly Pro Gly Phe Gly Pro Val Val Gly Val
            325                 330                 335

Pro Gly Ala Gly Val Pro Val Gly Val Pro Gly Ala Gly Ile Pro
        340                 345                 350

Val Val Pro Gly Ala Gly Ile Pro Gly Ala Ala Val Pro Gly Val Val
        355                 360                 365

Ser Pro Glu Ala Ala Ala Lys Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Ala Glu
        420                 425                 430

Ala Gln Ala Ala Ala Ala Lys Ala Ala Lys Tyr Gly Val Gly Thr
    435                 440                 445

Pro Ala Ala Ala Ala Lys Ala Ala Lys Ala Ala Gln Phe Gly
    450                 455                 460

Leu Val Pro Gly Val Gly Val Ala Pro Gly Val Gly Val Ala Pro Gly
465                 470                 475                 480

Val Gly Val Ala Pro Gly Val Gly Leu Ala Pro Gly Val Gly Val Ala
                485                 490                 495

Pro Gly Val Gly Val Ala Pro Gly Val Gly Val Ala Pro Gly Ile Gly
            500                 505                 510

Pro Gly Gly Val Ala Ala Ala Lys Ser Ala Ala Lys Val Ala Ala
            515                 520                 525

Lys Ala Gln Leu Arg Ala Ala Ala Gly Leu Gly Ala Gly Ile Pro Gly
    530                 535                 540

Leu Gly Val Gly Val Gly Val Pro Gly Leu Gly Val Gly Ala Gly Val
545                 550                 555                 560

Pro Gly Leu Gly Val Gly Ala Gly Val Pro Gly Phe Gly Ala Val Pro
                565                 570                 575

Gly Ala Leu Ala Ala Ala Lys Ala Ala Lys Tyr Ala Val Pro Gly Val
            580                 585                 590

Leu Gly Gly Leu Gly Ala Leu Gly Gly Val Gly Ile Pro Gly Gly Val
            595                 600                 605

Val Gly Ala Gly Pro Ala Ala Ala Ala Ala Lys Ala Ala
        610                 615                 620

Lys Ala Ala Gln Phe Gly Leu Val Gly Ala Ala Gly Leu Gly Gly Leu
625                 630                 635                 640

Gly Val Gly Gly Leu Gly Val Pro Gly Val Gly Gly Leu Gly Gly Ile
                645                 650                 655

Pro Pro Ala Ala Ala Lys Ala Ala Lys Tyr Gly Ala Ala Gly Leu
            660                 665                 670

Gly Gly Val Leu Gly Gly Ala Gly Gln Phe Pro Leu Gly Gly Val Ala
            675                 680                 685

Ala Arg Pro Gly Phe Gly Leu Ser Pro Ile Phe Pro Gly Gly Ala Cys
    690                 695                 700

Leu Gly Lys Ala Cys Gly Arg Lys Arg Lys
705                 710

<210> SEQ ID NO 29
<211> LENGTH: 721
```

<212> TYPE: PRT
<213> ORGANISM: Homo sapiens

<400> SEQUENCE: 29

```
Met Ala Gly Leu Thr Ala Ala Pro Arg Pro Gly Val Leu Leu Leu
1               5                   10                  15

Leu Leu Ser Ile Leu His Pro Ser Arg Pro Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Ala Pro Ser
            115                 120                 125

Val Pro Gly Ala Val Pro Gln Pro Gly Ala Gly Val Lys Pro Gly
    130                 135                 140

Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
                165                 170                 175

Gly Ala Gly Val Lys Pro Lys Ala Pro Gly Val Gly Gly Ala Phe Ala
                180                 185                 190

Gly Ile Pro Gly Val Gly Pro Phe Gly Gly Pro Gln Pro Gly Val Pro
            195                 200                 205

Leu Gly Tyr Pro Ile Lys Ala Pro Lys Leu Pro Gly Gly Tyr Gly Leu
    210                 215                 220

Pro Tyr Thr Thr Gly Lys Leu Pro Tyr Gly Tyr Gly Pro Gly Gly Val
225                 230                 235                 240

Ala Gly Ala Ala Gly Lys Ala Gly Tyr Pro Thr Gly Thr Gly Val Gly
                245                 250                 255

Pro Gln Ala Ala Ala Ala Ala Ala Lys Ala Ala Lys Phe Gly
    260                 265                 270

Ala Gly Ala Ala Gly Val Leu Pro Gly Val Gly Gly Ala Gly Val Pro
    275                 280                 285

Gly Val Pro Gly Ala Ile Pro Gly Ile Gly Gly Ile Ala Gly Val Gly
    290                 295                 300

Thr Pro Ala Ala Ala Ala Ala Ala Ala Lys Ala Ala Lys
305                 310                 315                 320

Tyr Gly Ala Ala Ala Gly Leu Val Pro Gly Gly Pro Gly Phe Gly Pro
                325                 330                 335

Gly Val Val Gly Val Pro Gly Ala Gly Val Pro Gly Val Gly Val Pro
                340                 345                 350

Gly Ala Gly Ile Pro Val Val Pro Gly Ala Gly Ile Pro Gly Ala Ala
            355                 360                 365

Val Pro Gly Val Val Ser Pro Glu Ala Ala Lys Ala Ala Ala Lys
    370                 375                 380

Ala Ala Lys Tyr Gly Ala Arg Pro Gly Val Gly Val Gly Gly Ile Pro
385                 390                 395                 400
```

-continued

```
Thr Tyr Gly Val Gly Ala Gly Phe Pro Gly Phe Gly Val Gly Val
                405                 410                 415

Gly Gly Ile Pro Gly Val Ala Gly Val Pro Gly Val Gly Val Pro
            420                 425                 430

Gly Val Gly Ala Glu Ala Gln Ala Ala Ala Lys Ala Ala Lys
        435                 440                 445

Tyr Gly Val Gly Thr Pro Ala Ala Ala Lys Ala Ala Lys
450                 455                 460

Ala Ala Gln Phe Gly Leu Val Pro Gly Val Gly Val Ala Pro Gly Val
465                 470                 475                 480

Gly Val Ala Pro Gly Val Gly Val Ala Pro Gly Val Gly Leu Ala Pro
                485                 490                 495

Gly Val Gly Val Ala Pro Gly Val Gly Val Ala Pro Gly Val Gly Val
            500                 505                 510

Ala Pro Gly Ile Gly Pro Gly Val Ala Ala Ala Lys Ser Ala
        515                 520                 525

Ala Lys Val Ala Ala Lys Ala Gln Leu Arg Ala Ala Ala Gly Leu Gly
            530                 535                 540

Ala Gly Ile Pro Gly Leu Gly Val Gly Val Gly Val Pro Gly Leu Gly
545                 550                 555                 560

Val Gly Ala Gly Val Pro Gly Leu Gly Val Gly Ala Gly Val Pro Gly
                565                 570                 575

Phe Gly Ala Val Pro Gly Ala Leu Ala Ala Ala Lys Ala Ala Lys Tyr
            580                 585                 590

Gly Ala Ala Val Pro Gly Val Leu Gly Gly Leu Gly Ala Leu Gly Gly
                595                 600                 605

Val Gly Ile Pro Gly Gly Val Val Gly Ala Gly Pro Ala Ala Ala Ala
610                 615                 620

Ala Ala Ala Lys Ala Ala Ala Lys Ala Ala Gln Phe Gly Leu Val Gly
625                 630                 635                 640

Ala Ala Gly Leu Gly Gly Leu Gly Val Gly Gly Leu Gly Val Pro Gly
                645                 650                 655

Val Gly Gly Leu Gly Gly Ile Pro Pro Ala Ala Ala Lys Ala Ala
                660                 665                 670

Lys Tyr Gly Ala Ala Gly Leu Gly Gly Val Leu Gly Gly Ala Gly Gln
675                 680                 685

Phe Pro Leu Gly Gly Val Ala Ala Arg Pro Gly Phe Gly Leu Ser Pro
            690                 695                 700

Ile Phe Pro Gly Gly Ala Cys Leu Gly Lys Ala Cys Gly Arg Lys Arg
705                 710                 715                 720

Lys

<210> SEQ ID NO 30
<211> LENGTH: 712
<212> TYPE: PRT
<213> ORGANISM: Homo sapiens

<400> SEQUENCE: 30

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45
```

-continued

```
Gly Ala Leu Gly Gly Ala Leu Gly Pro Gly Gly Lys Pro Leu Lys
         50                  55                  60
Pro Gly Leu Gly Ala Phe Pro Ala Val Thr Phe Pro Gly Ala Leu Val
 65                  70                  75                  80
Pro Gly Gly Val Ala Asp Ala Ala Ala Tyr Lys Ala Ala Lys Ala
                 85                  90                  95
Gly Ala Gly Leu Gly Gly Val Pro Gly Val Gly Leu Gly Val Ser
                100                 105                 110
Ala Gly Ala Val Val Pro Gln Pro Gly Ala Gly Val Lys Pro Gly Lys
                115                 120                 125
Val Pro Gly Val Gly Leu Pro Gly Val Tyr Pro Gly Gly Val Leu Pro
    130                 135                 140
Gly Ala Arg Phe Pro Gly Val Gly Val Leu Pro Gly Val Pro Thr Gly
145                 150                 155                 160
Ala Gly Val Lys Pro Lys Ala Pro Gly Val Gly Gly Ala Phe Ala Gly
                165                 170                 175
Ile Pro Gly Val Gly Pro Phe Gly Gly Pro Gln Pro Gly Val Pro Leu
                180                 185                 190
Gly Tyr Pro Ile Lys Ala Pro Lys Leu Pro Gly Gly Tyr Gly Leu Pro
                195                 200                 205
Tyr Thr Thr Gly Lys Leu Pro Tyr Gly Tyr Gly Pro Gly Gly Val Ala
    210                 215                 220
Gly Ala Ala Gly Lys Ala Gly Tyr Pro Thr Gly Thr Gly Val Gly Pro
225                 230                 235                 240
Gln Ala Ala Ala Ala Ala Ala Lys Ala Ala Lys Phe Gly Ala
                245                 250                 255
Gly Ala Ala Gly Val Leu Pro Gly Val Gly Gly Ala Gly Val Pro Gly
                260                 265                 270
Val Pro Gly Ala Ile Pro Gly Ile Gly Gly Ile Ala Gly Val Gly Thr
    275                 280                 285
Pro Ala Ala Ala Ala Ala Ala Ala Ala Lys Ala Ala Lys Tyr
290                 295                 300
Gly Ala Ala Ala Gly Leu Val Pro Gly Gly Pro Gly Phe Gly Pro Gly
305                 310                 315                 320
Val Val Gly Val Pro Gly Ala Gly Val Pro Gly Val Gly Val Pro Gly
                325                 330                 335
Ala Gly Ile Pro Val Val Pro Gly Ala Gly Ile Pro Gly Ala Ala Val
                340                 345                 350
Pro Gly Val Val Ser Pro Glu Ala Ala Ala Lys Ala Ala Ala Lys Ala
    355                 360                 365
Ala Lys Tyr Gly Ala Arg Pro Gly Val Gly Val Gly Gly Ile Pro Thr
    370                 375                 380
Tyr Gly Val Gly Ala Gly Gly Phe Pro Gly Phe Gly Val Gly Val Gly
385                 390                 395                 400
Gly Ile Pro Gly Val Ala Gly Val Pro Gly Val Gly Val Pro Gly
                405                 410                 415
Val Gly Gly Val Pro Gly Val Gly Ile Ser Pro Glu Ala Gln Ala Ala
                420                 425                 430
Ala Ala Ala Lys Ala Ala Lys Tyr Gly Val Gly Thr Pro Ala Ala Ala
                435                 440                 445
Ala Ala Lys Ala Ala Ala Lys Ala Ala Gln Phe Gly Leu Val Pro Gly
                450                 455                 460
```

```
Val Gly Val Ala Pro Gly Val Gly Val Ala Pro Gly Val Gly Val Ala
465                 470                 475                 480

Pro Gly Val Gly Leu Ala Pro Gly Val Gly Val Ala Pro Gly Val Gly
                485                 490                 495

Val Ala Pro Gly Val Gly Val Ala Pro Gly Ile Gly Pro Gly Gly Val
            500                 505                 510

Ala Ala Ala Ala Lys Ser Ala Ala Lys Val Ala Ala Lys Ala Gln Leu
        515                 520                 525

Arg Ala Ala Gly Leu Gly Ala Gly Ile Pro Gly Leu Gly Val Gly
    530                 535                 540

Val Gly Val Pro Gly Leu Gly Val Gly Ala Gly Val Pro Gly Leu Gly
545                 550                 555                 560

Val Gly Ala Gly Val Pro Gly Phe Gly Ala Val Pro Gly Ala Leu Ala
                565                 570                 575

Ala Ala Lys Ala Ala Lys Tyr Gly Ala Ala Val Pro Gly Val Leu Gly
            580                 585                 590

Gly Leu Gly Ala Leu Gly Gly Val Gly Ile Pro Gly Gly Val Val Gly
    595                 600                 605

Ala Gly Pro Ala Ala Ala Ala Ala Ala Lys Ala Ala Lys Ala
    610                 615                 620

Ala Gln Phe Gly Leu Val Gly Ala Ala Gly Leu Gly Gly Leu Gly Val
625                 630                 635                 640

Gly Gly Leu Gly Val Pro Gly Val Gly Gly Leu Gly Gly Ile Pro Pro
                645                 650                 655

Ala Ala Ala Ala Lys Ala Ala Lys Tyr Gly Ala Ala Gly Leu Gly Gly
            660                 665                 670

Val Leu Gly Gly Ala Gly Gln Phe Pro Leu Gly Gly Val Ala Ala Arg
        675                 680                 685

Pro Gly Phe Gly Leu Ser Pro Ile Phe Pro Gly Gly Ala Cys Leu Gly
    690                 695                 700

Lys Ala Cys Gly Arg Lys Arg Lys
705                 710

<210> SEQ ID NO 31
<211> LENGTH: 667
<212> TYPE: PRT
<213> ORGANISM: Homo sapiens

<400> SEQUENCE: 31

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu Gly Pro
            35                  40                  45

Gly Gly Lys Pro Leu Lys Pro Val Pro Gly Gly Leu Ala Gly Ala Gly
        50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                85                  90                  95

Lys Ala Gly Ala Gly Leu Gly Gly Val Pro Gly Val Gly Gly Leu Gly
            100                 105                 110

Val Ser Ala Gly Ala Val Val Pro Gln Pro Gly Ala Gly Val Lys Pro
        115                 120                 125
```

```
Gly Lys Val Pro Gly Val Gly Leu Pro Gly Val Tyr Pro Gly Gly Val
    130                 135                 140

Leu Pro Gly Ala Arg Phe Pro Gly Val Gly Val Leu Pro Gly Val Pro
145                 150                 155                 160

Thr Gly Ala Gly Val Lys Pro Lys Ala Pro Gly Val Gly Gly Ala Phe
                165                 170                 175

Ala Gly Ile Pro Gly Val Gly Pro Phe Gly Pro Gln Pro Gly Val
            180                 185                 190

Pro Leu Gly Tyr Pro Ile Lys Ala Pro Lys Leu Pro Gly Tyr Gly Pro
        195                 200                 205

Gly Gly Val Ala Gly Ala Gly Lys Ala Gly Tyr Pro Thr Gly Thr
    210                 215                 220

Gly Val Gly Pro Gln Ala Ala Ala Ala Ala Ala Lys Ala Ala Ala
225                 230                 235                 240

Lys Phe Gly Ala Gly Ala Ala Gly Val Leu Pro Gly Val Gly Ala
                245                 250                 255

Gly Val Pro Gly Val Pro Gly Ala Ile Pro Gly Ile Gly Gly Ile Ala
                260                 265                 270

Gly Val Gly Thr Pro Ala Ala Ala Ala Ala Ala Ala Ala Ala Lys
                275                 280                 285

Ala Ala Lys Tyr Gly Ala Ala Gly Leu Val Pro Gly Gly Pro Gly
        290                 295                 300

Phe Gly Pro Gly Val Val Gly Val Pro Gly Ala Gly Val Pro Gly Val
305                 310                 315                 320

Gly Val Pro Gly Ala Gly Ile Pro Val Val Pro Gly Ala Gly Ile Pro
                325                 330                 335

Gly Ala Ala Val Pro Gly Val Val Ser Pro Glu Ala Ala Ala Lys Ala
                340                 345                 350

Ala Ala Lys Ala Ala Lys Tyr Gly Ala Arg Pro Gly Val Gly Val Gly
            355                 360                 365

Gly Ile Pro Thr Tyr Gly Val Gly Ala Gly Gly Phe Pro Gly Phe Gly
        370                 375                 380

Val Gly Val Gly Gly Ile Pro Gly Val Ala Gly Val Pro Gly Val Gly
385                 390                 395                 400

Gly Val Pro Gly Val Gly Gly Val Pro Gly Val Gly Ile Ser Pro Glu
                405                 410                 415

Ala Gln Ala Ala Ala Ala Ala Lys Ala Ala Lys Tyr Gly Val Gly Thr
                420                 425                 430

Pro Ala Ala Ala Ala Lys Ala Ala Lys Ala Ala Gln Phe Gly
                435                 440                 445

Leu Val Pro Gly Val Gly Val Ala Pro Gly Val Gly Val Ala Pro Gly
    450                 455                 460

Val Gly Val Ala Pro Gly Val Gly Leu Ala Pro Gly Val Gly Val Ala
465                 470                 475                 480

Pro Gly Val Gly Val Ala Pro Gly Val Gly Val Ala Pro Gly Ile Gly
                485                 490                 495

Pro Gly Gly Val Ala Ala Ala Lys Ser Ala Ala Lys Val Ala Ala
                500                 505                 510

Lys Ala Gln Leu Arg Ala Ala Ala Gly Leu Gly Ala Gly Ile Pro Gly
            515                 520                 525

Leu Gly Val Gly Val Gly Val Pro Gly Leu Gly Val Gly Ala Gly Val
    530                 535                 540
```

```
Pro Gly Leu Gly Val Gly Ala Gly Val Pro Gly Phe Gly Ala Val Pro
545                 550                 555                 560

Gly Ala Leu Ala Ala Ala Lys Ala Ala Lys Tyr Gly Ala Ala Val Pro
            565                 570                 575

Gly Val Leu Gly Gly Leu Gly Ala Leu Gly Gly Val Gly Ile Pro Gly
            580                 585                 590

Gly Val Val Gly Ala Gly Pro Ala Ala Ala Ala Ala Ala Lys Ala
        595                 600                 605

Ala Ala Lys Ala Ala Gln Phe Gly Leu Val Gly Ala Ala Gly Leu Gly
        610                 615                 620

Gly Leu Gly Val Gly Gly Leu Gly Val Pro Gly Val Gly Gly Leu Gly
625                 630                 635                 640

Gly Ile Pro Pro Ala Ala Ala Lys Ala Ala Lys Tyr Gly Gly Ala
            645                 650                 655

Cys Leu Gly Lys Ala Cys Gly Arg Lys Arg Lys
            660                 665

<210> SEQ ID NO 32
<211> LENGTH: 682
<212> TYPE: PRT
<213> ORGANISM: Homo sapiens

<400> SEQUENCE: 32

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Ala Leu Gly Pro
        35                  40                  45

Gly Gly Lys Pro Leu Lys Pro Val Pro Gly Gly Leu Ala Gly Ala Gly
    50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                85                  90                  95

Lys Ala Gly Ala Gly Leu Gly Gly Val Pro Gly Val Gly Gly Leu Gly
            100                 105                 110

Val Ser Ala Gly Ala Val Val Pro Gln Pro Gly Ala Gly Val Lys Pro
        115                 120                 125

Gly Lys Val Pro Gly Val Gly Leu Pro Gly Val Tyr Pro Gly Gly Val
130                 135                 140

Leu Pro Gly Ala Arg Phe Pro Gly Val Gly Val Leu Pro Gly Val Pro
145                 150                 155                 160

Thr Gly Ala Gly Val Lys Pro Lys Ala Pro Gly Val Gly Gly Ala Phe
                165                 170                 175

Ala Gly Ile Pro Gly Val Gly Pro Phe Gly Pro Gln Pro Gly Val
            180                 185                 190

Pro Leu Gly Tyr Pro Ile Lys Ala Pro Lys Leu Pro Gly Tyr Gly Pro
        195                 200                 205

Gly Gly Val Ala Gly Ala Ala Gly Lys Ala Gly Tyr Pro Thr Gly Thr
    210                 215                 220

Gly Val Gly Pro Gln Ala Ala Ala Ala Ala Ala Lys Ala Ala Ala
225                 230                 235                 240

Lys Phe Gly Ala Gly Ala Ala Gly Val Leu Pro Gly Val Gly Gly Ala
                245                 250                 255
```

```
Gly Val Pro Gly Val Pro Gly Ala Ile Pro Gly Ile Gly Gly Ile Ala
            260                 265                 270

Gly Val Gly Thr Pro Ala Ala Ala Ala Ala Ala Ala Ala Ala Ala Lys
            275                 280                 285

Ala Ala Lys Tyr Gly Ala Ala Gly Leu Val Pro Gly Gly Pro Gly
    290                 295                 300

Phe Gly Pro Gly Val Val Gly Val Pro Gly Ala Gly Val Pro Gly Val
305                 310                 315                 320

Gly Val Pro Gly Ala Gly Ile Pro Val Val Pro Gly Ala Gly Ile Pro
                325                 330                 335

Gly Ala Ala Val Pro Gly Val Val Ser Pro Glu Ala Ala Lys Ala
                340                 345                 350

Ala Ala Lys Ala Ala Lys Tyr Gly Ala Arg Pro Gly Val Gly Val Gly
            355                 360                 365

Gly Ile Pro Thr Tyr Gly Val Gly Ala Gly Gly Phe Pro Gly Phe Gly
        370                 375                 380

Val Gly Val Gly Gly Ile Pro Gly Val Ala Gly Val Pro Gly Val Gly
385                 390                 395                 400

Gly Val Pro Gly Val Gly Val Pro Gly Val Gly Ile Ser Pro Glu
                405                 410                 415

Ala Gln Ala Ala Ala Ala Ala Lys Ala Ala Lys Tyr Gly Val Gly Thr
            420                 425                 430

Pro Ala Ala Ala Ala Lys Ala Ala Lys Ala Ala Gln Phe Gly
        435                 440                 445

Leu Val Pro Gly Val Gly Val Ala Pro Gly Val Gly Val Ala Pro Gly
        450                 455                 460

Val Gly Val Ala Pro Gly Val Gly Leu Ala Pro Gly Val Gly Val Ala
465                 470                 475                 480

Pro Gly Val Gly Val Ala Pro Gly Val Gly Val Ala Pro Gly Ile Gly
                485                 490                 495

Pro Gly Gly Val Ala Ala Ala Lys Ser Ala Ala Lys Val Ala Ala
            500                 505                 510

Lys Ala Gln Leu Arg Ala Ala Gly Leu Gly Ala Gly Ile Pro Gly
        515                 520                 525

Leu Gly Val Gly Val Gly Val Pro Gly Leu Gly Val Gly Ala Gly Val
        530                 535                 540

Pro Gly Leu Gly Val Gly Ala Gly Val Pro Gly Phe Gly Ala Val Pro
545                 550                 555                 560

Gly Ala Leu Ala Ala Lys Ala Ala Lys Tyr Gly Ala Ala Val Pro
                565                 570                 575

Gly Val Leu Gly Gly Leu Gly Ala Leu Gly Gly Val Gly Ile Pro Gly
            580                 585                 590

Gly Val Val Gly Ala Gly Pro Ala Ala Ala Ala Ala Ala Lys Ala
            595                 600                 605

Ala Ala Lys Ala Ala Gln Phe Gly Leu Val Gly Ala Ala Gly Leu Gly
    610                 615                 620

Gly Leu Gly Val Gly Gly Leu Gly Val Pro Gly Val Gly Gly Leu Gly
625                 630                 635                 640

Gly Ile Pro Pro Ala Ala Ala Lys Ala Ala Lys Tyr Gly Val Ala
                645                 650                 655

Ala Arg Pro Gly Phe Gly Leu Ser Pro Ile Phe Pro Gly Gly Ala Cys
            660                 665                 670
```

-continued

```
Leu Gly Lys Ala Cys Gly Arg Lys Arg Lys
        675                 680

<210> SEQ ID NO 33
<211> LENGTH: 662
<212> TYPE: PRT
<213> ORGANISM: Homo sapiens

<400> SEQUENCE: 33

Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Ala Leu Gly Pro
            35                  40                  45

Gly Gly Lys Pro Leu Lys Pro Val Pro Gly Gly Leu Ala Gly Ala Gly
        50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                85                  90                  95

Lys Ala Gly Ala Gly Leu Gly Gly Val Pro Gly Val Gly Gly Leu Gly
            100                 105                 110

Val Ser Ala Gly Ala Val Val Pro Gln Pro Gly Ala Gly Val Lys Pro
        115                 120                 125

Gly Lys Val Pro Gly Val Gly Leu Pro Gly Val Tyr Pro Gly Gly Val
    130                 135                 140

Leu Pro Gly Ala Arg Phe Pro Gly Val Gly Val Leu Pro Gly Val Pro
145                 150                 155                 160

Thr Gly Ala Gly Val Lys Pro Lys Ala Pro Gly Val Gly Gly Ala Phe
                165                 170                 175

Ala Gly Ile Pro Gly Val Gly Pro Phe Gly Gly Pro Gln Pro Gly Val
            180                 185                 190

Pro Leu Gly Tyr Pro Ile Lys Ala Pro Lys Leu Pro Gly Gly Tyr Gly
        195                 200                 205

Leu Pro Tyr Thr Thr Gly Lys Leu Pro Tyr Gly Tyr Gly Pro Gly Gly
    210                 215                 220

Val Ala Gly Ala Ala Gly Lys Ala Gly Tyr Pro Thr Gly Thr Gly Val
225                 230                 235                 240

Gly Pro Gln Ala Ala Ala Ala Ala Ala Lys Ala Ala Ala Lys Phe
                245                 250                 255

Gly Ala Gly Ala Ala Gly Val Leu Pro Gly Val Gly Gly Ala Gly Val
            260                 265                 270

Pro Gly Val Pro Gly Ala Ile Pro Gly Ile Gly Gly Ile Ala Gly Val
        275                 280                 285

Gly Thr Pro Ala Ala Ala Ala Ala Ala Ala Ala Lys Ala Ala
    290                 295                 300

Lys Tyr Gly Ala Ala Ala Gly Leu Val Pro Gly Gly Pro Gly Phe Gly
305                 310                 315                 320

Pro Gly Val Val Gly Val Pro Gly Ala Gly Val Pro Gly Val Gly Val
                325                 330                 335

Pro Gly Ala Gly Ile Pro Val Val Pro Gly Ala Gly Ile Pro Gly Ala
            340                 345                 350

Ala Val Pro Gly Val Val Ser Pro Glu Ala Ala Lys Ala Ala Ala
        355                 360                 365
```

```
Lys Ala Ala Lys Tyr Gly Ala Arg Pro Gly Val Gly Gly Ile
            370             375             380

Pro Thr Tyr Gly Val Gly Ala Gly Gly Phe Pro Gly Phe Gly Val Gly
385                 390                 395                 400

Val Gly Gly Ile Pro Gly Val Ala Gly Val Pro Gly Val Gly Gly Val
                405             410                 415

Pro Gly Val Gly Gly Val Pro Gly Val Gly Ile Ser Pro Glu Ala Gln
            420                 425                 430

Ala Ala Ala Ala Ala Lys Ala Ala Lys Tyr Gly Leu Val Pro Gly Val
            435                 440                 445

Gly Val Ala Pro Gly Val Gly Val Ala Pro Gly Val Gly Val Ala Pro
            450                 455                 460

Gly Val Gly Leu Ala Pro Gly Val Gly Val Ala Pro Gly Val Gly Val
465                 470                 475                 480

Ala Pro Gly Val Gly Val Ala Pro Gly Ile Gly Pro Gly Gly Val Ala
                485                 490                 495

Gly Ala Ala Ala Gly Leu Gly Ala Gly Ile Pro Gly Leu Gly Val Gly
            500                 505                 510

Val Gly Val Pro Gly Leu Gly Val Gly Ala Gly Val Pro Gly Leu Gly
            515                 520                 525

Val Gly Ala Gly Val Pro Gly Phe Gly Ala Val Pro Gly Ala Leu Ala
            530                 535                 540

Ala Ala Lys Ala Ala Lys Tyr Gly Ala Ala Val Pro Gly Val Leu Gly
545                 550                 555                 560

Gly Leu Gly Ala Leu Gly Gly Val Gly Ile Pro Gly Gly Val Val Gly
                565                 570                 575

Ala Gly Pro Ala Ala Ala Ala Ala Ala Lys Ala Ala Ala Lys Ala
            580                 585                 590

Ala Gln Phe Gly Leu Val Gly Ala Ala Gly Leu Gly Gly Leu Gly Val
            595                 600                 605

Gly Gly Leu Gly Val Pro Gly Val Gly Gly Leu Gly Gly Ile Pro Pro
            610                 615                 620

Ala Ala Ala Ala Lys Ala Ala Lys Tyr Gly Val Ala Ala Arg Pro Gly
625                 630                 635                 640

Phe Gly Leu Ser Pro Ile Phe Pro Gly Gly Ala Cys Leu Gly Lys Ala
                645                 650                 655

Cys Gly Arg Lys Arg Lys
            660

<210> SEQ ID NO 34
<211> LENGTH: 688
<212> TYPE: PRT
<213> ORGANISM: Homo sapiens

<400> SEQUENCE: 34

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
            50                  55                  60

Pro Val Pro Gly Gly Leu Ala Gly Ala Gly Leu Gly Ala Gly Leu Gly
```

```
                    65                  70                  75                  80
Ala Phe Pro Ala Val Thr Phe Pro Gly Ala Leu Val Pro Gly Gly Val
                    85                  90                  95
Ala Asp Ala Ala Ala Tyr Lys Ala Ala Lys Ala Gly Ala Gly Leu
               100                 105                 110
Gly Gly Val Pro Gly Val Gly Leu Gly Val Ser Ala Gly Ala Val
               115                 120                 125
Val Pro Gln Pro Gly Ala Gly Val Lys Pro Lys Val Pro Gly Val
               130                 135                 140
Gly Leu Pro Gly Val Tyr Pro Gly Val Leu Pro Gly Ala Arg Phe
145                 150                 155                 160
Pro Gly Val Gly Val Leu Pro Gly Val Pro Thr Gly Ala Gly Val Lys
                    165                 170                 175
Pro Lys Ala Pro Gly Val Gly Ala Phe Ala Gly Ile Pro Gly Val
               180                 185                 190
Gly Pro Phe Gly Gly Pro Gln Pro Gly Val Pro Leu Gly Tyr Pro Ile
                    195                 200                 205
Lys Ala Pro Lys Leu Pro Gly Gly Tyr Gly Leu Pro Tyr Thr Thr Gly
210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
               245                 250                 255
Ala Ala Ala Ala Lys Ala Ala Lys Phe Gly Ala Gly Ala Ala Gly
               260                 265                 270
Val Leu Pro Gly Val Gly Gly Ala Gly Val Pro Gly Val Pro Gly Ala
               275                 280                 285
Ile Pro Gly Ile Gly Gly Ile Ala Gly Val Gly Thr Pro Ala Ala Ala
               290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                    325                 330                 335
Pro Gly Ala Gly Val Pro Gly Val Gly Val Pro Gly Ala Gly Ile Pro
               340                 345                 350
Val Val Pro Gly Ala Gly Ile Pro Gly Ala Ala Val Pro Gly Ala Arg
               355                 360                 365
Pro Gly Val Gly Val Gly Ile Pro Thr Tyr Gly Val Gly Ala Gly
               370                 375                 380
Gly Phe Pro Gly Phe Gly Val Gly Val Gly Gly Ile Pro Gly Val Ala
385                 390                 395                 400
Gly Val Pro Gly Val Gly Val Pro Gly Val Gly Val Pro Gly
               405                 410                 415
Val Gly Ile Ser Pro Glu Ala Gln Ala Ala Ala Ala Lys Ala Ala
               420                 425                 430
Lys Tyr Gly Val Gly Thr Pro Ala Ala Ala Ala Lys Ala Ala Ala
               435                 440                 445
Lys Ala Ala Gln Phe Gly Leu Val Pro Gly Val Gly Val Ala Pro Gly
               450                 455                 460
Val Gly Val Ala Pro Gly Val Gly Val Ala Pro Gly Val Gly Leu Ala
465                 470                 475                 480
Pro Gly Val Gly Val Ala Pro Gly Val Gly Val Ala Pro Gly Val Gly
               485                 490                 495
```

```
Val Ala Pro Gly Ile Gly Pro Gly Gly Val Ala Ala Ala Lys Ser
            500                 505                 510

Ala Ala Lys Val Ala Ala Lys Ala Gln Leu Arg Ala Ala Ala Gly Leu
        515                 520                 525

Gly Ala Gly Ile Pro Gly Leu Gly Val Gly Val Gly Val Pro Gly Leu
    530                 535                 540

Gly Val Gly Ala Gly Val Pro Gly Leu Gly Val Gly Ala Gly Val Pro
545                 550                 555                 560

Gly Phe Arg Ala Val Pro Gly Ala Leu Ala Ala Ala Lys Ala Ala Lys
            565                 570                 575

Tyr Gly Ala Ala Val Pro Gly Val Leu Gly Gly Leu Gly Ala Leu Gly
        580                 585                 590

Gly Val Gly Ile Pro Gly Gly Val Val Gly Ala Gly Pro Ala Ala Ala
    595                 600                 605

Ala Ala Ala Ala Lys Ala Ala Ala Lys Ala Ala Gln Phe Gly Leu Val
610                 615                 620

Gly Ala Ala Gly Leu Gly Gly Leu Gly Val Gly Gly Leu Gly Val Pro
625                 630                 635                 640

Gly Val Gly Gly Leu Gly Gly Ile Pro Pro Ala Ala Ala Ala Lys Ala
            645                 650                 655

Ala Lys Tyr Gly Val Ala Ala Arg Pro Gly Phe Gly Leu Ser Pro Ile
        660                 665                 670

Phe Pro Gly Gly Ala Cys Leu Gly Lys Ala Cys Gly Arg Lys Arg Lys
    675                 680                 685

<210> SEQ ID NO 35
<211> LENGTH: 643
<212> TYPE: PRT
<213> ORGANISM: Homo sapiens

<400> SEQUENCE: 35

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Ala Leu Gly Pro
        35                  40                  45

Gly Gly Lys Pro Leu Lys Pro Val Pro Gly Gly Leu Ala Gly Ala Gly
    50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
            85                  90                  95

Lys Ala Gly Ala Gly Leu Gly Gly Val Pro Gly Val Gly Gly Leu Gly
        100                 105                 110

Val Ser Ala Gly Ala Val Val Pro Gln Pro Gly Ala Gly Val Lys Pro
    115                 120                 125

Gly Lys Val Pro Gly Val Gly Leu Pro Gly Val Tyr Pro Gly Gly Val
130                 135                 140

Leu Pro Gly Val Gly Pro Phe Gly Gly Pro Gln Pro Gly Val Pro Leu
145                 150                 155                 160

Gly Tyr Pro Ile Lys Ala Pro Lys Leu Pro Gly Gly Tyr Gly Leu Pro
            165                 170                 175

Tyr Thr Thr Gly Lys Leu Pro Tyr Gly Tyr Gly Pro Gly Gly Val Ala
```

-continued

```
                180                 185                 190
Gly Ala Ala Gly Lys Ala Gly Tyr Pro Thr Gly Thr Gly Val Gly Pro
            195                 200                 205
Gln Ala Ala Ala Ala Ala Ala Lys Ala Ala Ala Lys Phe Gly Ala
        210                 215                 220
Gly Ala Ala Gly Val Leu Pro Gly Val Gly Ala Gly Val Pro Gly
225                 230                 235                 240
Val Pro Gly Ala Ile Pro Gly Ile Gly Ile Ala Gly Val Gly Thr
            245                 250                 255
Pro Ala Ala Ala Ala Ala Ala Ala Lys Ala Ala Lys Tyr
        260                 265                 270
Gly Ala Ala Gly Leu Val Pro Gly Pro Gly Phe Gly Pro Gly
        275                 280                 285
Val Val Gly Val Pro Gly Ala Gly Val Pro Gly Val Gly Val Pro Gly
        290                 295                 300
Ala Gly Ile Pro Val Val Pro Gly Ala Gly Ile Pro Gly Ala Ala Val
305                 310                 315                 320
Pro Gly Val Val Ser Pro Glu Ala Ala Ala Lys Ala Ala Ala Lys Ala
            325                 330                 335
Ala Lys Tyr Gly Ala Arg Pro Gly Val Gly Val Gly Gly Ile Pro Thr
        340                 345                 350
Tyr Gly Val Gly Ala Gly Phe Pro Gly Phe Gly Val Gly Val Gly
        355                 360                 365
Gly Ile Pro Gly Val Ala Gly Val Pro Ser Val Gly Gly Val Pro Gly
        370                 375                 380
Val Gly Gly Val Pro Gly Val Gly Ile Ser Pro Glu Ala Gln Ala Ala
385                 390                 395                 400
Ala Ala Ala Lys Ala Ala Lys Tyr Gly Leu Val Pro Gly Val Gly Val
            405                 410                 415
Ala Pro Gly Val Gly Val Ala Pro Gly Val Gly Val Ala Pro Gly Val
        420                 425                 430
Gly Leu Ala Pro Gly Val Gly Val Ala Pro Gly Val Gly Val Ala Pro
        435                 440                 445
Gly Val Gly Val Ala Pro Gly Ile Gly Pro Gly Gly Val Ala Ala Ala
        450                 455                 460
Ala Lys Ser Ala Ala Lys Val Ala Ala Lys Ala Gln Leu Arg Ala Ala
465                 470                 475                 480
Ala Gly Leu Gly Ala Gly Ile Pro Gly Leu Gly Val Gly Val Gly Val
            485                 490                 495
Pro Gly Leu Gly Val Gly Ala Gly Val Pro Gly Leu Gly Val Gly Ala
        500                 505                 510
Gly Val Pro Gly Phe Gly Ala Val Pro Gly Ala Leu Ala Ala Ala Lys
        515                 520                 525
Ala Ala Lys Tyr Gly Ala Ala Val Pro Gly Val Leu Gly Gly Leu Gly
        530                 535                 540
Ala Leu Gly Gly Val Gly Ile Pro Gly Gly Val Val Gly Ala Gly Pro
545                 550                 555                 560
Ala Ala Ala Ala Ala Ala Lys Ala Ala Lys Ala Ala Gln Phe
            565                 570                 575
Gly Leu Val Gly Ala Ala Gly Leu Gly Gly Leu Gly Val Gly Gly Leu
        580                 585                 590
Gly Val Pro Gly Val Gly Gly Leu Gly Gly Ile Pro Pro Ala Ala Ala
        595                 600                 605
```

Ala Lys Ala Ala Lys Tyr Gly Val Ala Arg Pro Gly Phe Gly Leu
            610                 615                 620

Ser Pro Ile Phe Pro Gly Gly Ala Cys Leu Gly Lys Ala Cys Gly Arg
625                 630                 635                 640

Lys Arg Lys

<210> SEQ ID NO 36
<211> LENGTH: 688
<212> TYPE: PRT
<213> ORGANISM: Homo sapiens

<400> SEQUENCE: 36

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Val Phe Tyr Pro Gly
            20                  25                  30

Ala Gly Leu Gly Ala Leu Gly Gly Gly Ala Leu Gly Pro Gly Gly Lys
        35                  40                  45

Pro Leu Lys Pro Val Pro Gly Gly Leu Ala Gly Ala Gly Leu Gly Ala
50                  55                  60

Gly Leu Gly Ala Phe Pro Ala Val Thr Phe Pro Gly Ala Leu Val Pro
65                  70                  75                  80

Gly Gly Val Ala Asp Ala Ala Ala Tyr Lys Ala Ala Lys Ala Gly
                85                  90                  95

Ala Gly Leu Gly Gly Val Pro Gly Val Gly Gly Leu Gly Val Ser Ala
            100                 105                 110

Gly Ala Val Val Pro Gln Pro Gly Ala Gly Val Lys Pro Gly Lys Val
        115                 120                 125

Pro Gly Val Gly Leu Pro Gly Val Tyr Pro Gly Gly Val Leu Pro Gly
130                 135                 140

Ala Arg Phe Pro Gly Val Gly Val Leu Pro Gly Val Pro Thr Gly Ala
145                 150                 155                 160

Gly Val Lys Pro Lys Ala Pro Gly Val Gly Gly Ala Phe Ala Gly Ile
                165                 170                 175

Pro Gly Val Gly Pro Phe Gly Gly Pro Gln Pro Gly Val Pro Leu Gly
            180                 185                 190

Tyr Pro Ile Lys Ala Pro Lys Leu Pro Gly Gly Tyr Gly Leu Pro Tyr
        195                 200                 205

Thr Thr Gly Lys Leu Pro Tyr Gly Tyr Gly Pro Gly Gly Val Ala Gly
210                 215                 220

Ala Ala Gly Lys Ala Gly Tyr Pro Thr Gly Thr Gly Val Gly Pro Gln
225                 230                 235                 240

Ala Ala Ala Ala Ala Ala Lys Ala Ala Lys Phe Gly Ala Gly
                245                 250                 255

Ala Ala Gly Val Leu Pro Gly Val Gly Gly Ala Gly Val Pro Gly Val
            260                 265                 270

Pro Gly Ala Ile Pro Gly Ile Gly Gly Ile Ala Ala Ala Ala Ala
        275                 280                 285

Ala Ala Ala Ala Lys Ala Ala Lys Tyr Gly Ala Ala Ala Gly Leu
290                 295                 300

Val Pro Gly Gly Pro Gly Phe Gly Pro Gly Val Val Gly Val Pro Gly
305                 310                 315                 320

Ala Gly Val Pro Gly Val Gly Val Pro Gly Ala Gly Ile Pro Val Val
                325                 330                 335

-continued

```
Pro Gly Ala Gly Ile Pro Gly Ala Ala Val Pro Gly Val Val Ser Pro
            340                 345                 350

Glu Ala Ala Ala Lys Ala Ala Ala Lys Ala Ala Lys Tyr Gly Ala Arg
        355                 360                 365

Pro Gly Val Gly Val Gly Gly Ile Pro Thr Tyr Gly Val Gly Ala Gly
    370                 375                 380

Gly Phe Pro Gly Phe Gly Val Gly Val Gly Gly Ile Pro Gly Val Ala
385                 390                 395                 400

Gly Val Pro Gly Val Gly Gly Val Pro Gly Val Gly Gly Val Pro Gly
                405                 410                 415

Val Gly Ile Ser Pro Glu Ala Gln Ala Ala Ala Ala Lys Ala Ala
            420                 425                 430

Lys Tyr Gly Val Gly Thr Pro Ala Ala Ala Ala Lys Ala Ala Ala
        435                 440                 445

Lys Ala Ala Gln Phe Gly Leu Val Pro Gly Val Gly Val Ala Pro Gly
    450                 455                 460

Val Gly Val Ala Pro Gly Val Gly Val Ala Pro Gly Val Gly Leu Ala
465                 470                 475                 480

Pro Gly Val Gly Val Ala Pro Gly Val Gly Val Ala Pro Gly Val Gly
                485                 490                 495

Val Ala Pro Gly Ile Gly Pro Gly Gly Val Ala Ala Ala Ala Lys Ser
            500                 505                 510

Ala Ala Lys Val Ala Ala Lys Ala Gln Leu Arg Ala Ala Ala Gly Leu
        515                 520                 525

Gly Ala Gly Ile Pro Gly Leu Gly Val Gly Val Gly Val Pro Gly Leu
    530                 535                 540

Gly Val Gly Ala Gly Val Pro Gly Leu Gly Val Gly Ala Gly Val Pro
545                 550                 555                 560

Gly Phe Gly Ala Val Pro Gly Ala Leu Ala Ala Ala Lys Ala Ala Lys
                565                 570                 575

Tyr Gly Ala Ala Val Pro Gly Val Leu Gly Gly Leu Gly Ala Leu Gly
            580                 585                 590

Gly Val Gly Ile Pro Gly Gly Val Val Gly Ala Gly Pro Ala Ala Ala
        595                 600                 605

Ala Ala Ala Ala Lys Ala Ala Lys Ala Ala Gln Phe Gly Leu Val
    610                 615                 620

Gly Ala Ala Gly Leu Gly Gly Leu Gly Val Gly Gly Leu Gly Val Pro
625                 630                 635                 640

Gly Val Gly Gly Leu Gly Gly Ile Pro Pro Ala Ala Ala Ala Lys Ala
                645                 650                 655

Ala Lys Tyr Gly Val Ala Ala Arg Pro Gly Phe Gly Leu Ser Pro Ile
            660                 665                 670

Phe Pro Gly Gly Ala Cys Leu Gly Lys Ala Cys Gly Arg Lys Arg Lys
        675                 680                 685

<210> SEQ ID NO 37
<211> LENGTH: 687
<212> TYPE: PRT
<213> ORGANISM: Homo sapiens

<400> SEQUENCE: 37

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
```

```
                 20                  25                  30
Ile Pro Gly Gly Val Pro Gly Val Phe Tyr Pro Gly Ala Gly Leu
             35                  40                  45
Gly Ala Leu Gly Gly Ala Leu Gly Pro Gly Lys Pro Leu Lys
         50                  55                  60
Pro Val Pro Gly Gly Leu Ala Gly Ala Gly Leu Ala Gly Leu Gly
 65                  70                  75                  80
Ala Phe Pro Ala Val Thr Phe Pro Gly Ala Leu Val Pro Gly Val
                 85                  90                  95
Ala Asp Ala Ala Ala Tyr Lys Ala Ala Lys Ala Gly Ala Gly Leu
                100                 105                 110
Gly Gly Val Pro Gly Val Gly Leu Gly Val Ser Ala Gly Ala Val
            115                 120                 125
Val Pro Gln Pro Gly Ala Gly Val Lys Pro Gly Lys Val Pro Gly Val
            130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
            180                 185                 190
Gly Pro Phe Gly Gly Pro Gln Pro Gly Val Pro Leu Gly Tyr Pro Ile
            195                 200                 205
Lys Ala Pro Lys Leu Pro Gly Gly Tyr Gly Leu Pro Tyr Thr Thr Gly
        210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
            245                 250                 255
Ala Ala Ala Ala Lys Ala Ala Ala Lys Phe Gly Ala Gly Ala Ala Gly
            260                 265                 270
Val Leu Pro Gly Val Gly Gly Ala Gly Val Pro Gly Val Pro Gly Ala
        275                 280                 285
Ile Pro Gly Ile Gly Gly Ile Ala Gly Val Gly Thr Pro Ala Ala Ala
        290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
        355                 360                 365
Ser Pro Glu Ala Ala Ala Lys Ala Ala Ala Lys Ala Ala Lys Tyr Gly
        370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Gly Val Gly Val Pro Gly Val Gly Gly Val
        420                 425                 430
Pro Gly Val Gly Ile Ser Pro Glu Ala Gln Ala Ala Ala Ala Ala Lys
        435                 440                 445
```

```
Ala Ala Lys Tyr Gly Leu Val Pro Gly Val Gly Val Ala Pro Gly Val
        450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
                485                 490                 495

Ala Pro Gly Ile Gly Pro Gly Val Ala Ala Ala Lys Ser Ala
                500                 505                 510

Ala Lys Val Ala Ala Lys Ala Gln Leu Arg Ala Ala Gly Leu Gly
        515                 520                 525

Ala Gly Ile Pro Gly Leu Gly Val Gly Val Gly Val Pro Gly Leu Gly
        530                 535                 540

Val Gly Ala Gly Val Pro Gly Leu Gly Val Gly Ala Gly Val Pro Gly
545                 550                 555                 560

Phe Gly Ala Val Pro Gly Ala Leu Ala Ala Ala Lys Ala Ala Lys Tyr
                565                 570                 575

Gly Ala Ala Val Pro Gly Val Leu Gly Gly Leu Gly Ala Leu Gly Gly
                580                 585                 590

Val Gly Ile Pro Gly Gly Val Val Gly Ala Gly Pro Ala Ala Ala Ala
        595                 600                 605

Ala Ala Ala Lys Ala Ala Ala Lys Ala Ala Gln Phe Gly Leu Val Gly
        610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Pro Ala Ala Ala Lys Ala Ala
                645                 650                 655

Lys Tyr Gly Val Ala Ala Arg Pro Gly Phe Gly Leu Ser Pro Ile Phe
        660                 665                 670

Pro Gly Gly Ala Cys Leu Gly Lys Ala Cys Gly Arg Lys Arg Lys
                675                 680                 685

<210> SEQ ID NO 38
<211> LENGTH: 705
<212> TYPE: PRT
<213> ORGANISM: Homo sapiens

<400> SEQUENCE: 38

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
```

```
                130             135             140
Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
            195                 200                 205

Lys Ala Pro Lys Leu Pro Gly Gly Tyr Gly Leu Pro Tyr Thr Thr Gly
210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Ala Gly
                260                 265                 270

Val Leu Pro Gly Val Gly Gly Ala Gly Val Pro Gly Val Pro Gly Ala
                275                 280                 285

Ile Pro Gly Ile Gly Gly Ile Ala Gly Val Gly Thr Pro Ala Ala Ala
                290                 295                 300

Ala Ala Ala Ala Ala Ala Ala Lys Ala Ala Lys Tyr Gly Ala Ala Ala
305                 310                 315                 320

Gly Leu Val Pro Gly Gly Pro Gly Phe Gly Pro Gly Val Val Gly Val
                325                 330                 335

Pro Gly Ala Gly Val Pro Gly Val Gly Val Pro Gly Ala Gly Ile Pro
                340                 345                 350

Val Val Pro Gly Ala Gly Ile Pro Gly Ala Ala Val Pro Gly Val Val
                355                 360                 365

Ser Pro Glu Ala Ala Ala Lys Ala Ala Lys Ala Ala Lys Tyr Gly
            370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Gly Val Gly Val Pro Gly Val Gly Gly Val
                420                 425                 430

Pro Gly Val Gly Ile Ser Pro Glu Ala Gln Ala Ala Ala Ala Ala Lys
                435                 440                 445

Ala Ala Lys Tyr Gly Leu Val Pro Gly Val Gly Val Ala Pro Gly Val
450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
                485                 490                 495

Ala Pro Gly Ile Gly Pro Gly Gly Val Ala Ala Ala Lys Ser Ala
                500                 505                 510

Ala Lys Val Ala Ala Lys Ala Gln Leu Arg Ala Ala Ala Gly Leu Gly
            515                 520                 525

Ala Gly Ile Pro Gly Leu Gly Val Gly Val Gly Val Pro Gly Leu Gly
            530                 535                 540

Val Gly Ala Gly Val Pro Gly Leu Gly Val Gly Ala Gly Val Pro Gly
545                 550                 555                 560
```

-continued

```
Phe Gly Ala Val Pro Gly Ala Leu Ala Ala Lys Ala Ala Lys Tyr
            565                 570                 575

Gly Ala Ala Val Pro Gly Val Leu Gly Gly Leu Gly Ala Leu Gly Gly
            580                 585                 590

Val Gly Ile Pro Gly Gly Val Val Gly Ala Gly Pro Ala Ala Ala Ala
            595                 600                 605

Ala Ala Ala Lys Ala Ala Lys Ala Ala Gln Phe Gly Leu Val Gly
            610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Pro Ala Ala Ala Lys Ala Ala
            645                 650                 655

Lys Tyr Gly Ala Ala Gly Leu Gly Gly Val Leu Gly Ala Gly Gln
            660                 665                 670

Phe Pro Leu Gly Gly Val Ala Ala Arg Pro Gly Phe Gly Leu Ser Pro
            675                 680                 685

Ile Phe Pro Gly Gly Ala Cys Leu Gly Lys Ala Cys Gly Arg Lys Arg
            690                 695                 700

Lys
705

<210> SEQ ID NO 39
<211> LENGTH: 729
<212> TYPE: PRT
<213> ORGANISM: Homo sapiens

<400> SEQUENCE: 39

Met Ala Gly Leu Thr Ala Ala Pro Arg Pro Gly Val Leu Leu Leu
 1               5                  10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
            85                  90                  95

Ala Asp Ala Ala Ala Ala Tyr Lys Ala Ala Lys Ala Gly Ala Gly Leu
            100                 105                 110

Gly Gly Val Pro Gly Val Gly Gly Leu Gly Val Ser Ala Ala Pro Ser
            115                 120                 125

Val Pro Gly Ala Val Val Pro Gln Pro Ala Ala Gly Val Lys Pro Val
130                 135                 140

Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
            165                 170                 175

Gly Ala Gly Val Lys Pro Lys Ala Pro Gly Val Gly Gly Ala Phe Ala
            180                 185                 190

Gly Ile Pro Gly Val Gly Pro Phe Gly Gly Pro Gln Pro Gly Val Pro
            195                 200                 205

Leu Gly Tyr Pro Ile Lys Ala Pro Lys Leu Pro Gly Gly Tyr Gly Leu
```

```
               210                 215                 220
Pro Tyr Thr Gly Lys Leu Pro Gly Tyr Gly Pro Gly Gly Val
225                 230                 235                 240

Ala Gly Ala Ala Gly Lys Ala Gly Tyr Pro Thr Gly Thr Val Gly
                245                 250                 255

Pro Gln Ala Ala Ala Ala Ala Ala Lys Ala Ala Lys Phe Gly
                260                 265                 270

Ala Gly Ala Ala Gly Val Leu Pro Gly Val Gly Ala Gly Val Pro
                275                 280                 285

Gly Val Pro Gly Ala Ile Pro Gly Ile Gly Gly Ile Ala Gly Val Gly
        290                 295                 300

Thr Pro Ala Ala Ala Ala Ala Ala Ala Ala Lys Ala Ala Lys
305                 310                 315                 320

Tyr Gly Ala Ala Ala Gly Leu Val Pro Gly Pro Gly Phe Gly Pro
                325                 330                 335

Gly Val Val Gly Val Pro Gly Ala Gly Val Pro Gly Val Gly Val Pro
                340                 345                 350

Gly Ala Gly Ile Pro Val Val Pro Gly Ala Gly Ile Pro Gly Ala Ala
                355                 360                 365

Val Pro Gly Val Val Ser Pro Glu Ala Ala Lys Ala Ala Lys
        370                 375                 380

Ala Ala Lys Tyr Gly Ala Arg Pro Gly Val Gly Val Gly Gly Ile Pro
385                 390                 395                 400

Thr Tyr Gly Val Gly Ala Gly Gly Phe Pro Gly Phe Gly Val Gly Val
                405                 410                 415

Gly Gly Ile Pro Gly Val Ala Gly Val Pro Gly Val Gly Gly Val Pro
                420                 425                 430

Gly Val Gly Gly Val Pro Gly Val Gly Ile Ser Pro Glu Ala Gln Ala
                435                 440                 445

Ala Ala Ala Ala Lys Ala Ala Lys Tyr Gly Val Gly Thr Pro Ala Ala
                450                 455                 460

Ala Ala Ala Lys Ala Ala Ala Lys Ala Ala Gln Phe Gly Leu Val Pro
465                 470                 475                 480

Gly Val Gly Val Ala Pro Gly Val Gly Val Ala Pro Gly Val Gly Val
                485                 490                 495

Ala Pro Gly Val Gly Leu Ala Pro Gly Val Gly Val Ala Pro Gly Val
                500                 505                 510

Gly Val Ala Pro Gly Val Gly Val Ala Pro Gly Ile Gly Pro Gly Gly
                515                 520                 525

Val Ala Ala Ala Ala Lys Ser Ala Ala Lys Val Ala Ala Lys Ala Gln
530                 535                 540

Leu Arg Ala Ala Ala Gly Leu Gly Ala Gly Ile Pro Gly Leu Gly Val
545                 550                 555                 560

Gly Val Gly Val Pro Gly Leu Gly Val Gly Ala Gly Val Pro Gly Leu
                565                 570                 575

Gly Val Gly Ala Gly Val Pro Gly Phe Gly Ala Val Pro Gly Ala Leu
                580                 585                 590

Ala Ala Ala Lys Ala Ala Lys Tyr Gly Ala Ala Val Pro Gly Val Leu
                595                 600                 605

Gly Gly Leu Gly Ala Leu Gly Gly Val Gly Ile Pro Gly Gly Val Val
                610                 615                 620

Gly Ala Gly Pro Ala Ala Ala Ala Ala Ala Lys Ala Ala Ala Lys
625                 630                 635                 640
```

```
Ala Ala Gln Phe Gly Leu Val Gly Ala Gly Leu Gly Gly Leu Gly
                645                 650                 655

Val Gly Gly Leu Gly Val Pro Gly Val Gly Leu Gly Gly Ile Pro
            660                 665                 670

Pro Ala Ala Ala Ala Lys Ala Ala Lys Tyr Gly Ala Ala Gly Leu Gly
        675                 680                 685

Gly Val Leu Gly Gly Ala Gly Gln Phe Pro Leu Gly Gly Val Ala Ala
        690                 695                 700

Arg Pro Gly Phe Gly Leu Ser Pro Ile Phe Pro Gly Gly Ala Cys Leu
705             710                 715                 720

Gly Lys Ala Cys Gly Arg Lys Arg Lys
                725

<210> SEQ ID NO 40
<211> LENGTH: 661
<212> TYPE: PRT
<213> ORGANISM: Homo sapiens

<400> SEQUENCE: 40

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
        35                  40                  45

Gly Ala Leu Gly Gly Gly Ala Leu Gly Pro Gly Gly Lys Pro Leu Lys
    50                  55                  60

Pro Gly Leu Gly Ala Phe Pro Ala Val Thr Phe Pro Gly Ala Leu Val
65              70                  75                  80

Pro Gly Gly Val Ala Asp Ala Ala Ala Tyr Lys Ala Ala Lys Ala
            85                  90                  95

Gly Ala Gly Leu Gly Gly Val Pro Gly Val Gly Leu Gly Val Ser
        100                 105                 110

Ala Gly Ala Val Val Pro Gln Pro Gly Ala Gly Val Lys Pro Gly Lys
        115                 120                 125

Val Pro Gly Val Gly Leu Pro Gly Val Tyr Pro Gly Gly Val Leu Pro
130                 135                 140

Gly Ala Arg Phe Pro Gly Val Gly Val Leu Pro Gly Val Pro Thr Gly
145                 150                 155                 160

Ala Gly Val Lys Pro Lys Ala Pro Gly Val Gly Gly Ala Phe Ala Gly
                165                 170                 175

Ile Pro Gly Val Gly Pro Phe Gly Gly Pro Gln Pro Gly Val Pro Leu
            180                 185                 190

Gly Tyr Pro Ile Lys Ala Pro Lys Leu Pro Gly Tyr Gly Pro Gly Gly
        195                 200                 205

Val Ala Gly Ala Ala Gly Lys Ala Gly Tyr Pro Thr Gly Thr Gly Val
    210                 215                 220

Gly Pro Gln Ala Ala Ala Ala Ala Ala Lys Ala Ala Lys Phe
225                 230                 235                 240

Gly Ala Gly Ala Ala Gly Val Leu Pro Gly Val Gly Gly Ala Gly Val
                245                 250                 255

Pro Gly Val Pro Gly Ala Ile Pro Gly Ile Gly Gly Ile Ala Gly Val
            260                 265                 270

Gly Thr Pro Ala Ala Ala Ala Ala Ala Ala Ala Ala Ala Lys Ala Ala
```

```
            275                 280                 285
Lys Tyr Gly Ala Ala Gly Leu Val Pro Gly Pro Gly Phe Gly
            290                 295                 300
Pro Gly Val Val Gly Val Pro Gly Ala Gly Val Pro Gly Val Gly Val
305                 310                 315                 320
Pro Gly Ala Gly Ile Pro Val Val Pro Gly Ala Gly Ile Pro Gly Ala
                    325                 330                 335
Ala Val Pro Gly Val Val Ser Pro Glu Ala Ala Lys Ala Ala Ala
                340                 345                 350
Lys Ala Ala Lys Tyr Gly Ala Arg Pro Gly Val Gly Val Gly Gly Ile
                355                 360                 365
Pro Thr Tyr Gly Val Gly Ala Gly Gly Phe Pro Gly Phe Gly Val Gly
    370                 375                 380
Val Gly Gly Ile Pro Gly Val Ala Gly Val Pro Gly Val Gly Gly Val
385                 390                 395                 400
Pro Gly Val Gly Gly Val Pro Gly Val Gly Ile Ser Pro Glu Ala Gln
                    405                 410                 415
Ala Ala Ala Ala Ala Lys Ala Ala Lys Tyr Gly Leu Val Pro Gly Val
                420                 425                 430
Gly Val Ala Pro Gly Val Gly Val Ala Pro Gly Val Gly Val Ala Pro
                435                 440                 445
Gly Val Gly Leu Ala Pro Gly Val Gly Val Ala Pro Gly Val Gly Val
        450                 455                 460
Ala Pro Gly Val Gly Val Ala Pro Gly Ile Gly Pro Gly Gly Val Ala
465                 470                 475                 480
Ala Ala Ala Lys Ser Ala Ala Lys Val Ala Ala Lys Ala Gln Leu Arg
                    485                 490                 495
Ala Ala Ala Gly Leu Gly Ala Gly Ile Pro Gly Leu Gly Val Gly Val
                500                 505                 510
Gly Val Pro Gly Leu Gly Val Gly Ala Gly Val Pro Gly Leu Gly Val
                515                 520                 525
Gly Ala Gly Val Pro Gly Phe Gly Ala Val Pro Gly Ala Leu Ala Ala
        530                 535                 540
Ala Lys Ala Ala Lys Tyr Gly Ala Ala Val Pro Gly Val Leu Gly Gly
545                 550                 555                 560
Leu Gly Ala Leu Gly Gly Val Gly Ile Pro Gly Gly Val Val Gly Ala
                    565                 570                 575
Gly Pro Ala Ala Ala Ala Ala Ala Lys Ala Ala Ala Lys Ala Ala
                580                 585                 590
Gln Phe Gly Leu Val Gly Ala Ala Gly Leu Gly Gly Leu Gly Val Gly
        595                 600                 605
Gly Leu Gly Val Pro Gly Val Gly Gly Leu Gly Ile Pro Pro Ala
    610                 615                 620
Ala Ala Ala Lys Ala Ala Lys Tyr Gly Val Ala Ala Arg Pro Gly Phe
625                 630                 635                 640
Gly Leu Ser Pro Ile Phe Pro Gly Gly Ala Cys Leu Gly Lys Ala Cys
                    645                 650                 655
Gly Arg Lys Arg Lys
            660

<210> SEQ ID NO 41
<211> LENGTH: 714
<212> TYPE: PRT
<213> ORGANISM: Homo sapiens
```

<400> SEQUENCE: 41

```
Met Ala Gly Leu Thr Ala Ala Pro Arg Pro Gly Val Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Lys Pro Leu Lys
    50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Pro Phe Gly Gly Pro Gln Pro Gly Val
            180                 185                 190

Pro Leu Gly Tyr Pro Ile Lys Ala Pro Lys Leu Pro Gly Gly Tyr Gly
        195                 200                 205

Leu Pro Tyr Thr Thr Gly Lys Leu Pro Tyr Gly Tyr Gly Pro Gly Gly
    210                 215                 220

Val Ala Gly Ala Ala Gly Lys Ala Gly Tyr Pro Thr Gly Thr Gly Val
225                 230                 235                 240

Gly Pro Gln Ala Ala Ala Ala Ala Ala Lys Ala Ala Ala Lys Phe
                245                 250                 255

Gly Ala Gly Ala Ala Gly Val Leu Pro Gly Val Gly Gly Ala Gly Val
            260                 265                 270

Pro Gly Val Pro Gly Ala Ile Pro Gly Ile Gly Gly Ile Ala Gly Val
        275                 280                 285

Gly Thr Pro Ala Ala Ala Ala Ala Ala Ala Ala Lys Ala Ala
    290                 295                 300

Lys Tyr Gly Ala Ala Gly Leu Val Pro Gly Gly Pro Gly Phe Gly
305                 310                 315                 320

Pro Gly Val Val Gly Val Pro Gly Ala Gly Val Pro Gly Val Gly Val
            325                 330                 335

Pro Gly Ala Gly Ile Pro Val Val Pro Gly Ala Gly Ile Pro Gly Ala
            340                 345                 350

Ala Val Pro Gly Val Val Ser Pro Glu Ala Ala Lys Ala Ala Ala
            355                 360                 365

Lys Ala Ala Lys Tyr Gly Ala Arg Pro Gly Val Gly Val Gly Gly Ile
        370                 375                 380

Pro Thr Tyr Gly Val Gly Ala Gly Gly Phe Pro Gly Phe Gly Val Gly
385                 390                 395                 400

Val Gly Gly Ile Pro Gly Val Ala Gly Val Pro Gly Val Gly Gly Val
```

```
                405                 410                 415
Pro Gly Val Gly Gly Val Pro Val Gly Ile Ser Pro Glu Ala Gln
                420                 425                 430

Ala Ala Ala Ala Ala Lys Ala Ala Lys Tyr Gly Val Gly Thr Pro Ala
                435                 440                 445

Ala Ala Ala Ala Lys Ala Ala Lys Ala Ala Gln Phe Gly Leu Val
    450                 455                 460

Pro Gly Val Gly Val Ala Pro Gly Val Gly Val Ala Pro Gly Val Gly
465                 470                 475                 480

Val Ala Pro Gly Val Gly Leu Ala Pro Gly Val Gly Val Ala Pro Gly
                485                 490                 495

Val Gly Val Ala Pro Gly Val Gly Val Ala Pro Gly Ile Gly Pro Gly
                500                 505                 510

Gly Val Ala Ala Ala Lys Ser Ala Ala Lys Val Ala Ala Lys Ala
    515                 520                 525

Gln Leu Arg Ala Ala Gly Leu Gly Ala Gly Ile Pro Gly Leu Gly
    530                 535                 540

Val Gly Val Gly Val Pro Gly Leu Gly Val Gly Ala Gly Val Pro Gly
545                 550                 555                 560

Leu Gly Val Gly Ala Gly Val Pro Gly Phe Gly Ala Val Pro Gly Ala
                565                 570                 575

Leu Ala Ala Ala Lys Ala Ala Lys Tyr Gly Ala Ala Val Pro Gly Val
            580                 585                 590

Leu Gly Gly Leu Gly Ala Leu Gly Gly Val Gly Ile Pro Gly Gly Val
            595                 600                 605

Val Gly Ala Gly Pro Ala Ala Ala Ala Ala Ala Lys Ala Ala Ala
    610                 615                 620

Lys Ala Ala Gln Phe Gly Leu Val Gly Ala Ala Gly Leu Gly Gly Leu
625                 630                 635                 640

Gly Val Gly Gly Leu Gly Val Pro Gly Val Gly Gly Leu Gly Gly Ile
                645                 650                 655

Pro Pro Ala Ala Ala Ala Lys Ala Ala Lys Tyr Gly Ala Ala Gly Leu
                660                 665                 670

Gly Gly Val Leu Gly Gly Ala Gly Gln Phe Pro Leu Gly Gly Val Ala
            675                 680                 685

Ala Arg Pro Gly Phe Gly Leu Ser Pro Ile Phe Pro Gly Gly Ala Cys
            690                 695                 700

Leu Gly Lys Ala Cys Gly Arg Lys Arg Lys
705                 710

<210> SEQ ID NO 42
<211> LENGTH: 714
<212> TYPE: PRT
<213> ORGANISM: Homo sapiens

<400> SEQUENCE: 42

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Gly Lys Pro Leu Lys
        50                  55                  60
```

-continued

```
Pro Val Pro Gly Gly Leu Ala Gly Ala Gly Leu Ala Gly Leu Gly
 65                  70                  75                  80
Ala Phe Pro Ala Val Thr Phe Pro Gly Ala Leu Val Pro Gly Gly Val
                 85                  90                  95
Ala Asp Ala Ala Ala Ala Tyr Lys Ala Ala Lys Ala Gly Ala Gly Leu
                100                 105                 110
Gly Gly Val Pro Gly Val Gly Gly Leu Gly Val Ser Ala Gly Ala Val
            115                 120                 125
Val Pro Gln Pro Gly Ala Gly Val Lys Pro Gly Lys Val Pro Gly Val
    130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
            180                 185                 190
Gly Pro Phe Gly Gly Pro Gln Pro Gly Val Pro Leu Gly Tyr Pro Ile
            195                 200                 205
Lys Ala Pro Lys Leu Pro Gly Gly Tyr Gly Leu Pro Tyr Thr Thr Gly
    210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Lys Phe Gly Ala Gly Ala Ala Gly
            260                 265                 270
Val Leu Pro Gly Val Gly Gly Ala Gly Val Pro Gly Val Pro Gly Ala
    275                 280                 285
Ile Pro Gly Ile Gly Gly Ile Ala Val Gly Thr Pro Ala Ala Ala
            290                 295                 300
Ala Ala Ala Ala Ala Ala Ala Lys Ala Ala Lys Tyr Gly Ala Ala Ala
305                 310                 315                 320
Gly Leu Val Pro Gly Gly Pro Gly Phe Gly Pro Gly Val Val Gly Val
                325                 330                 335
Pro Gly Ala Gly Val Pro Gly Val Gly Val Pro Gly Ala Gly Ile Pro
            340                 345                 350
Val Val Pro Gly Ala Gly Ile Pro Gly Ala Ala Val Pro Gly Val Val
    355                 360                 365
Ser Pro Glu Ala Ala Ala Lys Ala Ala Ala Lys Ala Ala Lys Tyr Gly
    370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Gly Val Gly Val Pro Gly Val Gly Pro Glu
            420                 425                 430
Ala Gln Ala Ala Ala Ala Lys Ala Ala Lys Tyr Gly Val Gly Thr
    435                 440                 445
Pro Ala Ala Ala Ala Lys Ala Ala Lys Ala Ala Gln Phe Gly
    450                 455                 460
Leu Val Pro Gly Val Gly Val Ala Pro Gly Val Gly Val Ala Pro Gly
465                 470                 475                 480
Val Gly Val Ala Pro Gly Val Gly Leu Ala Pro Gly Val Gly Val Ala
```

```
                        485                 490                 495
Pro Gly Val Gly Val Ala Pro Gly Val Gly Val Ala Pro Gly Ile Gly
                    500                 505                 510

Pro Gly Gly Val Ala Ala Ala Lys Ser Ala Ala Lys Val Ala Ala
                515                 520                 525

Lys Ala Gln Leu Arg Ala Ala Gly Leu Gly Ala Gly Ile Pro Gly
            530                 535                 540

Leu Gly Val Gly Val Gly Val Pro Gly Leu Gly Val Gly Ala Gly Val
545                 550                 555                 560

Pro Gly Leu Gly Val Gly Ala Gly Val Pro Gly Phe Gly Ala Val Pro
                565                 570                 575

Gly Ala Leu Ala Ala Ala Lys Ala Ala Lys Tyr Ala Val Pro Gly Val
                580                 585                 590

Leu Gly Gly Leu Gly Ala Leu Gly Gly Val Gly Ile Pro Gly Gly Val
                595                 600                 605

Val Gly Ala Gly Pro Ala Ala Ala Ala Ala Ala Lys Ala Ala Ala
                610                 615                 620

Lys Ala Ala Gln Phe Gly Leu Val Gly Ala Ala Gly Leu Gly Gly Leu
625                 630                 635                 640

Gly Val Gly Gly Leu Gly Val Pro Gly Val Gly Gly Leu Gly Gly Ile
                    645                 650                 655

Pro Pro Ala Ala Ala Lys Ala Ala Lys Tyr Gly Ala Ala Gly Leu
                660                 665                 670

Gly Gly Val Leu Gly Gly Ala Gly Gln Phe Pro Leu Gly Gly Val Ala
                675                 680                 685

Ala Arg Pro Gly Phe Gly Leu Ser Pro Ile Phe Pro Gly Gly Ala Cys
                690                 695                 700

Leu Gly Lys Ala Cys Gly Arg Lys Arg Lys
705                 710

<210> SEQ ID NO 43
<211> LENGTH: 721
<212> TYPE: PRT
<213> ORGANISM: Homo sapiens

<400> SEQUENCE: 43

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
            35                  40                  45

Gly Ala Leu Gly Gly Gly Ala Leu Gly Pro Gly Gly Lys Pro Leu Lys
        50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Ala Pro Ser
            115                 120                 125

Val Pro Gly Ala Val Val Pro Gln Pro Gly Ala Gly Val Lys Pro Gly
        130                 135                 140
```

-continued

```
Lys Val Pro Gly Val Gly Leu Pro Gly Val Tyr Pro Gly Gly Val Leu
145                 150                 155                 160

Pro Gly Ala Arg Phe Pro Gly Val Gly Val Leu Pro Gly Val Pro Thr
            165                 170                 175

Gly Ala Gly Val Lys Pro Lys Ala Pro Gly Val Gly Gly Ala Phe Ala
        180                 185                 190

Gly Ile Pro Gly Val Gly Pro Phe Gly Gly Pro Gln Pro Gly Val Pro
    195                 200                 205

Leu Gly Tyr Pro Ile Lys Ala Pro Lys Leu Pro Gly Gly Tyr Gly Leu
        210                 215                 220

Pro Tyr Thr Thr Gly Lys Leu Pro Tyr Gly Tyr Gly Pro Gly Gly Val
225                 230                 235                 240

Ala Gly Ala Ala Gly Lys Ala Gly Tyr Pro Thr Gly Thr Gly Val Gly
            245                 250                 255

Pro Gln Ala Ala Ala Ala Ala Ala Lys Ala Ala Ala Lys Phe Gly
        260                 265                 270

Ala Gly Ala Ala Gly Val Leu Pro Gly Val Gly Ala Gly Val Pro
        275                 280                 285

Gly Val Pro Gly Ala Ile Pro Gly Ile Gly Gly Ile Ala Gly Val Gly
290                 295                 300

Thr Pro Ala Ala Ala Ala Ala Ala Ala Ala Lys Ala Ala Lys
305                 310                 315                 320

Tyr Gly Ala Ala Gly Leu Val Pro Gly Pro Gly Phe Gly Pro
            325                 330                 335

Gly Val Val Gly Val Pro Gly Ala Gly Val Pro Gly Val Gly Val Pro
        340                 345                 350

Gly Ala Gly Ile Pro Val Val Pro Gly Ala Gly Ile Pro Gly Ala Ala
        355                 360                 365

Val Pro Gly Val Val Ser Pro Glu Ala Ala Lys Ala Ala Ala Lys
        370                 375                 380

Ala Ala Lys Tyr Gly Ala Arg Pro Gly Val Gly Val Gly Ile Pro
385                 390                 395                 400

Thr Tyr Gly Val Gly Ala Gly Phe Pro Gly Phe Gly Val Gly Val
            405                 410                 415

Gly Gly Ile Pro Gly Val Ala Gly Val Pro Gly Val Gly Gly Val Pro
        420                 425                 430

Gly Val Gly Pro Glu Ala Gln Ala Ala Ala Ala Lys Ala Ala Lys
            435                 440                 445

Tyr Gly Val Gly Thr Pro Ala Ala Ala Ala Lys Ala Ala Ala Lys
450                 455                 460

Ala Ala Gln Phe Gly Leu Val Pro Gly Val Gly Val Ala Pro Gly Val
465                 470                 475                 480

Gly Val Ala Pro Gly Val Gly Val Ala Pro Gly Val Gly Leu Ala Pro
            485                 490                 495

Gly Val Gly Val Ala Pro Gly Val Gly Val Ala Pro Gly Val Gly Val
        500                 505                 510

Ala Pro Gly Ile Gly Pro Gly Gly Val Ala Ala Ala Lys Ser Ala
            515                 520                 525

Ala Lys Val Ala Ala Lys Ala Gln Leu Arg Ala Ala Gly Leu Gly
        530                 535                 540

Ala Gly Ile Pro Gly Leu Gly Val Gly Val Pro Gly Leu Gly
545                 550                 555                 560

Val Gly Ala Gly Val Pro Gly Leu Gly Val Gly Ala Gly Val Pro Gly
```

-continued

```
                    565                 570                 575

Phe Gly Ala Val Pro Gly Ala Leu Ala Ala Lys Ala Ala Lys Tyr
            580                 585                 590

Gly Ala Ala Val Pro Gly Val Leu Gly Gly Leu Gly Ala Leu Gly Gly
            595                 600                 605

Val Gly Ile Pro Gly Gly Val Val Gly Ala Gly Pro Ala Ala Ala
            610                 615                 620

Ala Ala Ala Lys Ala Ala Ala Lys Ala Ala Gln Phe Gly Leu Val Gly
625                 630                 635                 640

Ala Ala Gly Leu Gly Gly Leu Gly Val Gly Gly Leu Gly Val Pro Gly
                    645                 650                 655

Val Gly Gly Leu Gly Gly Ile Pro Pro Ala Ala Ala Lys Ala Ala
                    660                 665                 670

Lys Tyr Gly Ala Ala Gly Leu Gly Gly Val Leu Gly Gly Ala Gly Gln
                    675                 680                 685

Phe Pro Leu Gly Gly Val Ala Ala Arg Pro Gly Phe Gly Leu Ser Pro
            690                 695                 700

Ile Phe Pro Gly Gly Ala Cys Leu Gly Lys Ala Cys Gly Arg Lys Arg
705                 710                 715                 720

Lys

<210> SEQ ID NO 44
<211> LENGTH: 662
<212> TYPE: PRT
<213> ORGANISM: Homo sapiens

<400> SEQUENCE: 44

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
            20                  25                  30

Ile Pro Gly Gly Val Pro Gly Gly Val Phe Tyr Pro Ala Leu Gly Pro
            35                  40                  45

Gly Gly Lys Pro Leu Lys Pro Val Pro Gly Gly Leu Ala Gly Ala Gly
        50                  55                  60

Leu Gly Ala Gly Leu Gly Ala Phe Pro Ala Val Thr Phe Pro Gly Ala
65                  70                  75                  80

Leu Val Pro Gly Gly Val Ala Asp Ala Ala Ala Ala Tyr Lys Ala Ala
                    85                  90                  95

Lys Ala Gly Ala Gly Leu Gly Gly Val Pro Gly Val Gly Gly Leu Gly
                100                 105                 110

Val Ser Ala Gly Ala Val Val Pro Gln Pro Gly Ala Gly Val Lys Pro
            115                 120                 125

Gly Lys Val Pro Gly Val Gly Leu Pro Gly Val Tyr Pro Gly Gly Val
        130                 135                 140

Leu Pro Gly Ala Arg Phe Pro Gly Val Gly Val Leu Pro Gly Val Pro
145                 150                 155                 160

Thr Gly Ala Gly Val Lys Pro Lys Ala Pro Gly Val Gly Gly Ala Phe
                    165                 170                 175

Ala Gly Ile Pro Gly Val Gly Pro Phe Gly Gly Pro Gln Pro Gly Val
                180                 185                 190

Pro Leu Gly Tyr Pro Ile Lys Ala Pro Lys Leu Pro Gly Gly Tyr Gly
            195                 200                 205

Leu Pro Tyr Thr Thr Gly Lys Leu Pro Tyr Gly Tyr Gly Pro Gly Gly
```

```
              210                 215                 220
Val Ala Gly Ala Ala Gly Lys Ala Gly Tyr Pro Thr Gly Thr Gly Val
225                 230                 235                 240

Gly Pro Gln Ala Ala Ala Ala Ala Ala Lys Ala Ala Lys Phe
                245                 250                 255

Gly Ala Gly Ala Ala Gly Val Leu Pro Gly Val Gly Ala Gly Val
                260                 265                 270

Pro Gly Val Pro Gly Ala Ile Pro Gly Ile Gly Gly Ile Ala Gly Val
                275                 280                 285

Gly Thr Pro Ala Ala Ala Ala Ala Ala Ala Ala Lys Ala Ala
                290                 295                 300

Lys Tyr Gly Ala Ala Gly Leu Val Pro Gly Pro Gly Phe Gly
305                 310                 315                 320

Pro Gly Val Val Gly Val Pro Gly Ala Gly Val Pro Gly Val Gly Val
                325                 330                 335

Pro Gly Ala Gly Ile Pro Val Val Pro Gly Ala Gly Ile Pro Gly Ala
                340                 345                 350

Ala Val Pro Gly Val Val Ser Pro Glu Ala Ala Lys Ala Ala Ala
                355                 360                 365

Lys Ala Ala Lys Tyr Gly Ala Arg Pro Gly Val Gly Val Gly Gly Ile
                370                 375                 380

Pro Thr Tyr Gly Val Gly Ala Gly Gly Phe Pro Gly Phe Gly Val Gly
385                 390                 395                 400

Val Gly Gly Ile Pro Gly Val Ala Gly Val Pro Gly Val Gly Gly Val
                405                 410                 415

Pro Gly Val Gly Gly Val Pro Gly Val Gly Ile Ser Pro Glu Ala Gln
                420                 425                 430

Ala Ala Ala Ala Lys Ala Ala Lys Tyr Gly Leu Val Pro Gly Val
                435                 440                 445

Gly Val Ala Pro Gly Val Gly Val Ala Pro Gly Val Gly Val Ala Pro
450                 455                 460

Gly Val Gly Leu Ala Pro Gly Val Gly Val Ala Pro Gly Val Gly Val
465                 470                 475                 480

Ala Pro Gly Val Gly Val Ala Pro Gly Ile Pro Gly Gly Val Ala
                485                 490                 495

Arg Ala Ala Ala Gly Leu Gly Ala Gly Ile Pro Gly Leu Gly Val Gly
                500                 505                 510

Val Gly Val Pro Gly Leu Gly Val Gly Ala Gly Val Pro Gly Leu Gly
                515                 520                 525

Val Gly Ala Gly Val Pro Gly Phe Gly Ala Val Pro Gly Ala Leu Ala
                530                 535                 540

Ala Ala Lys Ala Ala Lys Tyr Gly Ala Ala Val Pro Gly Val Leu Gly
545                 550                 555                 560

Gly Leu Gly Ala Leu Gly Gly Val Gly Ile Pro Gly Gly Val Val Gly
                565                 570                 575

Ala Gly Pro Ala Ala Ala Ala Ala Ala Lys Ala Ala Ala Lys Ala
                580                 585                 590

Ala Gln Phe Gly Leu Val Gly Ala Ala Gly Leu Gly Gly Leu Gly Val
                595                 600                 605

Gly Gly Leu Gly Val Pro Gly Val Gly Gly Leu Gly Gly Ile Pro Pro
                610                 615                 620

Ala Ala Ala Ala Lys Ala Ala Lys Tyr Gly Val Ala Ala Arg Pro Gly
625                 630                 635                 640
```

```
Phe Gly Leu Ser Pro Ile Phe Pro Gly Gly Ala Cys Leu Lys Ala
                645                 650                 655
Cys Gly Arg Lys Arg Lys
            660

<210> SEQ ID NO 45
<211> LENGTH: 688
<212> TYPE: PRT
<213> ORGANISM: Homo sapiens

<400> SEQUENCE: 45

Met Ala Gly Leu Thr Ala Ala Pro Arg Pro Gly Val Leu Leu Leu
  1               5                  10                  15

Leu Leu Ser Ile Leu His Pro Ser Arg Pro Gly Gly Val Pro Gly Ala
                 20                  25                  30

Ile Pro Gly Gly Val Pro Gly Gly Val Phe Tyr Pro Gly Ala Gly Leu
                 35                  40                  45

Gly Ala Leu Gly Gly Gly Ala Leu Gly Pro Gly Gly Lys Pro Leu Lys
 50                  55                  60

Pro Val Pro Gly Gly Leu Ala Gly Ala Gly Leu Gly Ala Gly Leu Gly
 65                  70                  75                  80

Ala Phe Pro Ala Val Thr Phe Pro Gly Ala Leu Val Pro Gly Gly Val
                 85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
                115                 120                 125

Val Pro Gln Pro Gly Ala Gly Val Lys Pro Gly Lys Val Pro Gly Val
                130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
                180                 185                 190

Gly Pro Phe Gly Gly Pro Gln Pro Gly Val Pro Leu Gly Tyr Pro Ile
                195                 200                 205

Lys Ala Pro Lys Leu Pro Gly Gly Tyr Gly Leu Pro Tyr Thr Thr Gly
                210                 215                 220

Lys Leu Pro Tyr Gly Tyr Gly Pro Gly Gly Val Ala Gly Ala Ala Gly
225                 230                 235                 240

Lys Ala Gly Tyr Pro Thr Gly Thr Gly Val Gly Pro Gln Ala Ala Ala
                245                 250                 255

Ala Ala Ala Ala Lys Ala Ala Lys Phe Gly Ala Gly Ala Ala Gly
                260                 265                 270

Val Leu Pro Gly Val Gly Gly Ala Gly Val Pro Gly Val Pro Gly Ala
                275                 280                 285

Ile Pro Gly Ile Gly Gly Ile Ala Gly Val Gly Thr Pro Ala Ala Ala
                290                 295                 300

Ala Ala Ala Ala Ala Ala Lys Ala Ala Lys Tyr Gly Ala Ala Ala
305                 310                 315                 320

Gly Leu Val Pro Gly Pro Gly Phe Gly Pro Gly Val Val Gly Val
                325                 330                 335

Pro Gly Ala Gly Val Pro Gly Val Gly Val Pro Gly Ala Gly Ile Pro
```

```
                340                 345                 350
Val Val Pro Gly Ala Gly Ile Pro Gly Ala Val Pro Gly Ala Arg
            355                 360                 365

Pro Gly Val Gly Val Gly Gly Ile Pro Thr Tyr Gly Val Gly Ala Gly
        370                 375                 380

Gly Phe Pro Gly Phe Gly Val Gly Val Gly Ile Pro Gly Val Ala
385                 390                 395                 400

Gly Val Pro Gly Val Gly Val Pro Gly Val Gly Val Pro Gly
            405                 410                 415

Val Gly Ile Ser Pro Glu Ala Gln Ala Ala Ala Ala Lys Ala Ala
            420                 425                 430

Lys Tyr Gly Val Gly Thr Pro Ala Ala Ala Ala Lys Ala Ala Ala
            435                 440                 445

Lys Ala Ala Gln Phe Gly Leu Val Pro Gly Val Gly Val Ala Pro Gly
            450                 455                 460

Val Gly Val Ala Pro Gly Val Gly Val Ala Pro Gly Val Gly Leu Ala
465                 470                 475                 480

Pro Gly Val Gly Val Ala Pro Gly Val Gly Val Ala Pro Gly Val Gly
            485                 490                 495

Val Ala Pro Gly Ile Gly Pro Gly Gly Val Ala Ala Ala Lys Ser
            500                 505                 510

Ala Ala Lys Val Ala Ala Lys Ala Gln Leu Arg Ala Ala Ala Gly Leu
            515                 520                 525

Gly Ala Gly Ile Pro Gly Leu Gly Val Gly Val Gly Val Pro Gly Leu
            530                 535                 540

Gly Val Gly Ala Gly Val Pro Gly Leu Gly Val Gly Ala Gly Val Pro
545                 550                 555                 560

Gly Phe Gly Ala Val Pro Gly Ala Leu Ala Ala Lys Ala Ala Lys
            565                 570                 575

Tyr Gly Ala Ala Val Pro Gly Val Leu Gly Gly Leu Gly Ala Leu Gly
            580                 585                 590

Gly Val Gly Ile Pro Gly Gly Val Val Gly Ala Gly Pro Ala Ala Ala
            595                 600                 605

Ala Ala Ala Ala Lys Ala Ala Ala Lys Ala Ala Gln Phe Gly Leu Val
            610                 615                 620

Gly Ala Ala Gly Leu Gly Gly Leu Gly Val Gly Gly Leu Gly Val Pro
625                 630                 635                 640

Gly Val Gly Gly Leu Gly Gly Ile Pro Pro Ala Ala Ala Ala Lys Ala
                645                 650                 655

Ala Lys Tyr Gly Val Ala Ala Arg Pro Gly Phe Gly Leu Ser Pro Ile
            660                 665                 670

Phe Pro Gly Gly Ala Cys Leu Gly Lys Ala Cys Gly Arg Lys Arg Lys
            675                 680                 685

<210> SEQ ID NO 46
<211> LENGTH: 643
<212> TYPE: PRT
<213> ORGANISM: Homo sapiens

<400> SEQUENCE: 46

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30
```

-continued

```
Ile Pro Gly Gly Val Pro Gly Val Phe Tyr Pro Ala Leu Gly Pro
            35                  40                  45
Gly Gly Lys Pro Leu Lys Pro Val Pro Gly Gly Leu Ala Gly Ala Gly
 50                  55                  60
Leu Gly Ala Gly Leu Gly Ala Phe Pro Ala Val Thr Phe Pro Gly Ala
 65                  70                  75                  80
Leu Val Pro Gly Gly Val Ala Asp Ala Ala Ala Tyr Lys Ala Ala
                 85                  90                  95
Lys Ala Gly Ala Gly Leu Gly Gly Val Pro Gly Val Gly Leu Gly
                100                 105                 110
Val Ser Ala Gly Ala Val Pro Gln Pro Gly Ala Gly Val Lys Pro
             115                 120                 125
Gly Lys Val Pro Gly Val Gly Leu Pro Gly Val Tyr Pro Gly Gly Val
 130                 135                 140
Leu Pro Gly Val Gly Pro Phe Gly Gly Pro Gln Pro Gly Val Pro Leu
 145                 150                 155                 160
Gly Tyr Pro Ile Lys Ala Pro Lys Leu Pro Gly Tyr Gly Leu Pro
             165                 170                 175
Tyr Thr Thr Gly Lys Leu Pro Tyr Gly Tyr Gly Pro Gly Gly Val Ala
             180                 185                 190
Gly Ala Ala Gly Lys Ala Gly Tyr Pro Thr Gly Thr Gly Val Gly Pro
     195                 200                 205
Gln Ala Ala Ala Ala Ala Ala Lys Ala Ala Lys Phe Gly Ala
 210                 215                 220
Gly Ala Ala Gly Val Leu Pro Gly Val Gly Ala Gly Val Pro Gly
 225                 230                 235                 240
Val Pro Gly Ala Ile Pro Gly Ile Gly Gly Ile Ala Gly Val Gly Thr
                 245                 250                 255
Pro Ala Ala Ala Ala Ala Ala Ala Ala Lys Ala Ala Lys Tyr
             260                 265                 270
Gly Ala Ala Ala Gly Leu Val Pro Gly Gly Pro Gly Phe Gly Pro Gly
     275                 280                 285
Val Val Gly Val Pro Gly Ala Gly Val Pro Gly Val Gly Val Pro Gly
 290                 295                 300
Ala Gly Ile Pro Val Val Pro Gly Ala Gly Ile Pro Gly Ala Ala Val
 305                 310                 315                 320
Pro Gly Val Val Ser Pro Glu Ala Ala Ala Lys Ala Ala Lys Ala
                 325                 330                 335
Ala Lys Tyr Gly Ala Arg Pro Gly Val Gly Val Gly Gly Ile Pro Thr
         340                 345                 350
Tyr Gly Val Gly Ala Gly Gly Phe Pro Gly Phe Gly Val Gly Val Gly
             355                 360                 365
Gly Ile Pro Gly Val Ala Gly Val Pro Gly Val Gly Val Pro Gly
     370                 375                 380
Val Gly Gly Val Pro Gly Val Gly Ile Ser Pro Glu Ala Gln Ala Ala
 385                 390                 395                 400
Ala Ala Ala Lys Ala Ala Lys Tyr Gly Leu Val Pro Gly Val Gly Val
                 405                 410                 415
Ala Pro Gly Val Gly Val Ala Pro Gly Val Gly Val Ala Pro Gly Val
                 420                 425                 430
Gly Leu Ala Pro Gly Val Gly Val Ala Pro Gly Val Gly Val Ala Pro
             435                 440                 445
Gly Val Gly Val Ala Pro Gly Ile Gly Pro Gly Gly Val Ala Ala Ala
```

-continued

```
                450                 455                 460
Ala Lys Ser Ala Ala Lys Val Ala Ala Lys Ala Gln Leu Arg Ala Ala
465                 470                 475                 480

Ala Gly Leu Gly Ala Gly Ile Pro Gly Leu Gly Val Gly Val Gly Val
                485                 490                 495

Pro Gly Leu Gly Val Gly Ala Gly Val Pro Gly Leu Gly Val Gly Ala
                500                 505                 510

Gly Val Pro Gly Phe Gly Ala Val Pro Gly Ala Leu Ala Ala Ala Lys
                515                 520                 525

Ala Ala Lys Tyr Gly Ala Ala Val Pro Gly Val Leu Gly Gly Leu Gly
            530                 535                 540

Ala Leu Gly Gly Val Gly Ile Pro Gly Gly Val Val Gly Ala Gly Pro
545                 550                 555                 560

Ala Ala Ala Ala Ala Ala Lys Ala Ala Lys Ala Ala Gln Phe
                565                 570                 575

Gly Leu Val Gly Ala Ala Gly Leu Gly Gly Leu Gly Val Gly Gly Leu
            580                 585                 590

Gly Val Pro Gly Val Gly Gly Leu Gly Gly Ile Pro Pro Ala Ala Ala
            595                 600                 605

Ala Lys Ala Ala Lys Tyr Gly Val Ala Ala Arg Pro Gly Phe Gly Leu
    610                 615                 620

Ser Pro Ile Phe Pro Gly Gly Ala Cys Leu Gly Lys Ala Cys Gly Arg
625                 630                 635                 640

Lys Arg Lys

<210> SEQ ID NO 47
<211> LENGTH: 680
<212> TYPE: PRT
<213> ORGANISM: Homo sapiens

<400> SEQUENCE: 47

Met Ala Gly Leu Thr Ala Ala Ala Pro Arg Pro Gly Val Leu Leu Leu
1               5                   10                  15

Leu Leu Ser Ile Leu His Pro Ser Arg Pro Gly Gly Val Pro Gly Ala
                20                  25                  30

Ile Pro Gly Gly Val Pro Gly Gly Val Phe Tyr Pro Gly Ala Gly Leu
                35                  40                  45

Gly Ala Leu Gly Gly Gly Ala Leu Gly Pro Gly Gly Lys Pro Leu Lys
            50                  55                  60

Pro Val Pro Gly Gly Leu Ala Gly Ala Gly Leu Gly Ala Gly Leu Gly
65                  70                  75                  80

Ala Phe Pro Ala Val Thr Phe Pro Gly Ala Leu Val Pro Gly Gly Val
                85                  90                  95

Ala Asp Ala Ala Ala Ala Tyr Lys Ala Ala Lys Ala Gly Ala Gly Leu
                100                 105                 110

Gly Gly Val Pro Gly Val Gly Gly Leu Gly Val Ser Ala Gly Ala Val
            115                 120                 125

Val Pro Gln Pro Gly Ala Gly Val Lys Pro Gly Lys Val Pro Gly Val
        130                 135                 140

Gly Leu Pro Gly Val Tyr Pro Gly Gly Val Leu Pro Gly Ala Arg Phe
145                 150                 155                 160

Pro Gly Val Gly Val Leu Pro Gly Val Pro Thr Gly Ala Gly Val Lys
                165                 170                 175

Pro Lys Ala Pro Gly Val Gly Gly Ala Phe Ala Gly Ile Pro Gly Val
```

-continued

```
            180                 185                 190
Gly Pro Phe Gly Gly Pro Gln Pro Gly Val Pro Leu Gly Tyr Pro Ile
            195                 200                 205
Lys Ala Pro Lys Leu Pro Gly Gly Tyr Gly Leu Pro Tyr Thr Thr Gly
            210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Lys Phe Gly Ala Gly Ala Ala Gly
            260                 265                 270
Val Leu Pro Gly Val Gly Ala Gly Val Pro Gly Val Pro Gly Ala
            275                 280                 285
Ile Pro Gly Ile Gly Ile Ala Gly Val Gly Thr Pro Ala Ala Ala
            290                 295                 300
Ala Ala Ala Ala Ala Ala Lys Ala Ala Lys Tyr Gly Ala Ala Ala
305                 310                 315                 320
Gly Leu Val Pro Gly Pro Gly Phe Gly Pro Gly Val Val Gly Val
                325                 330                 335
Pro Gly Ala Gly Val Pro Val Gly Val Pro Gly Ala Gly Ile Pro
            340                 345                 350
Val Val Pro Gly Ala Gly Ile Pro Gly Ala Ala Val Pro Gly Val Val
            355                 360                 365
Ser Pro Glu Ala Ala Ala Lys Ala Ala Ala Lys Ala Ala Lys Tyr Gly
            370                 375                 380
Ala Arg Pro Gly Val Gly Val Gly Gly Ile Pro Thr Tyr Gly Val Gly
385                 390                 395                 400
Ala Gly Gly Phe Pro Gly Phe Gly Val Gly Val Gly Gly Ile Pro Gly
                405                 410                 415
Val Ala Gly Val Pro Ser Val Gly Gly Val Pro Gly Val Gly Gly Val
            420                 425                 430
Pro Gly Val Gly Ile Ser Pro Glu Ala Gln Ala Ala Ala Ala Lys
            435                 440                 445
Ala Ala Lys Tyr Gly Leu Val Pro Gly Val Gly Val Ala Pro Gly Val
            450                 455                 460
Gly Val Ala Pro Gly Val Gly Val Ala Pro Gly Val Gly Leu Ala Pro
465                 470                 475                 480
Gly Val Gly Val Ala Pro Gly Val Gly Val Ala Pro Gly Val Gly Val
                485                 490                 495
Ala Pro Gly Ile Gly Pro Gly Gly Val Ala Ala Ala Lys Ser Ala
            500                 505                 510
Ala Lys Val Ala Ala Lys Ala Gln Leu Arg Ala Ala Ala Gly Leu Gly
            515                 520                 525
Ala Gly Ile Pro Gly Leu Gly Val Gly Val Gly Val Pro Gly Leu Gly
            530                 535                 540
Val Gly Ala Gly Val Pro Gly Leu Gly Val Gly Ala Gly Val Pro Gly
545                 550                 555                 560
Phe Gly Ala Val Pro Gly Ala Leu Ala Ala Ala Lys Ala Ala Lys Tyr
                565                 570                 575
Gly Ala Ala Val Pro Gly Val Leu Gly Gly Leu Gly Ala Leu Gly Gly
            580                 585                 590
Val Gly Ile Pro Gly Gly Val Val Gly Ala Gly Pro Ala Ala Ala Ala
            595                 600                 605
```

```
Ala Ala Ala Lys Ala Ala Lys Ala Gln Phe Gly Leu Val Gly
        610             615             620
Ala Ala Gly Leu Gly Gly Leu Gly Val Gly Gly Leu Gly Val Pro Gly
625             630             635             640
Val Gly Gly Leu Gly Gly Ile Pro Pro Ala Ala Ala Lys Ala Ala
                645             650             655
Lys Tyr Gly Val Ala Ala Arg Pro Gly Phe Gly Leu Ser Pro Ile Phe
            660             665             670
Pro Gly Gly Ala Cys Leu Gly Lys
            675             680

<210> SEQ ID NO 48
<211> LENGTH: 681
<212> TYPE: PRT
<213> ORGANISM: Homo sapiens

<400> SEQUENCE: 48

Met Ala Gly Leu Thr Ala Ala Pro Arg Pro Gly Val Leu Leu Leu
 1               5                  10                  15
Leu Leu Ser Ile Leu His Pro Ser Arg Pro Gly Gly Val Pro Gly Ala
                20                  25                  30
Ile Pro Gly Gly Val Pro Gly Gly Val Phe Tyr Pro Gly Ala Gly Leu
            35                  40                  45
Gly Ala Leu Gly Gly Gly Ala Leu Gly Pro Gly Gly Lys Pro Leu Lys
        50                  55                  60
Pro Val Pro Gly Gly Leu Ala Gly Ala Gly Leu Gly Ala Gly Leu Gly
65                  70                  75                  80
Ala Phe Pro Ala Val Thr Phe Pro Gly Ala Leu Val Pro Gly Gly Val
                85                  90                  95
Ala Asp Ala Ala Ala Ala Tyr Lys Ala Ala Lys Ala Gly Ala Gly Leu
                100                 105                 110
Gly Gly Val Pro Gly Val Gly Gly Leu Gly Val Ser Ala Gly Ala Val
            115                 120                 125
Val Pro Gln Pro Gly Ala Gly Val Lys Pro Gly Lys Val Pro Gly Val
130                 135                 140
Gly Leu Pro Gly Val Tyr Pro Gly Gly Val Leu Pro Gly Ala Arg Phe
145                 150                 155                 160
Pro Gly Val Gly Val Leu Pro Gly Val Pro Thr Gly Ala Gly Val Lys
                165                 170                 175
Pro Lys Ala Pro Gly Val Gly Gly Ala Phe Ala Gly Ile Pro Gly Val
            180                 185                 190
Gly Pro Phe Gly Gly Pro Gln Pro Gly Val Pro Leu Gly Tyr Pro Ile
        195                 200                 205
Lys Ala Pro Lys Leu Pro Gly Gly Tyr Gly Leu Pro Tyr Thr Thr Gly
    210                 215                 220
Lys Leu Pro Tyr Gly Tyr Gly Pro Gly Gly Val Ala Gly Ala Ala Gly
225                 230                 235                 240
Lys Ala Gly Tyr Pro Thr Gly Thr Gly Val Gly Pro Gln Ala Ala Ala
                245                 250                 255
Ala Ala Ala Ala Lys Ala Ala Lys Phe Gly Ala Gly Ala Ala Gly
            260                 265                 270
Val Leu Pro Gly Val Gly Gly Ala Gly Val Pro Gly Val Pro Gly Ala
        275                 280                 285
Ile Pro Gly Ile Gly Gly Ile Ala Gly Val Gly Thr Pro Ala Ala Ala
```

```
            290                 295                 300
Ala Ala Ala Ala Ala Ala Lys Ala Ala Lys Tyr Gly Ala Ala
305                 310                 315                 320

Gly Leu Val Pro Gly Pro Gly Phe Gly Pro Gly Val Val Gly Val
                325                 330                 335

Pro Gly Ala Gly Val Pro Gly Val Gly Val Pro Gly Ala Gly Ile Pro
            340                 345                 350

Val Val Pro Gly Ala Gly Ile Pro Gly Ala Ala Val Pro Gly Val Val
        355                 360                 365

Ser Pro Glu Ala Ala Lys Ala Ala Lys Ala Ala Lys Tyr Gly
    370                 375                 380

Ala Arg Pro Gly Val Gly Val Gly Gly Ile Pro Thr Tyr Gly Val Gly
385                 390                 395                 400

Ala Gly Gly Phe Pro Gly Phe Gly Val Gly Val Gly Gly Ile Pro Gly
                405                 410                 415

Val Ala Gly Val Pro Ser Val Gly Gly Val Pro Gly Val Gly Gly Val
            420                 425                 430

Pro Gly Val Gly Ile Ser Pro Glu Ala Gln Ala Ala Ala Ala Lys
        435                 440                 445

Ala Ala Lys Tyr Gly Leu Val Pro Gly Val Gly Val Ala Pro Gly Val
    450                 455                 460

Gly Val Ala Pro Gly Val Gly Val Ala Pro Gly Val Gly Leu Ala Pro
465                 470                 475                 480

Gly Val Gly Val Ala Pro Gly Val Gly Val Ala Pro Gly Val Gly Val
                485                 490                 495

Ala Pro Gly Ile Gly Pro Gly Gly Val Ala Ala Ala Lys Ser Ala
            500                 505                 510

Ala Lys Val Ala Ala Lys Ala Gln Leu Arg Ala Ala Gly Leu Gly
        515                 520                 525

Ala Gly Ile Pro Gly Leu Gly Val Gly Val Gly Val Pro Gly Leu Gly
    530                 535                 540

Val Gly Ala Gly Val Pro Gly Leu Gly Val Gly Ala Gly Val Pro Gly
545                 550                 555                 560

Phe Gly Ala Val Pro Gly Ala Leu Ala Ala Ala Lys Ala Ala Lys Tyr
                565                 570                 575

Gly Ala Ala Val Pro Gly Val Leu Gly Gly Leu Gly Ala Leu Gly Gly
            580                 585                 590

Val Gly Ile Pro Gly Gly Val Val Gly Ala Gly Pro Ala Ala Ala
        595                 600                 605

Ala Ala Ala Lys Ala Ala Ala Lys Ala Ala Gln Phe Gly Leu Val Gly
    610                 615                 620

Ala Ala Gly Leu Gly Gly Leu Gly Val Gly Gly Leu Gly Val Pro Gly
625                 630                 635                 640

Val Gly Gly Leu Gly Gly Ile Pro Pro Ala Ala Ala Lys Ala Ala
                645                 650                 655

Lys Tyr Gly Val Ala Ala Arg Pro Gly Phe Gly Leu Ser Pro Ile Phe
            660                 665                 670

Pro Gly Gly Ala Cys Leu Gly Lys Ala
        675                 680

<210> SEQ ID NO 49
<211> LENGTH: 2469
<212> TYPE: DNA
<213> ORGANISM: Homo sapiens
```

<400> SEQUENCE: 49

```
atggcgggtc tgacggcggc ggccccgcgg cccggagtcc tcctgctcct gctgtccatc      60
ctccacccct ctcggcctgg aggggtccct ggggccattc ctggtggagt tcctggagga     120
gtcttttatc caggggctgg tctcggagcc cttggaggag gagcgctggg gcctggaggc     180
aaacctctta agccagttcc cggagggctt gcgggtgctg gccttggggc aggacctcac     240
cccatcctcc cctccgcagg gctcggcgcc ttccccgcag ttacctttcc gggggctctg     300
gtgcctggtg gagtggctga cgctgctgca gcctataaag ctgctaaggc tggcgctggg     360
cttggtggtg tcccaggagt tggtggctta ggagtgtctg cagcccctttc tgtgccaggt    420
gcggtggttc ctcagcctgg agccggagtg aagcctggga aagtgccggg tgtggggctg     480
ccaggtgtat acccaggtgg cgtgctccca gggcctgcaa ggcctgcctt cctacactca     540
ctgctttgtc ccccggcagg agctcggttc cccggtgtgg gggtgctccc tggagttccc     600
actggagcag gagttaagcc caaggctcca gtgtaggtg gagcttttgc tggaatccca     660
ggagttggac cctttggggg accgcaacct ggagtcccac tggggtatcc catcaaggcc     720
cccaagctgc ctggtggcta tggactgccc tacaccacag gaaaactgcc ctatggctat     780
gggcccggag gagtggctgg tgcagcgggc aaggctggtt acccaacagg gacaggggtt     840
ggcccccagg cagcagcagc agcggcagct aaagcagcag caaagttcgg tgctggagca     900
gccggagtcc tccctggtgt tggaggggct ggtgttcctg gcgtgcctgg ggcaattcct     960
ggaattggag gcatcgcagg cgttgggact ccagctgcag ctgcagctgc agcagcagcc    1020
gctaaggcag ccaagtatgg agctgctgca ggcttagtgc ctggtgggcc aggctttggc    1080
ccggagtag ttggtgtccc aggagctggc gttccaggtg ttggtgtccc aggagctggg    1140
attccagttg tcccaggtgc tgggatccca ggtgctgcgg ttccaggggt tgtgtcacca    1200
gaagcagctg ctaaggcagc tgcaaaggca gccaaatacg gggccaggcc cggagtcgga    1260
gttggaggca ttcctactta cggggttgga gctgggggct ttcccggctt tggtgtcgga    1320
gtcggaggta tccctggagt cgcaggtgtc cctggtgtcg gaggtgttcc cggagtcgga    1380
ggtgtcccgg gagttggcat ttccccgaa gctcaggcag cagctgccgc caaggctgcc    1440
aagtacggtg ctgcaggagc aggagtgctg gtgggctag tgccaggtgc cccaggcgca    1500
gtcccaggtg tgccgggcac gggaggagtg ccaggagtgg ggaccccagc agctgcagct    1560
gctaaagcag ccgccaaagc cgcccagttt gctcttctca atcttgcagg gttagttcct    1620
ggtgtcggcg tggctcctgg agttggcgtg gctcctggtg tcggtgtggc tcctggagtt    1680
ggcttggctc ctggagttgg cgtggctcct ggagttggtg tggctcctgg cgttggcgtg    1740
gctcccggca ttggccctgg tggagttgca gctgcagcaa aatccgctgc caaggtggct    1800
gccaaagccc agctccgagc tgcagctggg cttggtgctg gcatccctgg acttggagtt    1860
ggtgtcggcg tccctggact ggagttggt gctggtgttc ctggacttgg agttggtgct    1920
ggtgttcctg gcttcggggc aggtgcagat gagggagtta ggcggagcct gtcccctgag    1980
ctcagggaag gagatccctc ctcctctcag cacctcccca gcaccccctc atcacccagg    2040
gtacctggag ccctggctgc cgctaaagca gccaaatatg gagcagcagt gcctgggtc     2100
cttggagggc tcggggctct cggtggagta ggcatcccag gcggtgtggt gggagccgga    2160
cccgccgccg ccgctgccgc agccaaagct gctgccaaag ccgcccagtt tggcctagtg    2220
ggagccgctg ggctcggagg actcggagtc ggagggcttg gagttccagg tgttgggggc    2280
```

```
cttggaggta tacctccagc tgcagccgct aaagcagcta aatacggtgc tgctggcctt    2340
ggaggtgtcc taggggtgc cgggcagttc ccacttggag gagtggcagc aagacctggc     2400
ttcggattgt ctcccatttt cccaggtggg gcctgcctgg ggaaagcttg tggccggaag    2460
agaaaatga                                                             2469

<210> SEQ ID NO 50
<211> LENGTH: 2185
<212> TYPE: DNA
<213> ORGANISM: Homo sapiens

<400> SEQUENCE: 50 ctccctctttt ccctcacagc cgacgaggca acaattaggc tttggggata aaacgaggtg    60
cggagagcgg gctggggcat ttctccccga gatggcgggt ctgacggcgg cggccccgcg    120
gcccggagtc ctcctgctcc tgctgtccat cctccacccc tctcggcctg gagtctttta    180
tccaggggct ggtctcggag cccttggagg aggagcgctg gggcctggag gcaaacctct    240
taagccagtt cccggagggc ttgcgggtgc tggccttggg gcaggctcg gcgccttccc     300 cgcagttacc tttccggggg ctctggtgcc tggtggagtg gctgacgctg ctgcagccta    360
taaagctgct aaggctggcg ctgggcttgg tggtgtccca ggagttggtg gcttaggagt    420
gtctgcagcc ccttctgtgc caggtgcggt ggttcctcag cctggagccg gagtgaagcc    480
tgggaaagtg ccgggtgtgg ggctgccagg tgtataccca ggtggcgtgc tcccaggagc    540
tcggttcccc ggtgtggggg tgctccctgg agttcccact ggagcaggag ttaagcccaa    600
ggctccaggt gtaggtggag cttttgctgg aatcccagga gttggaccct ttgggggacc    660
gcaacctgga gtcccactgg ggtatcccat caaggccccc aagctgcctg gtggctatgg    720
actgccctac accacaggga aactgcccta tggctatggg ccggaggag tggctggtgc    780 agcgggcaag gctggttacc aacagggac aggggttggc cccaggcag cagcagcagc     840 ggcagctaaa gcagcagcaa agttcggtgc tggagcagcc ggagtcctcc ctggtgttgg    900
aggggctggt gttcctggcg tgcctggggc aattcctgga attggaggca tcgcaggcgt    960
tgggactcca gctgcagctg cagctgcagc agcagccgct aaggcagcca agtatggagc    1020
tgctgcaggc ttagtgcctg gtgggccagg cttggcccg ggagtagttg gtgtcccagg     1080
agctggcgtt ccaggtgttg gtgtcccagg agctgggatt ccagttgtcc caggtgctgg    1140
gatcccaggt gctgcggttc caggggttgt gtcaccagaa gcagctgcta aggcagctgc    1200
aaaggcagcc aaatacgggg ccaggcccgg agtcggagtt ggaggcattc ctacttacgg    1260
ggttggagct gggggctttc ccggctttgg tgtcggagtc ggaggtatcc ctggagtcgc    1320
aggtgtccct ggtgtcggag gtgttcccgg agtcggaggt gtcccgggag ttggcatttc    1380
ccccgaagct caggcagcag ctgccgccaa ggctgccaag tacgggttag ttcctggtgt    1440
cggcgtggct cctggagttg gcgtggctcc tggtgtcggt gtggctcctg gagttggctt    1500
ggctcctgga gttggcgtgg ctcctggagt tggtgtggct cctggcgttg gcgtggctcc    1560
cggcattggc cctggtggag ttgcagctgc agcaaaatcc gctgccaagg tggctgccaa    1620
agcccagctc cgagctgcag ctgggcttgg tgctggcatc cctggacttg gagttggtgt    1680
cggcgtccct ggacttggag ttggtgctgg tgttcctgga cttggagttg gtgctggtgt    1740
tcctggcttc ggggcagtac ctggagcccct ggctgccgct aaagcagcca atatggagc    1800 agcagtgcct ggggtccttg gagggctcgg ggctctcggt ggagtaggca tcccaggcgg    1860
tgtggtggga gccggacccg ccgccgccgc tgccgcagcc aaagctgctg ccaaagccgc    1920
```

```
ccagtttggc ctagtgggag ccgctgggct cggaggactc ggagtcggag ggcttggagt    1980
tccaggtgtt gggggccttg gaggtatacc tccagctgca gccgctaaag cagctaaata    2040
cggtgctgct ggccttggag gtgtcctagg gggtgccggg cagttcccac ttggaggagt    2100
ggcagcaaga cctggcttcg gattgtctcc cattttccca ggtggggcct gcctgggaa     2160 agcttgtggc cggaagagaa aatga                                          2185

<210> SEQ ID NO 51
<211> LENGTH: 2175
<212> TYPE: DNA
<213> ORGANISM: Homo sapiens

<400> SEQUENCE: 51
atggcgggtc tgacggcggc ggccccgcgg cccggagtcc tcctgctcct gctgtccatc      60
ctccaccctc tcggcctgga gggtccct ggggccattc ctggtggagt tcctggagga      120
gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttaccct tccgggggct ctggtgcctg gtggagtggc tgacgctgct    300
gcagcctata agctgctaa ggctggcgct gggcttggtg gtgtcccagg agttggtggc     360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggccccagg cagcagcagc agcggcagct    780
aaagcagcag caaagttcgg tgctggagca gccggagtcc tccctggtgt tggaggggct    840
ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc    1020
gttccaggtg ttgtgtccc aggagctggg attccagttg tcccaggtgc tgggatccca    1080
ggtgctgcgg ttccaggggt tgtgtcacca gaagcagctg ctaaggcagc tgcaaaggca    1140
gccaaatacg gggccaggcc cggagtcgga gttgaggca ttcctactta cggggttgga    1200 gctggggct ttcccggctt tggtgtcgga gtcggaggta tccctggagt cgcaggtgtc    1260
cctggtgtcg gaggtgttcc cggagtcgga ggtgtcccgg gagttggcat tccccccgaa    1320
gctcaggcag cagctgccgc caaggctgcc aagtacggag tggggacccc agcagctgca    1380
gctgctaaag cagccgccaa agccgcccac tttgggttag ttcctggtgt cggcgtggct    1440
cctggagttg gcgtggctcc tggtgtcggt gtggctcctg gagttggctt ggctcctgga    1500
gttggcgtgg ctcctggagt tggtgtggct cctggcgttg gcgtggctcc cggcattggc    1560
cctggtggag ttgcagctgc agcaaaatcc gctgccaagg tggctgccaa agcccagctc    1620
cgagctgcag ctgggcttgg tgctggcatc cctggacttg gagttggtgt cggcgtccct    1680
ggacttggag ttggtgctgg tgttcctgga cttgagttg gtgctggtgt tcctggcttc    1740
ggggcagtac ctggagcct ggctgccgct aaagcagcca aatatggagc agcagtgcct    1800
```

| | |
|---|---|
| gggtccttg agggctcgg ggctctcggt ggagtaggca tcccaggcgg tgtggtggga | 1860 |
| gccggacccg ccgccgccgc tgccgcagcc aaagctgctg ccaaagccgc ccagtttggc | 1920 |
| ctagtgggag ccgctgggct cggaggactc ggagtcggag ggcttggagt tccaggtgtt | 1980 |
| gggggccttg gaggtatacc tccagctgca gccgctaaag cagctaaata cggtgctgct | 2040 |
| ggccttggag gtgtcctagg gggtgccggg cagttcccac ttggaggagt ggcagcaaga | 2100 |
| cctggcttcg gattgtctcc cattttccca ggtggggcct gcctggggaa agcttgtggc | 2160 |
| cggaagagaa aatga | 2175 |

<210> SEQ ID NO 52
<211> LENGTH: 2175
<212> TYPE: DNA
<213> ORGANISM: Homo sapiens

<400> SEQUENCE: 52

| | |
|---|---|
| atggcgggtc tgacggcggc ggccccgcgg cccggagtcc tcctgctcct gctgtccatc | 60 |
| ctccacccct ctcggcctgg aggggtccct ggggccattc ctggtggagt tcctggagga | 120 |
| gtcttttatc caggggctgg tctcggagcc cttggaggag gagcgctggg gcctggaggc | 180 |
| aaacctctta agccagttcc cggagggctt gcggtgctg gccttggggc agggctcggc | 240 |
| gccttccccg cagttacctt tccggggggct ctggtgcctg gtggagtggc tgacgctgct | 300 |
| gcagcctata aagctgctaa ggctggcgct gggcttggtg gtgtcccagg agttggtggc | 360 |
| ttaggagtgt ctgcaggtgc ggtggttcct cagcctggag ccggagtgaa gcctgggaaa | 420 |
| gtgccgggtg tggggctgcc aggtgtatac ccaggtggcg tgctcccagg agctcggttc | 480 |
| cccggtgtgg gggtgctccc tggagttccc actggagcag gagttaagcc caaggctcca | 540 |
| ggtgtaggtg gagcttttgc tggaatccca ggagttggac cctttggggg accgcaacct | 600 |
| ggagtcccac tggggtatcc catcaaggcc cccaagctgc ctggtggcta tggactgccc | 660 |
| tacaccacag ggaaactgcc ctatggctat gggcccggag gagtggctgg tgcagcgggc | 720 |
| aaggctggtt acccaacagg gacagggggtt ggcccccagg cagcagcagc agcggcagct | 780 |
| aaagcagcag caaagttcgg tgctggagca gccgagtcc tccctggtgt ggagggggct | 840 |
| ggtgttcctg gcgtgcctgg ggcaattcct ggaattggag gcatcgcagg cgttgggact | 900 |
| ccagctgcag ctgcagctgc agcagcagcc gctaaggcag ccaagtatgg agctgctgca | 960 |
| ggcttagtgc ctggtgggcc aggctttggc ccgggagtag ttggtgtccc aggagctggc | 1020 |
| gttccaggtg ttggtgtccc aggagctggg attccagttg tcccaggtgc tgggatccca | 1080 |
| ggtgctgcgg ttcagggggt tgtgtcacca gaagcagctg ctaaggcagc tgcaaaggca | 1140 |
| gccaaatacg gggccaggcc cggagtcgga gttgaaggca ttcctactta cggggttgga | 1200 |
| gctgggggct ttcccggctt tggtgtcgga gtcgaggta tccctggagt cgcaggtgtc | 1260 |
| cctagtgtcg gaggtgttcc cggagtcgga ggtgtcccgg agttggcat ttcccccgaa | 1320 |
| gctcaggcag cagctgccgc caaggctgcc aagtacggag tggggacccc agcagctgca | 1380 |
| gctgctaaag cagccgccaa agccgcccag tttgggttag ttcctggtgt cggcgtggct | 1440 |
| cctggagttg gcgtggctcc tggtgtcggt gtggctcctg gagttggctt ggctcctgga | 1500 |
| gttggcgtgg ctcctggagt tggtgtggct cctggcgttg gcgtggctcc cggcattggc | 1560 |
| cctggtggag ttgcagctgc agcaaaatcc gctgccaagg tggctgccaa agccagctc | 1620 |
| cgagctgcag ctgggcttgg tgctggcatc cctggacttg gagttggtgt cggcgtccct | 1680 |
| ggacttggag ttggtgctgg tgttcctgga cttggagttg gtgctggtgt tcctggcttc | 1740 |

| | | |
|---|---|---|
| ggggcagtac ctggagccct ggctgccgct aaagcagcca aatatggagc agcagtgcct | 1800 | |
| ggggtccttg gagggctcgg ggctctcggt ggagtaggca tcccaggcgg tgtggtggga | 1860 | |
| gccggacccg ccgccgccgc tgccgcagcc aaagctgctg ccaaagccgc ccagtttggc | 1920 | |
| ctagtgggag ccgctgggct cggaggactc ggagtcggag ggcttggagt tccaggtgtt | 1980 | |
| gggggccttg gaggtatacc tccagctgca gccgctaaag cagctaaata cggtgctgct | 2040 | |
| ggccttggag gtgtcctagg gggtgccggg cagttcccac ttggaggagt ggcagcaaga | 2100 | |
| cctggcttcg gattgtctcc cattttccca ggtgggggcct gcctggggaa agcttgtggc | 2160 | |
| cggaagagaa aatga | 2175 | |

<210> SEQ ID NO 53
<211> LENGTH: 2175
<212> TYPE: DNA
<213> ORGANISM: Homo sapiens

<400> SEQUENCE: 53

| | | |
|---|---|---|
| atggcgggtc tgacggcggc ggccccgcgg cccggagtcc tcctgctcct gctgtccatc | 60 | |
| ctccacccct ctcggcctgg aggggtccct ggggccattc ctggtggagt tcctggagga | 120 | |
| gtcttttatc caggggctgg tctcggagcc cttggaggag gagcgctggg gcctggaggc | 180 | |
| aaacctctta agccagttcc cggagggctt gcggtgctg gccttggggc agggctcggc | 240 | |
| gccttccccg cagttacctt tccgggggct ctggtgcctg gtggagtggc tgacgctgct | 300 | |
| gcagcctata aagctgctaa ggctggcgct gggcttggtg gtgtcccagg agttggtggc | 360 | |
| ttaggagtgt ctgcaggtgc ggtggttcct cagcctggag ccggagtgaa gcctgggaaa | 420 | |
| gtgccgggtg tggggctgcc aggtgtatac ccaggtggcg tgctcccagg agctcggttc | 480 | |
| cccggtgtgg gggtgctccc tggagttccc actggagcag gagttaagcc caaggctcca | 540 | |
| ggtgtaggtg gagcttttgc tggaatccca ggagttggac cctttggggg accgcaacct | 600 | |
| ggagtcccac tgggggtatcc catcaaggcc cccaagctgc ctggtggcta tggactgccc | 660 | |
| tacaccacag ggaaactgcc ctatggctat gggcccggag gagtggctgg tgcagcgggc | 720 | |
| aaggctggtt acccaacagg gacaggggtt ggccccccagg cagcagcagc agcggcagct | 780 | |
| aaagcagcag caaagttcgg tgctggagca gccggagtcc tcctggtgt tggaggggct | 840 | |
| ggtgttcctg gcgtgcctgg gcaattcct ggaattggag gcatcgcagg cgttgggact | 900 | |
| ccagctgcag ctgcagctgc agcagcagcc gctaaggcag ccaagtatgg agctgctgca | 960 | |
| ggcttagtgc ctggtggggcc aggctttggc ccggagtag ttggtgtccc aggagctggc | 1020 | |
| gttccaggtg ttggtgtccc aggagctggg attccagttg tcccaggtgc tgggatccca | 1080 | |
| ggtgctgcgg ttcaggggt tgtgtcacca gaagcagctg ctaaggcagc tgcaaaggca | 1140 | |
| gccaaatacg gggccaggcc cggagtcgga gttggaggca ttcctactta cggggttgga | 1200 | |
| gctgggggct ttcccggctt tggtgtcgga gtcgaggta tccctggagt cgcaggtgtc | 1260 | |
| cctggtgtcg gaggtgttcc cggagtcgga ggtgtcccgg agttggcat ttccccgaa | 1320 | |
| gctcaggcag cagctgccgc caaggctgcc aagtacggag tggggacccc agcagctgca | 1380 | |
| gctgctaaag cagccgccaa agccgcccag tttgggttag ttcctggtgt cggcgtggct | 1440 | |
| cctggagttg gcgtggctcc tggtgtcggt gtggctcctg gagttggctt ggctcctgga | 1500 | |
| gttgcgtggg ctcctggagt tggtgtggct cctggcgttg gcgtggctcc cggcattggc | 1560 | |
| cctggtggag ttgcagctgc agcaaaatcc gctgccaagg tggctgccaa agcccagctc | 1620 | |

```
cgagctgcag ctgggcttgg tgctggcatc cctggacttg gagttggtgt cggcgtccct    1680
ggacttggag ttggtgctgg tgttcctgga cttggagttg gtgctggtgt tcctggcttc    1740
ggggcagtac ctggagccct ggctgccgct aaagcagcca aatatggagc agcagtgcct    1800
ggggtccttg gagggctcgg ggctctcggt ggagtaggca tcccaggcgg tgtggtggga    1860
gccggacccg ccgccgccgc tgccgcagcc aaagctgctg ccaaagccgc ccagtttggc    1920
ctagtgggag ccgctgggct cggaggactc ggagtcggag ggcttggagt tccaggtgtt    1980
gggggccttg gaggtatacc tccagctgca ccgctaaaag cagctaaata cggtgctgct    2040
ggccttggag gtgtcctagg gggtgccggg cagttcccac ttggaggagt ggcagcaaga    2100
cctggcttcg gattgtctcc cattttccca ggtggggcct gcctggggaa agcttgtggc    2160
cggaagagaa aatga                                                     2175
```

<210> SEQ ID NO 54
<211> LENGTH: 2173
<212> TYPE: DNA
<213> ORGANISM: Homo sapiens

<400> SEQUENCE: 54

```
ctccctcttt ccctcacagc cgacgaggca acaattaggc tttggggata aaacgaggtg      60
cggagagcgg gctggggcat ttctccccga gatggcgggt ctgacggcgg cggccccgcg     120 gccccggagtc ctcctgctcc tgctgtccat cctccacccc tctcggcctg gagtcttttta  180 tccaggggct ggtctcggag cccttggagg aggagcgctg gggcctggag gcaaacctct    240
taagccagtt cccggagggc ttgcgggtgc tggccttggg gcagggctcg cgccttcccc    300
cgcagttacc tttccggggg ctctggtgcc tggtggagtg gctgacgctg ctgcagccta    360
taaagctgct aaggctggcg ctgggcttgg tggtgtccca ggagttggtg cttaggagt     420 gtctgcaggt gcggtggttc ctcagcctgg agccggagtg aagcctggga aagtgccggg    480
tgtggggctg ccaggtgtat acccaggtgg cgtgctccca ggagctcggt tccccggtgt    540
gggggtgctc cctggagttc ccactggagc aggagttaag cccaaggctc aggtgtagg     600 tggagctttt gctggaatcc caggagttgg accctttggg ggaccgcaac ctggagtccc    660
actggggtat cccatcaagg cccccaagct gcctggtggc tatggactgc cctacaccac    720
agggaaactg ccctatggct atgggcccgg aggagtggct ggtgcagcgg caaggctgg     780 ttacccaaca gggacagggg ttggccccca ggcagcagca gcagcggcag ctaaagcagc    840
agcaaagttc ggtgctggag cagccggagt cctccctggt gttggagggg ctggtgttcc    900
tggcgtgcct ggggcaattc ctggaattgg aggcatcgca ggcgttggga ctccagctgc    960
agctgcagct gcagcagcag ccgctaaggc agccaagtat ggagctgctg caggcttagt   1020
gcctggtggg ccaggctttg gcccgggagt agttggtgtc ccaggagctg gcgttccagg   1080
tgttggtgtc ccaggagctg ggattccagt tgtcccaggt gctgggatcc caggtgctgc   1140
ggttccaggg gttgtgtcac cagaagcagc tgctaaggca gctgcaaagg cagccaaata   1200
cggggccagg cccggagtcg gagttggagg cattcctact tacggggttg gagctggggg   1260
ctttcccggc tttggtgtcg gagtcggagg tatccctgga gtcgcaggtg tccctggtgt   1320
cggaggtgtt cccggagtcg gaggtgtccc gggagttggc atttccccg aagctcaggc    1380 agcagctgcc gccaaggctg ccaagtacgg agtggggacc ccagcagctg cagctgctaa   1440
agcagccgcc aaagccgccc agtttgggtt agttcctggt gtcggcgtgg ctcctggagt   1500
tggcgtggct cctggtgtcg gtgtggctcc tggagttggc ttggctcctg gagttggcgt   1560
```

```
ggctcctgga gttggtgtgg ctcctggcgt tggcgtggct cccggcattg gccctggtgg    1620
agttgcagct gcagcaaaat ccgctgccaa ggtggctgcc aaagcccagc tccgagctgc    1680
agctgggctt ggtgctggca tccctggact tggagttggt gtcggcgtcc ctggacttgg    1740
agttggtgct ggtgttcctg gacttggagt tggtgctggt gttcctggct cggggcagt    1800 acctggagcc ctggctgccg ctaaagcagc caaatatgga gcagcagtgc ctggggtcct    1860
tggagggctc gggctctcg gtggagtagg catcccaggc ggtgtggtgg gagccggacc    1920
cgccgccgcc gctgccgcag ccaaagctgc tgccaaagcc gcccagtttg cctagtggg    1980 agccgctggg ctcggaggac tcggagtcgg agggcttgga gttccaggtg ttgggggcct    2040
tggaggtata cctccagctg cagccgctaa agcagctaaa tacggagtgg cagcaagacc    2100
tggcttcgga ttgtctccca ttttcccagg tggggcctgc ctggggaaag cttgtggccg    2160
gaagagaaaa tga                                                       2173
```

<210> SEQ ID NO 55
<211> LENGTH: 2121
<212> TYPE: DNA
<213> ORGANISM: Homo sapiens

<400> SEQUENCE: 55

```
atggcgggtc tgacggcggc ggccccgcgg cccggagtcc tcctgctcct gctgtccatc      60
ctccacccct ctcggcctgg aggggtccct ggggccattc ctggtggagt tcctggagga     120
gtcttttatc caggggctgg tctcggagcc cttggaggag gagcgctggg gcctggaggc     180
aaacctctta agccagttcc cggagggctt gcgggtgctg gccttggggc agggctcggc     240
gccttccccg cagttacctt tccggggggct ctggtgcctg gtggagtggc tgacgctgct     300
gcagcctata agctgctaa ggctggcgct gggcttggtg gtgtcccagg agttggtggc     360
ttaggagtgt ctgcaggtgc ggtggttcct cagcctggag ccggagtgaa gcctgggaaa     420
gtgccgggtg tggggctgcc aggtgtatac ccaggtggcg tgctcccagg agctcggttc     480
cccggtgtgg gggtgctccc tggagttccc actggagcag gagttaagcc caaggctcca     540
ggtgtaggtg gagcttttgc tggaatccca ggagttggac cctttggggg accgcaacct     600
ggagtcccac tggggtatcc catcaaggcc cccaagctgc ctggtggcta tggactgccc     660
tacaccacag ggaaactgcc ctatggctat gggcccggag gagtggctgg tgcagcgggc     720
aaggctggtt acccaacagg gacaggggtt ggccccccagg cagcagcagc agcggcagct     780
aaagcagcag caaagttcgg tgctggagca gccgagtcc tccctggtgt tggaggggct     840
ggtgttcctg gcgtgcctgg ggcaattcct ggaattggag gcatcgcagg cgttgggact     900
ccagctgcag ctgcagctgc agcagcagcc gctaaggcag ccaagtatgg agctgctgca     960
ggcttagtgc ctggtgggcc aggctttggc ccgggagtag ttggtgtccc aggagctggc    1020
gttccaggtt ttggtgtccc aggagctggg attccagttg tcccaggtgc tgggatccca    1080
ggtgctgcgg ttcaggggt tgtgtcacca gaagcagctg ctaaggcagc tgcaaaggca    1140
gccaaatacg gggccaggcc cggagtcgga gttggaggca ttcctactta cggggttgga    1200
gctgggggct ttcccggctt tggtgtcgga gtcgaggta tccctggagt cgcaggtgtc    1260
cctggtgtcg gaggtgttcc cggagtcgga ggtgtcccgg gagttggcat tccccccgaa    1320
gctcaggcag cagctgccgc caaggctgcc aagtacggag tggggacccc agcagctgca    1380
gctgctaaag cagccgccaa agccgcccag tttgggttag ttcctggtgt cggcgtggct    1440
```

```
cctggagttg gcgtggctcc tggtgtcggt gtggctcctg gagttggctt ggctcctgga    1500
gttggcgtgg ctcctggagt tggtgtggct cctggcgttg gcgtggctcc cggcattggc    1560
cctggtggag ttgcagctgc agcaaaatcc gctgccaagg tggctgccaa agcccagctc    1620
cgagctgcag ctgggcttgg tgctggcatc cctggacttg gagttggtgt cggcgtccct    1680
ggacttggag ttggtgctgg tgttcctgga cttggagttg gtgctggtgt tcctggcttc    1740
cgggcagtac ctggagccct ggctgccgct aaagcagcca aatatggagc agcagtgcct    1800
ggggtccttg gagggctcgg ggctctcggt ggagtaggca tcccaggcgg tgtggtggga    1860
gccggacccg ccgccgccgc tgccgcagcc aaagctgctg ccaaagccgc ccagtttggc    1920
ctagtgggag ccgctgggct cggaggactc ggagtcggag ggcttggagt tccaggtgtt    1980
gggggccttg gaggtatacc tccagctgca gccgctaaag cagctaaata cggagtggca    2040
gcaagacctg gcttcggatt gtctcccatt ttcccaggtg gggcctgcct ggggaaagct    2100
tgtggccgga agagaaaatg a                                              2121

<210> SEQ ID NO 56
<211> LENGTH: 2121
<212> TYPE: DNA
<213> ORGANISM: Homo sapiens

<400> SEQUENCE: 56
atggcgggtc tgacggcggc ggcccgcgg cccggagtcc tcctgctcct gctgtccatc      60
ctccacccct ctcggcctgg aggggtccct ggggccattc tggtggagt tcctggagga     120 gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttacctt tccggggct ctggtgcctg gtggagtggc tgacgctgct    300
gcagcctata agctgctaa ggctggcgct gggcttggtg gtgtcccagg agttggtggc    360
ttaggagtgt ctgcaggtgc ggtggttcct cagcctggag ccggagtgaa gcctgggaaa    420
gtgccgggtg tggggctgcc aggtgtatac caggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggccccagg cagcagcagc agcggcagct    780
aaagcagcag caaagttcgg tgctggagca gccggagtcc tccctggtgt tggaggggct    840
ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc    1020
gttccaggtg ttgtgtccc aggagctggg attccagttg tcccaggtgc tgggatccca    1080
ggtgctgcgg ttcagggggt tgtgtcacca gaagcagctg ctaaggcagc tgcaaaggca    1140
gccaaatacg gggccaggcc cggagtcgga gttggaggca ttcctactta cggggttgga    1200 gctggggct ttcccggctt tggtgtcgga gtcggaggta tcccctggagt cgcaggtgtc    1260 cctagtgtcg gaggtgttcc cggagtcgga ggtgtcccgg gagttggcat tccccccgaa    1320
gctcaggcag cagctgccgc caaggctgcc aagtacggag tggggacccc agcagctgca    1380
gctgctaaag cagccgccaa agccgcccag tttgggttag ttcctggtgt cggcgtggct    1440
```

```
cctggagttg gcgtggctcc tggtgtcggt gtggctcctg gagttggctt ggctcctgga    1500
gttggcgtgg ctcctggagt tggtgtggct cctggcgttg gcgtggctcc cggcattggc    1560
cctggtggag ttgcagctgc agcaaaatcc gctgccaagg tggctgccaa agcccagctc    1620
cgagctgcag ctgggcttgg tgctggcatc cctggacttg gagttggtgt cggcgtccct    1680
ggacttggag ttggtgccgg tgttcctgga cttggagttg gtgctggtgt tcctggcttc    1740
ggggcagtac ctggagccct ggctgccgct aaagcagcca aatatggagc agcagtgcct    1800
ggggtccttg gagggctcgg ggctctcggt ggagtaggca tcccaggcgg tgtggtggga    1860
gccggacccg ccgccgccgc tgccgcagcc aaagctgctg ccaaagccgc ccagtttggc    1920
ctagtgggag ccgctgggct cggaggactc ggagtcggag ggcttggagt tccaggtgtt    1980
gggggccttg gaggtatacc tccagctgca gccgctaaag cagctaaata cggagtggca    2040
gcaagacctg gcttcggatt gtctcccatt ttcccaggtg gggcctgcct ggggaaagct    2100
tgtggccgga agagaaaatg a                                              2121

<210> SEQ ID NO 57
<211> LENGTH: 2121
<212> TYPE: DNA
<213> ORGANISM: Homo sapiens

<400> SEQUENCE: 57
atggcgggtc tgacggcggc ggccccgcgg cccggagtcc tcctgctcct gctgtccatc      60
ctccacccct ctcggcctgg aggggtccct ggggccattc ctggtggagt tcctggagga    120
gtcttttatc caggggctgg tctcggagcc cttggaggag gagcgctggg gcctggaggc    180
aaacctctta agccagttcc cggagggctt gcggtgctgg gccttggggc agggctcggc    240
gccttccccg cagttacctt tccgggggct ctggtgcctg gtggagtggc tgacgctgct    300
gcagcctata aagctgctaa ggctggcgct gggcttggtg gtgtcccagg agttggtggc    360
ttaggagtgt ctgcaggtgc ggtggttcct cagcctggag ccggagtgaa gcctgggaaa    420
gtgccgggtg tggggctgcc aggtgtgtat accaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggcccccagg cagcagcagc agcggcagct    780
aaagcagcag caaagttcgg tgctggagca gccggagtcc tccctggtgt tgaggggct    840 ggtgttcctg gcgtgcctgg gcaattcct ggaattggag catcgcagg cgttgggact    900 ccagctgcag ctgcagctgc agcagcagcc gctaaggcag ccaagtatgg agctgctgca    960
ggcttagtgc ctggtgggcc aggctttggc ccggagtag ttggtgtccc aggagctggc    1020
gttccaggtg ttggtgtccc aggagctggg attccagttg tcccaggtgc tgggatccca    1080
ggtgctgcgg ttccaggggt tgtgtcacca gaagcagctg ctaaggcagc tgcaaaggca    1140
gccaaatacg gggccaggcc cggagtcgga gttggaggca ttcctactta cggggttgga    1200
gctgggggct ttcccggctt tggtgtcgga gtcggaggta tccctggagt cgcaggtgtc    1260
cctggtgtcg gaggtgttcc cggagtcgga ggtgtcccgg gagttggcat ttccccgaa    1320 gctcaggcag cagctgccgc caaggctgcc aagtacggag tggggacccc agcagctgca    1380
```

```
gctgctaaag cagccgccaa agccgcccag tttgggttag ttcctggtgt cggcgtggct   1440
cctggagttg gcgtggctcc tggtgtcggt gtggctcctg gagttggctt ggctcctgga   1500
gttggcgtgg ctcctggagt tggtgtggct cctggcgttg gcgtggctcc cggcattggc   1560
cctggtggag ttgcagctgc agcaaaatcc gctgccaagg tggctgccaa agcccagctc   1620
cgagctgcag ctgggcttgg tgctggcatc cctggacttg agttggtgt cggcgtccct   1680 ggacttggag ttggtgctgg tgttcctgga cttggagttg gtgctggtgt tcctggcttc   1740
ggggcagtac ctggagccct ggctgccgct aaagcagcca aatatggagc agcagtgcct   1800
ggggtccttg gagggctcgg ggctctcggt ggagtaggca tcccaggcgg tgtggtggga   1860
gccggacccg ccgccgccgc tgccgcagcc aaagctgctg ccaaagccgc ccagtttggc   1920
ctagtgggag ccgctgggct cggaggactc ggagtcggag gcttggagt tccaggtgtt   1980 gggggccttg gaggtatacc tccagctgca gccgctaaag cagctaaata cggagtggca   2040
gcaagacctg gcttcggatt gtctcccatt ttcccaggtg gggcctgcct ggggaaagct   2100
tgtggccgga agagaaaatg a                                            2121

<210> SEQ ID NO 58
<211> LENGTH: 2158
<212> TYPE: DNA
<213> ORGANISM: Homo sapiens

<400> SEQUENCE: 58
ctccctcttt ccctcacagc cgacgaggca acaattaggc tttggggata aaacgaggtg     60
cggagagcgg gctggggcat ttctccccga gatggcgggt ctgacggcgg cggccccgcg    120
gcccggagtc ctcctgctcc tgctgtccat cctccacccc tctcggcctg gagtctttta    180 tccagggggct ggtctcggag cccttggagg aggagcgctg gggcctggag gcaaaccttct  240 taagccagtt cccggagggc ttgcgggtgc tggccttggg cagggctcg gcgccttccc    300 cgcagttacc tttccggggg ctctggtgcc tggtggagtg gctgacgctg ctgcagccta   360
taaagctgct aaggctggcg ctgggcttgg tggtgtccca ggagttggtg gcttaggagt   420
gtctgcaggt gcggtggttc ctcagcctgg agcggagtg aagcctggga aagtgccggg   480
tgtggggctg ccaggtgtat acccaggtgg cgtgctccca ggagctcggt tccccggtgt   540
gggggtgctc cctggagttc ccactggagc aggagttaag cccaaggctc aggtgtagg    600 tggagctttt gctggaatcc caggagttgg acccttggg ggaccgcaac ctggagtccc    660
actggggtat cccatcaagg cccccaagct gcctggtggc tatggactgc ctacaccac    720 agggaaactg ccctatggct atgggcccgg aggagtggct ggtgcagcgg gcaaggctgg    780
ttacccaaca gggacagggg ttggccccca ggcagcagca gcagcggcag ctaaagcagc    840
agcaaagttc ggtgctggag cagccggagt cctccctggt gttggagggg ctggtgttcc    900
tggagtgcct ggggcaattc ctggagttgg aggcatcgca gctgcagctg cagctgcagc    960
agcagccgct acaggcagcc agtatggagc tgctgcaagc ttggtgcctg ctgggccagg   1020
ctttggcccg ggagtagttg gtgtcccagg agctggcgtt ccaggtgttg gtgtcccagg   1080
agctgggatt ccagttgtcc caggtgctgg gatcccaggt gctgcggttc caggggttgt   1140
gtcaccagaa gcagctgcta aggcagctgc aaaggcagcc aaatacgggg ccaggcccgg   1200
agtcggagtt ggaggcattc ctacttacgg ggttggagct gggggctttc ccggcttttg   1260
tgtcggagtc ggaggtatcc ctggagtcgc aggtgtccct ggtgtcggag gtgttcccgg   1320
agtcggaggt gtcccgggag ttggcatttc ccccgaagct caggcagcag ctgccgccaa   1380
```

```
ggctgccaag tacggagtgg ggaccccagc agctgcagct gctaaagcag ccgccaaagc   1440
cgcccagttt gggttagttc ctggtgtcgg cgtggctcct ggagttggcg tggctcctgg   1500
tgtcggtgtg gctcctggag ttggcttggc tcctggagtt ggcgtggctc ctggagttgg   1560
tgtggctcct ggcgttggcg tggctcccgg cattggccct ggtggagttg cagctgcagc   1620
aaaatccgct gccaaggtgg ctgccaaagc ccagctccga gctgcagctg gcttggtgc    1680 tggcatccct ggacttggag ttggtgtcgg cgtccctgga cttggagttg gtgctggtgt   1740
tcctggactt ggagttggtg ctggtgttcc tggcttcggg gcagtacctg gagccctggc   1800
tgccgctaaa gcagccaaat atggagcagc agtgcctggg gtccttggag ggctcggggc   1860
tctcggtgga gtaggcatcc caggcggtgt ggtgggagcc ggacccgccg ccgccgctgc   1920
cgcagccaaa gctgctgcca aagccgccca gtttggccta gtgggagccg ctgggctcgg   1980
aggactcgga gtcggagggc ttggagttcc aggtgttggg ggccttggag gtatacctcc   2040
agctgcagcc gctaaagcag ctaaatacga gtggcagca agacctggct tcggattgtc   2100
tcccattttc ccaggtgggg cctgcctggg gaaagcttgt ggccggaaga gaaaatga    2158
```

<210> SEQ ID NO 59
<211> LENGTH: 2116
<212> TYPE: DNA
<213> ORGANISM: Homo sapiens

<400> SEQUENCE: 59

```
ctccctctttt ccctcacagc cgacgaggca acaattaggc tttggggata aaacgaggtg     60
cggagagcgg gctggggcat ttctccccga gatggcgggt ctgacggcgg cggccccgcg    120
gcccggagtc ctcctgctcc tgctgtccat cctccacccc tctcggcctg gagtcttttta   180 tccagggct ggtctcggag cccttggagg aggagcgctg gggcctggag caaacctct     240 taagccagtt cccggagggc ttgcgggtgc tggccttggg gcagggctcg gcgccttccc   300
cgcagttacc tttccggggg ctctggtgcc tggtggagtg gctgacgctg ctgcagccta    360
taaagctgct aaggctggcg ctgggcttgg tggtgtccca ggagttggtg gcttaggagt    420
gtctgcaggt gcggtggttc ctcagcctgg agccggagtg aagcctggga aagtgccggg    480
tgtggggctg ccaggtgtat acccaggtgg cgtgctccca ggagctcggt tccccggtgt    540
gggggtgctc cctggagttc ccactggagc aggagttaag cccaaggctc caggtgtagg    600
tggagctttt gctggaatcc caggagttgg acccttttggg ggaccgcaac ctggagtccc   660
actggggtat cccatcaagg ccccccaagct gcctggtggc tatggactgc cctacaccac   720
agggaaactg ccctatggct atgggcccgg aggagtggct ggtgcagcgg gcaaggctgg    780
ttacccaaca gggacagggg ttggcccca ggcagcagca gcagcggcag ctaaagcagc     840
agcaaagttc ggtgctggag cagccggagt cctccctggt gttggagggg ctggtgttcc   900
tggcgtgcct ggggcaattc ctggaattgg aggcatcgca ggcgttggga ctccagctgc   960
agctgcagct gcagcagcag ccgctaaggc agccaagtat ggagctgctg caggcttagt   1020
gcctggtggg ccaggctttg gcccgggagt agttggtgtc caggagctg gcgttccagg   1080 tgttggtgtc ccaggagctg ggattccagt tgtcccaggt gctgggatcc caggtgctgc   1140
ggttccaggg gttgtgtcac cagaagcagc tgctaaggca gctgcaaagg cagccaaata   1200
cggggccagg cccggagtcg gagttggagg cattcctact tacggggttg gagctggggg   1260 cttttcccggc tttggtgtcg gagtcggagg tatccctgga gtcgcaggtg tccctggtgt   1320
```

| | |
|---|---|
| cggaggtgtt cccggagtcg gaggtgtccc gggagttggc atttccccg aagctcaggc | 1380 |
| agcagctgcc gccaaggctg ccaagtacgg gttagttcct ggtgtcggcg tggctcctgg | 1440 |
| agttggcgtg gctcctggtg tcggtgtggc tcctggagtt ggcttggctc ctggagttgg | 1500 |
| cgtggctcct ggagttggtg tggctcctgg cgttggcgtg gctcccggca ttggccctgg | 1560 |
| tggagttgca gctgcagcaa atccgctgc caaggtggct gccaaagccc agctccgagc | 1620 |
| tgcagctggg cttggtgctg gcatccctgg acttggagtt ggtgtcggcg tccctggact | 1680 |
| tggagttggt gctggtgttc ctggacttgg agttggtgct ggtgttcctg gcttcggggc | 1740 |
| agtacctgga gccctggctg ccgctaaagc agccaaatat ggagcagcag tgcctggggt | 1800 |
| ccttggaggg ctcggggctc tcggtggagt aggcatccca ggcggtgtgg tgggagccgg | 1860 |
| acccgccgcc gccgctgccg cagccaaagc tgctgccaaa gccgcccagt ttggcctagt | 1920 |
| gggagccgct gggctcggag gactcggagt cggagggctt ggagttccag gtgttggggg | 1980 |
| ccttggaggt atacctccag ctgcagccgc taaagcagct aaatacggag tggcagcaag | 2040 |
| acctggcttc ggattgtctc ccattttccc aggtggggcc tgcctgggga agcttgtgg | 2100 |
| ccggaagaga aaatga | 2116 |

<210> SEQ ID NO 60
<211> LENGTH: 2064
<212> TYPE: DNA
<213> ORGANISM: Homo sapiens

<400> SEQUENCE: 60

| | |
|---|---|
| atggcgggtc tgacggcggc ggccccgcgg cccggagtcc tcctgctcct gctgtccatc | 60 |
| ctccacccct ctcggcctgg aggggtccct ggggccattc ctggtggagt tcctggagga | 120 |
| gtcttttatc caggggctgg tctcggagcc cttggaggag gagcgctggg gcctggaggc | 180 |
| aaacctctta agccagttcc cggagggctt gcgggtgctg gccttggggc agggctcggc | 240 |
| gccttccccg cagttacctt tccggggget ctggtgcctg gtggagtggc tgacgctgct | 300 |
| gcagcctata agctgctaa ggctggcgct gggcttggtg gtgtcccagg agttggtggc | 360 |
| ttaggagtgt ctgcaggtgc ggtggttcct cagcctggag ccggagtgaa gcctgggaaa | 420 |
| gtgccgggtg tggggctgcc aggtgtatac ccaggtggcg tgctcccagg agctcggttc | 480 |
| cccggtgtgg gggtgctccc tggagttccc actggagcag gagttaagcc caaggctcca | 540 |
| ggtgtaggtg gagcttttgc tggaatccca ggagttggac ctttgggggg accgcaacct | 600 |
| ggagtcccac tggggtatcc catcaaggcc cccaagctgc ctggtggcta ggactgccc | 660 |
| tacaccacag ggaaactgcc ctatggctat gggcccggag gagtggctgg tgcagcgggc | 720 |
| aaggctggtt acccaacagg gacagggggtt ggccccagg cagcagcagc agcggcagct | 780 |
| aaagcagcag caaagttcgg tgctggagca gccggagtcc tccctggtgt ggaggggct | 840 |
| ggtgttcctg gcgtgcctgg ggcaattcct ggaattggag catcgcagg cgttgggact | 900 |
| ccagctgcag ctgcagctgc agcagcagcc gctaaggcag ccaagtatgg agctgctgca | 960 |
| ggcttagtgc ctggtgggcc aggctttggc ccgggagtag ttggtgtccc aggagctggc | 1020 |
| gttccaggtt ttggtatccc aggagctggg attccagttg tcccaggtgc tgggatccca | 1080 |
| ggtgctgcgg ttcaggggt tgtgtcacca gaagcagctg ctaaggcagc tgcaaaggca | 1140 |
| gccaaatacg gggccaggcc cggagtcgga gttggaggca ttcctactta cggggttgga | 1200 |
| gctgggggct ttcccggctt tggtgtcgga gtcgaggta tccctggagt cgcaggtgtc | 1260 |
| cctggtgtcg gaggtgttcc cggagtcgga ggtgtcccgg gagttggcat tccccccgaa | 1320 |

```
gctcaggcag cagctgccgc caaggctgcc aagtacgggt tagttcctgg tgtcggcgtg    1380
gctcctggag ttggcgtggc tcctggtgtc ggtgtggctc ctggagttgg cttggctcct    1440
ggagttggcg tggctcctgg agttggtgtg ctcctggcg ttggcgtggc tcccggcatt     1500
ggccctggtg gagttgcagc tgcagcaaaa tccgctgcca aggtggctgc caaagcccag    1560
ctccgagctg cagctgggct tggtgctggc atccctggac ttggagttgg tgtcggcgtc    1620
cctggacttg gagttggtgc tggtgttcct ggacttggag ttggtgctgg tgttcctggc    1680
ttcggggcag tacctggagc cctggctgcc gctaaagcag ccaaatatgg agcagcagtg    1740 cctgggtcc ttgagggct cggggctctc ggtggagtag gcatcccagg cggtgtggtg      1800
ggagccggac ccgccgccgc cgctgccgca gccaaagctg ctgccaaagc cgcccagttt    1860
ggcctagtgg gagccgctgg gctcggagga ctcggagtcg gagggcttgg agttccaggt    1920
gttgggggcc ttggaggtat acctccagct gcagccgcta aagcagctaa atacggagtg    1980
gcagcaagac ctggcttcgg attgtctccc attttcccag gtggggcctg cctggggaaa    2040
gcttgtggcc ggaagagaaa atga                                           2064

<210> SEQ ID NO 61
<211> LENGTH: 2064
<212> TYPE: DNA
<213> ORGANISM: Homo sapiens

<400> SEQUENCE: 61
atggcgggtc tgacggcggc ggccccgcgg cccggagtcc tcctgctcct gctgtccatc      60
ctccacccct ctcggcctgg aggggtccct ggggccattc ctggtggagt tcctggagga    120 gtctttatc caggggctgg tctcggagcc cttggaggag gagcgctggg gcctggaggc     180
aaacctctta agccagttcc cggagggctt gcgggtgctg gccttggggc agggctcggc    240
gccttccccg cagttacctt tccggggcct ctggtcctg tggagtggc tgacgctgct      300 gcagcctata agctgctaa ggctggcgct gggcttggtg gtgtcccagg agttggtggc     360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacagggtt ggccccagg cagcagcagc agcggcagct       780
aaagcagcag caaagttcgg tgctggagca gccgagtcc tccctggtgt ggaggggct      840 ggtgttcctg gcgtgcctgg ggcaattcct ggaattggag catcgcagg cgttgggact     900 ccagctgcag ctgcagctgc agcagcagcc gctaaggcag ccaagtatgg agctgctgca    960
ggcttagtgc ctggtgggcc aggctttggc ccgggagtag ttggtgtccc aggagctggc   1020
gttccaggtg ttggtgtccc aggagctggg attccagttg tcccaggtgc tgggatccca   1080
ggtgctgcgc ttcagggggt tgtgtcacca gaagcagctc taaggcagc tgcaaaggca    1140 gccaaatacg gggccaggcc cggagtcgga gttggaggca ttcctactta cggggttgga   1200
gctgggggct ttcccggctt tggtgtcgga gtcgaaggta tccctggagt cgcaggtgtc   1260
cctagtgtcg gaggtgttcc cggagtcgga ggtgtcccgg gagttggcat ttcccccgaa   1320
```

```
gctcaggcag cagctgccgc caaggctgcc aagtacgggt tagttcctgg tgtcggcgtg   1380
gctcctggag ttggcgtggc tcctggtgtc ggtgtggctc ctggagttgg cttggctcct   1440
ggagttggcg tggctcctgg agttggtgtg ctcctggcg ttggcgtggc tcccggcatt    1500
ggccctggtg gagttgcagc tgcagcaaaa tccgctgcca aggtggctgc caaagcccag   1560
ctccgagctg cagctgggct tggtgctggc atccctggac ttggagttgg tgtcggcgtc   1620
cctggacttg gagttggtgc tggtgttcct ggacttggag ttggtgctgg tgttcctggc   1680
ttcggggcag tacctggagc cctggctgcc gctaaagcag ccaaatatgg agcagcagtg   1740
cctggggtcc ttggagggct cggggctctc ggtggagtag gcatcccagg cggtgtggtg   1800
ggagccggac ccgccgccgc cgctgccgca gccaaagctg ctgccaaagc cgcccagttt   1860
ggcctagtgg gagccgctgg gctcggagga ctcggagtcg agggcttgg agttccaggt    1920 gttgggggcc ttggaggtat acctccagct gcagccgcta aagcagctaa atacggagtg   1980
gcagcaagac ctggcttcgg attgtctccc attttcccag gtggggcctg cctggggaaa   2040
gcttgtggcc ggaagagaaa atga                                          2064
```

<210> SEQ ID NO 62
<211> LENGTH: 2170
<212> TYPE: DNA
<213> ORGANISM: Homo sapiens

<400> SEQUENCE: 62

```
ctccctcttt ccctcacagc cgacgaggca acaattaggc tttgggata aaacgaggtg     60 cggagagcgg gctggggcat ttctccccga gatggcgggt ctgacggcgg cggccccgcg   120
gcccggagtc ctcctgctcc tgctgtccat cctccacccc tctcggcctg gagtcttta    180 tccaggggct ggtctcggag cccttggagg aggagcgctg gggcctggag caaacctct    240 taagccagtt cccggagggc ttgcgggtgc tggccttggg cagggctcg cgccttccc     300 cgcagttacc tttccggggg ctctggtgcc tggtggagtg gctgacgctg ctgcagccta   360
taaagctgct aaggctggcg ctgggcttgg tggtgtccca ggagttggtg gcttaggagt   420
gtctgcaggt gcggtggttc ctcagcctgg agcggagtg aagcctggga aagtgccggg    480
tgtggggctg ccaggtgtat acccaggtgg cgtgctccca ggagctcggt tccccggtgt   540
gggggtgctc cctggagttc ccactggagc aggagttaag cccaaggctc aggtgtagg    600 tggagctttt gctggaatcc caggagttgg acccttggg ggaccgcaac ctggagtccc    660 actgggtat cccatcaagg cccccaagct gcctggtggc tatggactgc cctacaccac    720
agggaaactg ccctatggct atgggcccgg aggagtggct ggtgcagcgg gcaaggctgg   780
ttacccaaca gggacagggg ttggcccca ggcagcagca gcagcggcag ctaaagcagc    840
agcaaagttc ggtgctggag cagccggagt cctccctggt gttggagggg ctggtgttcc   900
tggcgtgcct ggggcaattc ctggaattgg aggcatcgca ggcgttggga ctccagctgc   960
agctgcagct gcagcagcag ccgctaaggc agccaagtat ggagctgctg caggcttagt  1020
gcctggtggg ccaggctttg gcccgggagt agttggtgtc ccaggagctg gcgttccagg  1080
tgttggtgtc ccaggagctg ggattccagt tgtcccaggt gctgggatcc caggtgctgc  1140
ggttccaggg gttgtgtcac cagaagcagc tgctaaggca gctgcaaagg cagccaaata  1200
cggggccagg cccggagtcg gagttggagg cattcctact tacggggttg gagctggggg  1260
cttccccggc tttggtgtcg gagtcggagg tatccctgga gtcgcaggtg tcctggtgt   1320 cggaggtgtt cccggagtcg gaggtgtccc gggagttggc atttccccg aagctcaggc   1380
```

```
agcagctgcc gccaaggctg ccaagtacgg gttagttcct ggtgtcggcg tggctcctgg    1440
agttggcgtg gctcctggtg tcggtgtggc tcctggagtt ggcttggctc ctggagttgg    1500
cgtggctcct ggagttggtg tggctcctgg cgttggcgtg gctcccggca ttggccctgg    1560
tggagttgca gctgcagcaa atccgctgc caaggtggct gccaaagccc agctccgagc     1620
tgcagctggg cttggtgctg gcatccctgg acttggagtt ggtgtcggcg tccctggact    1680
tggagttggt gctggtgttc ctggacttgg agttggtgct ggtgttcctg gcttcggggc    1740
agtacctgga gccctggctg ccgctaaagc agccaaatat ggagcagcag tgcctggggt    1800
ccttggaggg ctcggggctc tcggtggagt aggcatccca ggcggtgtgg tgggagccgg    1860
acccgccgcc gccgctgccg cagccaaagc tgctgccaaa gccgcccagt tggcctagt     1920 gggagccgct gggctcggag gactcggagt cggagggctt ggagttccag tgttgggggg    1980
ccttggaggt atacctccag ctgcagccgc taaagcagct aaatacggtg ctgctggcct    2040 tgaggtgtc ctaggggtg ccgggcagtt cccacttgga ggagtggcag caagacctgg     2100
cttcggattg tctcccattt tcccaggtgg ggcctgcctg gggaaagctt gtggccggaa    2160
gagaaaatga                                                           2170

<210> SEQ ID NO 63
<211> LENGTH: 2170
<212> TYPE: DNA
<213> ORGANISM: Homo sapiens

<400> SEQUENCE: 63
ctccctcttt ccctcacagc cgacgaggca acaattaggc tttggggata aaacgaggtg      60
cggagagcgg gctggggcat ttctccccga gatggcgggt ctgacggcgg cggccccgcg     120
gcccggagtc ctcctgctcc tgctgtccat cctccacccc tctcggcctg gagtcttta     180 tccagggct ggtctcggag cccttggagg aggagcgctg gggcctggag gcaaacctct     240
taagccagtt cccggagggc ttgcgggtgc tggccttggg gcagggctcg gcgccttccc    300
cgcagttacc tttccggggg ctctggtgcc tggtggagtg gctgacgctg ctgcagccta    360
taaagctgct aaggctggcg ctgggcttgg tggtgtccca ggagttggtg gcttaggagt    420
gtctgcaggt gcggtggttc ctcagcctgg agcggagtg aagcctggga aagtgccggg     480 tgtgggctg ccaggtgtat acccaggtgg cgtgctccca ggagctcggt tccccggtgt     540
gggggtgctc cctggagttc ccactggagc aggagttaag cccaaggctc caggtgtagg    600
tggagctttt gctggaatcc caggagttgg accctttggg ggaccgcaac ctggagtccc    660
actggggtat cccatcaagg cccccaagct gcctggtggc tatggactgc cctacaccac    720
agggaaactg ccctatggct atgggccgg aggagtggct ggtgcagcgg caaggctgg      780 ttacccaaca gggacagggg ttggcccca ggcagcagca gcagcggcag ctaaagcagc     840
agcaaagttc ggtgctggag cagccggagt cctcctggt gttggagggg ctggtgttcc    900
tggcgtgcct ggggcaattc ctggaattgg aggcatcgca ggcgttggga ctccagctgc    960
agctgcagct gcagcagcag ccgctaaggc agccaagtat ggagctgctg caggcttagt   1020
gcctggtggg ccaggcttg gcccgggagt agttggtgtc ccaggagctg gcgttccagg    1080
tgttggtgtc ccaggagctg ggattccagt tgtcccaggt gctgggatcc caggtgctgc    1140
ggttccaggg gttgtgtcac cagaagcagc tgctaaggca gctgcaaagg cagccaaata   1200
cggggccagg cccggagtcg gagttggagg cattcctact tacggggttg gagctggggg   1260
```

| | |
|---|---|
| ctttcccggc tttggtgtcg gagtcggagg tatccctgga gtcgcaggtg tccctggtgt | 1320 |
| cggaggtgtt cccggagtcg gaggtgtccc gggagttggc atttcccccg aagctcaggc | 1380 |
| agcagctgcc gccaaggctg ccaagtacgg gttagttcct ggtgtcggcg tggctcctgg | 1440 |
| agttggcgtg gctcctggtg tcggtgtggc tcctggagtt ggcttggctc ctggagttgg | 1500 |
| cgtggctcct ggagttggtg tggctcctgg cgttggcgtg gctcccggca ttggccctgg | 1560 |
| tggagttgca gctgcagcaa atccgctgc caaggtggct gccaaagccc agctccgagc | 1620 |
| tgcagctggg cttggtgctg gcatccctgg acttggagtt ggtgtcggcg tccctggact | 1680 |
| tggagttggt gctggtgttc ctggacttgg agttggtgct ggtgttcctg gcttccgggc | 1740 |
| agtacctgga gccctggctg ccgctaaagc agccaaatat ggagcagcag tgcctggggt | 1800 |
| ccttggaggg ctcggggctc tcggtggagt aggcatccca ggcggtgtgg tgggagccgg | 1860 |
| acccgccgcc gccgctgccg cagccaaagc tgctgccaaa gtcgcccagt ttggcctagt | 1920 |
| gggagccgct gggctcggag gactcggagt cggagggctt ggagttccag gtgttggggg | 1980 |
| ccttggaggt atacctccag ctgcagccgc taaagcagct aaatacggtg ctgctggcct | 2040 |
| tggaggtgtc ctaggggtg ccgggcagtt cccacttgga ggagtggcag caagacctgg | 2100 |
| cttcggattg tctcccattt tcccaggtgg ggcctgcctg gggaaagctt gtggccggaa | 2160 |
| gagaaaatga | 2170 |

<210> SEQ ID NO 64
<211> LENGTH: 2118
<212> TYPE: DNA
<213> ORGANISM: Homo sapiens

<400> SEQUENCE: 64

| | |
|---|---|
| atggcgggtc tgacggcggc ggccccgcgg cccggagtcc tcctgctcct gctgtccatc | 60 |
| ctccacccct ctcggcctgg aggggtccct ggggccattc ctggtggagt tcctggagga | 120 |
| gtcttttatc caggggctgg tctcggagcc cttggaggag gagcgctggg gcctggaggc | 180 |
| aaacctctta agccagttcc cggagggctt gcgggtgctg gccttggggc agggctcggc | 240 |
| gccttccccg cagttacctt tccggggct ctggtgcctg gtggagtggc tgacgctgct | 300 |
| gcagcctata agctgctaa ggctggcgct gggcttggtg gtgtcccagg agttggtggc | 360 |
| ttaggagtgt ctgcaggtgc ggtggttcct cagcctggag ccggagtgaa gcctgggaaa | 420 |
| gtgccgggtg tggggctgcc aggtgtatac ccaggtggcg tgctcccagg agctcggttc | 480 |
| cccggtgtgg gggtgctccc tggagttccc actggagcag gagttaagcc caaggctcca | 540 |
| ggtgtaggtg gagcttttgc tggaatccca ggagttggac cctttggggg accgcaacct | 600 |
| ggagtcccac tggggtatcc catcaaggcc cccaagctgc ctggtggcta tggactgccc | 660 |
| tacaccacag ggaaactgcc ctatggctat gggcccggag gagtggctgg tgcagcgggc | 720 |
| aaggctggtt acccaacagg gacaggggtt ggccccccagg cagcagcagc agcggcagct | 780 |
| aaagcagcag caaagttcgg tgctggagca gccggagtcc tccctggtgt tggaggggct | 840 |
| ggtgttcctg gcgtgcctgg ggcaattcct ggaattggag gcatcgcagg cgttgggact | 900 |
| ccagctgcag ctgcagctgc agcagcagcc gctaaggcag ccaagtatgg agctgctgca | 960 |
| ggcttagtgc ctggtgggcc aggctttggc ccgggagtag ttggtgtccc aggagctggc | 1020 |
| gttccaggtg ttggtgtccc aggagctggg attccagttg tcccaggtgc tgggatccca | 1080 |
| ggtgctgcgg ttcagggggt tgtgtcacca gaagcagctg ctaaggcagc tgcaaaggca | 1140 |
| gccaaatacg gggccaggcc cggagtcgga gttggaggca ttcctactta cggggttgga | 1200 |

```
gctgggggct tcccggctt tggtgtcgga gtcggaggta tccctggagt cgcaggtgtc   1260
cctagtgtcg gaggtgttcc cggagtcgga ggtgtcccgg agttggcat ttcccccgaa    1320 gctcaggcag cagctgccgc caaggctgcc aagtacgggt tagttcctgg tgtcggcgtg   1380
gctcctggag ttggcgtggc tcctggtgtc ggtgtggctc ctggagttgg cttggctcct   1440
ggagttggcg tggctcctgg agttggtgtg ctcctggcg ttggcgtggc tcccggcatt    1500
ggccctggtg gagttgcagc tgcagcaaaa tccgctgcca aggtggctgc caaagcccag   1560
ctccgagctg cagctgggct tggtgctggc atccctggac ttggagttgg tgtcggcgtc   1620 cctgacttg gagttggtgc tggtgttcct ggacttggag ttggtgctgg tgttcctggc    1680
ttcggggcag tacctggagc cctggctgcc gctaaagcag ccaaatatgg agcagcagtg   1740 cctgggtcc ttggagggct cggggctctc ggtggagtag gcatcccagg cggtgtggtg    1800
ggagccggac ccgccgccgc cgctgccgca gccaaagctg ctgccaaagc cgcccagttt   1860
ggcctagtgg gagccgctgg gctcggagga ctcggagtcg gagggcttgg agttccaggt   1920
gttgggggcc ttggaggtat acctccagct gcagccgcta aagcagctaa atacggtgct   1980
gctggccttg gaggtgtcct aggggtgcc gggcagttcc cacttggagg agtggcagca    2040
agacctggct tcggattgtc tcccattttc ccaggtgggg cctgcctggg gaaagcttgt   2100
ggccggaaga gaaaatga                                                2118

<210> SEQ ID NO 65
<211> LENGTH: 2019
<212> TYPE: DNA
<213> ORGANISM: Homo sapiens

<400> SEQUENCE: 65
atggcgggtc tgacggcggc ggccccgcgg cccggagtcc tcctgctcct gctgtccatc     60
ctccacccct ctcggcctgg aggggtccct ggggccattc tggtggagt tcctggagga    120 gtctttatc caggggctgg tctcggagcc cttggaggag gagcgctggg gcctggaggc     180
aaacctctta agccagttcc cggagggctt gcgggtgctg gccttggggc agggctcggc    240
gccttccccg cagttacctt tccggggget ctggtgcctg tggagtggc tgacgctgct    300 gcagcctata agctgctaa ggctggcgct gggcttggtg gtgtcccagg agttggtggc     360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacaggggtt ggccccaagg cagcagcagc agcggcagct    780
aaagcagcag caaagttcgg tgctggagca gccggagtcc tccctggtgt ggagggggct    840
ggtgttcctg gcgtgcctgg ggcaattcct ggaattggag gcatcgcagg cgttgggact    900
ccagctgcag ctgcagctgc agcagcagcc gctaaggcag ccaagtatgg agctgctgca    960
ggcttagtgc ctggtgggcc aggctttggc ccgggagtag ttggtgtccc aggagctggc   1020
gttccaggtg ttggtgtccc aggagctggg attccagttg tcccaggtgc tgggatccca   1080
ggtgctgcgg ttccagggtgt tgtgtcacca gaagcagctg ctaaggcagc tgcaaaggca   1140
```

```
gccaaatacg gggccaggcc cggagtcgga gttggaggca ttcctactta cggggttgga      1200
gctgggggct ttcccggctt tggtgtcgga gtcggaggta tccctggagt cgcaggtgtc      1260
cctggtgtcg gaggtgttcc cggagtcgga ggtgtcccgg agttggcat  ttcccccgaa      1320 gctcaggcag cagctgccgc caaggctgcc aagtacgggt tagttcctgg tgtcggcgtg      1380
gctcctggag ttggcgtggc tcctggtgtc ggtgtggctc ctggagttgg cttggctcct      1440
ggagttggcg tggctcctgg agttggtgtg gctcctggcg ttggcgtggc tcccggcatt      1500
ggccctggtg agttgcagg  agctgcagct gggcttggtg ctggcatccc tggacttgga      1560
gttggtgtcg gcgtccctgg acttggagtt ggtgctggtg ttcctggact tggagttggt      1620
gctggtgttc ctggcttcgg ggcagtacct ggagccctgg ctgccgctaa agcagccaaa      1680
tatggagcag cagtgcctgg ggtccttgga gggctcgggg ctctcggtgg agtaggcatc      1740
ccaggcggtg tggtgggagc cggacccgcc gccgccgctg ccgcagccaa agctgctgcc      1800
aaagccgccc agtttggcct agtgggagcc gctgggctcg gaggactcgg agtcggaggg      1860
cttggagttc aggtgttgg  gggccttgga ggtataccctc cagctgcagc cgctaaagca      1920
gctaaatacg gagtggcagc aagacctggc ttcggattgt ctcccatttt cccaggtggg      1980
gcctgcctgg ggaaagcttg tggccggaag agaaaatga                            2019

<210> SEQ ID NO 66
<211> LENGTH: 2134
<212> TYPE: DNA
<213> ORGANISM: Homo sapiens

<400> SEQUENCE: 66
ctccctcttt ccctcacagc cgacgaggca acaattaggc tttggggata aaacgaggtg        60
cggagagcgg gctggggcat ttctccccga gatggcgggt ctgacggcgg cggccccgcg       120
gcccggagtc ctcctgctcc tgctgtccat cctccacccc tctcggcctg gagtcttttta     180 tccaggggct ggtctcggag cccttggagg aggagcgctg gggcctggag caaacctct       240 taagccaggg ctcggcgcct tccccgcagt tacctttccg gggctctgg  tgcctggtgg      300 agtggctgac gctgctgcag cctataaagc tgctaaggct ggcgctgggc ttggtggtgt      360
cccaggagtt ggtggcttag gagtgtctgc aggtgcggtg gttcctcagc ctggagccgg      420
agtgaagcct gggaaagtgc cgggtgtggg gctgccaggt gtatacccag gtggcgtgct      480
cccaggagct cggttccccg gtgtgggggt gctccctgga gttcccactg gagcaggagt      540
taagcccaag gctccaggtg taggtggagc ttttgctgga atcccaggag ttggaccctt      600
tgggggaccg caacctggag tcccactggg gtatcccatc aaggcccca  agctgcctgg      660 tggctatgga ctgccctaca ccacagggaa actgccctat ggctatgggc cggaggagt       720 ggctggtgca gcgggcaagg ctggttaccc aacagggaca ggggttggcc cccaggcagc      780
agcagcagcg gcagctaaag cagcagcaaa gttcggtgct ggagcagccg gagtcctccc      840
tggtgttgga ggggctggtg ttcctggcgt gcctgggca  attcctggaa ttggaggcat      900
cgcaggcgtt gggactccag ctgcagctgc agctgcagca gcagccgcta aggcagccaa      960
gtatggagct gctgcaggct tagtgcctgg tgggccaggc tttggcccgg agtagttgg      1020 tgtcccagga gctggcgttc caggtgttgg tgtcccagga gctgggattc cagttgtccc     1080
aggtgctggg atcccaggtg ctgcggttcc agggggttgtg tcaccagaag cagctgctaa      1140
ggcagctgca aaggcagcca aatacggggc caggcccgga gtcggagttg gaggcattcc      1200
tacttacggg gttggagctg ggggctttcc cggctttggt gtcggagtcg gaggtatccc      1260
```

-continued

```
tggagtcgca ggtgtccctg gtgtcggagg tgttcccgga gtcggaggtg tcccgggagt    1320
tggcatttcc cccgaagctc aggcagcagc tgccgccaag gctgccaagt acgggttagt    1380
tcctggtgtc ggcgtggctc ctggagttgg cgtggctcct ggtgtcggtg tggctcctgg    1440
agttggcttg gctcctggag ttggcgtggc tcctggagtt ggtgtggctc ctggcgttgg    1500
cgtggctccc ggcattggcc ctggtggagt tgcagctgca gcaaaatccg ctgccaaggt    1560
ggctgccaaa gcccagctcc gagctgcagc tgggcttggt gctggcatcc ctggacttgg    1620
agttggtgtc ggcgtccctg gacttggagt tggtgctggt gttcctggac ttggagttgg    1680
tgctggtgtt cctggcttcg gggcagtacc tggagccctg gctgccgcta aagcagccaa    1740
atatggagca gcagtgcctg gggtccttgg agggctcggg gctctcggtg gagtaggcat    1800
cccaggcggt gtggtgggag ccggacccgc cgccgccgct gccgcagcca agctgctgc    1860 caaagccgcc cagtttggcc tagtgggagc cgctgggctc ggaggactcg gagtcggagg    1920
gcttggagtt ccaggtgttg ggggccttgg aggtatacct ccagctgcag ccgctaaagc    1980
agctaaatac ggtgctgctg gccttggagg tgtcctaggg ggtgccgggc agttcccact    2040
tggaggagtg gcagcaagac ctggcttcgg attgtctccc attttcccag gtggggcctg    2100
cctggggaaa gcttgtggcc ggaagagaaa atga    2134
```

<210> SEQ ID NO 67
<211> LENGTH: 2092
<212> TYPE: DNA
<213> ORGANISM: Homo sapiens

<400> SEQUENCE: 67

```
ctccctcttt ccctcacagc cgacgaggca acaattaggc tttggggata aaacgaggtg      60
cggagagcgg gctggggcat ttctccccga gatggcgggt ctgacggcgg cggccccgcg     120
gcccggagtc ctcctgctcc tgctgtccat cctccacccc tctcggcctg gagtcttta     180 tccaggggct ggtctcggag cccttggagg aggagcgctg gggcctggag gcaaacctct     240
taagccaggg ctcggcgcct tccccgcagt tacctttccg ggggctctgg tgcctggtgg     300
agtggctgac gctgctgcag cctataaagc tgctaaggct ggcgctgggc ttggtggtgt     360
cccaggagtt ggtggcttag gagtgtctgc aggtgcggtg gttcctcagc ctggagccgg     420
agtgaagcct gggaaagtgc cgggtgtggg gctgccaggt gtataccag gtggcgtgct     480 cccaggagct cggttccccg gtgtgggggt gctccctgga gttcccactg gagcaggagt     540
taagcccaag gctccaggtg taggtggagc ttttgctgga atcccaggag ttggaccctt     600 tggggaccg caacctggag tcccactggg gtatcccatc aaggccccca gctgcctgg     660 ctatgggccc ggaggagtgg ctggtgcagc gggcaaggct ggttacccaa caggacagg     720 ggttggcccc caggcagcag cagcagcggc agctaaagca gcagcaaagt tcggtgctgg     780
agcagccgga gtcctccctg tgttggaggg gctggtgtt cctggcgtgc ctggggcaat     840
tcctggaatt ggaggcatcg caggcgttgg gactccagct gcagctgcag ctgcagcagc     900
agccgctaag gcagccaagt atggagctgc tgcaggctta gtgcctggtg gccaggctt     960 tggcccggga gtagttggtg tcccaggagc tggcgttcca ggtgttggtg tcccaggagc    1020
tgggattcca gttgtcccag gtgctgggat cccaggtgct gcggttccag gggttgtgtc    1080
accagaagca gctgctaagg cagctgcaaa ggcagccaaa tacggggcca ggcccggagt    1140
cggagttgga ggcattccta cttacggggt tggagctggg ggctttcccg gctttggtgt    1200
```

```
cggagtcgga ggtatccctg gagtcgcagg tgtccctggt gtcggaggtg ttcccggagt      1260
cggaggtgtc ccgggagttg gcatttcccc cgaagctcag gcagcagctg ccgccaaggc      1320
tgccaagtac gggttagttc ctggtgtcgg cgtggctcct ggagttggcg tggctcctgg      1380
tgtcggtgtg gctcctggag ttggcttggc tcctggagtt ggcgtggctc ctggagttgg      1440
tgtggctcct ggcgttggcg tggctcccgg cattggccct ggtggagttg cagctgcagc      1500
aaaatccgct gccaaggtgg ctgccaaagc ccagctccga gctgcagctg gcttggtgc       1560 tggcatccct ggacttggag ttggtgtcgg cgtccctgga cttggagttg gtgctggtgt      1620
tcctggactt ggagttggtg ctggtgttcc tggcttcggg gcagtacctg gagccctggc      1680
tgccgctaaa gcagccaaat atggagcagc agtgcctggg gtccttggag ggctcggggc      1740
tctcggtgga gtaggcatcc caggcggtgt ggtgggagcc ggacccgccg ccgccgctgc      1800
cgcagccaaa gctgctgcca aagccgccca gtttggccta gtgggagccg ctgggctcgg      1860
aggactcgga gtcggagggc ttggagttcc aggtgttggg ggccttggag gtatacctcc      1920
agctgcagcc gctaaagcag ctaaatacgg tgctgctggc cttggaggtg tcctaggggg      1980
tgccgggcag ttcccacttg gaggagtggc agcaagacct ggcttcggat tgtctcccat      2040
tttcccaggt ggggcctgcc tggggaaagc ttgtggccgg aagagaaaat ga              2092

<210> SEQ ID NO 68
<211> LENGTH: 2128
<212> TYPE: DNA
<213> ORGANISM: Homo sapiens

<400> SEQUENCE: 68
ctccctcttt ccctcacagc cgacgaggca acaattaggc tttggggata aaacgaggtg        60
cggagagcgg gctggggcat ttctccccga gatggcgggt ctgacggcgg cggccccgcg       120
gcccggagtc ctcctgctcc tgctgtccat cctccacccc tctcggcctg gagtcttta       180 tccaggggct ggtctcggag cccttggagg aggagcgctg gggcctggag gcaaacctct      240
taagccagtt cccggagggc ttgcgggtgc tggccttggg gcagggctcg gcgccttccc       300
cgcagttacc tttccgggggg ctctggtgcc tggtggagtg gctgacgctg ctgcagccta      360
taaagctgct aaggctggcg ctgggcttgg tggtgtccca ggagttggtg gcttaggagt       420
gtctgcaggt gcggtggttc ctcagcctgg agcggagtg aagcctggga aagtgccggg       480
tgtggggctg ccaggtgtat acccaggtgg cgtgctccca ggagctcggt tccccggtgt       540 ggggggtgctc cctggagttc ccactggagc aggagttaag cccaaggctc caggtgtagg       600
tggagctttt gctggaatcc caggagttgg acccttggg ggaccgcaac ctggagtccc        660
actggggtat cccatcaagg cccccaagct gcctggtggc tatggactgc cctacaccac       720
agggaaactg ccctatggct atgggcccgg aggagtggc ggtgcagcgg gcaaggctgg       780
ttacccaaca gggacagggg ttggccccca ggcagcagca gcagcggcag ctaaagcagc       840
agcaaagttc ggtgctggag cagccggagt cctccctggt gttggagggg ctggtgttcc       900
tggcgtgcct ggggcaattc ctggaattgg aggcatcgca ggcgttggga ctccagctgc       960
agctgcagct gcagcagcag ccgctaaggc agccaagtat ggagctgctg caggcttagt     1020
gcctggtggg ccaggctttg gcccgggagt agttggtgtc ccaggagctg cgttccagg       1080 tgttggtgtc ccaggagctg ggattccagt tgtcccaggt gctgggatcc caggtgctgc       1140
ggttccaggg gttgtgtcac cagaagcagc tgctaaggca gctgcaaagg cagccaaata     1200
cggggccagg cccggagtcg gagttggagg cattcctact tacggggttg gagctggggg       1260
```

```
ctttcccggc tttggtgtcg gagtcggagg tatccctgga gtcgcaggtg tccctggtgt    1320
cggaggtgtt cccggagtcg gaggtgtccc gggagttggc atttcccccg aagctcaggc    1380
agcagctgcc gccaaggctg ccaagtacgg agtggggacc ccagcagctg cagctgctaa    1440
agcagccgcc aaagccgccc agtttgggtt agttcctggt gtcggcgtgg ctcctggagt    1500
tggcgtggct cctggtgtcg gtgtggctcc tggagttggc ttggctcctg gagttggcgt    1560
ggctcctgga gttggtgtgg ctcctggcgt tggcgtggct cccggcattg ccctggtgg    1620 agttgcagct gcagcaaaat ccgctgccaa ggtggctgcc aaagcccagc tccgagctgc    1680
agctgggctt ggtgctggca tccctggact tggagttggt gtcggcgtcc ctggacttgg    1740
agttggtgct ggtgttcctg acttggagt tggtgctggt gttcctggct cggggcagt    1800 acctggagcc ctggctgccg ctaaagcagc caaatatgga gcagcagtgc ctggggtcct    1860
tggagggctc ggggctctcg gtggagtagg catcccaggc ggtgtggtgg gagccggacc    1920
cgccgccgcc gctgccgcag ccaaagctgc tgccaaagcc gcccagtttg gcctagtggg    1980
agccgctggg ctcggaggac tcggagtcgg agggcttgga gttccaggtg ttggggggcct    2040 tggaggtata cctccagctg cagccgctaa agcagctaaa tacggtgggg cctgcctggg    2100
gaaagcttgt ggccggaaga gaaaatga                                      2128

<210> SEQ ID NO 69
<211> LENGTH: 2190
<212> TYPE: DNA
<213> ORGANISM: Homo sapiens

<400> SEQUENCE: 69
atggcgggtc tgacggcggc ggccccgcgg cccggagtcc tcctgctcct gctgtccatc      60
ctccacccct ctcggcctgg agggggtccct ggggccattc ctggtggagt tcctggagga   120
gtcttttatc caggggctgg tctcggagcc cttggaggag gagcgctggg gcctggaggc   180
aaacctctta agccagttcc cggagggctt gcgggtgctg gccttggggc agggctcggc   240
gccttccccg cagttacctt tccgggggct ctggtgcctg gtggagtggc tgacgctgct   300
gcagcctata agctgctaa ggctggcgct gggcttggtg gtgtcccagg agttggtggc   360
ttaggagtgt ctgcagcccc ttctgtgcct cgtgcggtgg ttcctcagcc tgcagccgga   420
gtgaagcctg tgaaagtgcc gggtgtgggg ctgccaggtg tataccaggt ggcgtgctc   480 ccaggagctc ggttccccgg tgtgggggtg ctccctggag ttcccactgg agcaggagtt   540
aagcccaagg ctcaggtgt aggtggagct tttgctggaa tcccaggagt tggacccttt   600 ggggaccgc aacctggagt cccactgggg tatcccatca aggcccccaa gctgcctggt   660
ggctatggac tgccctacac cacagggaaa ctgccctatg ctatgggcc ggaggagtg   720 gctggtgcag cggggcaaggc tggttaccca acagggacag gggttggccc ccaggcagca   780
gcagcagcgg cagctaaagc agcagcaaag ttcggtgctg gagcagccgg agtcctccct   840
ggtgttggag gggctggtgt tcctggcgtg cctggggcaa ttcctggaat tggaggcatc   900
gcaggcgttg ggactccagc tgcagctgca gctgcagcag cagccgctaa ggcagccaag   960 tatgagctg ctgcaggctt agtgcctggt gggccaggct ttggcccggg agtagttgg   1020 gtcccaggag ctggcgttcc aggtgttggt gtcccaggag ctgggattcc agttgtccca   1080
ggtgctggga tccaggtgc tgcggttcca ggggttgtgt caccagaagc agctgctaag   1140
gcagctgcaa aggcagccaa atacgggggcc aggcccggag tcggagttgg aggcattcct   1200
```

```
acttacgggg ttggagctgg gggctttccc ggctttggtg tcggagtcgg aggtatccct    1260
ggagtcgcag gtgtccctgg tgtcggaggt gttcccggag tcggaggtgt cccgggagtt    1320
ggcatttccc ccgaagctca ggcagcagct gccgccaagg ctgccaagta cggagtgggg    1380
accgcagcag ctgcggctgc tgaagcagcc gccaaagccg cccagtatgg gttagttcct    1440
ggtgtcggcg tggctcctgg agttggcgtg gctcctggtg tcggtgtggc tcctggagtt    1500
ggcttggctc ctggagttgg cgtggctcct ggagttggtg tggctcctgg cgttggcgtg    1560
gctcccggca ttggccctgg tggagttgca gctgcagcaa atccgctgc caaggtggct    1620 gccaaagccc agctccgagc tgcagctggg cttggtgctg gcatccctgg acttggagtt    1680
ggtgtcggcg tccctggact tggagttggt gctggtgttc ctggacttgg agttggtgct    1740
ggtgttcctg gcttcgggc agtacctgga gccctggctg ccgctaaagc agccaaatat    1800
ggagcagcag tgcctggggt ccttggaggg ctcggggctc tcggtggagt aggcatccca    1860
ggcggtgtgg tgggagccgg acccgccgcc gccgctgccg cagccaaagc tgctgccaaa    1920
gccgcccagt ttggcctagt gggagccgct gggctcggag gactcggagt cggagggctt    1980
ggagttccag gtgttggggg ccttggaggt atacctccag ctgcagccgc taaagcagct    2040
aaatacggtg ctgctggcct tggaggtgtc ctaggggtg ccgggcagtt cccacttgga    2100
ggagtggcag caagacctgg cttcggattg tctcccattt tcccaggtgg ggcctgcctg    2160
gggaaagctt gtggccggaa gagaaaatga                                     2190

<210> SEQ ID NO 70
<211> LENGTH: 2037
<212> TYPE: DNA
<213> ORGANISM: Homo sapiens

<400> SEQUENCE: 70
atggcgggtc tgacggcggc ggccccgcgg cccggagtcc tcctgctcct gctgtccatc     60
ctccacccct ctcggcctgg aggggtccct ggggccattc ctggtggagt tcctggagga    120
gtcttttatc caggggctgg tctcggagcc cttggaggag gagcgctggg gcctggaggc    180
aaacctctta agccagttcc cggagggctt gcggtgctg gccttggggc agggctcggc    240
gccttccccg cagttacctt tccgggggct ctggtgcctg gtggagtggc tgacgctgct    300
gcagcctata aagctgctaa ggctggcgct gggcttggtg gtgtcccag agttggtggc    360 ttaggagtgt ctgcaggtgc ggtggttcct cagcctggag ccggagtgaa gcctgggaaa    420
gtgccgggtc tggggctgcc aggtgtatac ccaggtggcg tgctcccag agctcggttc    480 cccggtgtgg ggtgctcccc tggagttccc actggagcag gagttaagcc caaggctcca    540
ggtgtaggtg agcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacagggggtt ggccccccagg cagcagcagc agcggcagct    780
aaagcagcag caaagttcgg tgctggagca gactgagacc tccctggtgt tggagggggct    840 ggtgttcctg gcgtgcctgg gcaattcct ggaattggag catcgcagg cgttggagct    900 ccagctgcag ctgcagctgc agcagcagcc gctaaggcag ccaagtatgg agctgctgca    960
ggcttagtgc ctggtggggcc aggctttggc ccgggagtag ttggtgtccc aggagctggc    1020
gttccaggtg ttggtgtccc aggagctggg attccagttg tcccaggtgc tgggatccca    1080
ggtgctgcgg ttccaggggt tgtgtcacca gaagcagctg ctaaggcagc tgcaaaggca    1140
```

```
gccaaatacg gggccaggcc cggagtcgga gttggaggca ttcctactta cggggttgga   1200
gctgggggct ttcccggctt tggtgtcgga gtcggaggta tccctggagt cgcaggtgtc   1260
cctggtgtcg gaggtgttcc cggagtcgga ggtgtcccgg gagttggcat tcccccgaa    1320 gctcaggcag cagctgccgc caaggctgcc aagtacggga tggggacccc agcagctgca   1380
gctgctaaag cagccgccaa agccgcccag tttgggttag ttcctggtgt cggcgtggct   1440
cctggagttg gcgtggctcc tggtgtcggt gtggctcctg gagttggctt ggctcctgga   1500
gttggcgtgg ctcctggagt tggtgtggct cctggcgttg gcgtggctcc cggcattggc   1560
cctggtggag ttgcagctgc agcaaaatcc gctgccaagg tggctgccaa agcccagctc   1620
cgagctgcag ctgggcttgg tgctggcatc cctggacttg gagttggtgt cggcgtccct   1680
ggacttggag ttggtgctgg tgttcctgga cttggagttg gtgctggtgt tcctggcttc   1740
ggggcagtac ctggagccct ggctgccgct aaagcagcca aatatggagc agcagtgcct   1800
ggggtccttg gagggctcgg ggctctcggt ggagtaggca tcccaggcgg tgtggtggga   1860
gccggacccg ccgccgccgc tgccgcagcc aaagctgctg ccaaagccgc ccagtttggc   1920
ctagtgggag ccgctgggct cggaggactc ggagtcggag gcttggagt tccaggtgtt    1980 gggggccttg gaggtggggc ctgcctgggg aaagcttgtg gccggaagag aaaatga      2037

<210> SEQ ID NO 71
<211> LENGTH: 2037
<212> TYPE: DNA
<213> ORGANISM: Homo sapiens

<400> SEQUENCE: 71
atggcgggtc tgacggcggc ggccccgcgg cccggagtcc tcctgctcct gctgtccatc    60
ctccacccct ctcggcctgg aggggtccct ggggccattc tggtggagt tcctggagga    120 gtctttttatc caggggctgg tctcggagcc cttggaggag gagcgctggg gcctggaggc   180
aaacctctta agccagttcc cggagggctt gcgggtgctg gccttggggc agggctcggc   240
gccttccccg cagttacctt tccgggggct ctggtgcctg gtggagtggc tgacgctgct   300
gcagcctata aagctgctaa ggctggcgct gggcttggtg gtgtcccagg agttggtggc   360
ttaggagtgt ctgcaggtgc ggtggttcct cagcctggag ccggagtgaa gcctgggaaa   420
gtgccgggtg tgggctgcc aggtgtatac ccaggtggcg tgctcccagg agctcggttc   480
cccggtgtgg ggtgctccc tggagttccc actggagcag gagttaagcc caaggctcca   540
ggtgtaggtg gagcttttgc tggaatccca ggagttggac cctttggggg accgcaacct   600
ggagtcccac tggggtatcc catcaaggcc cccaagctgc ctggtggcta tggactgccc   660
tacaccacag ggaaactgcc ctatggctat gggcccggag gagtggctgg tgcagcgggc   720
aaggctggtt acccaacagg gacagggtt ggccccccagg cagcagcagc agcggcagct   780
aaagcagcag caaagttcgg tgctggagca gccgagtcc tcctggtgt tggaggggct    840 ggtgttcctg gcgtgcctgg ggcaattcct ggaattggag catcgcagg cgttgggact   900 ccagctgcag ctgcagctgc agcagcagcc gctaaggcag ccaagtatgg agctgctgca   960
ggcttagtgc ctggtgggcc aggctttggc ccggagtag ttggtgtccc aggagctggc   1020
gttccaggtg ttggtgtccc aggagctggg attccagttg tcccaggtgc tgggatccca   1080
ggtgctgcgg ttccagggt tgtgtcacca gaagcagctg ctaaggcagc tgcaaaggca   1140
gccaaatacg gggccaggcc cggagtcgga gttggaggca ttcctactta cggggttgga   1200
```

```
gctgggggct tcccggctt tggtgtcgga gtcggaggta tccctggagt cgcaggtgtc    1260
cctggtgtcg gaggtgttcc cggagtcgga ggtgtcccgg gagttggcat tccccccgaa    1320
gctcaggcag cagctgccgc caaggctgcc aagtacggag tggggacccc agcagctgca    1380
gctgctaaag cagccgccaa agccgcccag tttgggttag ttcctggtgt cggcgtggct    1440
cctggagttg gcgtggctcc tggtgtcggt gtggctcctg gagttggctt ggctcctgga    1500
gttggcgtgg ctcctggagt tggtgtggct cctggcgttg gcgtggctcc cggcattggc    1560
cctggtggag ttgcagctgc agcaaaatcc gctgccaagg tggctgccaa agcccagctc    1620
cgagctgcag ctgggcttgg tgctggcatc cctggacttg gagttggtgt cggcgtccct    1680
ggacttggag ttggtgctgg tgttcctgga cttggagttg gtgctggtgt tcctggcttc    1740
ggggcagtac ctggagccct ggctgccgct aaagcagcca aatatggagc agcagtgcct    1800
ggggtccttg gagggctcgg ggctctcggt ggagtaggca tcccaggcgg tgtggtggga    1860
gccggacccg ccgccgccgc tgccgcagcc aaagctgctg ccaaagccgc ccagtttggc    1920
ctagtgggag ccgctgggct cggaggactc ggagtcggag ggcttggagt tccaggtgtt    1980
gggggccttg gaggtgggc ctgcctgggg aaagcttgtg gccggaagag aaaatga        2037
```

<210> SEQ ID NO 72
<211> LENGTH: 2058
<212> TYPE: DNA
<213> ORGANISM: Homo sapiens

<400> SEQUENCE: 72

```
atggcgggtc tgacggcggc ggccccgcgg cccggagtcc tcctgctcct gctgtccatc      60
ctccacccct ctcggcctgg agggtcccct ggggccattc ctggtggagt tcctggagga    120
gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttacctt tccggggggct ctggtgcctg gtggagtggc tgacgctgct    300
gcagcctata agctgctaag gctggcgct gggcttggtg gtgtcccagg agttggtggc    360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggtggcta tggactgccc    660
tacaccacag ggaaactgcc ctatggctat gggcccggag gagtggctgg tgcagcgggc    720
aaggctggtt acccaacagg gacagggggtt ggccccagg cagcagcagc agcggcagct    780
aaagcagcag caaagttcgg tgctggagca gccggagtcc tccctggtgt tggagggggct    840 ggtgttcctg gcgtgcctgg gcaattcct ggaattggag catcgcagg agctgctgca    900 ggcttagtgc ctggtgggcc aggctttggc ccggagtag ttggtgtccc aggagctggc    960
gttccaggtg ttggtgtccc aggagctggg attccagttg tcccaggtgc tgggatccca   1020
ggtgctgcgg ttcagggggt tgtgtcacca gaagcagctg ctaaggcagc tgcaaaggca   1080
gccaaatacg gggccaggcc cggagtcgga gttggaggca ttcctactta cggggttgga   1140
gctgggggct ttcccggctt tggtgtcgga gtcggaggta tccctggagt cgcaggtgtc   1200
cctggtgtcg gaggtgttcc cggagtcgga ggtgtcccgg gagttggcat tccccccgaa   1260
gctcaggcag cagctgccgc caaggctgcc aagtacgggt tagttcctgg tgtcggcgtg   1320
```

```
gctcctggag ttggcgtggc tcctggtgtc ggtgtggctc ctggagttgg cttggctcct   1380
ggagttggcg tggctcctgg agttggtgtg gctcctggcg ttggcgtggc tcccggcatt   1440
ggccctggtg gagttgcagc tgcagcaaaa tccgctgcca aggtggctgc caaagcccag   1500
ctccgagctg cagctgggct tggtgctggc atccctggac ttggagttgg tgtcggcgtc   1560
cctggacttg gagttggtgc tggtgttcct ggacttggag ttggtgctgg tgttcctggc   1620
ttcggggcag tacctggagc cctggctgcc gctaaagcag ccaaatatgg agcagcagtg   1680
cctggggtcc ttggagggct cggggctctc ggtggagtag gcatcccagg cggtgtggtg   1740
ggagccggac ccgccgccgc cgctgccgca gccaaagctg ctgccaaagc cgcccagttt   1800
ggcctagtgg gagccgctgg gctcggagga ctcgagtcg agggcttgg agttccaggt   1860 gttgggggcc ttggaggtat acctccagct gcagccgcta aagcagctaa atacggtgct   1920
gctggccttg gaggtgtcct aggggggtgcc gggcagttcc cacttggagg agtggcagca   1980
agacctggct tcggattgtc tcccattttc ccaggtgggg cctgcctggg gaaagcttgt   2040
ggccggaaga gaaaatga                                                 2058

<210> SEQ ID NO 73
<211> LENGTH: 2016
<212> TYPE: DNA
<213> ORGANISM: Homo sapiens

<400> SEQUENCE: 73
atggcgggtc tgacggcggc ggccccgcgg cccggagtcc tcctgctcct gctgtccatc     60
ctccacccct ctcggcctgg aggggtccct ggggccattc ctggtggagt tcctggagga    120
gtcttttatc caggggctgg tctcggagcc cttggaggag gagcgctggg gcctggaggc    180
aaacctctta agccagttcc cggagggctt gcgggtgctg gccttggggc agggctcggc    240
gccttccccg cagttacctt tccgggggct ctggtgcctg gtggagtggc tgacgctgct    300
gcagcctata agctgctaa ggctggcgct gggcttggtg gtgtcccagg agttggtggc    360
ttaggagtgt ctgcaggtgc ggtggttcct cagcctggag ccggagtgaa gcctgggaaa    420
gtgccgggtg tggggctgcc aggtgtatac ccaggtggcg tgctcccagg agctcggttc    480
cccggtgtgg gggtgctccc tggagttccc actggagcag gagttaagcc caaggctcca    540
ggtgtaggtg gagcttttgc tggaatccca ggagttggac cctttggggg accgcaacct    600
ggagtcccac tggggtatcc catcaaggcc cccaagctgc ctggctatgg gcccggagga    660
gtggctggtg cagcgggcaa ggctggttac ccaacaggga caggggttgg ccccaggca    720 gcagcagcag cggcagctaa agcagcagca aagttcggtg ctggagcagc cggagtcctc    780
cctggtgttg gagggctgg tgttcctggc gtgcctgggg caattcctgg aattggaggc    840
atcgcaggag ctgctgcagg cttagtgcct ggtgggccag gctttggccc gggagtagtt    900
ggtgtcccag gagctggcgt tccaggtgtt ggtgtcccag gagctgggat tccagttgtc    960
ccaggtgctg ggatcccagg tgctgcggtt ccaggggttg tgtcaccaga agcagctgct   1020
aaggcagctg caaaggcagc caaatacggg gccaggcccg gagtcggagt tggaggcatt   1080
cctacttacg gggttggagc tggggctttt ccggctttg tgtcggagt cggaggtatc   1140 cctggagtcg caggtgtccc tggtgtcgga ggtgttcccg gagtcggagg tgtcccggga   1200
gttggcattt cccccgaagc tcaggcagca gctgccgcca aggctgccaa gtacgggtta   1260
gttcctggtg tcggcgtggc tcctggagtt ggcgtggctc ctggtgtcgg tgtggctcct   1320
```

```
ggagttggct tggctcctgg agttggcgtg gctcctggag ttggtgtggc tcctggcgtt    1380
ggcgtggctc ccggcattgg ccctggtgga gttgcagctg cagcaaaatc cgctgccaag    1440
gtggctgcca aagcccagct ccgagctgca gctgggcttg tgctggcat ccctggactt     1500 ggagttggtc tcgcgtccc tggacttgga gttggtgctg tgttcctgg acttggagtt      1560 ggtgctggtg ttcctggctt cggggcagta cctggagccc tggctgccgc taaagcagcc    1620
aaatatggag cagcagtgcc tggggtcctt ggagggctcg ggctctcgg tggagtaggc     1680 atcccaggcg gtgtggtggg agccggaccc gccgccgccg ctgccgcagc caaagctgct    1740
gccaaagccg cccagtttgg cctagtggga gccgctgggc tcggaggact cggagtcgga    1800
gggcttggag ttccaggtgt tgggggcctt ggaggtatac ctccagctgc agccgctaaa    1860
gcagctaaat acggtgctgc tggccttgga ggtgtcctag ggggtgccgg gcagttccca    1920
cttggaggag tggcagcaag acctggcttc ggattgtctc ccattttccc aggtgggggcc   1980 tgcctgggga agcttgtgg ccggaagaga aaatga                               2016
```

<210> SEQ ID NO 74  
<211> LENGTH: 1986  
<212> TYPE: DNA  
<213> ORGANISM: Homo sapiens

<400> SEQUENCE: 74

```
atggcgggtc tgacggcggc ggccccgcgg cccggagtcc tcctgctcct gctgtccatc      60 ctccaccct ctcggcctgg aggggtccct ggggccattc ctggtggagt tcctggagga    120
gtcttttatc caggggctgg tctcggagcc cttggaggag gagcgctggg gcctggaggc    180
aaacctctta agccagggct cggcgccttc cccgcagtta cctttccggg ggctctggtg    240
cctggtggag tggctgacgc tgctgcagcc tataaagctg ctaaggctgg cgctgggctt    300
ggtggtgtcc caggagttgg tggcttagga gtgtctgcag gtgcggtggt tcctcagcct    360
ggagccggag tgaagcctgg gaaagtgccg gtgtgtgggc tgccaggtgt atacccaggt    420
ggcgtgctcc caggagctcg gttccccggt gtgggggtgc tccctggagt tcccactgga    480
gcaggagtta agcccaaggc tccaggtgta ggtgagctt tgctggaat cccaggagtt     540 ggacccttg ggggaccgca accggagtc ccactggggt atcccatcaa ggccccaag      600 ctgcctggct atgggcccgg aggagtggct ggtgcagcgg gcaaggctgg ttacccaaca    660
gggacagggg ttggcccca ggcagcagca gcagcggcag ctaaagcagc agcaaagttc     720
ggtgctggag cagccggagt cctccctggt gttgagggg ctggtgttcc tggcgtgcct     780
ggggcaattc ctggaattgg aggcatcgca ggcgttggga ctccagctgc agctgcagct    840
gcagcagcag ccgctaaggc agccaagtat ggagctgctg caggcttagt gcctggtggg    900
ccaggctttg gcccgggagt agttggtgtc caggagctg gcgttccagg tgttggtgtc     960
ccaggagctg ggatccagt tgtcccaggt gctgggatcc aggtgctgc ggttccaggg     1020 gttgtgtcac cagaagcagc tgctaaggca gctgcaaagg cagccaaata cggggccagg    1080
cccggagtcg gagttggagg cattcctact tacggggttg gagctggggg ctttccggc     1140 tttggtgtcg gagtcggagg tatccctgga gtcgcaggtg tccctagtgt cggaggtgtt    1200
cccggagtcg gaggtgtccc gggagttggc atttcccccg aagctcaggc agcagctgcc    1260
gccaaggctg ccaagtacgg gttagttcct ggtgtcggcg tggctcctgg agttggcgtg    1320
gctcctggtg tcggtgtggc tcctggagtt ggcttggctc ctggagttgg cgtggctcct    1380
ggagttggtg tggctcctgg cgttggcgtg gctcccggca ttggccctgg tggagttgca    1440
```

```
gctgcagcaa aatccgctgc caaggtggct gccaaagccc agctccgagc tgcagctggg    1500
cttggtgctg gcatccctgg acttggagtt ggtgtcggcg tccctggact tggagttggt    1560
gctggtgttc ctggacttgg agttggtgct ggtgttcctg gcttcggggc agtacctgga    1620
gccctggctg ccgctaaagc agccaaatat ggagcagcag tgcctggggt ccttggaggg    1680
ctcggggctc tcggtggagt aggcatccca ggcggtgtgg tgggagccgg acccgccgcc    1740
gccgctgccg cagccaaagc tgctgccaaa gccgcccagt ttggcctagt gggagccgct    1800
gggctcggag gactcggagt cggagggctt ggagttccag gtgttggggg ccttggaggt    1860
atacctccag ctgcagccgc taaagcagct aaatacggag tggcagcaag acctggcttc    1920
ggattgtctc ccattttccc aggtggggcc tgcctgggga agcttgtggt ccggaagaga    1980
aaatga                                                              1986

<210> SEQ ID NO 75
<211> LENGTH: 2145
<212> TYPE: DNA
<213> ORGANISM: Homo sapiens

<400> SEQUENCE: 75
atggcgggtc tgacggcggc ggccccgcgg cccggagtcc tcctgctcct gctgtccatc      60
ctccacccct ctcggcctgg aggggtccct ggggccattc ctggtggagt tcctggagga     120
gtcttttatc caggggctgg tctcggagcc cttggaggag gagcgctggg gcctggaggc     180
aaacctctta agccagttcc cggagggctt gcgggtgctg gccttggggc agggctcggc     240
gccttccccg cagttacctt tccggggggct ctggtgcctg gtggagtggc tgacgctgct     300
gcagcctata agctgctaa ggctggcgct gggcttggtg gtgtcccagg agttggtggc     360
ttaggagtgt ctgcaggtgc ggtggttcct cagcctggag ccggagtgaa gcctgggaaa     420
gtgccgggtg tggggctgcc aggtgtatac ccaggtggcg tgctcccagg agctcggttc     480
cccggtgtgg gggtgctccc tggagttccc actggagcag gagttaagcc caaggctcca     540
ggagttggac cctttgggggg accgcaacct ggagtcccac tggggtatcc catcaaggcc     600
cccaagctgc ctggtggcta tggactgccc tacaccacag gaaaactgcc ctatggctat     660
gggcccggag gaatggctgg tgcagcgggc aaggctggtt acccaacagg tacaggggtt     720
ggcccccagg ccccaacagc agcggcagct aaagcagcag caaagttcgg tgctggagca     780
gccggagtcc tcctggtgt tggaggggct ggtgttcctg gcgtgcctgg ggcaattcct     840
ggaattggag gcatcgcagg cgttgggact ccagctgcag ctgcagctgc agcagcagcc     900
gctaaggcag ccaagtatgg agctgctgca ggcttagtgc ctggtgggcc aggctttggc     960 ccggagtag ttggtgtccc aggagctggc gttccaggtg ttggtgtccc aggagctggg     1020
attccagttg tcccaggtgc tgggatccca ggtgctgcgg ttccagggt tgtgtcacca     1080 gaagcagctg ctaaggcagc tgcaaaggca gccaaatacg ggccaggcc cggagtcgga     1140 gttggaggca ttcctactta cggggttgga gctgggggct ttcccggctt tggtgtcgga     1200 gtcgaggta tccctggagt cgcaggtgtc cctggtgtcg gaggtgttcc ggagtcggat     1260
ggtgtcccgg gagttggcat tccccccgaa gctcaggcag cagctgccgc caaggctgcc     1320
aagtacggag tggggacccc agcagctgca gctgctaaag cagccgccaa agccgcccag     1380
tttgggttag ttcctggtgt cggcgtggct cctgagttg gcgtggctcc tggtgtcggt     1440
gtggctcctg gagttggctt ggctcctgga gttggcgtgg ctcctggagt tggtgtggct     1500
```

```
cctggcgttg gcgtggctcc cggcattggc cctggtggag ttgcagctgc agcaaaatcc    1560
gctgccaagg tggctgccaa agcccagctc cgagctgcag ctgggcttgg tgctggcatc    1620
cctggacttg gagttggtgt cggcgtccct ggacttggag ttggtgctgg tgttcctgga    1680
cttggagttg gtgctggtgt tcctggcttc ggggcagtac ctggagccct ggctgccgct    1740
aaagcagcca aatatggagc agcagtgcct ggggtccttg gagggctcgg ggctctcggt    1800
ggagtaggca tcccaggcgg tgtggtggga gccggacccg ccgccgccgc tgccgcagcc    1860
aaagctgctg ccaaagccgc ccagtttggc ctagtgggag ccgctgggct cggaggactc    1920
ggagtcggag ggcttggagt tccaggtgtt gggggccttg gaggtatacc tccagctgca    1980
gccgctaaag cagctaaata cggtgctgct ggccttggag gtgtcctagg gggtgccggg    2040
cagttcccac ttggaggagt ggcagcaaga cctggcttcg gattgtctcc cattttccca    2100
ggtggggcct gcctggggaa agcttgtggc cggaagagaa aatga                    2145

<210> SEQ ID NO 76
<211> LENGTH: 2145
<212> TYPE: DNA
<213> ORGANISM: Homo sapiens

<400> SEQUENCE: 76
atggcgggtc tgacggcggc ggccccgcgg cccggagtcc tcctgctcct gctgtccatc      60
ctccacccct ctcggcctgg aggggtccct ggggccattc ctggtggagt tcctggagga     120
gtcttttatc caggggctgg tctcggagcc cttggaggag gagcgctggg gcctggaggc     180
aaacctctta agccagttcc cggagggctt gcggtgctg gccttggggc agggctcggc      240
gccttccccg cagttacctt tccggggct ctggtgcctg tggagtggc tgacgctgct      300 gcagcctata aagctgctaa ggctggcgct gggcttggtg gtgtcccagg agttggtggc     360
ttaggagtgt ctgcaggtgc ggtggttcct cagcctggag ccggagtgaa gcctgggaaa     420
gtgccgggtg tggggctgcc aggtgtatac ccaggtggcg tgctcccagg agctcggttc     480
cccggtgtgg gggtgctccc tggagttccc actggagcag gagttaagcc caaggctcca     540
ggtgtaggtg gagcttttgc tggaatccca ggagttggac cctttggggg accgcaacct     600
ggagtcccac tggggtatcc catcaaggcc cccaagctgc ctggtggcta tggactgccc     660
tacaccacag ggaaactgcc ctatggctat gggcccggag gagtggctgg tgcagcgggc     720
aaggctggtt acccaacagg gacaggggtt ggccccccagg cagcagcagc agcggcagct     780
aaagcagcag caaagttcgg tgctggagca gccggagtcc tccctggtgt ggaggggct     840 ggtgttcctg gcgtgcctgg ggcaattcct ggaattggag gcatcgcagg cgttgggact     900
ccagctgcag ctgcagctgc agcagcagcc gctaaggcag ccaagtatgg agctgctgca     960
ggcttagtgc ctggtgggcc aggctttggc ccggagtag ttggtgtccc aggagctggc     1020
gttccaggtg ttggtgtccc aggagctggg attccagttg tcccaggtgc tgggatccca     1080
ggtgctgcgg ttcaggggt tgtgtcacca gaagcagctg ctaaggcagc tgcaaaggca     1140
gccaaatacg gggccaggcc cggagtcgga gttggaggca ttcctactta cggggttgga     1200 gctggggct ttcccggctt tgtgtcgga gtcgaggta tccctggagt cgcaggtgtc     1260
cctggtgtcg gaggtgttcc cggagtcgga gccgaagctc aggcagcagc tgccgccaag     1320
gctgccaagt acgagtgggg accccagca gctgcagctg ctaaagcagc cgccaaagcc     1380
gcccagtttg ggttagttcc tggtgtcggc gtggctcctg gagttggcgt ggctcctggt     1440
gtcggtgtgg ctcctggagt tggcttggct cctggagttg gcgtggctcc tggagttggt     1500
```

```
gtggctcctg gcgttggcgt ggctcccggc attggccctg gtggagttgc agctgcagca    1560
aaatccgctg ccaaggtggc tgccaaagcc cagctccgag ctgcagctgg gcttggtgct    1620
ggcatccctg gacttggagt tggtgtcggc gtccctggac ttggagttgg tgctggtgtt    1680
cctggacttg gagttggtgc tggtgttcct ggcttcgggg cagtacctgg agccctggct    1740
gccgctaaag cagccaaata tgcagtgcct ggggtccttg gagggctcgg ggctctcggt    1800
ggagtaggca tcccaggcgg tgtggtggga gccggacccg ccgccgccgc tgccgcagcc    1860
aaagctgctg ccaaagccgc ccagtttggc ctagtgggag ccgctgggct cggaggactc    1920
ggagtcggag ggcttggagt tccaggtgtt gggggccttg gaggtatacc tccagctgca    1980
gccgctaaag cagctaaata cggtgctgct ggccttggag gtgtcctagg gggtgccggg    2040
cagttcccac ttggaggagt ggcagcaaga cctggcttcg gattgtctcc cattttccca    2100
ggtggggcct gcctggggaa agcttgtggc cggaagagaa aatga                    2145
```

<210> SEQ ID NO 77
<211> LENGTH: 2166
<212> TYPE: DNA
<213> ORGANISM: Homo sapiens

<400> SEQUENCE: 77

```
atggcgggtc tgacggcggc ggccccgcgg cccggagtcc tcctgctcct gctgtccatc      60
ctccacccct ctcggcctgg aggggtccct ggggccattc ctggtggagt tcctggagga     120
gtcttttatc caggggctgg tctcggagcc cttggaggag gagcgctggg gcctggaggc     180
aaacctctta agccagttcc cggagggctt gcgggtgctg gccttggggc agggctcggc     240
gccttccccg cagttacctt tccggggggct ctggtgcctg gtggagtggc tgacgctgct     300
```
(Note: line at 300 may vary)

```
gcagcctata agctgctaa ggctggcgct gggcttggtg gtgtcccagg agttggtggc     360
ttaggagtgt ctgcagcccc ttctgtgcca ggtgcggtgg ttcctcagcc tggagccgga     420
gtgaagcctg ggaaagtgcc gggtgtgggg ctgccaggtg tatacccagg tggcgtgctc     480
ccaggagctc ggttccccgg tgtggggtg ctccctggag ttcccactgg agcaggagtt     540
aagcccaagg ctcaggtgt aggtggagct tttgctggaa tccaggagt tggacccttt     600 gggggaccgc aacctggagt cccactgggg tatcccatca aggcccccaa gctgcctggt     660
ggctatggac tgccctacac cacagggaaa ctgccctatg ctatgggcc ggaggagtg     720 gctggtgcag cgggcaaggc tggttaccca acagggacag gggttggccc ccaggcagca     780
gcagcagcgg cagctaaagc agcagcaaag ttcggtgctg gagcagccgg agtcctccct     840
ggtgttggag gggctggtgt tcctggcgtg cctggggcaa ttcctggaat tggaggcatc     900
gcaggcgttg ggactccagc tgcagctgca gctgcagcag cagccgctaa ggcagccaag     960
tatggagctg ctgcaggctt agtgcctggt gggccaggct ttggcccggg agtagttggt    1020
gtcccaggag ctggcgttcc agtgttggt gtcccaggag ctgggattcc agttgtccca    1080
ggtgctggga tcccaggtgc tgcggttcca ggggttgtgt caccagaagc agctgctaag    1140
gcagctgcaa aggcagccaa atacgggcc aggccggag tcggagttgg aggcattcct    1200
acttacgggg ttgagctgg gggctttccc ggctttggtg tcggagtcgg aggtatccct    1260
ggagtcgcag gtgtccctgg tgtcggaggt gttcccggag tcggagccga agctcaggca    1320
gcagctgccg ccaaggctgc caagtacgga gtggggaccc cagcagctgc agctgctaaa    1380
gcagccgcca aagccgccca gtttgggtta gttcctggtg tcggcgtggc tcctggagtt    1440
```

```
ggcgtggctc ctggtgtcgg tgtggctcct ggagttggct tggctcctgg agttggcgtg      1500
gctcctggag ttggtgtggc tcctggcgtt ggcgtggctc ccggcattgg ccctggtgga      1560
gttgcagctg cagcaaaatc cgctgccaag gtggctgcca agcccagct ccgagctgca       1620 gctgggcttg gtgctggcat ccctggactt ggagttggtg tcggcgtccc tggacttgga      1680
gttggtgctg gtgttcctgg acttggagtt ggtgctggtg ttcctggctt cggggcagta      1740
cctggagccc tggctgccgc taaagcagcc aaatatggag cagcagtgcc tggggtcctt      1800
ggagggctcg gggctctcgg tggagtaggc atcccaggcg gtgtggtggg agccggaccc      1860
gccgccgccg ctgccgcagc caaagctgct gccaaagccg cccagtttgg cctagtggga      1920
gccgctgggc tcggaggact cggagtcgga gggcttggag ttccaggtgt tgggggcctt      1980
ggaggtatac ctccagctgc agccgctaaa gcagctaaat acggtgctgc tggccttgga      2040
ggtgtcctag ggggtgccgg gcagttccca cttggaggag tggcagcaag acctggcttc      2100
ggattgtctc ccattttccc aggtggggcc tgcctgggga agcttgtgg ccggaagaga       2160 aaatga                                                                 2166

<210> SEQ ID NO 78
<211> LENGTH: 2139
<212> TYPE: DNA
<213> ORGANISM: Homo sapiens

<400> SEQUENCE: 78
atggcgggtc tgacggcggc ggccccgcgg cccggagtcc tcctgctcct gctgtccatc        60
ctccacccct ctcggcctgg aggggtccct ggggccattc ctggtggagt tcctggagga      120
gtcttttatc caggggctgg tctcggagcc cttggaggag gagcgctggg gcctggaggc      180
aaacctctta agccagggct cggcgccttc cccgcagtta cctttccggg ggctctggtg      240
cctggtggag tggctgacgc tgctgcagcc tataaagctg ctaaggctgg cgctgggctt      300
ggtggtgtcc caggagttgg tggcttagga gtgtctgcag gtgcgtggt tcctcagcct       360 ggagccggag tgaagcctgg gaaagtgccg ggtgtggggc tgccaggtgt atacccaggt      420
ggcgtgctcc caggagctcg gttccccggt gtggggtgc tccctggagt tcccactgga       480
gcaggagtta agcccaaggc tccaggtgta ggtggagctt ttgctggaat cccaggagtt      540
ggaccctttg gggaccgcca acctggagtc ccactgggt atcccatcaa ggcccccaag       600
ctgcctggtg gctatggact gccctacacc acagggaaac tgcccatgg ctatgggccc       660 ggaggagtgg ctggtgcagc gggcaaggct ggttacccaa cagggacagg ggttggcccc      720
caggcagcag cagcagcggc agctaaagca gcagcaaagt tcggtgctgg agcagccgga      780
gtcctccctg gtgttggagg ggctggtgtt cctggcgtgc ctgggcaat tcctggaatt       840 ggaggcatcg caggcgttgg gactccagct gcagctgcag ctgcagcagc agccgctaag      900
gcagccaagt atgagctgc tgcaggctta gtgcctggtg gccaggctt tggcccggga       960 gtagttggtg tcccaggagc ctggcgttcca ggtgttggtg tcccaggagc tgggattcca     1020
gttgtcccag gtgctgggat cccaggtgct gcggttccag gggttgtgtc accagaagca     1080
gctgctaagg cagctgcaaa ggcagccaaa tacggggcca ggcccggagt cggagttgga     1140
ggcattccta cttacggggt tggagctggg ggcttttccg ctttggtgt cggagtcgga      1200 ggtatccctg gagtcgcagg tgtccctggt gtcggaggtg ttccgggagt cggaggtgtc     1260
ccgggagttg gcatttcccc cgaagctcag gcagcagctg ccgccaaggc tgccaagtac      1320
ggagtgggga ccccagcagc tgcagctgct aaagcagccg ccaaagccgc ccagtttggg     1380
```

-continued

```
ttagttcctg gtgtcggcgt ggctcctgga gttggcgtgg ctcctggtgt cggtgtggct    1440
cctggagttg gcttggctcc tggagttggc gtggctcctg gagttggtgt ggctcctggc    1500
gttggcgtgg ctcccggcat tggccctggt ggagttgcag ctgcagcaaa atccgctgcc    1560
aaggtggctg ccaaagccca gctccgagct gcagctgggc ttggtgctgg catccctgga    1620
cttggagttg gtgtcggcgt ccctggactt ggagttggtg ctggtgttcc tggacttgga    1680
gttggtgctg gtgttcctgg cttcggggca gtacctggag ccctggctgc cgctaaagca    1740
gccaaatatg agcagcagt gcctggggtc cttggagggc tcgggctct cggtggagta     1800 ggcatcccag gcgtgtggt gggagccgga cccgccgccg ccgctgccgc agccaaagct    1860
gctgccaaag ccgcccagtt tggcctagtg ggagccgctg ggctcggagg actcggagtc    1920
ggagggcttg gagttccagg tgttggggc cttggaggta tacctccagc tgcagccgct    1980
aaagcagcta aatacggtgc tgctggcctt ggaggtgtcc taggggtgc cgggcagttc    2040 ccacttggag gagtggcagc aagacctggc ttcggattgt ctcccatttt cccaggtggg    2100
gcctgcctgg ggaaagcttg tggccggaag agaaaatga                            2139
```

<210> SEQ ID NO 79
<211> LENGTH: 2004
<212> TYPE: DNA
<213> ORGANISM: Homo sapiens

<400> SEQUENCE: 79

```
atggcgggtc tgacggcggc ggccccgcgg cccggagtcc tcctgctcct gctgtccatc      60
ctccacccct ctcggcctgg aggggtccct ggggccattc ctggtggagt tcctggagga    120 gtctttatc cagcgctggg gcctggaggc aaacctctta agccagttcc cggagggctt     180
gcgggtgctg gccttggggc agggctcggc gccttccccg cagttacctt tccggggct     240 ctggtgcctg gtggagtggc tgacgctgct gcagcctata agctgctaa ggctggcgct     300 gggcttggtg gtgtcccagg agttggtggc ttaggagtgt ctgcaggtgc ggtggttcct    360
cagcctggag ccggagtgaa gcctgggaaa gtgccgggtg tggggctgcc aggtgtatac    420
ccaggtggcg tgctcccagg agctcggttc cccggtgtgg gggtgctccc tggagttccc    480
actggagcag gagttaagcc caaggctcca ggtgtaggtg agcttttgc tggaatccca    540 ggagttggac cctttgggg accgcaacct ggagtcccac tggggtatcc catcaaggcc    600
cccaagctgc ctggctatgg gcccggagga gtggctggtg cagcgggcaa ggctggttac    660
ccaacaggga caggggttgg cccccaggca gcagcagcag cggcagctaa agcagcagca    720
aagttcggtg ctggagcagc cggagtcctc cctggtgttg aggggctgg tgttcctggc    780 gtgcctgggg caattcctgg aattggaggc atcgcaggcg ttgggactcc agctgcagct    840
gcagctgcag cagcagccgc taaggcagcc aagtatggag ctgctgcagg cttagtgcct    900
ggtgggccag gctttggccc gggagtagtt ggtgtcccag gagctggcgt tccaggtgtt    960
ggtgtcccag gagctgggat tccagttgtc ccaggtgctg ggatcccagg tgctgcggtt   1020
ccaggggttg tgtcaccaga agcagctgct aaggcagctg caaaggcagc caaatacggg    1080
gccaggcccg gagtcggagt tggaggcatt cctacttacg gggttggagc tggggcttt    1140 cccggctttg gtgtcggagt cggaggtatc cctggagtcg caggtgtccc tggtgtcgga    1200
ggtgttcccg gagtcggagg tgtcccggga gttggcattt cccccgaagc tcaggcagca    1260
gctgccgcca aggctgccaa gtacggagtg gggaccccag cagctgcagc tgctaaagca    1320
```

```
gccgccaaag ccgcccagtt tgggttagtt cctggtgtcg gcgtggctcc tggagttggc    1380
gtggctcctg gtgtcggtgt ggctcctgga gttggcttgg ctcctggagt tggcgtggct    1440
cctggagttg gtgtggctcc tggcgttggc gtggctcccg gcattggccc tggtggagtt    1500
gcagctgcag caaaatccgc tgccaaggtg gctgccaaag cccagctccg agctgcagct    1560
gggcttggtg ctggcatccc tggacttgga gttggtgtcg gcgtccctgg acttggagtt    1620
ggtgctggtg ttcctggact tggagttggt gctggtgttc ctggcttcgg ggcagtacct    1680
ggagccctgg ctgccgctaa agcagccaaa tatggagcag cagtgcctgg ggtccttgga    1740
gggctcgggg ctctcggtgg agtaggcatc ccaggcggtg tggtgggagc cggacccgcc    1800
gccgccgctg ccgcagccaa agctgctgcc aaagccgccc agtttggcct agtgggagcc    1860
gctgggctcg gaggactcgg agtcggaggg cttggagttc caggtgttgg gggccttgga    1920
ggtatacctc cagctgcagc cgctaaagca gctaaatacg gtggggcctg cctggggaaa    1980
gcttgtggcc ggaagagaaa atga                                            2004

<210> SEQ ID NO 80
<211> LENGTH: 2049
<212> TYPE: DNA
<213> ORGANISM: Homo sapiens

<400> SEQUENCE: 80
atggcgggtc tgacggcggc ggccccgcgg cccggagtcc tcctgctcct gctgtccatc      60
ctccacccct ctcggcctgg aggggtccct ggggccattc tggtggagtt cctggagga     120 gtcttttatc cagcgctggg gcctggaggc aaacctctta agccagttcc cggagggctt    180
gcgggtgctg gccttgggggc agggctcggc gccttcccg cagttacctt tccggggct     240 ctggtgcctg gtgagtggc tgacgctgct gcagcctata aagctgctaa ggctggcgct    300
gggcttggtg gtgtcccagg agttggtggc ttaggagtgt ctgcaggtgc ggtggttcct    360
cagcctggag ccgagtgaa gcctgggaaa gtgccgggtg tggggctgcc aggtgtatac    420
ccaggtggcg tgctcccagg agctcggttc cccggtgtgg gggtgctccc tggagttccc    480
actggagcag gagttaagcc caaggctcca ggtgtaggtg gagcttttgc tggaatccca    540
ggagttggac cctttggggg accgcaacct ggagtcccac tggggtatcc catcaaggcc    600
cccaagctgc ctggctatgg gccggagga gtggctggtg cagcgggcaa ggctggttac    660
ccaacaggga caggggttgg cccccaggca gcagcagcag cggcagctaa agcagcagca    720
aagttcggtg ctggagcagc cggagtcctc cctggtgttg gagggggctgg tgttcctggc    780 gtgcctgggg caattcctgg aattggaggc atcgcaggcg ttgggactcc agctgcagct    840
gcagctgcag cagcagccgc taaggcagcc aagtatggag ctgctgcagg cttagtgcct    900
ggtgggccag gctttggccc gggagtagtt ggtgtcccag gagctggcgt tccaggtgtt    960
ggtgtcccag gagctgggat tccagttgtc ccaggtgctg gatcccagg tgctgcggtt   1020 ccaggggttg tgtcaccaga agcagctgct aaggcagctg caaaggcagc caaatacggg   1080
gccaggcccg gagtcggagt tggaggcatt cctacttacg ggttggagc tgggggctttт  1140 cccgggctttg tgtcggagt cggaggtatc cctgagtcg caggtgtccc tggtgtcgga   1200
ggtgttcccg gagtcggagg tgtcccggga gttggcattt cccccgaagc tcaggcagca   1260
gctgccgcca aggtgccaa gtacggagtg gggaccccag cagctgcagc tgctaaagca   1320
gccgccaaag ccgcccagtt tgggttagtt cctggtgtcg gcgtggctcc tggagttggc   1380
gtggctcctg gtgtcggtgt ggctcctgga gttggcttgg ctcctggagt tggcgtggct   1440
```

```
cctggagttg gtgtggctcc tggcgttggc gtggctcccg gcattggccc tggtggagtt    1500
gcagctgcag caaaatccgc tgccaaggtg gctgccaaag cccagctccg agctgcagct    1560
gggcttggtg ctggcatccc tggacttgga gttggtgtcg gcgtccctgg acttggagtt    1620
ggtgctggtg ttcctggact tggagttggt gctggtgttc ctggcttcgg ggcagtacct    1680
ggagccctgg ctgccgctaa agcagccaaa tatggagcag cagtgcctgg ggtccttgga    1740
gggctcgggc tctcggtgg agtaggcatc caggcggtg tggtgggagc cggacccgcc      1800
gccgccgctg ccgcagccaa agctgctgcc aaagccgccc agtttggcct agtgggagcc    1860
gctgggctcg gaggactcgg agtcggaggg cttggagttc caggtgttgg gggccttgga    1920
ggtatacctc cagctgcagc cgctaaagca gctaaatacg gagtggcagc aagacctggc    1980
ttcggattgt ctcccatttt cccaggtggg gcctgcctgg ggaaagcttg tggccggaag    2040
agaaaatga                                                            2049

<210> SEQ ID NO 81
<211> LENGTH: 1989
<212> TYPE: DNA
<213> ORGANISM: Homo sapiens

<400> SEQUENCE: 81
atggcgggtc tgacggcggc ggccccgcgg cccggagtcc tcctgctcct gctgtccatc     60
ctccacccct ctcggcctgg aggggtccct ggggccattc ctggtggagt tcctggagga    120
gtcttttatc cagcgctggg gcctggaggc aaacctctta agccagttcc cggagggctt    180
gcgggtgctg gccttggggc agggctcggc gccttccccg cagttacctt tccggggct     240 ctggtgcctg gtgagtggc tgacgctgct gcagcctata aagctgctaa ggctggcgct    300
gggcttggtg gtgtcccagg agttggtggc ttaggagtgt ctgcaggtgc ggtggttcct    360
cagcctggag ccggagtgaa gcctgggaaa gtgccgggtg tggggctgcc aggtgtatac    420
ccaggtggcg tgctcccagg agctcggttc cccggtgtgg gggtgctccc tggagttccc    480
actggagcag gagttaagcc caaggctcca ggtgtaggtg gagcttttgc tggaatccca    540
ggagttggac cctttgggg accgcaacct ggagtcccac tggggtatcc catcaaggcc     600
cccaagctgc ctggtggcta tggactgccc tacaccacag ggaaactgcc ctatggctat    660 gggccggag gagtggctgg tgcagcgggc aaggctggtt acccaacagg acaggggtt     720 ggcccccagg cagcagcagc agcggcagct aaagcagcag caaagttcgg tgctggagca    780
gccggagtcc tccctggtgt tggagggggct ggtgttcctg gcgtgcctgg ggcaattcct    840
ggaattggag gcatcgcagg cgttgggact ccagctgcag ctgcagctgc agcagcagcc    900
gctaaggcag ccaagtatgg agctgctgca ggcttagtgc ctggtgggcc aggctttggc    960
ccgggagtag ttggtgtccc aggagctggc gttccaggtg ttggtgtccc aggagctggg   1020
attccagttg tccaggtgc tgggatccca ggtgctgcgg ttccagggt tgtgtcacca     1080 gaagcagctg ctaaggcagc tgcaaaggca gccaaatacg gggccaggcc cggagtcgga   1140
gttggaggca ttcctactta cggggttgga gctggggct ttccggcgtt tggtgtcgga     1200 gtcgaggta tccctggagt cgcaggtgtc cctggtgtcg gaggtgttcc cggagtcgga   1260
ggtgtcccgg gagttggcat ttccccgaa gctcaggcag cagctgccgc caaggctgcc    1320
aagtacgggt tagttcctgg tgtcggcgtg gctcctggag ttggcgtggc tcctggtgtc    1380
ggtgtggctc ctggagttgg cttggctcct ggagttggcg tggctcctgg agttggtgtg    1440
```

| | |
|---|---|
| gctcctggcg ttggcgtggc tcccggcatt ggccctggtg gagttgcagg agctgcagct | 1500 |
| gggcttggtg ctggcatccc tggacttgga gttggtgtcg gcgtccctgg acttggagtt | 1560 |
| ggtgctggtg ttcctggact tggagttggt gctggtgttc ctggcttcgg ggcagtacct | 1620 |
| ggagccctgg ctgccgctaa agcagccaaa tatggagcag cagtgcctgg ggtccttgga | 1680 |
| gggctcgggg ctctcggtgg agtaggcatc ccaggcggtg tggtgggagc cggacccgcc | 1740 |
| gccgccgctg ccgcagccaa agctgctgcc aaagccgccc agtttggcct agtgggagcc | 1800 |
| gctgggctcg gaggactcgg agtcggaggg cttggagttc caggtgttgg gggccttgga | 1860 |
| ggtataccct cagctgcagc cgctaaagca gctaaatacg gagtggcagc aagacctggc | 1920 |
| ttcggattgt ctcccatttt cccaggtggg gcctgcctgg ggaaagcttg tggccggaag | 1980 |
| agaaaatga | 1989 |

<210> SEQ ID NO 82
<211> LENGTH: 2067
<212> TYPE: DNA
<213> ORGANISM: Homo sapiens
<400> SEQUENCE: 82

| | |
|---|---|
| atggcgggtc tgacggcggc ggccccgcgg cccggagtcc tcctgctcct gctgtccatc | 60 |
| ctccacccct ctcggcctgg aggggtccct ggggccattc ctggtggagt tcctggagga | 120 |
| gtcttttatc caggggctgg tctcggagcc cttggaggag gagcgctggg gcctggaggc | 180 |
| aaacctctta agccagttcc cggagggctt gcgggtgctg gccttggggc agggctcggc | 240 |
| gccttccccg cagttacctt tccggggggct ctggtgcctg gtggagtggc tgacgctgct | 300 |
| gcagcctata agctgctaa ggctggcgct gggcttggtg gtgtcccagg agttggtggc | 360 |
| ttaggagtgt ctgcaggtgc ggtggttcct cagcctggag ccggagtgaa gcctgggaaa | 420 |
| gtgccgggtg tggggctgcc aggtgtatac ccaggtggcg tgctcccagg agctcggttc | 480 |
| cccggtgtgg gggtgctccc tggagttccc actggagcag gagttaagcc caaggctcca | 540 |
| ggtgtaggtg gagcttttgc tggaatccca ggagttggac cctttggggg accgcaacct | 600 |
| ggagtcccac tggggtatcc catcaaggcc cccaagctgc ctggtggcta tggactgccc | 660 |
| tacaccacag ggaaactgcc ctatggctat gggcccggag gagtggctgg tgcagcgggc | 720 |
| aaggctggtt acccaacagg gacaggggtt ggccccagg cagcagcagc agcggcagct | 780 |
| aaagcagcag caaagttcgg tgctggagca gccggagtcc tccctggtgt ggaggggct | 840 |
| ggtgttcctg gcgtgcctgg ggcaattcct ggaattggag catcgcagg cgttgggact | 900 |
| ccagctgcag ctgcagctgc agcagcagcc gctaaggcag ccaagtatgg agctgctgca | 960 |
| ggcttagtgc ctggtgggcc aggctttggc ccgggagtag ttggtgtccc aggagctggc | 1020 |
| gttccaggtg ttggtgtccc aggagctggg attccagttg tccaggtgc tgggatccca | 1080 |
| ggtgctgcgg ttcagggggc caggcccgga gtcggagttg gaggcattcc tacttacggg | 1140 |
| gttggagctg ggggctttcc cggctttggt gtcggagtcg gaggtatccc tggagtcgca | 1200 |
| ggtgtccctg gtgtcggagg tgttcccgga gtcggaggtg tcccgggagt tggcatttcc | 1260 |
| cccgaagctc aggcagcagc tgccgccaag gctgccaagt acggagtggg gaccccagca | 1320 |
| gctgcagctg ctaaagcagc cgccaaagcc gcccagtttg ggttagttcc tggtgtcggc | 1380 |
| gtggctcctg gagttggcgt ggctcctggt gtcggtgtgg ctcctggagt tggcttggct | 1440 |
| cctggagttg gcgtggctcc tggagttggt gtggctcctg gcgttggcgt ggctcccggc | 1500 |
| attggccctg gtggagttgc agctgcagca aaatccgctg ccaaggtggc tgccaaagcc | 1560 |

```
cagctccgag ctgcagctgg gcttggtgct ggcatccctg gacttggagt tggtgtcggc 1620
gtccctggac ttggagttgg tgctggtgtt cctggacttg gagttggtgc tggtgttcct 1680
ggcttccggg cagtacctgg agccctggct gccgctaaag cagccaaata tggagcagca 1740
gtgcctgggg tccttggagg gctcggggct ctcggtggag taggcatccc aggcggtgtg 1800
```

gtgggagccg gacccgccgc cgccgctgcc gcagccaaag ctgctgccaa agccgcccag 1860
tttggcctag tgggagccgc tgggctcgga ggactcggag tcggagggct tggagttcca 1920
ggtgttgggg gccttggagg tatacctcca gctgcagccg ctaaagcagc taaatacgga 1980
gtggcagcaa gacctggctt cggattgtct cccattttcc caggtggggc ctgcctgggg 2040
aaagcttgtg gccggaagag aaaatga 2067

<210> SEQ ID NO 83
<211> LENGTH: 1932
<212> TYPE: DNA
<213> ORGANISM: Homo sapiens

<400> SEQUENCE: 83
atggcgggtc tgacggcggc ggccccgcgg cccggagtcc tcctgctcct gctgtccatc 60
ctccacccct ctcggcctgg aggggtccct ggggccattc ctggtggagt tcctggagga 120
gtcttttatc cagcgctggg gcctggaggc aaacctctta agccagttcc cggagggctt 180
gcgggtgctg gccttggggc agggctcggc gccttccccg cagttacctt tccgggggct 240
ctggtgcctg gtggagtggc tgacgctgct gcagcctata aagctgctaa ggctggcgct 300
gggcttggtg gtgtcccagg agttggtggc ttaggagtgt ctgcaggtgc ggtggttcct 360
cagcctggag ccggagtgaa gcctgggaaa gtgccgggtg tggggctgcc aggtgtatac 420
ccaggtggcg tgctcccagg agttggaccc tttgggggac cgcaacctgg agtcccactg 480
gggtatccca tcaaggcccc caagctgcct ggtggctatg gactgcccta caccacaggg 540
aaactgccct atggctatgg gcccggagga gtggctggtg cagcgggcaa ggctggttac 600
ccaacaggga caggggttgg cccccaggca gcagcagcag cggcagctaa agcagcagca 660
aagttcggtg ctggagcagc cggagtcctc cctggtgttg gaggggctgg tgttcctggc 720
gtgcctgggg caattcctgg aattggaggc atcgcaggcg ttgggactcc agctgcagct 780
gcagctgcag cagcagccgc taaggcagcc aagtatggag ctgctgcagg cttagtgcct 840
ggtgggccag gctttggccc gggagtagtt ggtgtcccag gagctggcgt tccaggtgtt 900
ggtgtcccag gagctgggat tccagttgtc ccaggtgctg ggatcccagg tgctgcggtt 960
ccaggggttg tgtcaccaga agcagctgct aaggcagctg caaaggcagc caaatacggg 1020
gccaggcccg gagtcggagt tggaggcatt cctacttacg ggttggagc tgggggcttt 1080
cccggctttg gtgtcggagt cggaggtatc cctggagtcg caggtgtccc tagtgtcgga 1140
ggtgttcccg gagtcggagg tgtcccggga gttggcattt cccccgaagc tcaggcagca 1200
gctgccgcca aggctgccaa gtacgggtta gttcctggtg tcggcgtggc tcctggagtt 1260
ggcgtggctc ctggtgtcgg tgtggctcct ggagttggct tggctcctgg agttggcgtg 1320
gctcctggag ttggtgtggc tcctggcgtt ggcgtggctc ccggcattgg ccctggtgga 1380
gttgcagctg cagcaaaatc cgctgccaag gtggctgcca aagcccagct ccgagctgca 1440
gctgggcttg gtgctggcat ccctggactt ggagttggtg tcggcgtccc tggacttgga 1500
gttggtgctg gtgttcctgg acttggagtt ggtgctggtg ttcctggctt cggggcagta 1560

| | |
|---|---:|
| cctggagccc tggctgccgc taaagcagcc aaatatggag cagcagtgcc tggggtcctt | 1620 |
| ggagggctcg gggctctcgg tggagtaggc atcccaggcg gtgtggtggg agccggaccc | 1680 |
| gccgccgccg ctgccgcagc caaagctgct gccaaagccg cccagtttgg cctagtggga | 1740 |
| gccgctgggc tcggaggact cggagtcgga gggcttggag ttccaggtgt gggggccttt | 1800 |
| ggaggtatac ctccagctgc agccgctaaa gcagctaaat acggagtggc agcaagacct | 1860 |
| ggcttcggat tgtctcccat tttcccaggt ggggcctgcc tggggaaagc ttgtggccgg | 1920 |
| aagagaaaat ga | 1932 |

<210> SEQ ID NO 84
<211> LENGTH: 2040
<212> TYPE: DNA
<213> ORGANISM: Homo sapiens

<400> SEQUENCE: 84

| | |
|---|---:|
| atggcaggtc tgactgccgc agcccctcgt ccaggtgtct tactgttgct gttatccatt | 60 |
| ctccatccat ctagacctgg tggcgttcca ggtgccattc caggtggcgt tccaggaggt | 120 |
| gtcttttatc ctggggctgg tttaggagcc cttggaggag gtgcgctggg tcctggtggc | 180 |
| aaaccactga aaccagttcc aggtggcctt gccggtgcag ccttggtgc aggcctgggt | 240 |
| gccttcccag cagtgacctt tcctggggct ctggtgcctg gtggcgtagc tgatgctgca | 300 |
| gcagcctaca aagcagctaa ggctggtgca ggtttagggg gtgtgccagg tgttggtggc | 360 |
| ttaggggtat ctgcaggtgc cgtggttcct caacctggtg ccggagtgaa gccagggaaa | 420 |
| gttccaggtg taggcctgcc aggtgtttac ccaggtggcg tgttgccagg agctcgtttt | 480 |
| ccaggtgtgg gggtgctacc tggcgttcca actggagccg tgtaaagcc aaaagctcca | 540 |
| ggtgtaggtg gagcatttgc tggcattcca ggtgttggac cttttggggg accacaacct | 600 |
| ggcgtcccat tgggatatcc aatcaaagcc ccaaaactgc caggtggcta cggtttaccc | 660 |
| tataccactg gtaagttgcc gtatggctat ggtcctggtg gcgtcgcagg tgcagccggt | 720 |
| aaggcaggtt accccaccgg tacaggtgta ggtccacagg cagcagcagc ggcagcagcg | 780 |
| aaagcagcag ccaagttcgg tgcaggagca gccggtgtgt tgccaggtgt tggtggcgca | 840 |
| ggtgttccag gtgtgcctgg tgcaatccct ggcattgggg gtatcgcagg cgtagggacc | 900 |
| ccagctgcag ccgcagccgc agcagcagcc gctaaggcag ccaagtacgg tgcagccgca | 960 |
| gggttagtgc caggtggccc aggttttggt ccaggagtag ttggtgttcc aggtgcaggt | 1020 |
| gttcctggtg ttggtgtccc aggtgcaggc attccagttg taccaggtgc aggcattcca | 1080 |
| ggtgcagccg ttcaggcgt tgtgtcacca gaagcagcag ccaaggcagc cgcaaaggca | 1140 |
| gccaagtatg cgcaaggcc aggcgtcggt gttgaggta ttcctactta tggcgtcgga | 1200 |
| gcaggggggtt ttccaggttt tggggtcgga gtaggaggta ttcctggtgt cgcaggtgtt | 1260 |
| ccaagtgtcg gaggtgttcc aggtgtcgga ggtgtaccgg cgtcggcat tagtccagag | 1320 |
| gcacaggctg cagctgcagc caaggcagcc aagtacgggt tagttccagg tgtaggtgtg | 1380 |
| gctccaggtg ttggtgtggc acctggtgtg ggtgtggcac caggtgttgg tttggctcca | 1440 |
| ggagttggcg ttgctccagg ggttggtgtt gctccaggcg ttggtgtggc acctggtatt | 1500 |
| ggaccaggtg gggtcgcagc tgcagcgaaa tccgctgcca agttgcagc caaagcacaa | 1560 |
| ctacgtgcgg cagctggcct gggtgcaggt attccaggct gggtgttgg cgttggcgtc | 1620 |
| cctggtcttg gagttggtgc cggtgtgcct ggtcttggtg ttggtgcagg ggttcctggt | 1680 |
| ttcggtgccg ttcctggtgc attagctgca gccaaggcag ccaaatatgg cgcggcagtg | 1740 |

```
cctggtgtct tgggaggtct cggagccttg ggtggcgtag gtattccagg cggtgtggtg      1800
ggagccggtc cagctgcagc agctgccgca gccaaggctg cagccaaagc agcccagttt      1860
ggcctggtgg gtgccgcagg tttaggaggt ttgggtgtcg gaggtttggg tgttccaggt      1920
gtcggtggct taggaggtat acctccagcc gcagccgcaa aagcagccaa atacggagtg      1980
gccgcacgtc ctggtttcgg cttatcaccc atcttcccag gtggagcctg cctgggtaaa      2040
```

<210> SEQ ID NO 85
<211> LENGTH: 2042
<212> TYPE: DNA
<213> ORGANISM: Homo sapiens

<400> SEQUENCE: 85

```
atggcaggtc tgactgccgc agcccctcgt ccaggtgtct tactgttgct gttatccatt       60
ctccatccat ctagacctgg tggcgttcca ggtgccattc caggtggcgt tccaggaggt      120
gtcttttatc ctggggctgg tttaggagcc cttggaggag gtgcgctggg tcctggtggc      180
aaaccactga aaccagttcc aggtggcctt gccggtgcag gccttggtgc aggcctgggt      240
gccttcccag cagtgacctt tcctggggct ctggtgcctg gtggcgtagc tgatgctgca      300
gcagcctaca aagcagctaa ggctggtgca ggtttagggg gtgtgccagg tgttggtggc      360
ttaggggtat ctgcaggtgc cgtggttcct caacctggtg ccggagtgaa gccagggaaa      420
gttccaggtg taggcctgcc aggtgtttac ccaggtggcg tgttgccagg agctcgtttt      480
ccaggtgtgg gggtgctacc tggcgttcca actggagccg gtgtaaagcc aaaagctcca      540
ggtgtaggtg gagcatttgc tggcattcca ggtgttggac cttttggggg accacaacct      600
ggcgtcccat gggatatcc aatcaaagcc ccaaaactgc caggtggcta cggtttaccc      660
tataccactg gtaagttgcc gtatggctat ggtcctggtg gcgtcgcagg tgcagccggt      720
aaggcaggtt accccaccgg tacaggtgta ggtccacagg cagcagcagc ggcagcagcg      780
aaagcagcag ccaagttcgg tgcaggagca gccggtgtgt tgccaggtgt tggtggcgca      840
ggtgttccag gtgtgcctgg tgcaatccct ggcattgggg gtatcgcagg cgtagggacc      900
ccagctgcag ccgcagccgc agcagcagcc gctaaggcag ccaagtacgg tgcagccgca      960
gggttagtgc caggtggccc aggttttggt ccaggagtag ttggtgttcc aggtgcaggt     1020
gttcctggtt tggtgtccc aggtgcaggc attccagttg taccaggtgc aggcattcca     1080
ggtgcagccg ttccaggcgt tgtgtcacca gaagcagcag ccaaggcagc cgcaaaggca     1140
gccaagtatg gcgcaaggcc aggcgtcggt gttggaggta ttcctactta tggcgtcgga     1200 gcaggggtt ttccaggttt tgggtcgga gtaggaggta ttcctggtgt cgcaggtgtt     1260
ccaagtgtcg gaggtgttcc agtgtcggt ggtgtaccgg cgtcggcat tagtccagag     1320 gcacaggctg cagctgcagc caaggcagcc aagtacgggt tagttccagg tgtaggtgtg     1380
gctccaggtg ttggtgtggc acctggtgtg ggtgtggcac aggtgttgg tttggctcca     1440 ggagttggcg ttgctccagg ggttggtgtt gctccaggcg ttggtgtggc acctggtatt     1500
ggaccaggtg gggtcgcagc tgcagcgaaa tccgctgcca aagttgcagc caaagcacaa     1560
ctacgtgcgg cagctggcct gggtgcaggt attccaggct ggtgttggg cgttggcgtc     1620 cctggtcttg gagttggtgc cggtgtgcct ggtcttggtg ttggtgcagg ggttcctggt     1680
ttcggtgccg ttcctggtgc attagctgca gccaaggcag ccaaatatgg cgcggcagtg     1740
cctggtgtct tgggaggtct cggagccttg ggtggcgtag gtattccagg cggtgtggtg     1800
```

```
ggagccggtc cagctgcagc agctgccgca gccaaggctg cagccaaagc agcccagttt    1860
ggcctggtgg gtgccgcagg tttaggaggt ttgggtgtcg gaggtttggg tgttccaggt    1920
gtcggtggct taggaggtat acctccagcc gcagccgcaa aagcagccaa atacggagtg    1980
gccgcacgtc ctggtttcgg cttatcaccc atcttcccag gtggagcctg cctgggtaaa    2040
gc                                                                   2042

<210> SEQ ID NO 86
<211> LENGTH: 2043
<212> TYPE: DNA
<213> ORGANISM: Homo sapiens

<400> SEQUENCE: 86
atggcaggtc tgactgccgc agcccctcgt ccaggtgtct tactgttgct gttatccatt      60
ctccatccat ctagacctgg tggcgttcca ggtgccattc aggtggcgt tccaggaggt     120
gtcttttatc ctggggctgg tttaggagcc cttggaggag gtgcgctggg tcctggtggc     180
aaaccactga accagttcc aggtggcctt gccggtgcag gccttggtgc aggcctgggt     240
gccttcccag cagtgacctt tcctggggct ctggtgcctg gtggcgtagc tgatgctgca     300
gcagcctaca agcagctaa ggctggtgca ggtttagggg gtgtgccagg tgttggtggc     360
ttaggggtat ctgcaggtgc cgtggttcct caacctggtg ccggagtgaa gccagggaaa     420
gttccaggtg taggcctgcc aggtgtttac ccaggtggcg tgttgccagg agctcgtttt     480
ccaggtgtgg gggtgctacc tggcgttcca actggagccg gtgtaaagcc aaaagctcca     540
ggtgtaggtg gagcatttgc tggcattcca ggtgttggac cttttggggg accacaacct     600
ggcgtcccat tggatatcc aatcaaagcc ccaaaactgc caggtggcta cggtttaccc     660
tataccactg gtaagttgcc gtatggctat ggtcctggtg gcgtcgcagg tgcagccggt     720
aaggcaggtt accccaccgg tacaggtgta ggtccacagg cagcagcagc ggcagcagcg     780
aaagcagcag ccaagttcgg tgcaggagca gccggtgtgt tgccaggtgt tggtggcgca     840
ggtgttccag gtgtgcctgg tgcaatccct ggcattgggg gtatcgcagg cgtagggacc     900
ccagctgcag ccgcagccgc agcagcagcc gctaaggcag ccaagtacgg tgcagccgca     960
gggttagtgc caggtggccc aggttttggt ccaggagtag ttggtgttcc aggtgcaggt    1020
gttcctggtg ttggtgtccc aggtgcaggc attccagttg taccaggtgc aggcattcca    1080
ggtgcagccg ttcaggcgt tgtgtcacca gaagcagcag ccaaggcagc cgcaaaggca    1140
gccaagtatg gcgcaaggcc aggcgtcggt gttgaggta ttcctactta tggcgtcgga    1200
gcaggggtt ttccaggttt tggggtcgga gtaggaggta ttcctggtgt cgcaggtgtt    1260
ccaagtgtcg gaggtgttcc aggtgtcgga ggtgtaccgg cgtcggcat tagtccagag    1320
gcacaggctg cagctgcagc caaggcagcc aagtacgggt tagttccagg tgtaggtgtg    1380
gctccaggtg ttggtgtggc acctggtgtg gtgtggcac aggtgttgg tttggctcca    1440
ggagttggcg ttgctccagg ggttggtgtt gctccaggcg ttggtgtggc acctggtatt    1500
ggaccaggtg gggtcgcagc tgcagcgaaa tccgctgcca agttgcagc caaagcacaa    1560
ctacgtgcgg cagctggcct gggtgcaggt attccaggct tgggtgttgg cgttggcgtc    1620
cctggtcttg gagttggtgc cggtgtgcct ggtcttggtg ttggtcagg ggttcctggt    1680
ttcggtgccg ttcctggtgc attagctgca gccaaggcag ccaaatatgg cgcggcagtg    1740
cctggtgtct tgggaggtct cggagccttg ggtggcgtag gtattccagg cggtgtggtg    1800
ggagccggtc cagctgcagc agctgccgca gccaaggctg cagccaaagc agcccagttt    1860
```

| | |
|---|---|
| ggcctggtgg gtgccgcagg tttaggaggt ttgggtgtcg gaggtttggg tgttccaggt | 1920 |
| gtcggtggct taggaggtat acctccagcc gcagccgcaa aagcagccaa atacggagtg | 1980 |
| gccgcacgtc ctggtttcgg cttatcaccc atcttcccag gtggagcctg cctgggtaaa | 2040 |
| gct | 2043 |

<210> SEQ ID NO 87
<211> LENGTH: 3774
<212> TYPE: DNA
<213> ORGANISM: Homo sapiens

<400> SEQUENCE: 87

| | |
|---|---|
| ctccctcttt ccctcacagc cgacgaggca acaattaggc tttggggata aaacgaggtg | 60 |
| cggagagcgg gctggggcat ttctccccga gatggcgggg ctgacggcgg cggccccgcg | 120 |
| gcccggagtc ctcctgctcc tgctgtccat cctccacccc tctcggcctg gagggtccc | 180 |
| tggggccatt cctggtggag ttcctggagg agtcttttat ccaggggctg gtctcggagc | 240 |
| ccttggagga ggagcgctgg ggcctggagg caaacctctt aagccagttc ccggagggct | 300 |
| tgcgggtgct ggccttgggg caggacctca ccccatcctc ccctccgcag gctcggcgc | 360 |
| cttccccgca gttacctttc cggggctct ggtgcctggt ggagtggctg acgctgctgc | 420 |
| agcctataaa gctgctaagg ctggcgctgg gcttggtggt gtcccaggag ttggtggctt | 480 |
| aggagtgtct gcagcccctt ctgtgccagg tgcggtggtt cctcagcctg agccggagt | 540 |
| gaagcctggg aaagtgccgg gtgtggggct gccaggtgta tacccaggtg gcgtgctccc | 600 |
| agggcctgca aggcctgcct tcctacactc actgctttgt cccccggcag gagctcggtt | 660 |
| ccccggtgtg ggggtgctcc ctggagttcc cactggagca ggagttaagc ccaaggctcc | 720 |
| aggtgtaggt ggagctttg ctggaatccc aggagttgga ccctttgggg gaccgcaacc | 780 |
| tggagtccca ctggggtatc ccatcaaggc cccaagctg cctggtggct atggactgcc | 840 |
| ctacaccaca gggaaactgc cctatggcta tgggcccgga ggagtggctg gtgcagcggg | 900 |
| caaggctggt tacccaacag ggacagggt tggccccag gcagcagcag cagcggcagc | 960 |
| taaagcagca gcaaagttcg gtgctggagc agccggagtc ctccctggtg ttggaggggc | 1020 |
| tggtgttcct ggcgtgcctg gggcaattcc tggaattgga ggcatcgcag gcgttgggac | 1080 |
| tccagctgca gctgcagctg cagcagcagc cgctaaggca gccaagtatg gagctgctgc | 1140 |
| aggcttagtg cctggtgggc caggcttttgg cccgggagta gttggtgtcc caggagctgg | 1200 |
| cgttccaggt gttggtgtcc caggagctgg gattccagtt gtcccaggtg ctgggatccc | 1260 |
| aggtgctgcg gttccagggg ttgtgtcacc agaagcagct gctaaggcag ctgcaaaggc | 1320 |
| agccaaatac ggggccaggc ccggagtcgg agttggaggc attcctactt acggggttgg | 1380 |
| agctgggggc tttcccggct ttggtgtcgg agtcggaggt atccctggag tcgcaggtgt | 1440 |
| ccctggtgtc ggaggtgttc ccggagtcgg aggtgtcccg ggagttggca tttcccccga | 1500 |
| agctcaggca gcagctgccg ccaaggctgc caagtacggt gctgcaggag caggagtgct | 1560 |
| gggtgggcta gtgccaggtg cccaggcgc agtcccaggt gtgccgggca cggaggagt | 1620 |
| gccaggagtg gggaccccag cagctgcagc tgctaaagca gccgccaaag ccgcccagtt | 1680 |
| tgctcttctc aatcttgcag ggttagttcc tggtgtcggc gtggctcctg gagttggcgt | 1740 |

```
ggctcctggt gtcggtgtgg ctcctggagt tggcttggct cctggagttg gcgtggctcc   1800
tggagttggt gtggctcctg gcgttggcgt ggctcccggc attggccctg gtggagttgc   1860
agctgcagca aaatccgctg ccaaggtggc tgccaaagcc cagctccgag ctgcagctgg   1920
gcttggtgct ggcatccctg gacttggagt tggtgtcggc gtccctggac ttggagttgg   1980
tgctggtgtt cctggacttg gagttggtgc tggtgttcct ggcttcgggg caggtgcaga   2040
tgagggagtt aggcggagcc tgtcccctga gctcagggaa ggagatccct cctcctctca   2100
gcacctcccc agcaccccct catcacccag ggtacctgga gccctggctg ccgctaaagc   2160
agccaaatat ggagcagcag tgcctggggt ccttggaggg ctcggggctc tcggtggagt   2220
aggcatccca gcggtgtggt gggagccgg accgccgcc gcgctgccg cagccaaagc      2280 tgctgccaaa ccgcccagt ttggcctagt gggagccgct gggctcggag gactcggagt    2340
cggagggctt ggagttccag gtgttggggg ccttggaggt atacctccag ctgcagccgc   2400
taaagcagct aaatacggtg ctgctggcct tggaggtgtc ctaggggtg ccgggcagtt    2460 cccacttgga ggagtggcag caagacctgg cttcggattg tctcccattt tcccaggtgg   2520
ggcctgcctg gggaaagctt gtggccggaa gagaaaatga gcttcctagg acccctgact   2580
cacgacctca tcaacgttgg tgctactgct tggtggagaa tgtaaaccct ttgtaacccc   2640
atcccatgcc cctccgactc cccacccag gagggaacgg gcaggccggg cggccttgca    2700
gatccacagg gcaaggaaac aagagggag cggccaagtg ccccgaccag gaggcccct     2760 acttcagagg caagggccat gtggtcctgg ccccccaccc catcccttcc cacctaggag   2820 ctcccctcc acacagcctc catctccagg ggaacttggt gctacacgct ggtgctctta    2880
tcttcctggg gggagggagg agggaagggt ggccctcgg ggaacccct acctggggct     2940 cctctaaaga tggtgcagac acttcctggg cagtcccagc tcccctgcc caccaggacc    3000 caccgttggc tgccatccag ttggtaccca agcacctgaa gcctcaaagc tggattcgct   3060
ctagcatccc tcctctcctg ggtccacttg gccgtctcct ccccaccgat cgctgttccc   3120
cacatctggg gcgcttttgg gttggaaaac caccccacac tgggaatagc accttgccc    3180 ttgtagaatc catccgccca tccgtccatt catccatcgg tccgtccatc catgtcccca   3240
gttgaccgcc cggcaccact agctggctgg gtgcacccac catcaacctg gttgacctgt   3300
catggccgcc tgtgccctgc ctccacccc atcctacact ccccagggc gtgcggggct     3360 gtgcagactg gggtgccagg catctcctcc ccacccgggg tgtccccaca tgcagtactg   3420
tatacccccc atccctccct cggtccactg aacttcagag cagttcccat tcctgccccg   3480
cccatctttt tgtgtctcgc tgtgatagat caataaatat tttattttt gtcctggata    3540 tttggggatt atttttgatt gttgatattc tcttttggtt ttattgttgt ggttcattga   3600 aaaaaaaga taatttttt ttctgatccg gggagctgta tccccagtag aaaaaacatt     3660
ttaatcactc taatataact ctggatgaaa cacaccttt tttttaataa gaaaagagaa    3720
ttaactgctt cagaaatgac taataaatga aaaaccttta aggaaaaaa aaaa           3774
```

TROPOELASTINS AND USES THEREOF

CROSS REFERENCE TO RELATED APPLICATIONS

This application claims the benefit under 35 U.S.C. 119(e) of U.S. Provisional Application No. 61/451,696, filed Sep. 30, 2011, which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DERM_001_01 US_ST25.txt. The text file is 369 KB, was created on Dec. 28, 2012, and is being submitted electronically via EFS-Web.

BACKGROUND

1. Technical Field

The present invention generally relates to tropoelastin polynucleotides and polypeptides and methods of making and using the same to prepare biocompatible polymeric scaffold materials. More particularly, the present invention relates to alternative spliced tropoelastin isoforms, and to implants and grafts comprising polymeric scaffold materials of cross-linked human tropoelastin polypeptides and methods of making and using the same.

2. Description of the Related Art

Regenerative medicine has the potential to repair or replace any diseased cell, tissue, or organ; thus revolutionizing the practice of medicine. One important goal of regenerative medicine is to repair, maintain, improve or even restore the function of damaged or diseased cells, tissues, and organs. However, to date, there have a limited number of successful examples applying these concepts in a human clinical setting. In addition, many of compositions and materials used in regenerative medicine are currently cost-prohibitive, inefficient, and/or unsafe.

Surgical means have been used to regenerate tissue in a certain, controlled manner. Common reasons for surgical intervention include, a fractured bone, the regeneration of new tissue to replace tissue lost due to traumatic or surgical causes or an infection, atrophy or for congenital reasons. Success of surgical interventions often requires that the affected tissue be separated from other tissues surrounding it and that around the tissue a certain space is created, to which tissue can regenerate.

The inadequacy of existing polymeric graft materials has constantly been challenged by the development of new materials, particularly those with more favorable physical properties. The use of polyurethane biomaterials has been limited by questions surrounding long-term stability of implanted materials. The combined susceptibility of polyurethanes to hydrolysis, cracking, enzymatic degradation, calcification and corrosion to varying degrees depending on the formulation (Santerre et al., (2005), Biomaterials, 26, 7457-70) has led to doubts regarding biostability and bi-product toxicity. The problems faced by polyurethane biomaterials are common to this field.

Currently available biocompatible membranes also lack ideal shapeability and rigidity. These two properties of biocompatible membranes are contrary to each other. For example, a biocompatible membrane must naturally be shaped to fit the tissue structure in such a manner that it separates the tissues from each other exactly as desired so as to allow the regenerating tissue to grow in the correct shape with no damage to the surrounding tissue. On the other hand, the membrane must be sufficiently rigid that its shape does not change under the pressure caused by the growing tissue or that possible external stress does not cause a movement hampering the healing of the tissue. The prior art does not provide a satisfactory solution to fulfilling both requirements.

For example, synthetic biocompatible membranes made of expanded polytetrafluoroethylene (ePTFE) such as Gore-Tex®, Impra, or Atrium have increased rigidity when supported by titanium support threads or other metal alloys. Such membranes are often rigid and therefore keep their form well under the pressure of tissue, but correspondingly, their shaping is arduous. In contrast shaping support thread-free PTFE membranes is quite easy, but their rigidity is not sufficient. Another significant problem with such membranes is that they require surgical removal from the organ system after the tissue has healed. Surgical removal of such membranes increases patient costs, discomfort, and adds to the patient's risk of obtaining an infection from the operation.

Biocompatible membranes made of biodegradable polymers need not be surgically removed from the organ system, as they dissipate slowly from the organ system via normal biochemical and metabolic pathways. A significant problem with biodegradable materials is that the thin, easily shaping membranes are not rigid enough to maintain space for the regenerating tissue to grow undisturbed. Thus, there is a significant risk the membrane bends under pressure against the healing tissue so that there is insufficient space for the regenerating tissue to adequately grow. To achieve sufficient rigidity, the membrane can naturally be made thicker. However, when the thickness of the membrane is increased to achieve a sufficient rigidity, the membrane becomes so thick that shaping it is very difficult and arduous.

It is clear that there is a large unmet need in regenerative medicine for a more biocompatible, durable, and clinically effective polymeric biomaterial. The compositions, implants, and methods of the present invention address these needs and offer other related advantages.

BRIEF SUMMARY

The present invention generally provides biocompatible polymeric scaffold materials comprising novel tropoelastin compositions, methods for making the materials and methods of using the materials.

In various embodiments, the present invention provides implants and grafts comprising polymeric scaffold materials of cross-linked human tropoelastin polypeptides. In various other embodiments, methods of making polymeric scaffold materials are provided. In addition, the present invention provides alternatively spliced tropoelastin polynucleotides and polypeptides and compositions comprising the same.

In various embodiments, the present invention contemplates, in part, a method for repairing, replacing, or regenerating an injured or damaged tissue comprising: providing an amount of one or more tropoelastin polypeptides; casting the tropoelastin polypeptides into a desired shape to form a scaffold; culturing cells on the shaped tropoelastin polymer scaffold to form an implant; and providing the implant to a subject; thereby repairing, replacing, or regenerating the injured or damaged tissue.

In one embodiment, at least one of the one or more tropoelastin polypeptides comprises an alternatively spliced tropoelastin polypeptide.

In a particular embodiment, at least one or more alternatively spliced tropoelastin polypeptides comprises an amino acid sequence as set forth in any one of SEQ ID NOs: 2-48.

In an additional embodiment, at least one or more alternatively spliced tropoelastin polypeptides comprises an amino acid sequence as set forth in any one of SEQ ID NOs: 13, 47, and 48.

In a certain embodiment, at least one or more alternatively spliced tropoelastin polypeptides comprises an amino acid sequence as set forth in SEQ ID NOs: 13.

In a further embodiment, the at least one or more alternatively spliced tropoelastin polypeptides comprises an N-terminal or C-terminal truncation of 1, 2, 3, 4, 5, 6, 7, 8, 9, or 10 amino acids.

In a particular embodiment, the tissue is selected from the group consisting of: odontic tissue, periodontal tissue, pancreatic tissue, neural tissue, cardiac tissue, bone marrow, muscle tissue, bone tissue, skin tissue, liver tissue, hair follicles, vascular tissue, adipose tissue, lung tissue, retinal tissue, corneal tissue, and kidney tissue.

In one embodiment, the scaffold comprises one or more co-polymers.

In another embodiment, the scaffold comprises one or more resorbable co-polymers.

In yet another embodiment, the scaffold comprises one or more non-resorbable co-polymers.

In still yet another embodiment, the scaffold comprises both a resorbable and a non-resorbable co-polymer.

In a certain embodiment, the one or more co-polymers comprises a collagen protein.

In a certain particular embodiment, the desired shape is a three dimensional shape In another certain particular embodiment, the desired shape is a sheet or a tube.

In an additional particular embodiment, the cells comprise stem cells, progenitor cells, and/or differentiated cells.

In various embodiments, the present invention contemplates, in part, a method for making an implant comprising: providing an amount of one or more tropoelastin polypeptides; casting the tropoelastin polypeptides into a desired shape to form a scaffold; culturing cells on the shaped tropoelastin polymer scaffold to form an implant.

In one embodiment, at least one of the one or more tropoelastin polypeptides comprises an alternatively spliced tropoelastin polypeptide.

In a particular embodiment, at least one or more alternatively spliced tropoelastin polypeptides comprises an amino acid sequence as set forth in any one of SEQ ID NOs: 2-48.

In a certain embodiment, at least one or more alternatively spliced tropoelastin polypeptides comprises an amino acid sequence as set forth in any one of SEQ ID NOs: 13, 47, and 48.

In an additional embodiment, at least one or more alternatively spliced tropoelastin polypeptides comprises an amino acid sequence as set forth in SEQ ID NOs: 13.

In a further embodiment, the at least one or more alternatively spliced tropoelastin polypeptides comprises an N-terminal or C-terminal truncation of 1, 2, 3, 4, 5, 6, 7, 8, 9, or 10 amino acids.

In one embodiment, the scaffold comprises one or more co-polymers.

In another embodiment, the scaffold comprises one or more resorbable co-polymers.

In yet another embodiment, the scaffold comprises one or more non-resorbable co-polymers.

In still yet another embodiment, the scaffold comprises both a resorbable and a non-resorbable co-polymer.

In a further particular embodiment, the one or more co-polymers comprises a collagen protein.

In an additional particular embodiment, the desired shape is a three dimensional shape In a certain particular embodiment, the desired shape is a sheet or a tube.

In one embodiment, the cells are stem/progenitor cells.

In a further embodiment, the stem/progenitor cells are selected from the group consisting of: bone marrow stem/progenitor cells, umbilical cord stem/progenitor cells, adipose tissue derived stem/progenitor cells, hematopoietic stem/progenitor cells (HSGs), mesenchymal stem/progenitor cells, muscle stem/progenitor cells, liver stem/progenitor cells, pancreatic stem/progenitor cells, skin stem/progenitor cells, neural stem/progenitor cells, kidney stem/progenitor cells, osteoblast stem/progenitor cells, and chondrocyte stem/progenitor cells In an additional embodiment, the cells comprises one or more of odontic cells, periodontic cells, gingival cells, pancreatic islet cells, CNS cells, PNS cells, cardiac muscle cells, skeletal muscle cells, smooth muscle cells, hematopoietic cells, bone cells, liver cells, an adipose cells, renal cells, lung cells, chondrocyte, skin cells, keratinocytes, fibroblasts, follicular cells, vascular cells, epithelial cells, immune cells, and endothelial cells.

In various other embodiments, the present invention contemplates, in part, an implant comprising: a biocompatible polymer scaffold comprising one or more tropoelastin polypeptides; one or more populations of cells; and a co-polymer polypeptide, wherein the implant is substantially endotoxin free.

In a particular embodiment, at least one of the one or more tropoelastin polypeptides comprises an alternatively spliced tropoelastin polypeptide.

In an additional embodiment, the at least one or more alternatively spliced tropoelastin polypeptides comprises an amino acid sequence as set forth in any one of SEQ ID NOs: 2-48.

In a certain embodiment, the at least one or more alternatively spliced tropoelastin polypeptides comprises an amino acid sequence as set forth in any one of SEQ ID NOs: 13, 47, and 48.

In a further embodiment, the at least one or more alternatively spliced tropoelastin polypeptides comprises an amino acid sequence as set forth in SEQ ID NOs: 13.

In a particular additional embodiment, the at least one or more alternatively spliced tropoelastin polypeptides comprises an N-terminal or C-terminal truncation of 1, 2, 3, 4, 5, 6, 7, 8, 9, or 10 amino acids.

In a certain additional embodiment, the one or more co-polymers comprises a collagen protein.

In a further additional embodiment, the scaffold is cast into a desired shape.

In another further additional embodiment, the desired shape is a three dimensional shape.

In one embodiment, the cells are stem/progenitor cells.

In another embodiment, the stem/progenitor cells are selected from the group consisting of: bone marrow stem/progenitor cells, umbilical cord stem/progenitor cells, adipose tissue derived stem/progenitor cells, hematopoietic stem/progenitor cells (HSGs), mesenchymal stem/progenitor cells, muscle stem/progenitor cells, liver stem/progenitor cells, pancreatic stem/progenitor cells, skin stem/progenitor cells, neural stem/progenitor cells, kidney stem/progenitor cells, osteoblast stem/progenitor cells, and chondrocyte stem/progenitor cells In yet another embodiment, the cells comprises one or more of odontic cells, periodontic cells, gingival cells, pancreatic islet cells, CNS cells, PNS cells, cardiac muscle cells, skeletal muscle cells, smooth muscle cells, hematopoietic cells, bone cells, liver cells, an adipose cells, renal cells, lung cells, chondrocyte, skin cells, keratinocytes, fibroblasts, follicular cells, vascular cells, epithelial cells, immune cells, and endothelial cells.

In various embodiments, the present invention contemplates, in part, a polynucleotide comprising a nucleotide sequence as set forth in any one of SEQ ID NOs: 50-86 or a variant thereof.

In a particular embodiment, the polynucleotide has a nucleotide sequence that is at least 95% identical to a nucleotide sequence as set forth in any one of SEQ ID NOs: 50-86.

In another particular embodiment, the polynucleotide encodes a tropoelastin polypeptide as set forth in any one of SEQ ID NOs: 2-48.

In a certain particular embodiment, at least one or more alternatively spliced tropoelastin polypeptides comprises an amino acid sequence as set forth in any one of SEQ ID NOs: 13, 47, and 48.

In an additional particular embodiment, the at least one or more alternatively spliced tropoelastin polypeptides comprises an amino acid sequence as set forth in SEQ ID NOs: 13.

In a further particular embodiment, the polynucleotide encodes a tropoelastin polypeptide that has an amino acid sequence that is at least 95% identical to an amino acid sequence as set forth in any one of SEQ ID NOs: 2-48.

In one embodiment, the nucleotide sequence is codon optimized for expression in *Escherichia coli*, yeast, or insect cells.

In various embodiments, the present invention contemplates, in part, a polypeptide encoded by a polynucleotide.

In one embodiment, the polypeptide comprises one or more amino acid substitutions, deletions, or insertions.

In a particular embodiment, the polypeptide comprises an N-terminal or C-terminal truncation of 1, 2, 3, 4, 5, 6, 7, 8, 9, or 10 amino acids.

In a certain embodiment, the polypeptide comprises a C-terminal truncation of 1, 2, 3, 4, 5, 6, 7, 8, 9, or 10 amino acids.

BRIEF DESCRIPTION OF THE SEQUENCE IDENTIFIERS

Figure 1:
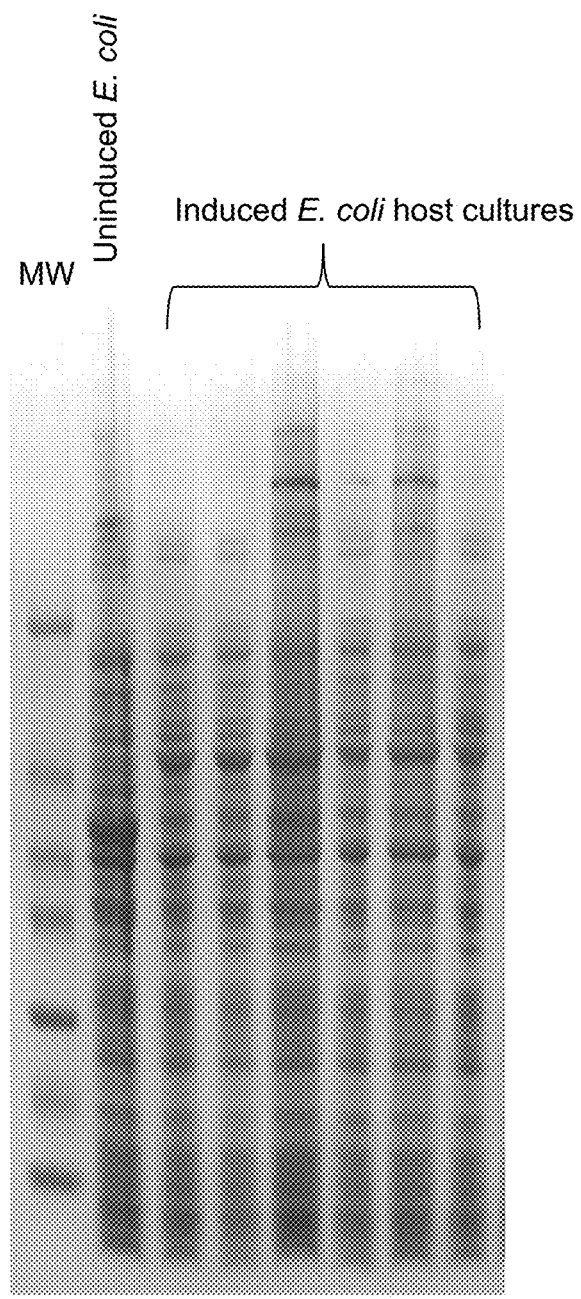
FIG. 1 shows an SDS PAGE analysis of tropoelastin expression. Lane 1 is a molecular weight marker; lane 2 is uninduced *E. coli* host cultures; and lanes 3-8 are induced *E. coli* host cultures. The arrow identifies the region of the gel corresponding to tropoelastin having a molecular weight (MW) of 62,000 Daltons.

SEQ ID NOs: 1-48 represent amino acid sequences of tropoelastin polypeptides.

SEQ ID NOs: 49-87 represent polynucleotide sequences of tropoelastin cDNAs.

DETAILED DESCRIPTION

All publications, patents and patent applications cited herein, whether supra or infra, are hereby incorporated by reference in their entirety.

The articles "a," "an," and "the" are used herein to refer to one or to more than one (i.e. to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As noted above, the invention generally relates to alternatively spliced tropoelastins, and their production and use in biocompatible polymeric scaffold materials for regenerative medicine. The materials are shapeable into various forms, including, but not limited to sheets, tubes, and any other three-dimensional spatial pieces. The shapeable scaffolds are used in constructing grafts and implants to provide aspects of regenerative medicine and promote regeneration by repairing, replacing or restoring damaged tissues or organs.

An objective in the development of bioengineered materials for regenerative medicine is the generation of polymer scaffolds with desirable properties, including strength, elasticity, and biocompatibility. The use of natural or near-natural starting materials in the manufacture of polymer scaffolds with low resorption has the advantages of providing an established level of performance and congruence. Implants and grafts comprising such scaffolds are more biocompatible, last longer, provide a more efficient means of regeneration, and are less toxic than existing biomaterials. An important example of a natural polymer scaffold with low or slow resorption is human elastin. Elastin is one of the most abundant protein polymers in organs that require flexibility as part of their essential functions, including the skin, lungs, blood vessels, and bladder, among others.

Elastin is a polymer of tropoelastin. However, to date only a single form of tropoelastin has been studied and its properties characterized. The present inventors have discovered that many forms of tropoelastin exist in the human body. Clearly, an advantage exists for the human body to have evolved such a complex of multiple tropoelastin forms. These different forms differ in tensile strength, elasticity, stiffness, cross-linking potential, ability to attract populating cells (chemotaxis) and wound healing properties. In various embodiments, fibers composed of two or more tropoelastin isoforms display different and unique properties compared to those fibers composed of a single isoform.

Thus, one significant advantage of the invention is the development of elastins with unique properties, e.g., tensile strength, elasticity, and flexibiltiy/stiffness, generated by combining 2, 3, 4, 5, 6, 7, 8, 9, 10 or more individual tropoelastin isoforms, themselves having unique properties. Such unique elastins can be tailored for use at locations in the body where their unique properties are the most advantageous. For example, the strongest fibers can be used to repair muscles, the most elastic fibers can be used to construct bladders and other flexible organs, e.g, blood vessels, and the stiffest fibers can be used in cartilage repair.

A. Elastin

The elastin protein polymer is synthesized from tropoelastin monomers, soluble polypeptides of about 72 kDa (Parks et al., *Am. J. Respir. Cell Mol. Biol.* 2:399, 1990). During elastin synthesis, newly synthesized tropoelastin monomers are secreted into the extracellular space, assembled into functional fibers, and cross-linked to form insoluble elastin. Following secretion, tropoelastin monomers self-associate in a process called coacervation, which arises from hydrophobic interactions. Coacervation concentrates and aligns tropoelastin for cross-linking and is a precursor to fiber formation (fibrillogenesis). Fibrillogenesis takes place at unique sites close to the cell membrane where tropoelastin is secreted within microfibrillar bundles surrounding the cell. Lysyl oxidase then oxidizes terminal amino groups on lysine residues and cross-links form as the oxidized side chains undergo condensation reactions.

Elastin has been used in combination with other supporting components to form biocompatible structures. Elastin, digested from animal sources has been combined with gelatin, collagen (Buttafoco et al., (2006) *Biomaterials,* 27, 724-34) and polymers such as poly(lactide-co-glycolide) (Stitzel et al., (2006) *Biomaterials,* 27, 1088-94) using electrospinning and producing fibers with improved tensile characteristics. Elastin from porcine arteries has also been used as the scaffold for a graft material, reinforced by physically wrapping the construct with small intestinal submucosa (essentially decellularized collagen) (Hinds et al., (2006) *J. Biomed. Mater. Res. Part A,* 77, 458-69). However, these materials are limited by the low quality and supply of animal elastin, infectious organisms associated with animal tissue sources, and also by the thrombogenicity of the supporting material.

B. Tropoelastin

The human tropoelastin gene has been isolated and the sequence has been determined (Indik et al., *P.N.A.S. USA* (1987), 84, pp. 5680-5684; Indik et al., *Connect. Tissue Res.* (1987), 16; pp. 197-211). The human tropoelastin gene has at least 34 separate exons spanning a total of 45 kbp of genomic DNA. Previously, others have identified alternative splicing of 6 of the 34 exons, which leads to at least 11 alternatively spliced protein isoforms (e.g., polymorphic polypeptides) of human tropoelastin (Boyd et al. *Matrix* (1991), 11; pp. 235-241; Shapiro, *Am. J. Respir. Crit. Care Med.* (1994) 150; pp. S160-S164; Fazio et al. *J. Invest. Dermatol.* (1988), 91; pp. 458-464; Fazio et al. *Lab. Invest.* (1988), 58; pp. 270-277). Applicants have conducted a detailed polymorphism analysis of tropoelastin mRNAs obtained from four independent human fibroblast cell lines revealed the presence of many different exon mRNA polymorphisms (see, e.g., Example 1). Illustrative tropoelastin polypeptides, including alternatively spliced tropoelastins and tropoelastins having point mutations, are set in SEQ ID NOs: 2-48. Illustrative polynucleotides sequences that represent tropoelastin cDNAs are set in SEQ ID NOs: 50-86.

The various polymorphic forms of tropoelastin can interact in ways that enhance specific roles of the resulting fiber. For example, some forms can provide a higher degree of elasticity, while other forms can promote hydrophobic interactions, increased tensile strength or chemotaxis by skin cells. These different forms can display unique affinities for cell surface receptors or in their ability to bind other proteins during fibrillogenesis. For example, particular tropoelastin polymorphisms affect the tensile strength in vascular tissue. In addition, carotid artery elasticity parameters (distensibility and elastic modulus) correlates with the presence of a particular elastin polymorph. Individuals carrying this polymorph show a decrease in distensibility and an increase in the elastic modulus of the carotid artery, linking the elasticity and tensile strength of tissues to the presence of specific elastin polymorphisms.

C. Biocompatible Polymer Scaffolds

In various embodiments, a biocompatible polymer scaffold with desirable properties, including, but not limited to strength, elasticity and biocompatibility comprises one or more tropoelastin polypeptides, as discussed elsewhere herein. As used herein, the terms "tropoelastin," "tropoelastin polypeptides," "tropoelastin polymorphic polypeptides," "tropoelastin polymorphs," "alternatively spliced tropoelastin polypeptides," "alternatively spliced tropoelastin isoforms," and "tropoelastin protein isoforms" refer to any of a variety of different isolated or recombinant human tropoelastin polypeptides, e.g., SEQ ID NOs: 2-48, encoded by "normally" spliced mRNAs, alternatively spliced tropoelastin mRNAs or tropoelastin mRNAs comprising polymorphic exons or single nucleotide polymorphisms (SNPs), as well as fusion proteins thereof. In various embodiments, the term "tropoelastin polypeptides," includes "normally" spliced tropoelastin, alternatively spliced tropoelastin, and variants and fragments thereof. The normally spliced form of tropoelastin includes all exons and for purposes of comparison, is set forth in SEQ ID NO: 1. A full length tropoelastin cDNA including 5' and 3' UTR and all exons is set forth in SEQ ID NO: 87. Additional illustrative embodiments of tropoelastin polypeptides includes the amino acid sequences set forth in SEQ ID NOs: 2-48.

In particular preferred embodiments, compositions and methods of the present invention comprise one or more tropoelastin polypeptides having an amino acid sequence as set forth in SEQ ID NO: 2-48, including variants thereof.

In particular embodiments, the polypeptides and biocompatible scaffolds are "endotoxin free." As used herein, the term "endotoxin free" refers to compositions that contain at most trace amounts (i.e., amounts having no adverse physiological effects to a subject) of endotoxin, and preferably undetectable amounts of endotoxin. In one embodiment, the term "endotoxin free" or "substantially endotoxin free" refers to a composition that is at least 95%, at least 96%, at least 97%, at least 98%, at least 99%, or 100% endotoxin free. In one embodiment, the term "endotoxin free" refers to endotoxin levels or an endotoxin profile that may be less than about 0.001, 0.005, 0.01, 0.02, 0.03, 0.04, 0.05, 0.06, 0.08. 0.09, 0.1, 0.5, 1.0, 1.5, 2, 2.5, 3, 4, 5, 6, 7, 8, 9, or 10 endotoxin units (EU)/ml or EU/mg. Typically, 1 ng lipopolysaccharude (LPS) corresponds to about 1-10 EU.

In other embodiments, non-human tropoelastin may be employed; however, it is generally desirable to match the species of animal being treated to the species of the tropoelastin being used to ensure biocompatability.

In particular embodiments, a non-human tropoelastin polypeptide is isolated from; or a non-human tropoelastin cDNA is obtained from a bovine, an equine, a sheep, a goat, a pig, a dog, a cat, rodent, or a non-human primate.

In a preferred embodiment, the tropoelastin polypeptides are human.

In another preferred embodiment, the present invention provides human tropoelastins codon optimized for recombinant expression in various hosts, methods for recombinantly producing the codon optimized tropoelastins, and the recombinant tropoelastin polypeptides for use in preparing biocompatible polymer scaffolds.

Various properties of the polymer scaffold that can affect the strength, elasticity, cross-linking potential and other physical and biochemical behavior of tropoelastin polymers, include, but are not limited to, the number and identity of the tropoelastin polymorphs in the scaffold, co-polymers included in the tropoelastin polymer scaffold, the thickness and/or shape of the scaffold, and the degree of cross-linking, among others.

In one embodiment, the polymer scaffolds are tailored to suit particular needs in the human body. The properties of the scaffold are tailored by incorporation of tropoelastin isoforms having different properties in tensile strength, elasticity, and flexibility/rigidity. In this way, the scaffold can be reliably designed for a particular purpose. For example, highly flexible elastin can be used in the construction of vascular structures (e.g., veins and arteries). The ability of elastin polymers to attract the growth of capillaries and promote the population of the scaffolds by the migration and growth of nearby cells (chemotaxis) are an important advantage of the invention in the context of wound healing.

Mechanical tests, such as uniaxial tensile testing, ultimate stresses and linear moduli parameters, yield and failure energies, and other tests (e.g., creep tests) known to those skilled in the art can be used to determine the mechanical characteristics of the devices.

1. Number and Identity of Tropoelastin Polymorphs

In particular embodiments, a scaffold comprises a single type of tropoelastin polypeptide, or a combination of tropoelastin polypeptides. The combination of tropoelastin polypeptides can comprise 1, 2, 3, 4, 5, 6, 7, 9, 10, or more, different types of tropoelastin polypeptides. In another particular embodiment, the scaffold can comprise at least 1, at least 2, at least 3, at least 4, at least 5, at least 6, at least 7, at least 8, at least 9, at least 10 or more, different tropoelastin polypeptides. In another particular embodiment, the scaffold can comprise 1 or more, 2 or more, 3 or more, 4 or more, 5 or more, 6 or more, 7 or more, 8 or more, 9 or more, or 10 or more different types of tropoelastin polypeptides, e.g., SEQ ID NOs: 2-48.

In certain embodiments, a scaffold comprises a single tropoelastin polypeptide, such as an alternatively spliced tropoelastin, or a combination of alternatively spliced tropoelastin polypeptides, wherein the tropoelastin polypeptides are human. In other certain embodiments, the tropoelastin polypeptides are any number or combination of human, non-human primate, bovine, an equine, a sheep, a goat, a pig, a dog, a cat, or rodent tropoelastin polypeptides.

In other particular embodiments, suitable tropoelastin polypeptides for use in manufacturing biocompatible polymer scaffolds include tropoelastin polypeptides, polypeptides encoded by alternatively spliced tropoelastin mRNAs, polypeptides encoded by tropoelastin mRNAs with one or more polymorphic exons and/or amino acid mutations, and genetically engineered tropoelastin polypeptides (e.g., fusion polypeptides) including any of the foregoing tropoelastin polypeptides.

Furthermore, one having ordinary skill in the art would appreciate that varying the ratio and/or identity of each of the tropoelastin polymorphs present in a combination can generate tropoelastin-based scaffolds with desired elasticity, tensile strength, and shapeability. For example, polymers based on particular combinations of tropoelastin exons that resulted in 3 different polymorphic forms, displayed tensile strength and elasticity reflecting the presence or absence of certain portions of the tropoelastin molecules. Thus, the strength, elasticity, cross-linking potential and other physical and biochemical behavior of tropoelastin polymers can be varied and possibly controlled by incorporating various polymorphic forms of tropoelastin into polymeric scaffolds.

In another embodiment, the ratio and/or identity of each of the tropoelastin polymorphs present in a combination can be varied so as to match the tropoelastin polymorphs present in the tissue being repaired, replaced, or regenerated.

2. Co-Polymers

In particular embodiments, a biocompatible polymer scaffold comprises one or more tropoelastin polypeptides and a co-polymer. An exemplary and in some cases preferred co-polymer is collagen. The presence and association of tropoelastin with collagen in biocompatible polymer scaffolds can significantly increase the durability of the scaffolds and decrease the rate of collagen degradation and resorption, which is a major advance and benefit over current collagen membranes. In one embodiment, the co-polymer is resorbable. In another embodiment, the co-polymer is non-resorbable. In a particular embodiment, the scaffold comprises one or more resorbable and non-resorbable co-polymers and one or more tropoelastin polypeptides.

In particular embodiments, a collagen co-polymer suitable for use in the biocompatible polymer scaffolds, includes, but is not limited to Collagen Type I, Collagen Type II, Collagen Type III, Collagen Type IV, Collagen Type V, Collagen Type VI, Collagen Type VII, Collagen Type VIII, Collagen Type IX, Collagen Type X, Collagen Type XI, Collagen Type XII, Collagen Type XIII, Collagen Type XIV, Collagen Type XV, Collagen Type XVI, Collagen Type XVII, Collagen Type XVIII, Collagen Type XIX, Collagen Type XX, Collagen Type XXI, Collagen Type XXII, Collagen Type XXIII, Collagen Type XXIV, Collagen Type XXV, Collagen Type XXVI, Collagen Type XXVII, Collagen Type XXVIII, and Collagen Type XXIX.

In other particular embodiments, the collagen co-polymer is selected from the group consisting of Collagen Type I, Collagen Type II, Collagen Type III, and Collagen Type IV.

In other particular embodiments, the collagen co-polymer is selected from the group consisting of: Collagen Type I and Collagen Type III.

In other particular embodiments, the collagen co-polymer is Collagen Type I and/or Collagen Type III.

In other embodiments, a biocompatible polymer scaffolds comprises one or more tropoelastin polypeptides in combination with 1, 2, 3, 4, 5, 6, 7, 8, 9, 10, or more collagens One having skill in the art would appreciate that varying the ratio and/or identity of tropoelastin polypeptides and collagen co-polymers in a biocompatible polymer scaffold can generate scaffolds with desired elasticity, tensile strength, and shapeability and/or to match the tropoelastins and collagens present in the tissue being repaired, replaced, or regenerated.

In particular embodiments, exemplary molar ratios of tropoelastin to collagen include about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10 or any intervening ratio.

Other co-polymers suitable for use in particular embodiments, include hyaluronic acid, hyaluronates, chitosan, chitosan derivatives, polyrotaxane, polyrotaxane derivatives, polyglycolic acid, chitin, chitin derivatives, gelatin, fibronectin, heparin, laminin, and alginate In particular embodiments, suitable co-polymers are resorbable synthetics including, but not limited to, polylactone, polylcaprolactone, polylactic acid, polyglycolic acid, or any combination thereof.

In certain embodiments, suitable copolymers are non-resorbable synthetics, including, but not limited to, metals, e.g., titanium, stainless steel, nickel, aluminum alloys, and alloys of nickel-iron, or any combination there of; ceramics e.g., silicon and silicon oxide, or any combination there of; plastics, e.g., polypropylene (PP), polystyrene (PS), nylon, high impact polystyrene (HIPS), acrylonitrile butadiene styrene (ABS), polyethylene terephthalate (PET), poly(vinyl chloride) (PVC), polyurethanes (PU), polycarbonate (PC), polyvinylidene chloride (PVDC), polyethylene (PE), polycarbonate/acrylonitrile butadiene styrene (PC/ABS), polymethyl methacrylate (PMMA), polytetrafluoroethylene (PTFE), and polyetheretherketone (PEEK), or any combination there of; and rubbers, e.g., polybutadiene, chloro isobutylene isoprene, polychloroprene, chlorosulphonated polyethylene, epichlorohydrin, epichlorohydrin, ethylene propylene, ethylene propylene diene, ethylene vinyl acetate, fluoronated hydrocarbon, hydrogenated nitrile butadiene, polyisoprene, isoprene butylene butyl, butadiene acrylonitrile, polyurethane, styrene butadiene, and poly-siloxane, or any combination there of.

3. Casts/Molds

In particular embodiments, a biocompatible polymer scaffold is formed into a desired shape, for example by casting in a mold or electrospinning. One having ordinary skill in the art would appreciate that the preferred shape will depend, in part, the particular tissue or organ being repaired, replaced, or regenerated.

In a certain embodiment, a biocompatible polymer scaffold is formed in a subject, in a wound or in an area of space wherein new tissue is needed. In particular embodiments, one or more cell populations may be mixed with one or more tropoelastin polypeptides and the implant formed in vivo. In another embodiment, the implants are formed from molds in vitro or ex vivo. In related embodiments, the mixture comprises a co-polymer, e.g., a collagen polypeptide.

Exemplary molds and casts can be formed from many different materials or their combinations including, but not limited to, metals, ceramics, plastics, rubbers, glass, and fiberglass. In one embodiment, the mold is formed from plastic or metal.

Illustrative examples of metals include, but are not limited to, titanium, stainless steel, nickel, aluminum alloys, and alloys of nickel-iron, or any combination there of.

Illustrative examples of ceramics include, but are not limited to, silicon and silicon oxide, or any combination there of.

Illustrative examples of plastics include, but are not limited to, polypropylene (PP), polystyrene (PS), nylon, high impact polystyrene (HIPS), acrylonitrile butadiene styrene (ABS), polyethylene terephthalate (PET), poly(vinyl chloride) (PVC), polyurethanes (PU), polycarbonate (PC), polyvinylidene chloride (PVDC), polyethylene (PE), polycarbonate/acrylonitrile butadiene styrene (PC/ABS), polymethyl methacrylate (PMMA), polytetrafluoroethylene (PTFE), and polyetheretherketone (PEEK), or any combination there of.

Illustrative examples of rubbers include, but are not limited to, polybutadiene, chloro isobutylene isoprene, polychloroprene, chlorosulphonated polyethylene, epichlorohydrin, epichlorohydrin, ethylene propylene, ethylene propylene diene, ethylene vinyl acetate, fluoronated hydrocarbon, hydrogenated nitrile butadiene, polyisoprene, isoprene butylene butyl, butadiene acrylonitrile, polyurethane, styrene butadiene, and poly-siloxane, or any combination there of.

Exemplary desired shapes of the biocompatible polymer scaffold, include, but are not limited to sheets, tubes, any other three dimensional shape. Scaffolds formed in the shape of a sheet can be used in the preparation of implants and grafts to provide reparative, replacement, and/or regenerative therapy for dermal tissues, membranes for tooth root coverage procedures, membranous tissues (e.g., dura mater), and the like. Scaffolds formed in the shape of a tube can be used in the preparation of implants and grafts to provide reparative, replacement, and/or regenerative therapy for arteries, veins, ureters, urethras, nerves, long bones, and the like. Scaffolds formed in the shape of any other three dimensional can be used in the preparation of implants and grafts to provide reparative, replacement, and/or regenerative therapy for organ transplants, bone remodeling or mending, dental implants, or for muscle, tendon, ligament, and cartilage grafts.

A biocompatible polymer scaffold formed, cast, or molded in the shape of a sheet, can be a flat sheet, or a sheet having curvatures to closely match the contours of the injured, damaged, or diseased tissue or organ being repaired, replaced, or regenerated. The sheets may be of any geometrical shape, including but not limited to squares, rectangles, trapezoids, triangles, circles, ellipses, and the like.

Exemplary areas of the sheets include areas of about 1 $mm^2$ to about 1 $m^2$, about 1 $mm^2$ to about 50 $cm^2$, about 1 $mm^2$ to about 25 $cm^2$, about 1 $mm^2$ to about 10 $cm^2$, about 1 $mm^2$ to about 1 $cm^2$, about 1 $cm^2$ to about 1 $m^2$, about 1 $cm^2$ 1 $cm^2$ to about 500 $cm^2$, 1 $cm^2$ to about 250 $cm^2$, 1 $cm^2$ to about 200 $cm^2$, 1 $cm^2$ to about 150 $cm^2$, to about 100 $cm^2$, about 1 $cm^2$ to about 50 $cm^2$, about 1 $cm^2$ to about 25 $cm^2$, about 1 $cm^2$ to about 10 $cm^2$, about 1 $cm^2$ to about 5 $cm^2$, about 1 $cm^2$ to about 2.5 $cm^2$, about 10 $mm^2$ to about 10 $cm^2$, about 0.1 $cm^2$ to about 10 $cm^2$, about 0.1 $cm^2$ to about 1 $cm^2$, or any intervening range thereof. For example, the range of areas of 1 $cm^2$ to 100 $cm^2$ of an exemplary sheet includes about areas of about 1 $cm^2$, about 5 $cm^2$, about 10 $cm^2$, about 20 $cm^2$, about 30 $cm^2$, about 40 $cm^2$, about 50 $cm^2$, about 60 $cm^2$, about 70 $cm^2$, about 80 $cm^2$, about 90 $cm^2$, and about 100 $cm^2$.

Exemplary degrees of thickness of a biocompatible polymer scaffold formed, cast, or molded in the shape of a sheet, include a range of about 0.1 mm to about 10 mm, about 0.25 mm to about 7.5 mm, about 0.5 mm to about 5 mm, about 0.75 mm to about 2.5 mm, about 1 mm to about 2 mm or any intervening range thereof.

In another embodiment, the thickness can be about 0.1 mm, about 0.25 mm, about 0.5 mm, about 0.75 mm, about 1 mm, about 2 mm, about 3 mm, about 4 mm, about 5 mm, about 7.5 mm, or about 10 mm or more.

A biocompatible polymer scaffold formed, cast, or molded in the shape of a tube, can have any desired length, diameter, and thickness such that the size of the scaffold is suitable to repair, replace, and/or regenerate an injured, damaged, or diseased tissue or organ.

Exemplary lengths of the tube include about 0.5 cm, about 1 cm, about 2.5 cm, about 5 cm, about 10 cm, about 25 cm, about 50 cm, about 100 cm, about 150 cm, about 200 cm, about 250 cm, about 300 cm, about 350 cm, about 400 cm, about 450 cm, about 500 cm, or longer.

Exemplary diameters of the tube include about 0 mm (e.g., a solid fiber), 0.5 mm, about 1 mm, about 1.5 mm, about 2 mm, about 2.5 mm, about 3 mm, about 3.5 mm, about 4 mm, about 4.5 mm, about 5 mm, about 5.5 mm, about 6 mm, about 6.5 mm, about 7 mm, about 7.5 mm, about 8 mm, about 8.5 mm, about 9 mm, about 9.5 mm, about 10 mm, about 11 mm, about 12 mm or more mm in diameter. In a preferred embodiment, a tube of the invention has about 1 mm to about 10 mm diameter.

A biocompatible polymer scaffold formed, cast, or molded in the shape of other three dimensional objects can have any desired volume and/shape such that the size of the scaffold is suitable to repair, replace, and/or regenerate an injured, damaged, or diseased tissue or organ.

Exemplary volumes of the three dimensional shape scaffolds of about 100 mm$^3$ to about 5 m$^3$, about 100 mm$^3$ to about 1000 cm$^3$, about 1 cm$^3$ to about 1000 cm$^3$, about 1 cm$^3$ to about 100 cm$^3$, about 1 cm$^3$ to about 10 cm$^3$, about 10 cm$^3$ to about 1000 m$^3$, about 10 cm$^3$ to about 100 cm$^3$, about 500 cm$^3$ to about 1000 cm$^3$, about 100 mm$^3$ to about 5 cm$^3$, about 100 mm$^3$ to about 2.5 cm$^3$, about 1 cm$^3$ to about 5 cm$^3$, about 1 cm$^3$ to about 2.5 cm$^3$, about 750 cm$^3$ to about 1250 cm$^3$, about 850 cm$^3$ to about 1150 cm$^3$, about 950 cm$^3$ to about 1050 cm$^3$, about 900 cm$^3$ to about 1000 cm$^3$, or any intervening range thereof. For example, the range of volumes of 1 cm$^3$ to 10 cm$^3$ of an exemplary three dimensional shape includes about volumes of about 1 cm3, about 2 cm$^3$, about 3 cm$^3$, about 4 cm$^3$, about 5 cm$^3$, about 6 cm$^3$, about 7 cm$^3$, about 8 cm$^3$, about 9 cm$^3$, and about 10 cm$^3$.

4. Polymer/Co-Polymer Cross-Linking Agents

In particular embodiments, polymer/co-polymer cross-linking agents agent are employed to modulate the porosity, hardness, density, rigidity, and/or elasticity of the biocompatible polymer scaffold.

In particular embodiments, the cross-linking agent is an enzyme. Exemplary enzymatic cross-linking agents include, but are not limited to, any lysyl oxidase capable of converting epsilon amines to adipic semi-aldehydes or through the enzyme catalysis of transglutaminase.

In other particular embodiments, the cross-linking agent is a chemical cross-linking agent. Exemplary chemical cross-linking agents include, but are not limited to, bipyridylruthenium(II) in the presence of ammonium persulfate and visible light, tris-Cobalt-60 γ-irradiation, *Arthromyces ramosus* peroxidase treatment, pyrroloqinoline quinone in the presence of copper, methacrylamide anhydride, dimethyl adipimidate, bis(sulfosuccinimidyl)suberate (BS3), 1-Ethyl-3-[3-dimethylaminopropyl]carbodiimide Hydrochloride) (EDC), glutaraldehyde, N-hydroxysuccinimide) (NHS), NHS-polyethylene glycol (NHS-PEG), NHS-PEG-NHS, and 1,6-diisocyanatohexane (HMDI) and combinations thereof.

Cross-linking may be performed at the time the scaffold is being cast. For example, cross-linking agents can be added to a tropoelastin polypeptide composition just prior to molding, at the time the scaffold is being molded, or after molding of the scaffold is completed.

In another embodiment, a modified version of tropoelastin polypeptide is provided which is not susceptible to cross-linking. The tropoelastin polypeptide may not be susceptible to cross-linking for a number of reasons including, mutating one or more lysine residues in the tropoelastin polypeptide. The high degree of cross-linking found in the elastic fibers contributes to their proper function. Lysyl oxidase is the enzyme that catalyzes the oxidative deamination of lysine residues leading to the non-enzymatic condensation of the modified lysine side chains. This same enzyme is involved in collagen cross-link formation as well. All but about 5 of the 34 lysine residues of tropoelastin participate in some form of cross-link resulting in a highly insoluble polymer (Rosenbloom et al., *FASEB J.* (1993), 7: p. 1208).

Thus, by modulating the lysine available for cross-linking provides another method for modulating the porosity, hardness, density, rigidity, and/or elasticity of the biocompatible polymer scaffold.

5. Strength and Elasticity

In particular embodiments, a biocompatible polymer scaffold is formed with a desired strength and elasticity. One having ordinary skill in the art would appreciate that the preferred strength and elasticity will depend, in part, the particular tissue or organ being repaired, replaced, or regenerated.

Without being bound to any particular theory, the present invention contemplates, in part, that the static and dynamic mechanical properties, including, but not limited to strength and elasticity, of biocompatible polymer scaffold comprising tropoelastins, including, but not limited to, sheets and tubes, can approximate the static and dynamic mechanical properties of the native target tissue or biological end location.

In one non-limiting example, the mechanical parameters of the native target tissue, e.g., stress/strain characteristics, Young's modulus, yield point, and any other biologically relevant mechanical parameter can be modeled and matched by the tropoelastin scaffold.

Illustrative mechanical parameters of the biocompatible polymer scaffolds of the invention can be about 25% to about 125%, about 50% to about 100%, about 75% to about 100% of the mechanical parameters of the corresponding native tissue or any intervening range thereof. In one embodiment, the mechanical parameters of the biocompatible polymer scaffolds of the invention can be about 10%, 20%, 30%, 40%, 50%, 60%, 70%, 80%, 90%, 100%, 110%, 120%, or more of the mechanical parameters of the corresponding native tissue or any intervening percentage thereof.

However, in some circumstances lower values or higher values may be required and necessary for end use of the implant. For example, end device design characteristics may require higher yield point or failure point values than normal healthy tissue due to disease processes within the patient.

D. Implants and Grafts

In various embodiments, an implant or graft is provided to promote repair, replacement, and/or regeneration of a damaged, injured, or diseased tissue or organ.

In one embodiment, an implant or graft comprises a cast or formed biocompatible polymer scaffold and a population of cells. The implant or graft can comprise one or more cell populations that are seeded, grown, or cultured on the scaffold. The cell populations can be developmentally mature or restricted, developmentally potent or plastic, or a combination of the foregoing cell types. As used herein, the terms "implant" and "graft" are used interchangeably and refer to a biocompatible natural and/or synthetic polymer scaffold that has any of the characteristics described for scaffolds, supra or infra, one or more tropoelastin polymorphs and one or more of co-polymers, cell populations, and other polypeptides, e.g., cytokines, growth factors, etc.

In particular embodiments, an implant or graft comprises a biocompatible polymer scaffold that can be molded into any suitable form or shape, as described elsewhere herein throughout. In a certain embodiment, an implant or graft is formed in a subject, in a wound, or in an area of space wherein new tissue is needed. In particular embodiments, one or more cell populations may be mixed with one or more tropoelastin polymorphic polypeptides and the implant formed in vivo. In related embodiments, the mixture comprises a co-polymer, e.g., a collagen polypeptide.

Thus, implants or grafts comprising biocompatible polymer scaffolds comprising one or more tropoelastin polymorphs and one or more populations of cells growing thereon, can accelerate tissue growth and regeneration and participate as a reinforcing material in a newly constructed, cell-based tissue, which usually lack elastin during adult tissue regeneration. The presence of elastin would more closely resemble the provisional matrix that is created during the development of tissues in utero.

Sheet-like implants and grafts provide reparative, replacement, and/or regenerative therapy for dermal tissues, membranes for tooth root coverage procedures, membranous tissues (e.g., dura mater), flat bones (e.g., skull, breast-bone) and the like. Tubular implants and grafts provide reparative, replacement, and/or regenerative therapy for arteries, veins, ureters, urethras, nerves, long bones (e.g., femur, fibula, tibia, humerus, radius, ulna, metacarpals, metatarsals, etc.) and the like. Other three dimensional implants and grafts provide reparative, replacement, and/or regenerative therapy for organ transplants (e.g., liver, lung, skin, heart, pancreas, etc.), bone remodeling or mending of all types of bones, dental implants, or for muscle, tendon, ligament, and cartilage grafts.

The physical properties of the tropoelastin polymers can be modulated to create scaffolds of specific strengths, elasticity, and density. Thus, in certain embodiments, implants or grafts comprising biocompatible polymer scaffolds comprising one or more tropoelastin polypeptides and one or more populations of cells growing thereon are stable in vivo and will remain in a patient's body for up to 1, 2, 3, 4, 5, 10, 15 or more years.

In various embodiments, implants or grafts disclosed herein, comprise at least one cell or population of cells.

In particular embodiments, a cell or population of cells is cultured in or seeded onto a biocompatible polymer scaffold to form an implant or graft. Such implants or grafts can also include, by way of non-limiting example, cytokines, growth factors, hormones, or other compounds/agents that may provide therapeutic benefit in a method of repairing, replacing, or regenerating a tissue or organ.

Exemplary growth factors and cytokines include, but are not limited to, brain derived neurotropihic factor (BDNF), bone morphogenetic protein 2 (BMP-2), bone morphogenetic protein 6 (BMP-6), bone morphogenetic protein 7 (BMP-7), cardiotrophin 1 (BMP-2), CD22, CD40, ciliary neurotrophic factor (CNTF), CCL1-CCL28, CXCL1-CXCL17, XCL1, XCL2, CX3CL1, vascular endothelial cell growth factor (VEGF), epidermal growth factor (EGF), FAS-ligand, fibroblast growth factor 1 (FGF-1), fibroblast growth factor 2 (FGF-2), fibroblast growth factor 4 (FGF-4), fibroblast growth factor 5 (FGF-5), fibroblast growth factor 6 (FGF-6), fibroblast growth factor 1 (FGF-7), fibroblast growth factor 1 (FGF-10), Flt-3, granulocyte colony-stimulating factor (G-CSF), granulocyte macrophage stimulating factor (GM-CSF), hepatocyte growth factor (HGF), interferon alpha (IFN-a), interferon beta (IFN-b), interferon gamma (IFNg), insulin-like growth factor 1(IGF-1), insulin-like growth factor 2 (IGF-2), interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 15 (IL-15), interleukin 17 (IL-17), interleukin 19 (IL-19), macrophage colony-stimulating factor (M-CSF), monocyte chemotactic protein 1 (MCP-1), macrophage inflammatory protein 3a (MIP-3a), macrophage inflammatory protein 3b (MIP-3b), nerve growth factor (NGF), neurotrophin 3 (NT-3), neurotrophin 4 (NT-4), platelet derived growth factor AA (PDGF-AA), platelet derived growth factor AB (PDGF-AB), platelet derived growth factor BB (PDGF-BB), platelet derived growth factor CC(PDGF-CC), platelet derived growth factor DD (PDGF-DD), RANTES, stem cell factor (SCF), stromal cell derived factor 1 (SDF-1), transforming growth factor alpha (TGF-a), transforming growth factor beta (TGF-b), tumor necrosis factor alpha (TNF-a), WntI, Wnt2, Wnt2b/13, Wnt3, Wnt3a, Wnt4, Wnt5a, Wnt5b, Wnt6, Wnt7a, Wnt7b, Wnt7c, Wnt8, Wnt8a, Wnt8b, Wnt8c, WntIOa, WntIOb, WntII, WntI4, WntI5, or WntI6, Sonic hedgehog, Desert hedgehog, and Indian hedgehog.

Exemplary hormones include, but are not limited to, Anti-mullerian hormone (or mullerian inhibiting factor or hormone), Adiponectin, Adrenocorticotropic hormone (or corticotropin), Angiotensinogen and angiotensin, Antidiuretic hormone (or vasopressin, arginine vasopressin), Atrial-natriuretic peptide (or atriopeptin), Calcitonin, Cholecystokinin, Corticotropin-releasing hormone, Erythropoietin, Follicle-stimulating hormone, Gastrin, Ghrelin, Glucagon, Gonadotropin-releasing hormone, Growth hormone-releasing hormone, Human chorionic gonadotropin, Human placental lactogen, Growth hormone, Insulin-like growth factor 1, Insulin-like growth factor (or somatomedin), Leptin, Luteinizing hormone, Melanocyte stimulating hormone MSH, Orexin, Oxytocin, Parathyroid hormone, Prolactin, Relaxin, Secretin, Somatostatin, Thrombopoietin, Thyroid-stimulating hormone (or thyrotropin), and Thyrotropin-releasing hormone.

In particular embodiments, implants or grafts comprise cells that are genetically modified to express increased amounts of a particular extracellular material, cytokine, and/or growth factor to promote or facilitate the repair, regeneration, or replacement of a tissue or organ.

Alternatively, or in addition, particular embodiments provide implants or grafts comprising cells that natively express the desired cytokine, and/or growth factor to promote or facilitate the repair, regeneration, or replacement of a tissue, or organ.

In another embodiment, an implant or grafts comprises a biocompatible polymer scaffold, a population of multipotent or pluripotent stem cells, and hormones, growth factors, cytokines, morphogens (e.g., retinoic acid etc), extracellular matrix materials (e.g., fibronectin, laminin, collagen, etc.) or other materials (e.g., DNA, viruses, other cell types, etc.) that facilitate the differentiation of the cell population along a particular developmental pathway once the implant has been implanted in the patient. Alternatively, or in addition, the cells may be differentiated in vitro during cell culturing with the biocompatible polymer scaffold.

In various embodiments, an implant or graft comprising the inventive biocompatible polymer scaffold and a population of cells growing thereon supports guided tissue engineering and regeneration in a patient or subject. Thus, the present invention contemplates, in part, to use an implant or graft comprising a biocompatible polymer scaffold in combination a population of cells cultured thereon, and incorporating any of the features disclosed herein. The exact nature of the implant (e.g., the size, shape, elasticity, strength, cell type growing thereon, etc.) will vary according to the use desired.

In various embodiments, methods of providing reparative, replacement, or regenerative therapy to a site in vivo comprises introducing the implant or grafts into the individual at or near the site of tissue or organ injury, wherein the regenerative, restorative, preventative, or ameliorative therapy is desired and/or required.

For example, an implant or grafts of the present invention can be implanted or grafted in odontic tissue, periodontic tissue, pancreatic tissue, neural tissue, cardiac tissue, bone marrow, muscle tissue, bone tissue, skin tissue, liver tissue, hair follicles, vascular tissue, adipose tissue, lung tissue, retinal tissue, corneal tissue, and kidney tissue, as required to direct the appropriate therapy.

E. Cells

Various embodiments provide implants or grafts comprising one or more population of cells. The population of cells may be made up of any number and/or combination of homogenous or heterogeneous cell types, as described elsewhere herein or that are known to those having ordinary skill in the art. Those having ordinary skill in the art would appreciate that any of the cell types discussed herein, supra or infra, are suitable for seeding, growing, or culturing said cells on particular biocompatible polymer scaffolds as discussed elsewhere herein throughout.

The cell populations can be isolated primary cells or cell lines, either of which may further comprise one or more genetic modifications and/or transgenes.

In preferred embodiments, the cell population comprises mammalian cells. Illustrative examples of mammals include bovines, equines, sheep, goats, pigs, dogs, cats, primates, and rodents.

In particular embodiments, a population of cells seeded on, growing on, and/or cultured on a biocompatible polymer scaffold, as described elsewhere herein throughout, comprises one or more cell types selected from the group consisting of: a stem cell, a progenitor cell, a reprogrammed cell, and a differentiated cell. In other embodiments, a population of cells seeded on, growing on, and/or cultured on a biocompatible polymer scaffold comprises a mixture or combination of stem cells, progenitor cells, and differentiated cells.

In one embodiment, the population of cells is selected from adult, neonatal, or embryonic stem/progenitor cells.

In particular embodiments, the population of cells is selected from the group consisting of: mesodermal stem/progenitor cells, endodermal stem/progenitor cells, and ectodermal stem/progenitor cells.

In related embodiments, the population of cells comprises a mesodermal stem/progenitor cell. Illustrative examples of mesodermal stem/progenitor cells include, but are not limited to mesodermal stem/progenitor cells, endothelial stem/progenitor cells, bone marrow stem/progenitor cells, umbilical cord stem/progenitor cells, adipose tissue derived stem/progenitor cells, hematopoietic stem/progenitor cells (HSGs), mesenchymal stem/progenitor cells, muscle stem/progenitor cells, kidney stem/progenitor cells, osteoblast stem/progenitor cells, chondrocyte stem/progenitor cells, and the like.

In other related embodiments, the population of cells comprises an ectodermal stem/progenitor cell. Illustrative examples of ectodermal stem/progenitor cells include, but are not limited to neural stem/progenitor cells, retinal stem/progenitor cells, skin stem/progenitor cells, and the like.

In other related embodiments, the population of cells comprises an endodermal stem/progenitor cell. Illustrative examples of endodermal stem/progenitor cells include, but are not limited to liver stem/progenitor cells, pancreatic stem/progenitor cells, epithelial stem/progenitor cells, and the like.

In certain embodiments, the population of cells includes a heterogeneous or homogeneous population of cells selected from the group consisting of: odontic cells, periodontic cells, gingival cells, pancreatic islet cells, CNS cells, PNS cells, cardiac muscle cells, skeletal muscle cells, smooth muscle cells, hematopoietic cells, bone cells, liver cells, an adipose cells, renal cells, lung cells, chondrocyte, skin cells, keratinocytes, fibroblasts, follicular cells, vascular cells, epithelial cells, immune cells, endothelial cells, and the like.

In certain other embodiments, the population of cells comprises a cell isolated from an in vivo tissue selected from the group consisting of: odontic tissue, periodontic tissue, gingival tissue, pancreatic tissue, neural tissue, cardiac tissue, bone marrow, muscle tissue, bone tissue, skin tissue, liver tissue, hair follicles, vascular tissue, adipose tissue, lung tissue, retinal tissue, corneal tissue, and kidney tissue. The cell isolate from the foregoing in vivo tissues can be an adult stem cell, progenitor cell, or somatic cell.

In certain other embodiments, the population of cells comprises a cell isolated from an in vivo tissue selected from the group consisting of: odontic tissue, periodontic tissue, and gingival tissue. In related embodiments, the population of cells comprises: gingival fibroblasts, periodontal ligament fibroblasts, osteoblasts, and osteoblast like cells.

In certain other embodiments, the population of cells comprises a cell isolated from bone marrow. In related embodiments, the population of cells comprises: bone marrow stromal cells, bone marrow stem cells, hematopoietic stem cells, and/or mesenchymal stem cells.

In certain other embodiments, the population of cells comprises a cell isolated from the skin of an individual. In related embodiments, the population of cells comprises: keratinocytes and/or fibroblasts.

In other illustrative embodiments, implants comprise cell populations obtained from a different donor (allogeneic), obtained from the individual to be treated (autologous), or obtained from an entirely different species (xenogeneic).

One of ordinary skill in the art is familiar with methods for isolating and culturing the different types of cells described herein (e.g., Embryonic Stem Cells: Methods and Protocols (Methods in Molecular Biology) (Kurstad Turksen, Ed., 2002); Embryonic Stem Cell Protocols: Volume I: Isolation and Characterization (Methods in Molecular Biology) (Kurstad Turksen, Ed., 2006); Embryonic Stem Cell Protocols: Volume II: Differentiation Models (Methods in Molecular Biology) (Kurstad Turksen, Ed., 2006); Human Embryonic Stem Cell Protocols (Methods in Molecular Biology) (Kursad Turksen Ed., 2006); Mesenchymal Stem Cells: Methods and Protocols (Methods in Molecular Biology) (Darwin J. Prockop, Donald G. Phinney, and Bruce A. Bunnell Eds., 2008); Hematopoietic Stem Cell Protocols (Methods in Molecular Medicine) (Christopher A. Klug, and Craig T. Jordan Eds., 2001); Hematopoietic Stem Cell Protocols (Methods in Molecular Biology) (Kevin D. Bunting Ed., 2008) Neural Stem Cells: Methods and Protocols (Methods in Molecular Biology) (Leslie P. Weiner Ed., 2008)).

Cells may be cultured in growth-promoting conditions, which can include any set of conditions (temperature, atmosphere, growth medium composition, humidity, degree of agitation, etc.) under which cells normally proliferate. None of these conditions are critical. The temperature should be near that of normal human body temperature (i.e., about 37° C.), but can be any temperature at which cells can proliferate (e.g., 30 to 43° C.). Cells can be grown in an air atmosphere, or an air atmosphere supplemented with 5% $CO_2$, for example. The growth medium can be any liquid medium which contains nutrients and factors sufficient to support proliferation of cells. Such media contain, for example, a carbon source (e.g., glucose) and minimal essential nutrients, and preferably contain one or more of a mammalian serum (e.g., fetal calf serum), an antibiotic (e.g., penicillin or streptomycin), and L-glutamine (i.e., to improve amino acid supply for protein biosynthesis).

Mammalian serum can be used at a concentration of 1% to 20%, by volume, of the total growth medium. The serum is preferably pre-screened to ensure that it supports vigorous growth of cells; some lots, even lots provided from the same supplier, do not support vigorous growth of cells. Alternatively, the mammalian serum can be replaced with one or more growth factors (e.g., fibroblast growth factor, platelet derived growth factor, insulin growth factor, or endothelial growth factor). The growth medium can, for example, be Minimal Essential Medium-alpha without deoxyribonucleotides or ribonucleotides, supplemented with fetal calf serum, antibiotics, and L-glutamine; Dulbecco's minimal essential medium; and others well known to one of ordinary skill in the art. The growth medium is preferably replaced one or more times (e.g., every 3 or 4 days) during culture of the cells.

F. Polynucleotides

The present invention also provides isolated tropoelastin polynucleotides and polynucleotides encoding tropoelastin polypeptides (e.g., tropoelastin polymorphic polypeptides from alternatively spliced transcripts or transcripts having exon polymorphisms, tropoelastin fusion polypeptides) of the invention, as described elsewhere herein, e.g., SEQ ID NOs: 2-48. Isolated polynucleotides of the present invention, include, but are not limited to, alternatively spliced tropoelastin polynucleotides (e.g., alternatively spliced exons 2, 3, 5, 6, 8, 10, 11, 13, 17, 19, 20, 22, 23, 24, 25, 26, 28, 31, 32, and 33). In addition, Applicants identified partially deleted isoforms of that represent tropoelastin cDNAs, tropoelastin cDNAs comprising deleted or partially deleted exons (e.g., tropoelastin exons 2, 6, 8, 10, 17, 20, 24, 26, and 28), and engineered tropoelastin cDNAs, as described elsewhere herein e.g., SEQ ID NOs: 50-86. Fusion polynucleotides that encode fusion polypeptides are also included in the present invention, as described elsewhere herein.

As used herein, the terms "polynucleotide" or "nucleic acid" refers to messenger RNA (mRNA), RNA, genomic DNA (gDNA), complementary DNA (cDNA) or DNA. The term typically refers to polymeric form of nucleotides of at least 100, at least 200, at least 300, at least 400, at least 500, at least 600, at least 700, at least 800, at least 900, at least 1000, at least 1250, at least 1500, at least 1750, at least 2000, at least 2250, at least 2500, at least 2750, at least 3000, at least 3250, at least 3500, at least 3750, at least 4000 or more bases in length, or any intermediate length of either ribonucleotides or deoxynucleotides or a modified form of either type of nucleotide. The term includes single and double stranded forms of DNA. The term also includes sense, non-sense, antisense DNA strands, and plus and minus RNA strands.

In particular embodiments, polynucleotides are provided by this invention that encode at least about 50, 100, 200, 250, 300, 400, 500, 600, 625, 650, 675, 700, 725, 750, 800, or 822 or more contiguous amino acid residues of a polypeptide of the invention, as well as all intermediate lengths. It will be readily understood that "intermediate lengths," in this context, means any length between the quoted values, such as 650, 651, 652, 653, 654, 655, 656, 657, 658, 659, 660, 661, 662, 663, 664, 665, 666, 667, 668, 669, 670, 671, 672, 673, 674, and 675, etc., 675, 676, 677, 678, 679, 680, 681, 682, 683, 684, 685, 686, 687, 688, 689, 690, 691, 692, 693, 694, 695, 696, 697, 698, 699, and 700, etc.; and 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, and 730, etc.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides.

In certain embodiments, a variant tropoelastin polynucleotide encodes a polypeptide having an amino acid sequence having at least about 50%, 55%, 60%, 65%, 70%, 75%, 80%, 85%, 90%, 91%, 92%, 93%, 94%, 95%, 96%, 97%, 98% or more identical to a corresponding sequence of a tropoelastin reference polypeptide, as described herein, and substantially retains the desired properties of that reference polypeptide. Also included are tropoelastin polynucleotide sequences that encode tropoelastin polypeptides having 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids additions, deletions, or substitutions, and that substantially retain the desired properties of that reference polypeptide. In certain embodiments, tropoelastin polynucleotides encode tropoelastin polypeptides having additions or deletions that occur at the C-terminal end and/or the N-terminal end of the reference polypeptide. In certain embodiments, tropoelastin polynucleotides encode tropoelastin polypeptides having 1, 2, 3, 4, 5, 6, 7, 8, 9, 10, 11, 12, 13, 14, 15, 16, 17, 18, 19, 20, 30, 40, 50 N-terminal and/or C-terminal amino acid deletions or additions. In certain embodiments polynucleotide variants encode tropoelastin polypeptides comprising 1, 2, 3, 4, 5, 6, 7, 8, 9, 10, 11, 12, 13, 14, 15, 16, 17, 18, 19, 20, 30, 40, 50 N-terminal and/or C-terminal amino acid deletions.

In this regard, it is well understood in the art that certain alterations inclusive of mutations, additions, deletions and substitutions can be made to a reference polynucleotide whereby the altered polynucleotide retains the biological function or activity of the reference polynucleotide.

In various illustrative embodiments, the present invention provides isolated polynucleotides as set forth in SEQ ID NOs: 50-86 that encode tropoelastin polypeptides of the invention, including, but not limited to those polypeptides set forth in SEQ ID NOs: 2-48. Tropoelastin polypeptides of the invention are used to direct cell-based compositions to a particular cellular environment to repair, replace, restore and/or regenerate damaged or diseased mammalian cells, tissues and organs.

Polynucleotides can be synthesized using protocols known in the art as described in Caruthers et al., 1992, Methods in Enzymology 211, 3-19; Thompson et al., International PCT Publication No. WO 99/54459; Wincott et al., 1995, Polynucleotides Res. 23, 2677-2684; Wincott et al., 1997, Methods Mol. Bio., 74, 59-68; Brennan et al., 1998, Biotechnol Bioeng., 61, 33-45; and Brennan, U.S. Pat. No. 6,001,311.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of a polypeptide of the present invention. The polynucleotides of the present invention, regardless of the length of the coding sequence itself, may be combined with other DNA sequences, such as 5' and 3' untranslated sequences (UTRs), promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide, or fragment of variant thereof, as described herein. Some of these polynucleotides bear minimal homology to the nucleotide sequence of any native gene. As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product. Further, alleles of the genes comprising the polynucleotide sequences provided herein may also be used. Alleles are endogenous genes that are altered as a result of one or more mutations, such as deletions, additions and/or substitutions of nucleotides.

In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination.

Such techniques are described in the literature. See, e.g., Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001; Maniatis et al. *Molecular Cloning: A Laboratory Manual* (1982); DNA Cloning: *A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); Perbal, *A Practical Guide to Molecular Cloning* (1984).

G. Polypeptides

As noted above, the present invention, in certain aspects, provides for the prevention, treatment, cure, amelioration, or mitigation of disease or injuries in humans by the introducing implants comprising a biocompatible polymer scaffold that comprises one or more tropoelastin polypeptides, e.g., alternatively spliced tropoelastin polypeptides as disclosed herein, and one or more populations of cells. In particular embodiments, the present invention provides therapeutic implants comprising tropoelastin polypeptides and methods of using the same to effect tissue, and or organ regenerative, preventative, restorative, and/or ameliorative therapy.

As used herein, the terms "polypeptide," "peptide," and "protein" are used interchangeably, unless specified to the contrary, and according to conventional meaning, i.e., as a sequence of amino acids. Polypeptides are not limited to a specific length, e.g., they may comprise a full length protein sequence or a fragment of a full length protein, and may include post-translational modifications of the polypeptide, for example, glycosylations, acetylations, phosphorylations and the like, as well as other modifications known in the art, both naturally occurring and non-naturally occurring. Polypeptides can be prepared using any of a variety of well known recombinant and/or synthetic techniques, illustrative examples of which are further discussed below. Illustrative examples of tropoelastin polypeptides for use in the present invention are set forth in SEQ ID NOs: 2-48. Tropoelastins can be selected according to the desired elasticity, tensile strength, and shapeability and/or to match the tropoelastins and collagens present in the tissue being repaired, replaced, or regenerated.

Tropoelastin polypeptides are often alternatively spliced polypeptides. The present invention contemplates, in part, a core tropoelastin polypeptide comprising exons that are present in most, if not all isoforms. In one embodiment, the core tropoelastin comprises exons 1, 4, 7, 9, 12, 14, 15, 16, 18, 21, 27, 29, and 34. In another embodiment, the present invention contemplates, in part, a core tropoelastin polypeptide comprising one or more exons that are partially deleted, but that are also included in many tropoelastin polypeptide isoforms. In one embodiment, the core tropoelastin comprises exons 1, 4, 6B, 7, 9, 12, 14, 15, 16, 18, 21, 24B, 26A, 27, 29, and 34.

As used herein, the term "partially deleted exon" refers to a exon that has at least one long form and at least one short form; the short form comprising a partial deletion long form. The naming convention used herein, for partially deleted exons names the long form the "A form" and the short or partially deleted form, the "B form." For example, exon 2A refers to the tropoelastin exon that begins at nucleotide position 83 and ends at nucleotide position 133 of SEQ ID NO: 49 and exon 2B refers to the tropoelastin exon that begins at nucleotide position 122 and ends at nucleotide position 133 of SEQ ID NO: 49. Illustrative partially deleted exons include exons 2A/B, 6A/B, 8A/B, 10A/B, 17A/B, 24A/B, 26A/B, and 28A/B.

As used herein, the term "tropoelastin fragment," refers to a fragment, e.g., biologically active fragment, of a reference polypeptide sequence. In particular embodiments, tropoelastin fragments comprise at least about 50, 100, 200, 250, 300, 400, 500, 600, 625, 650, 675, 700, 725, 750, 800, or 822 or more contiguous amino acid residues of a polypeptide of the invention, as well as all intermediate lengths. It will be readily understood that "intermediate lengths," in this context, means any length between the quoted values, such as 650, 651, 652, 653, 654, 655, 656, 657, 658, 659, 660, 661, 662, 663, 664, 665, 666, 667, 668, 669, 670, 671, 672, 673, 674, and 675, etc., 675, 676, 677, 678, 679, 680, 681, 682, 683, 684, 685, 686, 687, 688, 689, 690, 691, 692, 693, 694, 695, 696, 697, 698, 699, and 700, etc.; and 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, and 730, etc.

Also included are tropoelastin polypeptides having 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids additions, deletions, or substitutions, and that substantially retain the desired properties of that reference polypeptide. In certain embodiments, tropoelastin polypeptides have additions or deletions that occur at the C-terminal end and/or the N-terminal end of the reference polypeptide. In certain embodiments, tropoelastin polypeptides having 1, 2, 3, 4, 5, 6, 7, 8, 9, 10, 11, 12, 13, 14, 15, 16, 17, 18, 19, 20, 30, 40, 50 N-terminal and/or C-terminal amino acid deletions or additions. In certain embodiments, tropoelastin polypeptides comprise 1, 2, 3, 4, 5, 6, 7, 8, 9, 10, 11, 12, 13, 14, 15, 16, 17, 18, 19, 20, 30, 40, 50 N-terminal and/or C-terminal amino acid deletions.

In various embodiments, the invention contemplates polypeptide fragments that retain at least one biological activity of tropoelastin. Fragments may also be selected according to the tropoelastin properties desired, e.g., desired elasticity, tensile strength, and shapeability and/or to match the tropoelastins and collagens present in a tissue being repaired, replaced, or regenerated.

Polypeptides include polypeptide variants. Polypeptide variants may differ from a naturally occurring polypeptide in one or more substitutions, deletions, additions and/or insertions. Such variants may be naturally occurring or may be synthetically generated, for example, by modifying one or more of the above polypeptide sequences used in the methods of the invention and evaluating their effects using any of a number of techniques well known in the art. Preferably, polypeptides of the invention include polypeptides having at least about 65%, 70%, 75%, 85%, 90%, 95%, 98%, or 99% amino acid identity thereto.

Further, the present invention contemplates, tropoelastin polypeptides comprising one or more, two or more, three or more, four or more, or five or more amino acid substitutions in polypeptides encoded by particular exons. Illustrative example of exons and corresponding amino acid substitutions with reference to the unsubstituted polypeptide sequence set forth in SEQ ID NO: 1, include, without limitation: exon 8A, glycine (G) arginine→ (R), glycine (G)→ alanine (A), glycine (G)→ valine (V); exon 14, valine (V)→ methionine (M); exon 15, alanine (A)→ proline (P), alanine (A)→ threonine (T); exon 16, isoleucine (I)→ valine (V); exon 17B, lysine (K)→ threonine(T), alanine (A)→ glycine (G), alanine (A)→ serine (S), lysine (K)→glutamine (Q); exon 18, glycine (G)→alanine (A), glycine (G)→ serine (S), valine (V)→isoleucine (I); exon 20B, glycine (G)→ serine (S); exon 21, proline (P)→ alanine (A); exon 23, proline (P)→ alanine (A), lysine (K)→ glutamate (E), phenylalanine (F)→ tyrosine (Y), glutamine (Q)→ histidine (H); exon 26A, arginine (R)→ glycine (G), glycine (G)→ arginine (R); and exon 29, alanine (A)→ valine(V).

In certain embodiments, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides of the present invention and still obtain a functional molecule that encodes a variant or derivative polypeptide with desirable characteristics, e.g., with an ability to modulate, induce and/or maintain pluripotency as described herein. When it is desired to alter the amino acid sequence of a polypeptide to create an equivalent, or even an improved, variant polypeptide of the invention, one skilled in the art, for example, can change one or more of the codons of the encoding DNA sequence, e.g., according to Table 1.

TABLE 1

AMINO ACID CODONS

| Amino Acids | One letter code | Three letter code | Codons | | | |
|---|---|---|---|---|---|---|
| Alanine | A | Ala | GCA | GCC | GCG | GCU |
| Cysteine | C | Cys | UGC | UGU | | |
| Aspartic acid | D | Asp | GAC | GAU | | |
| Glutamic acid | E | Glu | GAA | GAG | | |
| Phenylalanine | F | Phe | UUC | UUU | | |
| Glycine | G | Gly | GGA | GGC | GGG | GGU |
| Histidine | H | His | CAC | CAU | | |
| Isoleucine | I | Iso | AUA | AUC | AUU | |
| Lysine | K | Lys | AAA | AAG | | |
| Leucine | L | Leu | UUA | UUG | CUA | CUC | CUG | CUU |
| Methionine | M | Met | AUG | | | |
| Asparagine | N | Asn | AAC | AAU | | |
| Proline | P | Pro | CCA | CCC | CCG | CCU |
| Glutamine | Q | Gln | CAA | CAG | | |

TABLE 1-continued

AMINO ACID CODONS

| Amino Acids | One letter code | Three letter code | Codons | | | | | |
|---|---|---|---|---|---|---|---|---|
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU | | |
| Valine | V | Val | GUA | GUC | GUG | GUU | | |
| Tryptophan | W | Trp | UGG | | | | | |
| Tyrosine | Y | Tyr | UAC | UAU | | | | |

Guidance in determining which amino acid residues can be substituted, inserted, or deleted without abolishing biological activity can be found using computer programs well known in the art, such as DNASTAR™ software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cystine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Exemplary conservative substitutions are described in U.S. Provisional Patent Application No. 61/241,647, the disclosure of which is herein incorporated by reference.

In making such changes, the hydropathic index of amino acids may be considered. The importance of the hydropathic amino acid index in conferring interactive biologic function on a protein is generally understood in the art (Kyte and Doolittle, 1982, incorporated herein by reference). Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

Polypeptide variants further include glycosylated forms, aggregative conjugates with other molecules, and covalent conjugates with unrelated chemical moieties (e.g., pegylated molecules). Covalent variants can be prepared by linking functionalities to groups which are found in the amino acid chain or at the N- or C-terminal residue, as is known in the art. Variants also include allelic variants, species variants, and muteins. Truncations or deletions of regions which do not affect functional activity of the proteins are also variants.

Optimal alignment of sequences for comparison may be conducted using the Megalign program in the Lasergene suite of bioinformatics software (DNASTAR, Inc., Madison, Wis.), using default parameters. Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Nat'l Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection. Examples of algorithms that are suitable for determining percent sequence identity and sequence similarity are the BLAST and BLAST 2.0 algorithms, which are described in Altschul et al. (1977) *Nucl.*

Acids Res. 25:3389-3402 and Altschul et al. (1990) *J. Mol. Biol.* 215:403-410, respectively.

Polypeptides of the present invention include fusion polypeptides. In preferred embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments. Tropoelastin domains associated with desired properties may be multimerized or concatenated and used to provide a desired elasticity, tensile strength, and shapeability and/or to match the tropoelastins and collagens present in a tissue being repaired, replaced, or regenerated.

The polypeptide domains or segments of the fusion protein can be in any order. Fusion polypeptides or fusion proteins can also include conservatively modified variants, polymorphic variants, alleles, mutants, subsequences, and interspecies homologs, so long as the desired transcriptional activity of the fusion polypeptide is preserved.

Amino acids in polypeptides of the present invention that are essential for function can be identified by methods known in the art, such as site-directed mutagenesis or alanine-scanning mutagenesis (Cunningham and Wells, Science 244: 1081-1085, 1989). The latter procedure introduces single alanine mutations at every residue in the molecule. The resulting mutant molecules are then tested for biological activity such as binding to a natural or synthetic binding partner (e.g., polynucleotide transcription factor binding site; EMSA assays). Furthermore, transcriptional activity of fusion polypeptides, mutants, and variants thereof can be assayed in vitro using CAT or luciferase reporter assays as generally described in the art. Sites that are critical for protein-DNA binding can also be determined by structural analysis such as crystallization, nuclear magnetic resonance or photoaffinity labeling (Smith et al., J. Mol. Biol. 224:899-904, 1992 and de Vos et al. Science 255:306-312,1992). Polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support.

The fusion partner may be designed and included for essentially any desired purpose provided they do not adversely affect the desired activity of the polypeptide. For example, a fusion partner comprises a sequence that assists in expressing the protein (an expression enhancer) at higher yields than the native recombinant protein. Other fusion partners may be selected so as to increase the solubility of the protein or to enable the protein to be targeted to desired intracellular compartments. Still further fusion partners include affinity tags, which facilitate purification of the protein. Fusion polypeptides may be produced by chemical synthetic methods or by chemical linkage between the two moieties or may generally be prepared using other standard techniques.

In general, polypeptides and fusion polypeptides (as well as polynucleotides encoding them) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., Serological Methods, a Laboratory Manual (1990) and Maddox et al., J. Exp. Med. 158:1211-1216 (1983).

H. Methods

As noted above, the invention generally relates, in part, to production of implants and grafts comprising biocompatible polymeric scaffold materials and one or more cell populations for use in regenerative medicine. The implants or grafts are shapeable into various forms, including, but not limited to sheets, tubes, and any other three-dimensional spatial pieces. Further, the cells growing on the implants or grafts promote regeneration by repairing, replacing or restoring damaged tissues or organs.

1. Wound Treatment

In one embodiment, implants and grafts are used for treating wounds. Exemplary wounds that can be treated by implants and grafts described herein, include, but are not limited to: blast injuries suffered during combat such as blunt trauma, shrapnel wounds and burns; burns, cuts (superficial and deep), scrapes, abrasions, gashes, and punctures.

After a wound has been cleaned and disinfected, it is closed to promote healing and reduce the risk of infection. The most frequently used closures are sutures and staples. These devices have the advantages of excellent tensile strength, a low dehiscence rate and rapid and simple application. However, the disadvantages are requiring removal and leaving scars on the tissue. Sutures and staples cannot be used to completely close wounds that have gaps in their proximate edges and do not seal the wound nor promote wound healing.

Recently, adhesives such as cyanoacrylate glues and fibrin biological adhesives have been introduced to close traumatic injuries and surgical incisions. N-butyl-1,2-cyanoacrylate (Histoacryl) and 2-octyl-cyanoacrylate (Dermabond) are widely used to close surface wounds and incisions. These adhesives cure rapidly upon contact with water, provide excellent tensile strength (30.6 N) and are sloughed off during the healing process. Tooth enamel bonded with cyanoacrylate has a shear bond strength of up to 7 MPa.

However, the contraindications for their use are inadequate hemostasis, areas of the skin under high tension, such as over the joints, or proximity to moist areas, which reduces tensile strength. Because cyanoacrylate adhesives are toxic and release formaldehyde during their breakdown by the body, they are not recommended for closing deep incisions or wounds. Infected or heavily contaminated wounds should not be closed with these adhesives.

Fibrin sealants include fibrinogen and thrombin as separate components. When these two proteins are mixed, the fibrinogen is cleaved and a fibrin clot forms, sealing and closing the wound. Additional components such as human factor XIII and aprotinin are often included in the preparations to increase the tensile strength of the clot and reduce fibrinoloysis. However, fibrin sealants can be limited in their application as wound adhesives by their relatively low tensile strength (30 kPa). In addition, fibrin sealants do not have adequate tensile strength to close skin injuries. In some instances, adverse immunologic reactions are observed with repeated use of fibrin preparations that contain bovine blood products such as aprotinin.

Tropoelastin is synthesized as a natural monomer and then catalytically polymerized; thus, the monomer can be applied to the edges of a wound and polymerized in vivo on the surface or within the edges of a wound, physically closing and sealing the wound.

During polymerization, tropoelastin-based scaffolds, as described elsewhere herein, are conducive to cell attachment and growth, and can promote the wound healing process. Thus, in addition to performing as a strong wound adhesive and sealant, tropoelastin-based implants may also contribute to accelerated wound healing by attracting regenerative cells into a supporting scaffold that self-assembles during fibrillogenesis. Tropelastin itself can participate as a reinforcing material in a newly forming scar.

Thus, in one embodiment, an implant or graft comprising a biocompatible polymer scaffold comprising one or more tropoelastin polypeptides and one or more cell populations is grafted to a wound of a subject to repair, replace, or regenerate the wounded tissue.

Without wishing to be bound by any particular theory, the foregoing implant or graft provides a regenerative phase that continues for days, weeks, or months, and further provides an increased rate of epithelial cell growth that helps repair the wound with new tissue. Implants and grafts used in particular embodiments of the present invention provide more rapid wound healing, more perfect reconstruction of the damaged parts of the wound, and minimize wound contraction.

In a particular embodiment, a wound of a subject is treated by providing an implant or graft comprising a biocompatible polymer scaffold comprising one or more tropoelastin polypeptides. The scaffold or graft can be molded into any form. In one embodiment, the scaffold is cast as a sheet, with a thickness that matches that of the wounded area.

In another particular embodiment, the scaffold is cast directly in the wound.

In another particular, embodiment, the scaffold is seeded with one or more cell populations. In a related embodiment, the cell populations comprise fibroblasts, keratinocytes, and other cell types that can promote wound healing and tissues regeneration (e.g., stem cells).

In certain embodiments, the implant comprises growth factors, co-polymers, and a distribution of tropoelastin polypeptides similar to the wounded tissue.

Without wishing to be bound by any particular theory, it is contemplated that providing an implant comprising a tropoelastin polypeptide profile similar to the wounded tissue will result in a repaired wound whose tissue is indistinguishable from normal tissue, aesthetically and functionally.

2. Guided Tissue and Bone Regeneration

In various embodiments, the biocompatible polymer scaffolds described herein are used in regenerative medicine for osteopathic applications, including, but not limited to craniofacial, odontic, and periodontic applications.

In one embodiment, implants and grafts are provided that comprise biocompatible polymer scaffolds comprising one or more tropoelastin polypeptides for use in reconstruction and regeneration of oral and craniofacial tissues.

In particular embodiments, a biocompatible polymer scaffold comprises one or more tropoelastin polypeptides and a human collagen co-polymer. The resulting scaffolds are engineered for the desired surface topography, porosity, strength and elasticity.

In one embodiment, the biocompatible polymer scaffold is cast in the form of a sheet and can be used as a regenerative membrane in various clinical applications, e.g., guided tissue regeneration (GTR) or root coverage procedures.

In one embodiment, the biocompatible polymer scaffold is cast as a sheet and seeded with periodontal ligament cells (PDL) forming an implant or graft that is suitable for use in a root coverage procedure. Once the implant has formed, a surgeon engrafts the implant in a root coverage procedure using methods known to those having ordinary skill in the art.

In another embodiment, the biocompatible polymer scaffold is cast in a three dimensional shape for use as a bone filling material. Virtually any shape can be achieved because the unpolymerized scaffold material is in a shapeable putty-like form. Once molded, the scaffold can be hardened by cross-linking. In addition, the shapeable scaffold can support unique clinical applications in periodontal medicine for guided bone regeneration (GBR) procedures and eliminate the need for a bone filler and a membrane to contain the bone graft.

In a particular embodiment, an implant comprises a biocompatible polymer scaffold as described herein, molded into a desired shape, and one or populations of cells.

In a certain embodiment, an implant or graft comprises one or more cell populations comprises bone marrow stem cells, mesenchymal stem cells, or pre-osteoblast cells to facilitate tissue or bone regeneration. Additionally, the osteogenic potential of the shapeable scaffold/implant can be used as a sole therapy or in combination with currently available commercial bone filler products or primary autologous bone harvests.

One having ordinary skill in the art would recognize that any type of bones can be repaired, replace, or regenerated using the foregoing techniques.

3. Vasculature Regeneration

As noted above, in particular embodiments, biocompatible polymer scaffolds are cast into the form of tubes. The dimensions, elasticity, and strength of the tubular scaffolds can be engineered to be useful as arteries, veins, ducts, ureters, urethras, and virtually any other tubular structure in the body wherein reparative, replacement, or regenerative therapy is desired or required.

In one embodiment, an implant or graft is provided to repair, replacement or regenerate a vessel within the peripheral vascular system, cardiac vasculature, or cardiac tissue itself. The implant or graft can comprise a biocompatible polymer scaffold having one or more tropoelastin polypeptides, and one or more populations of cells. Exemplary cell populations used in an implant or graft to repair, replacement or regenerate a vessel within the vascular system comprise smooth muscle cells, fibroblasts, mesenchymal stem cells, bone marrow stem cells, and the like.

Thus, one significant advantage of the invention is the development of elastins with unique properties, e.g., tensile strength, elasticity, and flexibiltiy/stiffness, generated by combining 2, 3, 4, 5, 6, 7, 8, 9, 10 or more individual tropoelastin isoforms, themselves having unique properties. Such unique elastins can be tailored for use at locations in the body where their unique properties are the most advantageous. For example, the strongest fibers can be used to repair muscles, the most elastic fibers can be used to construct bladders and other flexible organs, e.g, blood vessels, and the stiffest fibers can be used in cartilage repair.

In particular embodiments, the vessel being repaired, replace, or regenerated is selected from the group consisting of: veins, venules, capillaries, arterioles, and arteries.

In other particular embodiments, the vessel being repaired, replace, or regenerated is selected from the group consisting of: coronary vessels, vessels in the brain, or any other vessel that has been damaged and/or injured and is in need of repair, replacement, or regeneration.

EXAMPLES

Example 1

Cloning and Sequence Analysis of Tropoelastin Isoforms

Genetic Analysis

Four non-fetal skin fibroblast cell lines from healthy donors were purchased from the Corriel Institute for Medical Research. Total RNA was extracted from the four cell lines. cDNA was synthesized from the RNA using reverse transcriptase, and the cDNA was amplified using PCR with specifically designed primers. The amplified DNA was then ligated into a plasmid and transformed into *Escherichia coli* (*E. coli*). Colonies containing the cloned cDNA were picked and the size of the inserted cDNA determined. Only colonies containing full length inserts were further evaluated. The cDNA was isolated from the host and subjected to full length DNA sequencing. A total of 96 distinct cDNA clones were sequenced.

A comparison of the sequences revealed that a total of 34 separate tropoelastin polymorphs were present in the mRNA from 4 human cell lines. A detailed polymorphism analysis of tropoelastin mRNAs obtained from four independent human fibroblast cell lines revealed the presence of many different exon mRNA polymorphisms. Applicants have discovered that at least 17 exons are involved in the alternative splicing of tropoelastin, including exons 2, 3, 5, 6, 8, 10, 11, 13, 17, 19, 20, 22, 23, 24, 25, 26, 28, 31, 32, and 33. In addition, Applicants identified partially deleted isoforms of exons 2, 6, 8, 10, 17, 20, 24, 26, and 28. In total, human tropoelastin comprises at least 29 exons, including partially deleted exons, that can be alternatively spliced; thus, potentially encoding a total of 841 alternatively spliced tropoelastin polypeptides. The following table shows the polynucleotide positions for each of the exons with reference to a tropoelastin cDNA, as set forth in SEQ ID NO: 49.

TABLE 2 human tropoelastin exons (to STOP codon)

| Exon number | Start polynucleotide | End polynucleotide |
|---|---|---|
| 1 | 1 | 82 |
| 2A | 83 | 133 |
| 2B | 122 | 133 |
| 3 | 134 | 163 |
| 4 | 164 | 196 |
| 5 | 197 | 232 |
| 6A | 233 | 352 |
| 6B | 260 | 352 |
| 7 | 353 | 403 |
| 8A | 404 | 469 |
| 8B | 419 | 469 |
| 9 | 470 | 511 |
| 10A | 512 | 631 |
| 10B | 560 | 631 |
| 11 | 632 | 661 |
| 12 | 662 | 733 |
| 13 | 734 | 775 |
| 14 | 776 | 835 |
| 15 | 836 | 889 |
| 16 | 890 | 979 |
| 17A | 980 | 1039 |
| 17B | 995 | 1039 |

TABLE 2-continued human tropoelastin exons (to STOP codon)

| Exon number | Start polynucleotide | End polynucleotide |
|---|---|---|
| 18 | 1040 | 1186 |
| 19 | 1187 | 1240 |
| 20A | 1241 | 1405 |
| 20B | 1241 | 1381 |
| 21 | 1406 | 1447 |
| 22 | 1448 | 1534 |
| 23 | 1535 | 1591 |
| 24A | 1592 | 1771 |
| 24B | 1610 | 1771 |
| 25 | 1772 | 1816 |
| 26A | 1817 | 2041 |
| 26B | 1817 | 1942 |
| 27 | 2042 | 2080 |
| 28A | 2081 | 2152 |
| 28B | 2086 | 2152 |
| 29 | 2153 | 2212 |
| 30 | 2213 | 2287 |
| 31 | 2288 | 2326 |
| 32 | 2327 | 2380 |
| 33 | 2381 | 2425 |
| 34 | 2426 | 2469 |

Moreover, a number of amino acid substitutions were identified that further increases the diversity of the tropoelastin polypeptides disclosed by Applicants. Illustrative tropoelastin polypeptides, including alternatively spliced tropoelastins and tropoelastins having amino acids mutations, are set forth in SEQ ID NOs: 2-48.

Example 2

Design of Tropoelastin Gene for Optimization of Protein Expression

Tropoelastin Gene Optimization and Design

The sequence of the human tropoelastin gene was originally published in 1987 (Indik et al. *P.N.A.S. USA* (1987); 84: pp. 5680-5684.). The gene encoding tropoelastin is large, spanning more than 41.5 kilobases and contains an extensive number of tandem repeated nucleotides. Moreover, the codon usage of the tropoelastin gene is highly biased toward expression in human cells. All of these factors contribute to the difficulty of successfully synthesizing this protein in alternative hosts. As a result, attempts to express the human gene in *E. coli* have largely been unsuccessful and yield only small amounts of tropoelastin protein (Indik et al. *Arch. Biochem. Biophys.* (1990); 280: (1): pp. 80-86).

The highly biased codon usage in the human tropoelastin gene interferes with assembly of the protein during translation, because the necessary tRNA molecules are not abundant in alternative hosts such as bacteria, yeasts or plants. Therefore, the rate of tropoelastin synthesis during gene expression is limited by the concentration of the appropriate tRNAs. For example, there are 79 glycine codons that are encoded as GGA in the human tropoelastin gene (Fazio et al. *J. Invest. Dermatol.* (1988);91: pp. 458-464). However, in alternative hosts the glycine codons GGU, GGG and GGC are used more frequently than GGA; thus, the rate of tropoelastin synthesis in these alternative hosts is compromised.

In addition, the human tropoelastin gene contains other features that contribute to the inefficient translation of mRNA into protein, including a large number of tandem repeating identical codons and long stretches of AT/GC sequences. The human tropoelastin mRNA also contains several self-complementary regions, which is conducive to the formation of stable helical structures that impede translation of mRNA into protein. Previous attempts by others have been made to address the codon bias with a synthetic tropoelastin gene containing a more universal codon usage have been largely unsuccessful (Martin S L, Vrhovski B, Weiss A. Total synthesis and expression in *Escherichia coli* of a gene encoding human tropoelastin. Gene. 1995; 154: 159-166.). The previous methods are only effective at a laboratory scale, producing human tropoelastin sporadically and in very limited quantities.

Applicants took a more comprehensive approach and designed a human tropoelastin DNA sequence that simultaneously addressed biased codon usage, tandem repeats, AT/GC stretches and unwanted helix formation. A final DNA sequence was designed with putative improved functional characteristics in all known structural aspects by using an iterative algorithm.

TABLE 3

Examples of Codon Preference Optimization

| Codon | | Human Gene | Alternative Host | Optimized Gene |
|---|---|---|---|---|
| Glycine | GGA | 43.3% | 34.6% | 34.3% |
| | GGU | 56.6% | 33.7% | 33.3% |
| | GGG | 0 | 15.4% | 14.8% |
| | GGC | 0 | 16.2% | 17.6% |
| Valine | GUA | 0 | 18.6% | 18.5% |
| | GUU | 100% | 40.3% | 40.2% |
| | GUG | 0 | 24.2% | 23.9% |
| | GUC | 0 | 16.9% | 17.4% |

The codon usage of the tropoelastin coding sequence was optimized to closely mimic the endogenous codon usage of the alternative host used for protein expression.

The number of tandem repeats of identical codons in the optimized sequence was simultaneously reduced during the gene design process. The original sequence contained 23 tandem repeats with up to 4 identical codons. The optimized sequence was engineered to contain 9 tandem repeats with 3 identical codons. Further, the number of AT/GC stretches was reduced from 62 stretches with more than 4 nucleotides to 38 stretches with more than 4 nucleotides. Secondary structure (Amarzguioui M, G. Brede E, Babaie M, Grotli B, Sproat H, Prydz E. Secondary structure prediction and in vitro accessibility of mRNA as tools in the selection of target sites for ribozymes. Nucleic Acids Res. 2000; 28(21): 4113-24.) was optimized by reducing the number of complimentary sequences that would tend to form helices by 36%.

One having skill in the art would appreciate that all of the tropoelastin polynucleotide sequences disclosed herein can be codon optimized for expression in any number of species.

Example 3

Expression of Tropoelastin Protein

Gene Synthesis and Expression

A codon optimized version of a human tropoelastin coding sequence, e.g., SEQ ID NOs: 84-86, was synthesized and was used to efficiently produce human tropoelastin, e.g., SEQ ID NOs: 47-48, in alternative hosts such as bacteria, yeasts and plants. The correct DNA sequence for the optimized tropoelastin polynucleotide was confirmed by sequencing, the optimized tropoelastin polynucleotide was ligated into an *E. coli* expression vector, and the optimized tropoelastin polynucleotide containing expression vector was transformed into *E. coli*. Several clones of the *E. coli* transformant were cultured, induced to express protein, and harvested. The expression of tropoelastin was analyzed by SDS PAGE. FIG. 1 shows that when the codon optimized version of the human tropoelastin coding sequence was expressed in *E. coli*, tropoelastin was efficiently expressed in the cell. The efficient expression of the optimized tropoelastin coding sequence validates the strategy used in re-designing the tropoelastin gene.

Example 4

Purification of Tropoelastin Protein

Protein Production and Purification

For use in composition and methods directed to guided regeneration, (e.g., guided tissue regeneration (GTR), guided bone regeneration (GBR)), we tropoelastin protein was produced at low cost and in large quantities using the following exemplary methods. A simple and efficient purification process was designed to purify tropoelastin protein in a few steps. A series of four histidine residues ("poly-His tag") was incorporated at the carboxy terminus of the tropoelastin protein to facilitate purification of the protein.

Figure 2:
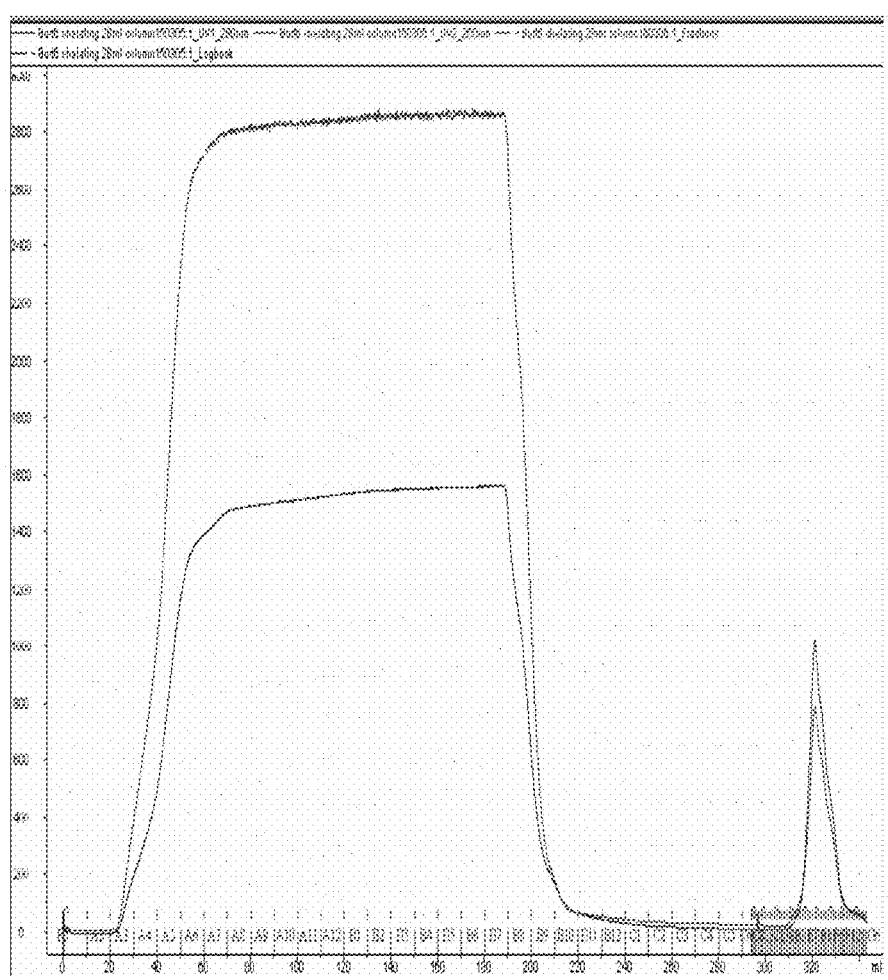
FIG. 2 shows a chromatographic profile of tropoelastin protein purification.

Cell paste containing the expressed tropoelastin was homogenized, extracted, clarified by centrifugation, and the supernatant passed over a column containing a nickel resin (HiTrap). The tropoelastin protein was eluted from the column as a single peak with 250 millimolar (mM) imidazole. The resulting chromatographic profile is shown in FIG. 2. Column fractions containing the tropoelastin protein were pooled and analyzed for purity by SDS PAGE. This analysis demonstrated that the optimized tropoelastin as designed and synthesized was purified to over 95% homogeneity by the use of a single chromatographic step on a Ni resin. Approximately 100 milligrams (mg) (dry weight) of tropoelastin protein was recovered from 100 milliliters (mL) of cell extract in this example. The manufacturing is scalable up to kilogram (kg) quantities of purified material. One kg of purified tropoelastin is sufficient to produce about 10,000 $cm^3$ of polymer membranes.

Example 5

Polymerization of Tropoelastin

Polymerization Studies

Figure 3:
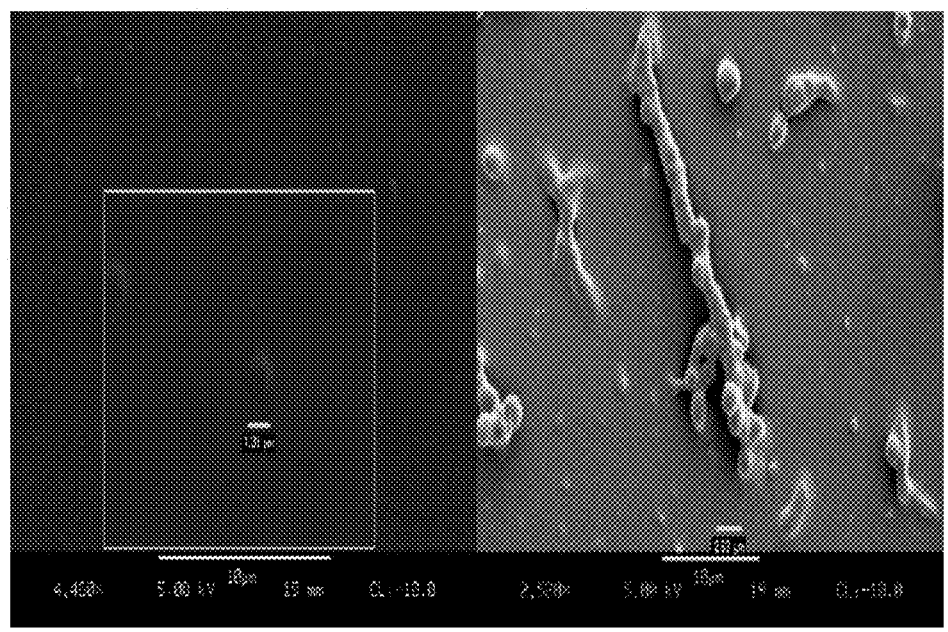
FIG. 3 shows SEM images that illustrate the self-assembly and subsequent formation of tropoelastin fibers up to 30 μm in length in the presence of a succinimide-PEG crosslinking reaction.

Purified tropoelastin was dialyzed into phosphate buffered saline (PBS) and polymerized with the crosslinking reagent N-hydroxy succinimide-PEG-N-hydroxy succinimide and allowed to react to completion. The reaction mixture was dried, fixed and prepared for SEM imaging. The images obtained from unreacted and crosslinked tropoelastin are shown in FIG. 3. These results indicated that purified tropoelastin formed cross-linkable fibers in vitro.

Example 6

Results of Clinical Trials with Tropoelastin Cream

Clinical Testing

A composition comprising purified tropoelastin protein was formulated with an emulsion cream carrier at a concentration of 200 μg tropoelastin protein per ounce of emulsion cream carrier and transferred to Clinical Research Laboratories, Inc. and the potential for dermal irritation and also dermal sensitization were assessed. A total of 54 adult subjects signed Informed Consent Forms in compliance with 21 CFR Part 50: "Protection of Human Subjects" and a HIPAA Authorization Form in compliance with 45 CFR Parts 160 and 164. All subjects completed a Subject Profile/Medical History Form provided by Clinical Research Laboratories, Inc. prior to the study.

Test Method

A patch comprising the tropoelastin in a carrier cream was applied to the upper back of the patients (between the scapulae) and allowed to remain in direct skin contact for a period of 24 hours.

Patches were Applied to the Same Site on Monday, Wednesday, and

Friday for a total of 9 applications during the Induction Period. The sites were graded by a CRL technician for dermal irritation 24 hours after removal of the patches on Tuesday and Thursday and 48 hours after removal of the patches on Saturday.

The sites were graded according to the following scoring system:

Dermal Scoring Scale

| Score | Skin Reactions |
|---|---|
| 0 | No visible skin reaction |
| ± | Barely perceptible erythema |
| + | Mild erythema |
| ++ | Well defined erythema |
| +++ | Erythema and edema |
| ++++ | Erythema and edema with vesiculation |

Following approximately a 2-week rest period, the challenge patches were applied to previously untreated test sites on the back. After 24 hours, the patches were removed by a CRL technician and the test sites were evaluated for dermal reactions. The test sites were re-evaluated at 48 and 72 hours.

Results

The results of the irritation study showed that the tropoelastin composition is non-irritating. None of the 54 subjects received an irritancy score above "0". The results of the challenge study indicated that the tropoelastin composition is non-sensitizing. None of the 54 subjects received a challenge score above "0" after 24, 48 or 72 hours of observation. Therefore, the tropoelastin composition described above was non-irritating and non-sensitizing to patients.

Example 7

Recombinant Human Tropoelastins as a Material for Use in Wound Care

Recombinant human tropoelastin and/or tropoelastin polymorphs are characterized as a crossed-linked material for use in wound care. In vitro and in vivo tests are performed to evaluate the structure, tensile strength, and biocompatibility of the cross-linked tropoelastin material.

Scanning Electron Microscopy (SEM) is used to evaluate the surface structure of the cross-linked tropoelastin material using three different cross-linkers. Tensile strength of the three different tropoelastin cross-linked materials is characterized using an Instron device and is compared to currently available materials (e.g. Dermabond). A well characterized in vivo subcutaneous implant model in a rodent is used to evaluate the biocompatibility of the cross-linked tropoelastin materials. Standard outcome measures of fibrous capsule formation, activated tissue macrophages, foreign body giant cell presence, and the resulting vascular response to the material are evaluated (Kellar et al., *Journal of Biomedical Materials Research.* 61 (2): 226-233; 2002 and Kidd et al. *Journal of Biomedical Materials Research.* 59 (4): 682-689; 2002).

Example 8

Recombinant Human Tropoelastins as a Wound Adhesive

Recombinant human tropoelastin and/or tropoelastin polymorphs are cross-linked then evaluated as a wound adhesive. Currently available wound adhesives use synthetic components (e.g. cyanoacrylate) which have toxic properties to healing tissues. Other currently available options include biological solutions such as fibrin from animal sources. However, fibrin obtained from animal sources raises concerns for patient use based on animal-source disease transmission or allergies to animal-source materials. Human tropoelastin as a wound adhesive can help promote wound healing and thus reduces the incidence of infection in wounds.

In addition, a wound adhesive based on human tropoelastin and/or tropoelastin polymorphs can also accelerate healing and assist in wound edge approximation. The cross-linked tropoelastin material is tested for efficacy in vivo using an incisional wound model in the rat (Kapoor, M. et. al., *Am. J. Path.* 2004. 165: 299-307). Outcome measures that are evaluated in this wound model include: wound closure rates, re-epithelialization, wound strength, and scar formation.

Example 9

Generation and Characterization of Tropoelastin Scaffolds

Experimental Overview

Tropoelastin sheet scaffolds and tropoelastin shapeable scaffolds will be created. These two types of scaffolds will be evaluated using in vitro techniques to assay the affinity of periodontal ligament (PDL) cells and cryopreserved human bone marrow-derived mesenchymal stem cells (MSCs) for the respective scaffold prototypes.

PDL cells were selected for biocompatibility evaluation of the sheet scaffolds in guided tissue regeneration (GTR) applications such as dental root coverage procedures. Additionally, cryopreserved human bone marrow-derived MSCs were selected for applications incorporating stem cell therapies for GTR and guided bone regeneration (GBR) procedures.

Recombinant human tropoelastin can be cross-linked to create new materials suitable for use as membranes in GTR and GTB applications. The type and degree of crosslinking and presence of human collagen can alter the physical and biological characteristics of these new membranes.

Methods

The human extracellular matrix protein tropoelastin (monomeric) is co-polymerized with human collagen, and cross-linked membranes for guided tissue and bone regeneration are fabricated. The resulting structures are characterized for surface topography, porosity, strength and elasticity. Microscopy and mechanical testing are used to measure and compare mechanical properties and surface topography of tropoelastin polymer membranes with varying degrees of crosslinking and as a copolymer with human collagen.

Human tropoelastin monomer will be synthesized by and obtained by methods described herein. Tropoelastin monomer is cross-linked using bis(sulfosuccinimidyl) suberate (11.4 A° (Mithieux J, Rasko E, Weiss AS, Synthetic elastin hydrogels derived from massive elastic assemblies of self-organized human protein monomers. Biomaterials. 2004; 25:

4921-4927.) or dimethyl adipimidate (8.6 A° at crosslinker: tropoelastin molar ratios ranging from 2:1 to 10:1 and allowed to polymerize at 37° C., the temperature at which tropoelastin coacervates (Clark A. Arnspang E. Mithieux S. Korkmaz E. Braet P. Weiss A. Tropoelastin massively associates during coacervation to form quantized protein spheres. Biochemistry. 2006. 45: 9989-9996.).

In particular embodiments, tropoelastin monomer is mixed with human collagen (e.g., Fibrogen) at tropoelastin:collagen molar ratios ranging from about 10:1 to about 1:1 and crosslinked using bis suberate.

Polymerized structures are cast as membranes of varying thicknesses of about 0.5 mm to about 5 mm between glass sheets. Optimized selection of crosslinking and copolymerization conditions for GTR and GBR membranes is performed by characterizing the mechanical properties of the sample. Scanning Electron Microscopy and Atomic Force Microscopy are used to characterize the surface topography of the samples, which is important for fostering cell attachment. Uniaxial tensile testing is performed using a material testing apparatus designed specifically for biomaterials testing. Mechanical measurements are obtained from human tropoelastin membranes and membranes comprising copolymer blends of tropoelastin and collagen.

Results

The static and dynamic mechanical properties of each of the tropoelastin membranes will be evaluated as noted above. Crosslinked tropoelastin polymers and copolymers comprising collagen could exhibit variations in their mechanical properties.

Example 10

Tropoelastin Sheet Scaffolds Comprising Tropoelastin Polymorphs and PDLs

Experimental Overview

Tropoelastin sheet scaffolds are generated using tropoelastin polymorphs. The scaffold supports the growth and maintenance of PDL cells in in vitro tissue culture. The growth of PDL cells on these scaffolds indicates that the tropoelastin scaffolds comprising tropoelastin polymorphs can be used as GTR membranes for root coverage procedures. Recombinant tropoelastin scaffolds can support the growth and maintenance of PDL cells over currently available membrane technologies alone (e.g. AlloDerm®).

Methods

PDL cells are obtained from human teeth using routine extractions from consenting patients. Extracted teeth are stored in I-MEM (Biochrom, Berlin, Germany) at 37° C. PDL explants are dissected from the cervical root thirds using methods commonly known in the art. PDL cells will be cultured without enzymatic treatment according to Ragnarsson et al. (Ragnarsson B, Carr G, Daniel J C *Isolation and growth of human periodontal ligament cells in vitro*. Journal of Dental Research. 1985. 64: 1026-1030.) at 37° C. in a humidified incubator with 5% $CO_2$/95% air. All cultures are incubated with a-minimum essential-medium (a-MEM) (Biochrom) supplemented with 10% heat-inactivated fetal calf serum (FCS) (Nunc, Wiesbaden, Germany), 2 mg/ml sodium hydrogencarbonate (Merck, Darmstadt, Germany), 100 mg/ml ascorbic acid (Merck), 50 mg/ml b-aminoproprionitrile (Sigma, Munich, Germany), 100 U/ml penicillin G (Sigma), 100 mg/ml streptomycin (Sigma) and 40 U/ml of nystatin (Sigma) at pH 7.4. Media is changed every three days and cells are subcultured at a density of 2500 cells/mm³. Typical cell passage conditions include incubating cell cultures in a solution of phosphate-buffered saline (PBS), without any $Ca^{2+}$ or Mg2+ ions, containing 0.05% trypsin/0.02 (:)/0 EDTA (Nunc). This solution is inactivated with FCS prior to cell centrifugation (1200 r.p.m. for 5 minutes).

PDL cells are resuspended at a density of $10^5$ cells per 3 ml of I-MEM. PDL cells are cultured on the tropoelastin sheet scaffolds that are the size of cell culture disk inserts that fit into 12-well tissue culture plates. Control tissue culture wells contain commercially available AlloDerm® (BioHorizons, Birmingham, Ala.). Cell culture experiments are performed in triplicate and are characterized for cell viability and number at 24, 48, 72 hours, and 1 week timepoints. Cell viability is monitored by trypan blue exclusion. Subsequently, the cells will be counted in triplicate in a Coulter Counter.

Results

Tropoelastin sheet scaffolds could support PDL cell growth and maintenance over the course of an experiment (24, 48, 72 hours, and 1 week). Initial cell populations will be compared to cell numbers at the various timepoints. Cell viability data is an important indicator of PDL cell affinity toward the tropoelastin sheet scaffold. Comparisons to AlloDerm® will be made at the various timepoints and could demonstrate equivalence of the tropoelastin scaffold to a well established, widely clinical-used periodontal membrane (Gapski R, Parks Calif., Wang H L. *Acellular Dermal Matrix for Mucogingival Surgery: A Meta-Analysis*. J Periodontol November 2005, Vol. 76, No. 11: 1814-1822; Papageorgakopoulos G, Greenwell H, Hill M, Vidal R, Scheetz JP. Root coverage using acellular dermal matrix and comparing a coronally positioned tunnel to a coronally positioned flap approach. J Periodontol. 2008 June; 79(6):1022-30; and Cummings L C, Kaldahl W B, Allen E P. Histologic evaluation of autogenous connective tissue and acellular dermal matrix grafts in humans. J Periodontol. 2005 February; 76(2): 178-86).

Example 11

Tropoelastin Shapeable Scaffolds Comprising Tropoelastin Polymorphs and MSCs

Experimental Overview

Tropoelastin shapeable scaffolds are generated using tropoelastin polymorphs. Tropoelastin shapeable scaffolds support growth and maintenance of cryopreserved human bone marrow-derived mesenchymal stem cells (MSCs) in in vitro tissue culture. Tropoelastin shapeable scaffolds are manufactured in a variety of shapes and forms, as described elsewhere herein. The scaffolds are used as delivery vehicles for or as a sole therapy for repairing and/or regenerating bone in GBR and GTR procedures. Recombinant tropoelastin scaffolds comprising tropoelastin polymorphs support the growth and maintenance of cryopreserved MSCs over currently available bone filler materials alone (e.g. Grafton®).

Methods

Methods for culturing cryopreserved human bone marrow-derived MSCs are known to those having ordinary skill in the art, for example, in the methods published by Kundu et al. (Kundu A K, Khatiwala C B, Putnam A J. *Extracellular Matrix Remodeling, Integrin Expression, and Downstream Signaling Pathways Influence the Osteogenic Differentiation of Mesenchymal Stem Cells on Poly(Lactide-Co-Glycolide) Substrates*. Tissue Engineering. 2008. Part A, Vol 14. 1-11). Cells are purchased from Lonza (Walkersville, Md.) at passage 2. The manufacturer tests these cells for purity using flow cytometry and for their ability to differentiate into osteogenic, chondrogenic, and adipogenic lineages. The cells are positive for the cell surface markers CD105, CD166, CD29, and CD44 and negative for CD14, CD34, and CD45.

MSCs are routinely cultured and expanded in a non-differentiating growth medium consisting of Dulbecco's modified Eagle medium (DMEM) supplemented with 10% fetal bovine serum (FBS), 4 mM of L-glutamine, 100 units/mL of penicillin and 0.1 mg/mL of streptomycin. Cells are grown in a 5% $CO_2$ atmosphere at 37° C., and the medium is renewed every 2 to 3 days. Before confluence, cells are trypsinized using trypsin-ethylenediaminetetraacetic acid (Tryp-EDTA; Invitrogen) and passaged 1:3 into fresh culture flasks. Experiments are conducted using cells below passage 8.

The osteogenic differentiation of MSCs on tropoelastin shapeable scaffolds vs. Grafton® (BioHorizons, Birmingham, Ala.) is monitored using an ALP activity assay and the von Kossa method to stain for deposited calcium phosphate mineral (Kundu A K and Putnam A J. *Vitronectin and collagen I differentially regulate osteogenesis in mesenchymal stem cells.* Biochem Biophys Res Commun. 2006. 347). For both assays, MSCs ($2.5 \times 10^4$ cells/cm3) are seeded on shapeable tropoelastin scaffolds in 12 well culture dishes in serum-containing medium for 24 h. The culture medium is replaced with OS medium and is changed every other day.

For the ALP assay, MSCs are lysed after 7 and 14 days in passive lysis buffer (Promega Corporation) for 15 min at room temperature. Lysates are scraped from the wells of the tissue culture plates of tropoelastin shapeable scaffolds and Grafton® controls and then incubated with 50 mM of p-nitrophenylphosphate in assay buffer (containing 100 mM glycine, 1 mM $MgCl_2$, pH 10.5) at 37° C. for 25 minutes. The reaction is stopped by adding 0.5 mL 0.1 N sodium hydroxide and the absorbance read at 405 nm. The specific ALP activity is determined using the extinction coefficient for p-nitrophenylphosphate ($1.85 \times 10^4$/M per cm) and then expressed in units of ALP activity per mg of protein.

For von Kossa staining, a commercially available kit (American MasterTech Scientific Inc, Lodi, Calif.) is used to stain calcium phosphate mineral deposited by MSCs cultured on tropoelastin shapeable scaffolds in OS medium. As in the ALP assays, medium with fresh inhibitors is provided every other day. After 14 days, cells are washed twice with warmed PBS pH 7.4, followed by fixation using 4% formaldehyde in PBS at 25° C. for 40 min. Samples are then extensively rinsed with double distilled water and incubated in the presence of 5% silver nitrate, followed by exposure to ultraviolet light for 40 min. After extensive rinsing with water, the cells are treated with 5% sodium thiosulphate for 3 min, rinsed, and then incubated in Nuclear Fast Red stain for 5 min before a final rinse with water. Staining results are visualized on a Nikon E800 (Nikon, Melville, N.Y.) microscope using a 10× objective and the images compiled with using a standard image analysis software program.

Results

Tropoelastin shapeable scaffolds could demonstrate equal or superior ability to culture cryopreserved human bone marrow-derived MSCs and facilitate osteogenic differentiation than presently available methods. Results can be compared to Graftoecontrols, a commercially available bone graft material that has shapeable characteristics. The tropoelastin shapeable scaffolds could afford the same shapeable properties of existing methods with an added benefit of stable cross-linking which can eliminate the need for a secondary membrane covering.

Example 12

Cross-Linked Tropoelastin Material for Use as a Tissue Culture Scaffold

Experimental Overview

Recombinant tropoelastin and/or tropoelastin polymorphs are manufactured, cross-linked, and characterized for use as a tissue culture scaffold. Microscopy and mechanical testing are used to measure and compare mechanical properties and surface topography of three cross-linked tropoelastin polymorphs. The different cross-linked polymorphs can exhibit variation in mechanical properties.

Methods

The different tropoelastin polymorphs (monomeric) will be synthesized by and obtained by the methods described elsewhere herein. Each monomeric polymorph will be catalytically cross-linked either with the established bis(sulfosuccinimidyl) suberate (11.4 A° (Mithieux et al., 2004)), dimethyl adipimidate (8.6 A° or thiol-cleavable 3,3"-dithiobis (sulfosuccinimidylpropionate) (12 A° at crosslinker: tropoelastin molar ratios ranging from 2:1 to 10:1 and allowed to polymerize at 37° C., the temperature at which tropoelastin coacervates (Clark et al., 2006).

Polymerized materials are cast as solid rods and barbells. SEM and Atomic Force Microscopy (AFM) are used to characterize the surface topography of the samples, which is important for fostering cell attachment. Uniaxial tensile testing is performed using a material testing apparatus designed specifically for biomaterials testing, capable of applying both static and dynamic loads with high accuracy at low forces and high strains. Such a device is necessary because tropoelastin is highly extensible, has an elastic modulus of 220–280 kPa, and the polymerized materials have a cross-sectional area on the order of about 5 mm3 to about 50 mm3.

Dynamic testing is used to measure fatigue and endurance properties of the samples under cyclic loading. Creep behavior is assessed by measuring strain while subjecting the sample to constant applied loads. These measurements are performed both with the sample dry as well as immersed in a fluid environment that can simulate biological conditions.

Mechanical measurements are performed on three types of polymerized tropoelastin materials. The first type of polymerized tropoelastin material is solid tropoelastin of a single polymorph, which is used for correlating mechanical properties with genetic variation. The second type of polymerized tropoelastin material is for testing is porous tropoelastin. Porosity and void volumes of fabricated biomaterials such as tropoelastin influence cell attachment, migration, and proliferation onto material surfaces. Different porosities and void volumes for each tropoelastin polymorphs are tested. The third type of polymerized tropoelastin material is a copolymer blend of multiple tropoelastin polymorphs, prepared in both solid and porous configurations. Different configurations of copolymer blends of multiple tropoelastin polymorphs are tested. Thorough characterization of the mechanical properties polymerized tropoelastin materials allows for optimized selection of materials for tissue culture scaffolds. Testing multiple blends of polymorphs allows for creating potentially novel optimal materials.

Results

Methods for evaluating the static and dynamic mechanical properties of each of the tropoelastin polymorphs are disclosed. The different tropoelastin polymorphs or combinations thereof, could exhibit variations in their mechanical properties due to the variations in genetic sequence.

Example 13

Biocompatibility of Tropoelastin Scaffolds

Experimental Overview

The biocompatibility is evaluated as a vehicle for tissue culture scaffolds for three different cross-linked tropoelastin scaffold prototypes, e.g., the scaffolds produced in Example 12. The current methods for culturing of various cell types, including pluripotent stem cell populations require specialized protein surfaces for cellular attachment. In the case of certain stem cell populations, feeder layers are also required. A novel tropoelastin scaffold provides an appropriate protein interface for cellular attachment and obviate the need for other more specialized scaffolds known in the art.

Methods

Commercially available fibroblasts are obtained and cultured using standard cell culture techniques. Established cell cultures are harvested and cultured onto the tropoelastin scaffold prototypes in 12 well plates. Cell populations are determined 24, 48, and 72 hours post-culture on the three different scaffold prototypes. Experiments are done in triplicate and means and standard deviations are calculated for comparisons.

In another embodiment, bone marrow-derived stem cells are harvested from rats, purified and frozen using existing protocols. Methods of subculture/expansion, analysis and cryopreservation of the whole stem cell fraction are evaluated and optimized. Additionally, clonal selection is performed to isolate pure cultures of stem cells. Researcher's Working Cell Banks (RWCB) are produced.

Briefly, male Sprague Dawley rats of various ages are anesthetized and both femurs are removed. The ends of each femur are cut off and flushed with 10-30 mL of sterile 10% FBS in Dulbecco's modified Eagle's Medium-Low Glucose (DMEM-LG). Bone spicules and clots are allowed to settle briefly after which the cell suspension is decanted into a sterile 50 mL tube. The bone marrow mononuclear cell (BM-MNC) fraction is isolated using Ficoll density gradient centrifugation. The cells of the BMMNC fraction are plated at $1 \times 10^5$ cells per well in 24 well plates grown in an incubator at 37° C. with 5% CO2. The cells are trypsinized using 0.25% Trypsin-EDTA and subsequently counted using a coulter counter. Cells bearing CD34, CD90, and CD44 markers are identified and purified using dynal beads. Purity of the purified cells is verified using flow cytometry. The cells are labeled using both Dil and CFD SE.

Conditions are optimized for subculture, expansion, analysis, cryopreservation and subsequent revival of these cells. These procedures yield the cells of the RWCB.

Bone marrow-derived stem cells from the RWCB are grown on tropoelastin scaffolds. Ranging studies are performed to optimize culturing conditions (e.g. media composition, culture time). Engraftment of the stem cells onto tropoelastin scaffolds is visualized microscopically. Labeling of stem cells is used to trace cells in vitro and for in vivo experiments.

Labeling of the BMMNC cells in culture is performed using standards methods known to those having ordinary skill in the art. An exemplary method uses a commercially available Vybrant® CFDA SE (carboxyfluorescein diacetate, succinimidyl ester) Cell Tracer Kit provided by Invitrogen. This kit provides a versatile and well-retained cell-tracing reagent in a convenient and easy-to-use form. CFDA SE passively diffuses into cells. CFDA SE is colorless and nonfluorescent until undergoing cleavage of the acetate groups by intracellular esterases to yield highly fluorescent, amine-reactive carboxyfluorescein succinimidyl ester. The succinimidyl ester group reacts with intracellular amines, forming fluorescent conjugates that are well-retained and can be fixed with aldehyde fixatives. Excess unconjugated reagent and by-products passively diffuse to the extracellular medium, where they are washed away. The dye-protein adducts that form in labeled cells are retained by the cells throughout development, meiosis, and allow in vivo tracing.

Harvested BMMNC cells are centrifuged to obtain a cell pellet and the supernatant is aspirated. BMMNC cells are resuspended in prewarmed (37° C.) PBS containing the labeling probe. The BMMNC cells and the labeling probe are incubated together for 15 minutes at 37° C. The BMMNC cells are re-pelleted by centrifugation and resuspended in fresh prewarmed medium. The BMMNC cells are subsequently incubated for another 30 minutes to ensure complete modification of the probe and then the BMMNC cells are washed again. Visualization of the harvested BMMNC is possible within the tropoelastin scaffold.

Results

Methods for determining biocompatibility of the tropoelastin scaffolds using standard fibroblast cell culturing experiments are disclosed. A Researcher's Working Cell Bank of a mixed population of stem cells could be established in sufficient quantities to carryout the experiments described herein. In addition, this example shows that bone marrow-derived stem cells could be cultured on the tropoelastin scaffolds Example 14

A Tropoelastin Scaffold Seeded with Bone Marrow-Derived Stem Cells as a Treatment for Chronic Heart Failure Experimental Overview Cell-seeded bioengineered tropoelastin scaffolds are evaluated as a regenerative medicine therapy in vivo. Treatment with tropoelastin scaffolds seeded with bone marrow-derived stem cells are used to improve measureable outcomes in an existing rat model of heart failure model.

Methods

The effect of a tropoelastin scaffold seeded with bone marrow-derived stem cells as a treatment for chronic heart failure is evaluated. Left coronary artery ligation is used to infarct rat hearts, thus creating a model of chronic heart failure. The 3 week timepoint has previously been shown as a point in time where chronic heart failure is established. These rats have stable heart failure with elevated LV-EDPs, dilated LV, with ventricular remodeling, decreased LV dP/dt, decreased cardiac output and decreased survival. A control group of infarcted-only rats is used as a control group. Hemodynamics of the coronary vessels, echocardiography, and histology of the heart tissue and vasculature will be evaluated in this study.

Results

Treatment of myocardial infarction with tropoelastin scaffolds seeded with bone marrow-derived stem cells could positively influence LV remodeling. Other positive treatment outcomes include, but are not limited to altered LV dilatation, an improved EF, a lower LV end-diastolic pressure, an improved cardiac output and a higher LV dP/dt. Treatment with tro poelastin scaffolds seeded with bone marrow-derived stem cells could alter infarct size and stimulate angiogenesis.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A complementary DNA (cDNA) comprising a nucleotide sequence that has at least 95% identity to a nucleotide sequence as set forth in any one of SEQ ID NOs: 84-86.

2. The cDNA of claim 1, wherein the cDNA has the nucleotide sequence set forth in any one of SEQ ID NOs: 84-86.

3. The cDNA of claim 1, wherein the cDNA encodes a tropoelastin polypeptide comprising an amino acid sequence as set forth in any one of SEQ ID NOs: 13, 47, and 48.

4. The cDNA of claim 1, wherein the cDNA encodes a tropoelastin polypeptide comprising an amino acid sequence as set forth in SEQ ID NO: 13.

5. The cDNA of claim 2, wherein the cDNA encodes a tropoelastin polypeptide comprising an amino acid sequence as set forth in any one of SEQ ID NOs: 13, 47, and 48.

6. The cDNA of claim 1, wherein the nucleotide sequence is codon optimized for expression in *Escherichia coli*, yeast, or insect cells.

7. A complementary DNA (cDNA) comprising a nucleotide sequence that has at least 85% identity to a nucleotide sequence as set forth in any one of SEQ ID NOs: 84-86.

8. A complementary DNA (cDNA) comprising a nucleotide sequence that has at least 90% identity to a nucleotide sequence as set forth in any one of SEQ ID NOs: 84-86.

* * * * *